(12) United States Patent
Maures et al.

(10) Patent No.: US 12,139,707 B2
(45) Date of Patent: Nov. 12, 2024

(54) STABILIZED CRISPR COMPLEXES

(71) Applicant: Synthego Corporation, Redwood City, CA (US)

(72) Inventors: Travis Maures, La Jolla, CA (US); Jared Carlson-Stevermer, Burlingame, CA (US); Sahil Joshi, Somerville, MA (US); Reed Kelso, San Francisco, CA (US); Anastasia Kadina, Sunnyvale, CA (US); John Andrew Walker, II, San Leandro, CA (US)

(73) Assignee: Synthego Corporation, Redwood City, CA (US)

( * ) Notice: Subject to any disclaimer, the term of this patent is extended or adjusted under 35 U.S.C. 154(b) by 378 days.

(21) Appl. No.: 17/384,417

(22) Filed: Jul. 23, 2021

(65) Prior Publication Data

US 2022/0056436 A1  Feb. 24, 2022

Related U.S. Application Data

(63) Continuation of application No. PCT/US2020/042681, filed on Jul. 17, 2020.

(60) Provisional application No. 63/010,465, filed on Apr. 15, 2020, provisional application No. 62/939,554, filed on Nov. 22, 2019, provisional application No. 62/939,553, filed on Nov. 22, 2019, provisional application No. 62/876,204, filed on Jul. 19, 2019, provisional application No. 62/876,177, filed on Jul. 19, 2019.

(51) Int. Cl.
C12N 15/11 (2006.01)
C07F 9/655 (2006.01)

(52) U.S. Cl.
CPC .......... *C12N 15/11* (2013.01); *C07F 9/65522* (2013.01); *C12N 2310/20* (2017.05); *C12N 2310/321* (2013.01); *C12N 2310/3513* (2013.01); *C12N 2310/53* (2013.01)

(58) Field of Classification Search
CPC ........................... C12N 15/11; C12N 2310/20
See application file for complete search history.

(56) References Cited

U.S. PATENT DOCUMENTS

| | | | |
|---|---|---|---|
| 5,849,902 | A | 12/1998 | Arrow |
| 7,897,737 | B2 | 3/2011 | Wu |
| 8,603,996 | B2 | 12/2013 | Galloway |
| 9,932,566 | B2 | 4/2018 | Kennedy |
| 2008/0227742 | A1 | 9/2008 | Dmochowski |
| 2010/0022761 | A1 | 1/2010 | Chen |
| 2010/0216804 | A1 | 8/2010 | Zale |
| 2010/0303850 | A1 | 12/2010 | Lipford |
| 2011/0020388 | A1 | 1/2011 | Zepp |
| 2011/0027217 | A1 | 2/2011 | Zepp |
| 2011/0217377 | A1 | 9/2011 | Zale |
| 2012/0171229 | A1 | 7/2012 | Zepp |
| 2012/0178702 | A1 | 7/2012 | Huang |

FOREIGN PATENT DOCUMENTS

| | | |
|---|---|---|
| WO | 1998013526 A1 | 4/1998 |
| WO | 2008103276 | 8/2008 |
| WO | 2010005740 | 1/2010 |
| WO | 2010030763 | 3/2010 |
| WO | 2010075072 | 7/2010 |
| WO | 2010138192 | 12/2010 |
| WO | 2010138193 | 12/2010 |
| WO | 2010138194 | 12/2010 |
| WO | 2011084518 | 7/2011 |
| WO | 2011127255 | 10/2011 |
| WO | 2012092552 | 7/2012 |
| WO | 2012099755 | 7/2012 |
| WO | 2017155408 A1 | 9/2017 |
| WO | 2017184799 A1 | 10/2017 |

OTHER PUBLICATIONS

McGregor et al (Nucleic Acids Research, 1996, vol. 24, No. 16 3173-3180) (Year: 1996).*
Sanchez et al (Org. Biomol. Chem., 2012, 10, 8478) (Year: 2012).*
Rouet et al (J. Am. Chem. Soc. 2018, 140, 6596-6603) (Year: 2018).*
Reyes et al (Cell Biochem Biophys (2017) 75:203-210) (Year: 2017).*
Jin et al (J. Org. Chem. 2005, 70, 4284-4299) (Year: 2005).*
Smith et al (RSC Adv., 2014, 4, 48228) (Year: 2014).*
Henkel et al (Bioconjugate Chem. 2016, 27, 2260-2265) (Year: 2016).*
Akinc, A., et al. "A combinatorial library of lipid-like materials for delivery of RNAi therapeutics." Nature biotechnology 26.5 (2008): 561-569.
Beaucage, S. L., et al. De-oxynucleoside phosphoramidites—a new class of key intermediates for deoxypolynucleotide syn. Tetrahedron Lett. 22: 1859-1862, 1981.
Behlke, M. A. "Chemical modification of siRNAs for in vivo use." Oligonucleotides 18.4 (2008): 305-320.
Beloglazova, N., et al. "A novel family of sequence-specific endoribonucleases associated with the clustered regularly interspaced short palindromic repeats." Journal of Biological Chemistry 283.29 (2008): 20361-20371.
Biosynthesis. Maleimide Oligonucleotide Modification. 2018. [online]. [Version dated Jun. 20, 2018]. Retrieved from the internet URL https://web.archive.org/web/20180620150124/https://www.biosyn.com/oligonucleotideproduct/maleimide-oligonucleotide-modification.aspx.

(Continued)

Primary Examiner — Richard A Schnizer
(74) Attorney, Agent, or Firm — Quarles & Brady, LLP

(57) ABSTRACT

Provided herein are polynucleotides and CRISPR effector proteins configured to be covalently bound together in a CRISPR complex. The polynucleotides can be further modified to modulate the activity of the CRISPR complex. Modification of the polynucleotide and CRISPR effector protein can be used to improve the efficacy of target binding and/or cleavage.

8 Claims, 66 Drawing Sheets

Specification includes a Sequence Listing.

(56) References Cited

OTHER PUBLICATIONS

Bohacova, S., et al. "Protected 5-(hydroxymethyl) uracil nucleotides bearing visible-light photocleavable groups as building blocks for polymerase synthesis of photocaged DNA." Organic & biomolecular chemistry 16.9 (2018): 1527-1535.

Boyle, E. A. et al. High-throughput biochemical profiling reveals sequence determinants of dCas9 off-target binding and unbinding. Proc. Natl Acad. Sci. USA 114, 5461-5466 (2017).

Briner, A. E. et al. Guide RNA functional modules direct Cas9 activity and orthogonality. Mol. Cell 56, 333-339 (2014).

Brinkman, E. K. et al. Kinetics and fidelity of the repair of Cas9-induced double-strand DNA breaks. Mol. Cell 70, 801-813.e6 (2018).

Buckup, T., et al. Optimisation of two-photon induced cleavage of molecular linker systems for drug delivery. J. Photochem. Photobiol. Chem. 210, 188-192 (2010).

Carlson-Stevermer, J., et al. "CRISPRoff enables spatio-temporal control of CRISPR editing." Nature communications 11.1 (2020): 1-7.

Chen, B., et al. "Dynamic imaging of genomic loci in living human cells by an optimized CRISPR/Cas system." Cell 155.7 (2013): 1479-1491.

Chen, C. H., et al. "Chemical conversion of a DNA-binding protein into a site-specific nuclease." Science 237.4819 (1987): 1197-1201.

Chylinski, K. et al. CRISPR-Switch regulates sgRNA activity by Cre recombination for sequential editing of two loci. Nat. Commun. 10, 1-12 (2019).

De Koker, S., et al. "Polymeric multilayer capsules delivering biotherapeutics." Advanced drug delivery reviews 63.9 (2011): 748-761.

Dellinger, D. J., et al. "Solid-phase chemical synthesis of phosphonoacetate and thiophosphonoacetate oligodeoxynucleotides." Journal of the American Chemical Society 125.4 (2003): 940-950.

Dellinger, D. J., et al. "Streamlined process for the chemical synthesis of RNA using 2'-O-thionocarbamate-protected nucleoside phosphoramidites in the solid phase." Journal of the American Chemical Society 133.30 (2011): 11540-11556.

Dow, L. E. et al. Inducible in vivo genome editing with CRISPR-Cas9. Nat. Biotechnol. 33, 390-394 (2015).

Endres, T. K., et al. "Self-assembled biodegradable amphiphilic PEG-PCL-lPEI triblock copolymers at the borderline between micelles and nanoparticles designed for drug and gene delivery." Biomaterials 32.30 (2011): 7721-7731.

Fu, Y. et al. High-frequency off-target mutagenesis induced by CRISPR-Cas nucleases in human cells. Nat. Biotechnol. 31, 822-826 (2013).

Fukuma, T., et al. "Conjugation of an antisense oligodeoxynucleotide to ribonuclease H results in sequence-specific cleavage and intracellular inhibition of HCV gene expression." Bioconjugate chemistry 14.2 (2003): 295-301.

Fuller, J. E., et al. "Intracellular delivery of core-shell fluorescent silica nanoparticles." Biomaterials 29.10 (2008): 1526-1532.

Gangopadhyay, S. A. et al. Precision control of CRISPR-Cas9 using small molecules and light. Biochemistry 58, 234-244 (2019).

Garcia, B. et al. Anti-CRISPR AcrIIA5 potently inhibits all Cas9 homologs used for genome editing. Cell Rep. 29, 1739-1746.e5 (2019).

Glów, D., et al. "Sequence-specific cleavage of dsRNA by Mini-III RNase." Nucleic acids research 43.5 (2015): 2864-2873.

Gnaccarini, C., et al. "Site-specific cleavage of RNA by a metal-free artificial nuclease attached to antisense oligonucleotides." Journal of the American Chemical Society 128.24 (2006): 8063-8067.

González, F et al. An iCRISPR platform for rapid, multiplexable, and inducible genome editing in human pluripotent stem cells. Cell Stem Cell 15, 215-226 (2014).

Hendel, A., et al. "Chemically modified guide RNAs enhance CRISPR-Cas genome editing in human primary cells." Nature biotechnology 33.9 (2015): 985-989.

Hoffmann, M. D. et al. Optogenetic control of Neisseria meningitidis Cas9 genome editing using an engineered, light-switchable anti-CRISPR protein. Preprint at https://doi.org/10.1101/858589 (2019).

Hisiau, T., et al. "Inference of CRISPR edits from Sanger trace data." BioRxiv (2018): 251082.

International Searching Authority. International Search Report and Written Opinion for application PCT/US2020/042681. Mailed on Dec. 3, 2020. 14 pages.

Jain, P. K., et al. "Development of Light-Activated CRISPR Using Guide RNAs with Photocleavable Protectors." Angewandte Chemie International Edition 55.40 (2016): 12440-12444.

Jeffs, L. B., et al. "A scalable, extrusion-free method for efficient liposomal encapsulation of plasmid DNA." Pharmaceutical research 22.3 (2005): 362-372.

Jinek, M. et al. A programmable dual RNA-guided DNA endonuclease in adaptive bacterial immunity. Science 337, 816-821 (2012).

Kim, S., et al. Highly efficient RNA-guided genome editing in human cells via delivery of purified Cas9 ribonucleoproteins. Genome Res. 24, 1012-1019 (2014).

Klein, M., et al. Hybridization kinetics explains CRISPR-Cas off-targeting rules. Cell Rep. 22, 1413-1423 (2018).

Kleinstiver, B. P. et al. High-fidelity CRISPR-Cas9 variants with undetectable genome-wide off-targets. Nature 529, 490-495 (2016).

Kundert, K. et al. Controlling CRISPR-Cas9 with ligand-activated and liganddeactivated sgRNAs. Nat. Commun. 10, 1-11 (2019).

Levy, M., et al. "Direct selection of trans-acting ligase ribozymes by in vitro compartmentalization." Rna 11.10 (2005): 1555-1562.

Li, H. "Structural principles of CRISPR RNA processing." Structure 23.1 (2015): 13-20.

Liu, Y et al. Very fast CRISPR on demand. Science 368, 1265-1269 (2020).

Love, K. T., et al. "Lipid-like materials for low-dose, in vivo gene silencing." Proceedings of the National Academy of Sciences of the United States of America 107.5 (2010): 1864.

Mahon, K. P., et al. "Combinatorial approach to determine functional group effects on lipidoid-mediated siRNA delivery." Bioconjugate chemistry 21.8 (2010): 1448-1454.

Manoharan, M. "RNA interference and chemically modified small interfering RNAs." Current opinion in chemical biology 8.6 (2004): 570-579.

Matteucci, M. D., et al. "Synthesis of deoxyoligonucleotides on a polymer support." Journal of the American Chemical Society 103.11 (1981): 3185-3191.

Morrissey, D. V., et al. "Potent and persistent in vivo anti-HBV activity of chemically modified siRNAs." Nature biotechnology 23.8 (2005): 1002-1007.

Needleman, S. B., et al. "A general method applicable to the search for similarities in the amino acid sequence of two proteins." Journal of molecular biology 48.3 (1970): 443-453.

Nguyen, D. P. et al. Ligand-binding domains of nuclear receptors facilitate tight control of split CRISPR activity. Nat. Commun. 7, 1-10 (2016).

Nihongaki, Y., et al. Photoactivatable CRISPRCas9 for optogenetic genome editing. Nat. Biotechnol. 33, 755-760 (2015).

Nishimasu, H. et al. Crystal structure of Cas9 in complex with guide RNA and target DNA. Cell 156, 935-949 (2014).

Olejnik, J., et al. "Photocleavable aminotag phosphoramidites for 5'-termini DNA/RNA labeling." Nucleic acids research 26.15 (1998): 3572-3576.

Ordoukhanian, P. et al. Design and synthesis of a versatile photocleavable DNA building block. Application to phototriggered hybridization. J. Am. Chem. Soc. 117, 9570-9571 (1995).

Ortigao, J. F. R. et al. "Antisense effect of oligodeoxynucleotides with inverted terminal internucleotidic linkages: a minimal modification protecting against nucleolytic degradation." Antisense research and development 2.2 (1992): 129-146.

Pearson, W. R., et al. "Improved tools for biological sequence comparison." Proceedings of the National Academy of Sciences 85.8 (1988): 2444-2448.

RCSB Protein Data Bank. 4OO8 Crystal Structure of Strep. Version dated May 9, 2019. Available online at http://web.archive.org/web/20190509184951/https://www.rcsb.org/structure/4oo8.

(56) References Cited

OTHER PUBLICATIONS

Rose, J. C. et al. Rapidly inducible Cas9 and DSB-ddPCR to probe editing kinetics. Nat. Methods 14, 891-896 (2017).
Samarsky, D. A., et al. "A small nucleolar RNA: ribozyme hybrid cleaves a nucleolar RNA target in vivo with near-perfect efficiency." Proceedings of the National Academy of Sciences 96.12 (1999): 6609-6614.
Scaringe, S. A. "[1] Advanced 5'-silyl-2'-orthoester approach to RNA oligonucleotide synthesis." (2000): 3-18.
Scaringe, S. A., et al. "Novel RNA synthesis method using 5'-O-Silyl-2'-O-orthoester protecting groups." Journal of the American Chemical Society 120.45 (1998): 11820-11821.
Schroeder, A., et al. "Lipid-based nanotherapeutics for siRNA delivery." Journal of internal medicine 267.1 (2010): 9-21.
Shen, C.-C. et al. Synthetic switch to minimize CRISPR off-target effects by self-restricting Cas9 transcription and translation. Nucleic Acids Res. 47, e13-e13 (2019).
Shukla, S. et al. "Exploring chemical modifications for siRNA therapeutics: a structural and functional outlook." ChemMedChem 5.3 (2010): 328-349.
Siegwart, D. J., et al. "Combinatorial synthesis of chemically diverse core-shell nanoparticles for intracellular delivery." Proceedings of the National Academy of Sciences 108.32 (2011): 12996-13001.
Sigman, D. S., et al. "Chemical nucleases." Chemical Reviews 93.6 (1993): 2295-2316.
Sigman, D. S., et al. "Targeted chemical nucleases." Accounts of Chemical Research 26.3 (1993): 98-104.
Slaymaker, I. M. et al. Rationally engineered Cas9 nucleases with improved specificity. Science 351, 84-88 (2016).
Sletten, E.M. et al. "Bioorthogonal chemistry: fishing for selectivity in a sea of functionality." Angewandte Chemie International Edition 48.38 (2009): 6974-6998.
Smith, T. F., et al. "Comparison of biosequences." Advances in applied mathematics 2.4 (1981): 482-489.
Su, X., et al. "In vitro and in vivo mRNA delivery using lipid-enveloped pH-responsive polymer nanoparticles." Molecular pharmaceutics 8.3 (2011): 774-787.
Sulej, A. A., et al. "Sequence-specific cleavage of the RNA strand in DNA-RNA hybrids by the fusion of ribonuclease H with a zinc finger." Nucleic acids research 40.22 (2012): 11563-11570.
Tatusova, T. A., et al. "BLAST 2 Sequences, a new tool for comparing protein and nucleotide sequences." FEMS microbiology letters 174.2 (1999): 247-250.
Threlfall, R. N., et al. "Synthesis and biological activity of phosphonoacetate-and thiophosphonoacetate-modified 2'-O-methyl oligoribonucleotides." Organic & biomolecular chemistry 10.4 (2012): 746-754.
Tsai et al. "GUIDE-seq enables genome-wide profiling of off-target cleavage by CRISPR-Cas nucleases", Nature Biotechnology 33, 187-197 (2015).
Van Devanter, et al. "Characterization of an adduct between CC-1065 and a defined oligodeoxynucleotide duplex." Nucleic acids research 12.15 (1984): 6159-6168.
Wang, Y., et al. "Co-delivery of drugs and DNA from cationic core-shell nanoparticles self-assembled from a biodegradable copolymer." Nature materials 5.10 (2006): 791-796.
Watts, J. K. et al. "Chemically modified siRNA: tools and applications." Drug discovery today 13.19-20 (2008): 842-855.
Wenzel, T., et al. "Genosnip: SNP genotyping by MALDI-TOF MS using photocleavable oligonucleotides." Nucleosides, Nucleotides and Nucleic Acids 22.5-8 (2003): 1579-1581.
Werner M et al. "Short oligonucleotides as external guide sequences for site-specific cleavage of RNA molecules with human RNase P." Rna 4.7 (1998): 847-855.
Weyel, X. M. M., et al. A two-photon-photocleavable linker for triggering light-induced strand breaks in oligonucleotides. ACS Chem. Biol. 12, 2183-2190 (2017).
Wheeler, J. J., et al. "Stabilized plasmid-lipid particles: construction and characterization." Gene therapy 6.2 (1999): 271-281.
Xu, J., et al. "Evolution and characterization of a benzylguanine-binding RNA aptamer." Chemical Communications 52.3 (2016): 549-552.
Zaug et. al, "Sequence-specific endoribonuclease activity of the Tetrahymena ribozyme: enhanced cleavage of certain oligonucleotide substrates that form mismatched ribozyme-substrate complexes." Biochemistry 27.25 (1988): 8924-8931.
Zetsche, B. et al. (2016), "Multiplex gene editing by CRISPR-Cpf1 using a single crRNA array", Nature Biotechnology (2016) doi: 10.1038/nbt.3737.
Zhang, L., et al. "Self-assembled lipid-polymer hybrid nanoparticles: a robust drug delivery platform." ACS nano 2.8 (2008): 1696-1702.
Zhang, Y. P., et al. "Stabilized plasmid-lipid particles for regional gene therapy: formulation and transfection properties." Gene therapy 6.8 (1999): 1438-1447.
Zhou, W. et al. Spatiotemporal control of CRISPR/Cas9 function in cells and zebrafish using light-activated guide RNA. Angew. Chem. 132, 9083-9088 (2020).

\* cited by examiner

*5 different UV Photocleavable gRNAs

-b21; inactive

-b24; inactive

-b50; inactive

-b57; active, UV attenuates activity

-b74; active UV attenuates activity

SEQUENCE LISTING

<160> NUMBER OF SEQ ID NOS: 187

<210> SEQ ID NO 1
<211> LENGTH: 5
<212> TYPE: DNA

```
<213> ORGANISM: Artificial Sequence
<220> FEATURE:
<223> OTHER INFORMATION: Synthetic- CAS9 PAM sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 1 nggng                                                                    5

<210> SEQ ID NO 2
<211> LENGTH: 7
<212> TYPE: DNA
<213> ORGANISM: Artificial Sequence
<220> FEATURE:
<223> OTHER INFORMATION: Synthetic- Cas9 PAM sequence
<220> FEATURE:
<221> NAME/KEY: misc_feature
<222> LOCATION: (1)..(2)
<223> OTHER INFORMATION: n is a, c, g, or t

<400> SEQUENCE: 2 nnagaaw                                                                  7

<210> SEQ ID NO 3
<211> LENGTH: 4
<212> TYPE: DNA
<213> ORGANISM: Artificial Sequence
<220> FEATURE:
<223> OTHER INFORMATION: Synthetic- Cas9 PAM sequence

<400> SEQUENCE: 3 acay                                                                     4

<210> SEQ ID NO 4
<211> LENGTH: 20
<212> TYPE: DNA
<213> ORGANISM: Artificial Sequence
<220> FEATURE:
<223> OTHER INFORMATION: Synthetic- EMX1

<400> SEQUENCE: 4
gagtccgagc agaagaagaa                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic- FANCF

<400> SEQUENCE: 5
gctgcagaag ggattccatg                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic- PRGN

<400> SEQUENCE: 6
cagatgcctg ctcagtgttg                                                   20
```

<210> SEQ ID NO 7
<211> LENGTH: 20
<212> TYPE: DNA
<213> ORGANISM: Artificial Sequence
<220> FEATURE:
<223> OTHER INFORMATION: Synthetic- VEGFA

<400> SEQUENCE: 7
ggtgagtgag tgtgtgcgtg                                               20

<210> SEQ ID NO 8
<211> LENGTH: 100
<212> TYPE: RNA
<213> ORGANISM: Artificial Sequence
<220> FEATURE:
<223> OTHER INFORMATION: Synthetic- Control sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (98)..(100)
<223> OTHER INFORMATION: 2'-O-methyl analogs and 3' phosphorothioate
      internucleotide linkages

<400> SEQUENCE: 8
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 9
<211> LENGTH: 104
<212> TYPE: RNA
<213> ORGANISM: Artificial Sequence
<220> FEATURE:
<223> OTHER INFORMATION: Synthetic- No 2nd sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (5)..(24)
<223> OTHER INFORMATION: n is a, c, g, or u
<220> FEATURE:
<221> NAME/KEY: misc_feature
<222> LOCATION: (102)..(104)
<223> OTHER INFORMATION: 2'-O-methyl analogs and 3' phosphorothioate
      internucleotide linkages

<400> SEQUENCE: 9
gaaannnnnn nnnnnnnnnn nnnnguuuua gagcuagaaa uagcaaguua aaauaaggcu    60
aguccguuau caacuugaaa aaguggcacc gagucggugc uuuu                    104

<210> SEQ ID NO 10
<211> LENGTH: 110
<212> TYPE: RNA
<213> ORGANISM: Artificial Sequence
<220> FEATURE:
<223> OTHER INFORMATION: Synthetic- 3 bp Stem sgRNA
<220> FEATURE:
<221> NAME/KEY: misc_feature
<222> LOCATION: (1)..(3)

```
<223> OTHER INFORMATION: 2'-O-methyl analogs and 3' phosphorothioate
      internucleotide linkages
<220> FEATURE:
<221> NAME/KEY: misc_feature
<222> LOCATION: (11)..(30)
<223> OTHER INFORMATION: n is a, c, g, or u
<220> FEATURE:
<221> NAME/KEY: misc_feature
<222> LOCATION: (108)..(110)
<223> OTHER INFORMATION: 2'-O-methyl analogs and 3' phosphorothioate
      internucleotide linkages

<400> SEQUENCE: 10
ugagaaauca nnnnnnnnnn nnnnnnnnnn guuuuagagc uagaaauagc aaguuaaaau      60
aaggcuaguc cguuaucaac uugaaaaagu ggcaccgagu cggugcuuuu               110

<210> SEQ ID NO 11
<211> LENGTH: 116
<212> TYPE: RNA
<213> ORGANISM: Artificial Sequence
<220> FEATURE:
<223> OTHER INFORMATION: Synthetic- 6 bp Stem sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (17)..(36)
<223> OTHER INFORMATION: n is a, c, g, or u
<220> FEATURE:
<221> NAME/KEY: misc_feature
<222> LOCATION: (114)..(116)
<223> OTHER INFORMATION: 2'-O-methyl analogs and 3' phosphorothioate
      internucleotide linkages

<400> SEQUENCE: 11
cacugagaaa ucagugnnnn nnnnnnnnnn nnnnnnguuu uagagcuaga aauagcaagu      60
uaaaauaagg cuaguccguu aucaacuuga aaaaguggca ccgagucggu gcuuuu        116

<210> SEQ ID NO 12
<211> LENGTH: 100
<212> TYPE: RNA
<213> ORGANISM: Artificial Sequence
<220> FEATURE:
<223> OTHER INFORMATION: Synthetic- sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (98)..(100)
<223> OTHER INFORMATION: 2'-O-methyl analogs and 3' phosphorothioate
      internucleotide linkages

<400> SEQUENCE: 12
nnnnnnnnnn nnnnnnnnnn guuuuagagc uagaaauagc aaguuaaaau aaggcuaguc      60
cguuaucaac uugaaaaagu ggcaccgagu cggugcuuuu                          100

<210> SEQ ID NO 13
<211> LENGTH: 99
<212> TYPE: RNA
<213> ORGANISM: Artificial Sequence
```

```
<220> FEATURE:
<223> OTHER INFORMATION: Synthetic- sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (21)..(21)
<223> OTHER INFORMATION: Photocleavable bond
<220> FEATURE:
<221> NAME/KEY: misc_feature
<222> LOCATION: (97)..(99)
<223> OTHER INFORMATION: 2'-O-methyl analogs and 3' phosphorothioate
      internucleotide linkages

<400> SEQUENCE: 13
nnnnnnnnnn nnnnnnnnnn uuuuagagcu agaaauagca aguuaaaaua aggcuagucc      60
guuaucaacu ugaaaaagug gcaccgaguc ggugcuuuu                             99

<210> SEQ ID NO 14
<211> LENGTH: 99
<212> TYPE: RNA
<213> ORGANISM: Artificial Sequence
<220> FEATURE:
<223> OTHER INFORMATION: Synthetic- sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (24)..(24)
<223> OTHER INFORMATION: photocleavable bond
<220> FEATURE:
<221> NAME/KEY: misc_feature
<222> LOCATION: (97)..(99)
<223> OTHER INFORMATION: 2'-O-methyl analogs and 3' phosphorothioate
      internucleotide linkages

<400> SEQUENCE: 14
nnnnnnnnnn nnnnnnnnnn guuuagagcu agaaauagca aguuaaaaua aggcuagucc      60
guuaucaacu ugaaaaagug gcaccgaguc ggugcuuuu                             99

<210> SEQ ID NO 15
<211> LENGTH: 99
<212> TYPE: RNA
<213> ORGANISM: Artificial Sequence
<220> FEATURE:
<223> OTHER INFORMATION: Synthetic- sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (50)..(50)
<223> OTHER INFORMATION: photocleavable bond
```

```
<220> FEATURE:
<221> NAME/KEY: misc_feature
<222> LOCATION: (97)..(99)
<223> OTHER INFORMATION: 2'-O-methyl analogs and 3' phosphorothioate
      internucleotide linkages

<400> SEQUENCE: 15
nnnnnnnnnn nnnnnnnnnn guuuuagagc uagaaauagc aaguuaaaaa aggcuagucc    60
guuaucaacu ugaaaaagug gcaccgaguc ggugcuuuu                           99

<210> SEQ ID NO 16
<211> LENGTH: 99
<212> TYPE: RNA
<213> ORGANISM: Artificial Sequence
<220> FEATURE:
<223> OTHER INFORMATION: Synthetic- sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (57)..(57)
<223> OTHER INFORMATION: photocleavable bond
<220> FEATURE:
<221> NAME/KEY: misc_feature
<222> LOCATION: (97)..(99)
<223> OTHER INFORMATION: 2'-O-methyl analogs and 3' phosphorothioate
      internucleotide linkages

<400> SEQUENCE: 16
nnnnnnnnnn nnnnnnnnnn guuuuagagc uagaaauagc aaguuaaaau aaggcugucc    60
guuaucaacu ugaaaaagug gcaccgaguc ggugcuuuu                           99

<210> SEQ ID NO 17
<211> LENGTH: 99
<212> TYPE: RNA
<213> ORGANISM: Artificial Sequence
<220> FEATURE:
<223> OTHER INFORMATION: Synthetic- sgRNA
<220> FEATURE:
<221> NAME/KEY: misc_feature
<222> LOCATION: (1)..(3)
<223> OTHER INFORMATION: 2'-O-methyl analogs and 3' phosphorothioate
      internucleotide linkages
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (74)..(74)
<223> OTHER INFORMATION: photocleavable bond
<220> FEATURE:
<221> NAME/KEY: misc_feature
<222> LOCATION: (97)..(99)
<223> OTHER INFORMATION: 2'-O-methyl analogs and 3' phosphorothioate
      internucleotide linkages

<400> SEQUENCE: 17
nnnnnnnnnn nnnnnnnnnn guuuuagagc uagaaauagc aaguuaaaau aaggcuaguc    60
cguuaucaac uugaaaaagug gcaccgaguc ggugcuuuu                          99

<210> SEQ ID NO 18
<211> LENGTH: 20
```

```
<212> TYPE: DNA
<213> ORGANISM: Artificial Sequence
<220> FEATURE:
<223> OTHER INFORMATION: Synthetic- BUB1B target binding region

<400> SEQUENCE: 18
agtgaagcca tgtccctgga                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic- CAMK1 target binding region

<400> SEQUENCE: 19
tgccaggatc acctccgaga                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic- PRKAG3 target binding regoin

<400> SEQUENCE: 20
agcaagaaaa cagcagctca                                              20

<210> SEQ ID NO 21
<211> LENGTH: 20
<212> TYPE: RNA
<213> ORGANISM: Artificial Sequence
<220> FEATURE:
<223> OTHER INFORMATION: Synthetic- PRKAG3 sg2 target binding region

<400> SEQUENCE: 21
agcaagaaaa cagcagcuca                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic- STK3 target binding region

<400> SEQUENCE: 22
tcctgaagat ctgattcaac                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic- STK3 sg2 target binding region

<400> SEQUENCE: 23
aaagcaatac acaaggaatc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic- STK3 sg3 target binding region

<400> SEQUENCE: 24
```
ccataatgca gcaatgtgac					20

<210> SEQ ID NO 25
<211> LENGTH: 20
<212> TYPE: RNA
<213> ORGANISM: Artificial Sequence
<220> FEATURE:
<223> OTHER INFORMATION: Synthetic- STK3 sg4 target binding region

<400> SEQUENCE: 25
uuuaauugcg acaacuugac					20

<210> SEQ ID NO 26
<211> LENGTH: 20
<212> TYPE: DNA
<213> ORGANISM: Artificial Sequence
<220> FEATURE:
<223> OTHER INFORMATION: Synthetic- IRAK4 target binding region

<400> SEQUENCE: 26
gtcctgtctt tgtcacagaa					20

<210> SEQ ID NO 27
<211> LENGTH: 20
<212> TYPE: DNA
<213> ORGANISM: Artificial Sequence
<220> FEATURE:
<223> OTHER INFORMATION: Synthetic- Chr8q23 target binding region

<400> SEQUENCE: 27
agtctactat gagttttctg					20

<210> SEQ ID NO 28
<211> LENGTH: 20
<212> TYPE: DNA
<213> ORGANISM: Artificial Sequence
<220> FEATURE:
<223> OTHER INFORMATION: Synthetic- Chr8q23 sg2 target binding region

<400> SEQUENCE: 28
ttatagttac gatgtttgat					20

<210> SEQ ID NO 29
<211> LENGTH: 20
<212> TYPE: DNA
<213> ORGANISM: Artificial Sequence
<220> FEATURE:
<223> OTHER INFORMATION: Synthetic- Chr8q23 sg3 target binding region

<400> SEQUENCE: 29
aagcctcaaa ttaggagaaa					20

<210> SEQ ID NO 30
<211> LENGTH: 20
<212> TYPE: DNA
<213> ORGANISM: Artificial Sequence
<220> FEATURE:
<223> OTHER INFORMATION: Synthetic- DNMT1 target binding region

<400> SEQUENCE: 30
ggagtgaggg aaacggcccc					20

<210> SEQ ID NO 31
<211> LENGTH: 20
<212> TYPE: DNA
<213> ORGANISM: Artificial Sequence

```
<220> FEATURE:
<223> OTHER INFORMATION: Synthetic- EMX1 target binding region

<400> SEQUENCE: 31
gagtccgagc agaagaagaa                                                    20

<210> SEQ ID NO 32
<211> LENGTH: 20
<212> TYPE: DNA
<213> ORGANISM: Artificial Sequence
<220> FEATURE:
<223> OTHER INFORMATION: Synthetic- FANCF target binding region

<400> SEQUENCE: 32
gctgcagaag ggattccatg                                                    20

<210> SEQ ID NO 33
<211> LENGTH: 20
<212> TYPE: DNA
<213> ORGANISM: Artificial Sequence
<220> FEATURE:
<223> OTHER INFORMATION: Synthetic- GRK1 target binding region

<400> SEQUENCE: 33
gccgtcaaag ctgcctcggg                                                    20

<210> SEQ ID NO 34
<211> LENGTH: 20
<212> TYPE: DNA
<213> ORGANISM: Artificial Sequence
<220> FEATURE:
<223> OTHER INFORMATION: Synthetic- PRGN target binding region

<400> SEQUENCE: 34
cagatgcctg ctcagtgttg                                                    20

<210> SEQ ID NO 35
<211> LENGTH: 20
<212> TYPE: DNA
<213> ORGANISM: Artificial Sequence
<220> FEATURE:
<223> OTHER INFORMATION: Synthetic- VEGFA target binding region

<400> SEQUENCE: 35
ggtgagtgag tgtgtgcgtg                                                    20

<210> SEQ ID NO 36
<211> LENGTH: 100
<212> TYPE: DNA
<213> ORGANISM: Artificial Sequence
<220> FEATURE:
<223> OTHER INFORMATION: Synthetic- on-target sgRNA

<400> SEQUENCE: 36
ggagtgaggg aaacggcccc gttttagagc tagaaatagc aagttaaaat aaggctagtc         60
cgttatcaac ttgaaaaagt ggcaccgagt cggtgctttt                              100

<210> SEQ ID NO 37
<211> LENGTH: 98
<212> TYPE: DNA
<213> ORGANISM: Artificial Sequence
<220> FEATURE:
<223> OTHER INFORMATION: Synthetic- on-target CRISPR OFF
<220> FEATURE:
<221> NAME/KEY: misc_feature
<222> LOCATION: (57)..(57)
```

```
<223> OTHER INFORMATION: (3-(4,4'-Dimethoxytrityl)-1-(2-nitrophenyl)-
      propan-1-yl-[(2-cyano ethyl)-(N,N-diisopropyl)]-phosphoramidite)
      linker
<220> FEATURE:
<221> NAME/KEY: misc_feature
<222> LOCATION: (74)..(74)
<223> OTHER INFORMATION: (3-(4,4'-Dimethoxytrityl)-1-(2-nitrophenyl)-
      propan-1-yl-[(2-cyano ethyl)-(N,N-diisopropyl)]-phosphoramidite)
      linker

<400> SEQUENCE: 37
ggagtgaggg aaacggcccc gttttagagc tagaaatagc aagttaaaat aaggctgtcc       60
gttatcaact tgaaaagtgg caccgagtcg gtgctttt                              98

<210> SEQ ID NO 38
<211> LENGTH: 20
<212> TYPE: DNA
<213> ORGANISM: Artificial Sequence
<220> FEATURE:
<223> OTHER INFORMATION: Synthetic- Off-target 1

<400> SEQUENCE: 38
ggagggaggg aaacagcccc                                                  20

<210> SEQ ID NO 39
<211> LENGTH: 100
<212> TYPE: DNA
<213> ORGANISM: Artificial Sequence
<220> FEATURE:
<223> OTHER INFORMATION: Synthetic- On-target sgRNA

<400> SEQUENCE: 39
gctgcagaag ggattccatg gttttagagc tagaaatagc aagttaaaat aaggctagtc      60
cgttatcaac ttgaaaaagt ggcaccgagt cggtgctttt                           100

<210> SEQ ID NO 40
<211> LENGTH: 98
<212> TYPE: DNA
<213> ORGANISM: Artificial Sequence
<220> FEATURE:
<223> OTHER INFORMATION: Synthetic- On-target CRISPR OFF
<220> FEATURE:
<221> NAME/KEY: misc_feature
<222> LOCATION: (57)..(57)
<223> OTHER INFORMATION: (3-(4,4'-Dimethoxytrityl)-1-(2-nitrophenyl)-
      propan-1-yl-[(2-cyano ethyl)-(N,N-diisopropyl)]-phosphoramidite)
      linker
<220> FEATURE:
<221> NAME/KEY: misc_feature
<222> LOCATION: (74)..(74)
<223> OTHER INFORMATION: (3-(4,4'-Dimethoxytrityl)-1-(2-nitrophenyl)-
      propan-1-yl-[(2-cyano ethyl)-(N,N-diisopropyl)]-phosphoramidite)
      linker

<400> SEQUENCE: 40
gctgcagaag ggattccatg gttttagagc tagaaatagc aagttaaaat aaggctgtcc      60
gttatcaact tgaaaagtgg caccgagtcg gtgctttt                              98

<210> SEQ ID NO 41
<211> LENGTH: 20
<212> TYPE: DNA
<213> ORGANISM: Artificial Sequence
<220> FEATURE:
<223> OTHER INFORMATION: Synthetic- Off-target 2

<400> SEQUENCE: 41
gctgcagaag ggattccaag                                                  20
```

<210> SEQ ID NO 42
<211> LENGTH: 100
<212> TYPE: DNA
<213> ORGANISM: Artificial Sequence
<220> FEATURE:
<223> OTHER INFORMATION: Synthetic- On target sgRNA

<400> SEQUENCE: 42
ggtgagtgag tgtgtgcgtg gttttagagc tagaaatagc aagttaaaat aaggctagtc    60
cgttatcaac ttgaaaaagt ggcaccgagt cggtgctttt                         100

<210> SEQ ID NO 43
<211> LENGTH: 98
<212> TYPE: DNA
<213> ORGANISM: Artificial Sequence
<220> FEATURE:
<223> OTHER INFORMATION: Synthetic- On-target CRISPR OFF
<220> FEATURE:
<221> NAME/KEY: misc_feature
<222> LOCATION: (57)..(57)
<223> OTHER INFORMATION: (3-(4,4'-Dimethoxytrityl)-1-(2-nitrophenyl)-
      propan-1-yl-[(2-cyano ethyl)-(N,N-diisopropyl)]-phosphoramidite)
      linker
<220> FEATURE:
<221> NAME/KEY: misc_feature
<222> LOCATION: (74)..(74)
<223> OTHER INFORMATION: (3-(4,4'-Dimethoxytrityl)-1-(2-nitrophenyl)-
      propan-1-yl-[(2-cyano ethyl)-(N,N-diisopropyl)]-phosphoramidite)
      linker

<400> SEQUENCE: 43
ggtgagtgag tgtgtgcgtg gttttagagc tagaaatagc aagttaaaat aaggctgtcc    60
gttatcaact tgaaaagtgg caccgagtcg gtgctttt                            98

<210> SEQ ID NO 44
<211> LENGTH: 20
<212> TYPE: DNA
<213> ORGANISM: Artificial Sequence
<220> FEATURE:
<223> OTHER INFORMATION: Synthetic- Off-target 3

<400> SEQUENCE: 44
gctgagtgag tgtatgcgtg                                                20

<210> SEQ ID NO 45
<211> LENGTH: 20
<212> TYPE: RNA
<213> ORGANISM: Artificial Sequence
<220> FEATURE:
<223> OTHER INFORMATION: Synthetic- AAVS target binding region

<400> SEQUENCE: 45
ggggccacua gggacaggau                                                20

<210> SEQ ID NO 46
<211> LENGTH: 20
<212> TYPE: RNA
<213> ORGANISM: Artificial Sequence
<220> FEATURE:
<223> OTHER INFORMATION: Synthetic- BUB1B target binding region

<400> SEQUENCE: 46
agugaagcca ugucccugga                                                20

<210> SEQ ID NO 47

```
<211> LENGTH: 20
<212> TYPE: RNA
<213> ORGANISM: Artificial Sequence
<220> FEATURE:
<223> OTHER INFORMATION: Synthetic- CAMK1_sg1 target binding region

<400> SEQUENCE: 47
ugccaggauc accuccgaga                                                      20

<210> SEQ ID NO 48
<211> LENGTH: 20
<212> TYPE: RNA
<213> ORGANISM: Artificial Sequence
<220> FEATURE:
<223> OTHER INFORMATION: Synthetic- CAMK1_sg2 target binding region

<400> SEQUENCE: 48
gcguccucuu aucuucugcc                                                      20

<210> SEQ ID NO 49
<211> LENGTH: 20
<212> TYPE: RNA
<213> ORGANISM: Artificial Sequence
<220> FEATURE:
<223> OTHER INFORMATION: Synthetic- CEL target binding region

<400> SEQUENCE: 49
aaccaguugc aggcgcccca                                                      20

<210> SEQ ID NO 50
<211> LENGTH: 20
<212> TYPE: RNA
<213> ORGANISM: Artificial Sequence
<220> FEATURE:
<223> OTHER INFORMATION: Synthetic- Chr8q23 sg1

<400> SEQUENCE: 50
uuauaguuac gauguuugau                                                      20

<210> SEQ ID NO 51
<211> LENGTH: 20
<212> TYPE: RNA
<213> ORGANISM: Artificial Sequence
<220> FEATURE:
<223> OTHER INFORMATION: Synthetic- CXCR4 target binding region

<400> SEQUENCE: 51
gauaacuaca ccgaggaaau                                                      20

<210> SEQ ID NO 52
<211> LENGTH: 20
<212> TYPE: RNA
<213> ORGANISM: Artificial Sequence
<220> FEATURE:
<223> OTHER INFORMATION: Synthetic- DNMT1 target binding region

<400> SEQUENCE: 52
ggagugaggg aaacggcccc                                                      20

<210> SEQ ID NO 53
<211> LENGTH: 20
<212> TYPE: RNA
<213> ORGANISM: Artificial Sequence
<220> FEATURE:
<223> OTHER INFORMATION: Synthetic- EMX1 target binding region

<400> SEQUENCE: 53
```
gaguccgagc agaagaagaa                                              20

<210> SEQ ID NO 54
<211> LENGTH: 20
<212> TYPE: RNA
<213> ORGANISM: Artificial Sequence
<220> FEATURE:
<223> OTHER INFORMATION: Synthetic- FAM163A target binding region

<400> SEQUENCE: 54
cugcagggcu cgcuggugag                                              20

<210> SEQ ID NO 55
<211> LENGTH: 20
<212> TYPE: RNA
<213> ORGANISM: Artificial Sequence
<220> FEATURE:
<223> OTHER INFORMATION: Synthetic- FANCF target binding region

<400> SEQUENCE: 55
gcugcagaag ggauuccaug                                              20

<210> SEQ ID NO 56
<211> LENGTH: 20
<212> TYPE: RNA
<213> ORGANISM: Artificial Sequence
<220> FEATURE:
<223> OTHER INFORMATION: Synthetic- GAA target binding region

<400> SEQUENCE: 56
aggagccggu gggagcaggg                                              20

<210> SEQ ID NO 57
<211> LENGTH: 20
<212> TYPE: RNA
<213> ORGANISM: Artificial Sequence
<220> FEATURE:
<223> OTHER INFORMATION: Synthetic- GRK1 target binding region

<400> SEQUENCE: 57
gccgucaaag cugccucggg                                              20

<210> SEQ ID NO 58
<211> LENGTH: 20
<212> TYPE: RNA
<213> ORGANISM: Artificial Sequence
<220> FEATURE:
<223> OTHER INFORMATION: Synthetic- ITGA7 target binding region

<400> SEQUENCE: 58
ggugcuggag ggcgaggcug                                              20

<210> SEQ ID NO 59
<211> LENGTH: 20
<212> TYPE: RNA
<213> ORGANISM: Artificial Sequence
<220> FEATURE:
<223> OTHER INFORMATION: Synthetic- IRAK4 target binding region

<400> SEQUENCE: 59
guccugucuu ugucacagaa                                              20

<210> SEQ ID NO 60
<211> LENGTH: 20
<212> TYPE: RNA

```
<213> ORGANISM: Artificial Sequence
<220> FEATURE:
<223> OTHER INFORMATION: Synthetic- MAPRE1 target binding region

<400> SEQUENCE: 60
uucucugcag auaauuccug                                                  20

<210> SEQ ID NO 61
<211> LENGTH: 20
<212> TYPE: RNA
<213> ORGANISM: Artificial Sequence
<220> FEATURE:
<223> OTHER INFORMATION: Synthetic- MIP target binding region

<400> SEQUENCE: 61
gcugggaucc ucacugcgcu                                                  20

<210> SEQ ID NO 62
<211> LENGTH: 20
<212> TYPE: RNA
<213> ORGANISM: Artificial Sequence
<220> FEATURE:
<223> OTHER INFORMATION: Synthetic- OMP target binding region

<400> SEQUENCE: 62
gaacuguagc cgcugcugcu                                                  20

<210> SEQ ID NO 63
<211> LENGTH: 20
<212> TYPE: RNA
<213> ORGANISM: Artificial Sequence
<220> FEATURE:
<223> OTHER INFORMATION: Synthetic- OPN1SW target binding region

<400> SEQUENCE: 63
acaggggcaa ugugguacug                                                  20

<210> SEQ ID NO 64
<211> LENGTH: 20
<212> TYPE: RNA
<213> ORGANISM: Artificial Sequence
<220> FEATURE:
<223> OTHER INFORMATION: Synthetic- PRGN target binding region

<400> SEQUENCE: 64
cagaugccug cucaguguug                                                  20

<210> SEQ ID NO 65
<211> LENGTH: 20
<212> TYPE: RNA
<213> ORGANISM: Artificial Sequence
<220> FEATURE:
<223> OTHER INFORMATION: Synthetic- PRKAG3 target binding region

<400> SEQUENCE: 65
agcaagaaaa cagcagcuca                                                  20

<210> SEQ ID NO 66
<211> LENGTH: 20
<212> TYPE: RNA
<213> ORGANISM: Artificial Sequence
<220> FEATURE:
<223> OTHER INFORMATION: Sythetic- STK3 sg1

<400> SEQUENCE: 66
aaagcaauac acaaggaauc                                                  20
```

<210> SEQ ID NO 67
<211> LENGTH: 20
<212> TYPE: RNA
<213> ORGANISM: Artificial Sequence
<220> FEATURE:
<223> OTHER INFORMATION: Synthetic- STK3 sg2

<400> SEQUENCE: 67
ccauaaugca gcaaugugac                                              20

<210> SEQ ID NO 68
<211> LENGTH: 20
<212> TYPE: RNA
<213> ORGANISM: Artificial Sequence
<220> FEATURE:
<223> OTHER INFORMATION: Synthetic- VEGFA target binding region

<400> SEQUENCE: 68
ggugagugag ugugugcgug                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic- AAVS F

<400> SEQUENCE: 69
gcccctatgt ccacttcagg                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic- AAVS R

<400> SEQUENCE: 70
ctcaggttct gggagagggt                                              20

<210> SEQ ID NO 71
<211> LENGTH: 25
<212> TYPE: DNA
<213> ORGANISM: Artificial Sequence
<220> FEATURE:
<223> OTHER INFORMATION: Synthetic- AAVS Primer seq

<400> SEQUENCE: 71
ctccatcgta agcaaacctt agagg                                        25

<210> SEQ ID NO 72
<211> LENGTH: 20
<212> TYPE: DNA
<213> ORGANISM: Artificial Sequence
<220> FEATURE:
<223> OTHER INFORMATION: Synthetic- BUB1B F

<400> SEQUENCE: 72
agaaatcctc ccacttcggc                                              20

<210> SEQ ID NO 73
<211> LENGTH: 20
<212> TYPE: DNA
<213> ORGANISM: Artificial Sequence
<220> FEATURE:

<223> OTHER INFORMATION: Synthetic- BUB1B R

<400> SEQUENCE: 73
gcagattctt gtgccagtgc                                          20

<210> SEQ ID NO 74
<211> LENGTH: 30
<212> TYPE: DNA
<213> ORGANISM: Artificial Sequence
<220> FEATURE:
<223> OTHER INFORMATION: Synthetic- BUB1B primer seq

<400> SEQUENCE: 74
cagctaacaa agaagcttag gcatataata                               30

<210> SEQ ID NO 75
<211> LENGTH: 20
<212> TYPE: DNA
<213> ORGANISM: Artificial Sequence
<220> FEATURE:
<223> OTHER INFORMATION: Synthetic- CAMK1_sg1F

<400> SEQUENCE: 75
acaaccctgc caagtggaaa                                          20

<210> SEQ ID NO 76
<211> LENGTH: 20
<212> TYPE: DNA
<213> ORGANISM: Artificial Sequence
<220> FEATURE:
<223> OTHER INFORMATION: Synthetic- CAMK1_sg1R

<400> SEQUENCE: 76
actaggggag ggtcatccac                                          20

<210> SEQ ID NO 77
<211> LENGTH: 30
<212> TYPE: DNA
<213> ORGANISM: Artificial Sequence
<220> FEATURE:
<223> OTHER INFORMATION: Synthetic- CAMK1_sg1 primer seq

<400> SEQUENCE: 77
cattttataa agggcaatt taaggcttag                                30

<210> SEQ ID NO 78
<211> LENGTH: 20
<212> TYPE: DNA
<213> ORGANISM: Artificial Sequence
<220> FEATURE:
<223> OTHER INFORMATION: Synthetic- CAMK1_sg2F

<400> SEQUENCE: 78
acaaccctgc caagtggaaa                                          20

<210> SEQ ID NO 79
<211> LENGTH: 20
<212> TYPE: DNA
<213> ORGANISM: Artificial Sequence
<220> FEATURE:
<223> OTHER INFORMATION: Synthetic- CAMK1_sg2R

<400> SEQUENCE: 79
actaggggag ggtcatccac                                          20

```
<210> SEQ ID NO 80
<211> LENGTH: 30
<212> TYPE: DNA
<213> ORGANISM: Artificial Sequence
<220> FEATURE:
<223> OTHER INFORMATION: Synthetic- CAMK1_sg2 primer seq

<400> SEQUENCE: 80
cattttataa aggggcaatt taaggcttag                                   30

<210> SEQ ID NO 81
<211> LENGTH: 20
<212> TYPE: DNA
<213> ORGANISM: Artificial Sequence
<220> FEATURE:
<223> OTHER INFORMATION: Synthetic- CEL F

<400> SEQUENCE: 81
ctgagggtgt agaggggagg                                              20

<210> SEQ ID NO 82
<211> LENGTH: 20
<212> TYPE: DNA
<213> ORGANISM: Artificial Sequence
<220> FEATURE:
<223> OTHER INFORMATION: Synthetic- CEL R

<400> SEQUENCE: 82
gttctacctg gcacctgtcc                                              20

<210> SEQ ID NO 83
<211> LENGTH: 23
<212> TYPE: DNA
<213> ORGANISM: Artificial Sequence
<220> FEATURE:
<223> OTHER INFORMATION: Synthetic- CEL primer seq

<400> SEQUENCE: 83
cctgagagct catgaacaag cat                                          23

<210> SEQ ID NO 84
<211> LENGTH: 22
<212> TYPE: DNA
<213> ORGANISM: Artificial Sequence
<220> FEATURE:
<223> OTHER INFORMATION: Synthetic- Chr8q23_sg1 F

<400> SEQUENCE: 84
ctcgtcaaaa caagggtaag ca                                           22

<210> SEQ ID NO 85
<211> LENGTH: 20
<212> TYPE: DNA
<213> ORGANISM: Artificial Sequence
<220> FEATURE:
<223> OTHER INFORMATION: Synthetic- Chr8q23_sg1 R

<400> SEQUENCE: 85
gtttgagttg accaaacgca                                              20

<210> SEQ ID NO 86
<211> LENGTH: 30
<212> TYPE: DNA
<213> ORGANISM: Artificial Sequence
<220> FEATURE:
<223> OTHER INFORMATION: Synthetic- Chr8q23_sg1 primer seq
```

```
<400> SEQUENCE: 86
caagggtaag caaagaaata aaatctcttc                                      30

<210> SEQ ID NO 87
<211> LENGTH: 20
<212> TYPE: DNA
<213> ORGANISM: Artificial Sequence
<220> FEATURE:
<223> OTHER INFORMATION: Synthetic- Chr8q23_sg2 F

<400> SEQUENCE: 87
acctgtcaca ttgctgcatt                                                 20

<210> SEQ ID NO 88
<211> LENGTH: 20
<212> TYPE: DNA
<213> ORGANISM: Artificial Sequence
<220> FEATURE:
<223> OTHER INFORMATION: Synthetic- Chr8q23_sg2 R

<400> SEQUENCE: 88
gtttgagttg accaaacgca                                                 20

<210> SEQ ID NO 89
<211> LENGTH: 30
<212> TYPE: DNA
<213> ORGANISM: Artificial Sequence
<220> FEATURE:
<223> OTHER INFORMATION: Synthetic- Chr8q23_sg2 primer seq

<400> SEQUENCE: 89
ttgattattt cctgaagatc tgattcaaca                                      30

<210> SEQ ID NO 90
<211> LENGTH: 20
<212> TYPE: DNA
<213> ORGANISM: Artificial Sequence
<220> FEATURE:
<223> OTHER INFORMATION: Synthetic- CXCR4 F

<400> SEQUENCE: 90
ttgtgccctt agcccactac                                                 20

<210> SEQ ID NO 91
<211> LENGTH: 20
<212> TYPE: DNA
<213> ORGANISM: Artificial Sequence
<220> FEATURE:
<223> OTHER INFORMATION: Synthetic- CXCR4 R

<400> SEQUENCE: 91
ccagaaggga agcgtgatga                                                 20

<210> SEQ ID NO 92
<211> LENGTH: 27
<212> TYPE: DNA
<213> ORGANISM: Artificial Sequence
<220> FEATURE:
<223> OTHER INFORMATION: Synthetic- CXCR4 primer seq

<400> SEQUENCE: 92
gtacttgtcc gtcatgcttc tcagttt                                         27

<210> SEQ ID NO 93
<211> LENGTH: 24
```

```
<212> TYPE: DNA
<213> ORGANISM: Artificial Sequence
<220> FEATURE:
<223> OTHER INFORMATION: Synthetic- DNMT1  F

<400> SEQUENCE: 93
gatcaagctt tgtatgttgg ccaa                                          24

<210> SEQ ID NO 94
<211> LENGTH: 24
<212> TYPE: DNA
<213> ORGANISM: Artificial Sequence
<220> FEATURE:
<223> OTHER INFORMATION: Synthetic- DNMT1 R

<400> SEQUENCE: 94
aatccagaat gcacaaagta ctgc                                          24

<210> SEQ ID NO 95
<211> LENGTH: 24
<212> TYPE: DNA
<213> ORGANISM: Artificial Sequence
<220> FEATURE:
<223> OTHER INFORMATION: Synthetic- DNMT1 primer seq

<400> SEQUENCE: 95
gatcaagctt tgtatgttgg ccaa                                          24

<210> SEQ ID NO 96
<211> LENGTH: 22
<212> TYPE: DNA
<213> ORGANISM: Artificial Sequence
<220> FEATURE:
<223> OTHER INFORMATION: Synthetic- EMX1 F

<400> SEQUENCE: 96
cagctctgtg accctttgtt tg                                            22

<210> SEQ ID NO 97
<211> LENGTH: 22
<212> TYPE: DNA
<213> ORGANISM: Artificial Sequence
<220> FEATURE:
<223> OTHER INFORMATION: Synthetic- EMX1 R

<400> SEQUENCE: 97
actaaactac agtggtgcct gg                                            22

<210> SEQ ID NO 98
<211> LENGTH: 22
<212> TYPE: DNA
<213> ORGANISM: Artificial Sequence
<220> FEATURE:
<223> OTHER INFORMATION: Synthetic- EMX1 primer seq

<400> SEQUENCE: 98
cagctctgtg accctttgtt tg                                            22

<210> SEQ ID NO 99
<211> LENGTH: 20
<212> TYPE: DNA
<213> ORGANISM: Artificial Sequence
<220> FEATURE:
<223> OTHER INFORMATION: Synthetic- FAM163A F

<400> SEQUENCE: 99
```
gagtggtggg aggggaaaag                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic- FAM163A R

<400> SEQUENCE: 100
catgtcagcc gtccgtatgt                                               20

<210> SEQ ID NO 101
<211> LENGTH: 25
<212> TYPE: DNA
<213> ORGANISM: Artificial Sequence
<220> FEATURE:
<223> OTHER INFORMATION: Synthetic- FAM163A primer seq

<400> SEQUENCE: 101
cttgcaaagc tgggattaga aactt                                         25

<210> SEQ ID NO 102
<211> LENGTH: 24
<212> TYPE: DNA
<213> ORGANISM: Artificial Sequence
<220> FEATURE:
<223> OTHER INFORMATION: Synthetic- FANCF F

<400> SEQUENCE: 102
gatatttcca aagcgaaagg aagc                                          24

<210> SEQ ID NO 103
<211> LENGTH: 24
<212> TYPE: DNA
<213> ORGANISM: Artificial Sequence
<220> FEATURE:
<223> OTHER INFORMATION: Synthetic- FANCF R

<400> SEQUENCE: 103
atcagagagt cctcctggag attt                                          24

<210> SEQ ID NO 104
<211> LENGTH: 24
<212> TYPE: DNA
<213> ORGANISM: Artificial Sequence
<220> FEATURE:
<223> OTHER INFORMATION: Synthetic- FANCF primer seq

<400> SEQUENCE: 104
gatatttcca aagcgaaagg aagc                                          24

<210> SEQ ID NO 105
<211> LENGTH: 20
<212> TYPE: DNA
<213> ORGANISM: Artificial Sequence
<220> FEATURE:
<223> OTHER INFORMATION: Synthetic- GAA F

<400> SEQUENCE: 105
ggtgagtctc ctccaggact                                               20

<210> SEQ ID NO 106
<211> LENGTH: 20
<212> TYPE: DNA
<213> ORGANISM: Artificial Sequence

```
<220> FEATURE:
<223> OTHER INFORMATION: Synthetic- GAA R

<400> SEQUENCE: 106
cagactgtgc aagtgctctg                                                   20

<210> SEQ ID NO 107
<211> LENGTH: 22
<212> TYPE: DNA
<213> ORGANISM: Artificial Sequence
<220> FEATURE:
<223> OTHER INFORMATION: Synthetic- GAA primer seq

<400> SEQUENCE: 107
cttttctcgc ccttccttct gg                                                22

<210> SEQ ID NO 108
<211> LENGTH: 21
<212> TYPE: DNA
<213> ORGANISM: Artificial Sequence
<220> FEATURE:
<223> OTHER INFORMATION: Synthetic- GRK1 F

<400> SEQUENCE: 108
gtctctctcg tccagcaagg g                                                 21

<210> SEQ ID NO 109
<211> LENGTH: 22
<212> TYPE: DNA
<213> ORGANISM: Artificial Sequence
<220> FEATURE:
<223> OTHER INFORMATION: Synthetic- GRK1 R

<400> SEQUENCE: 109
atgtctttcc agagctccag gg                                                22

<210> SEQ ID NO 110
<211> LENGTH: 21
<212> TYPE: DNA
<213> ORGANISM: Artificial Sequence
<220> FEATURE:
<223> OTHER INFORMATION: Synthetic- GRK1 primer seq

<400> SEQUENCE: 110
gtctctctcg tccagcaagg g                                                 21

<210> SEQ ID NO 111
<211> LENGTH: 20
<212> TYPE: DNA
<213> ORGANISM: Artificial Sequence
<220> FEATURE:
<223> OTHER INFORMATION: Synthetic- ITGA7 F

<400> SEQUENCE: 111
ggttgtcgcc aaaccttcac                                                   20

<210> SEQ ID NO 112
<211> LENGTH: 20
<212> TYPE: DNA
<213> ORGANISM: Artificial Sequence
<220> FEATURE:
<223> OTHER INFORMATION: Synthetic- ITGA7 R

<400> SEQUENCE: 112
gggattgggg agtcaagagc                                                   20
```

<210> SEQ ID NO 113
<211> LENGTH: 30
<212> TYPE: DNA
<213> ORGANISM: Artificial Sequence
<220> FEATURE:
<223> OTHER INFORMATION: Synthetic- ITGA7 primer seq

<400> SEQUENCE: 113
gagtcaagag cacaagaaac atgagaacat          30

<210> SEQ ID NO 114
<211> LENGTH: 21
<212> TYPE: DNA
<213> ORGANISM: Artificial Sequence
<220> FEATURE:
<223> OTHER INFORMATION: Synthetic- IRAK4 F

<400> SEQUENCE: 114
gcttcttgtg tgtgctgtga g          21

<210> SEQ ID NO 115
<211> LENGTH: 20
<212> TYPE: DNA
<213> ORGANISM: Artificial Sequence
<220> FEATURE:
<223> OTHER INFORMATION: Synthetic- IRAK4 R

<400> SEQUENCE: 115
gcctgtgatt gctgcacaaa          20

<210> SEQ ID NO 116
<211> LENGTH: 30
<212> TYPE: DNA
<213> ORGANISM: Artificial Sequence
<220> FEATURE:
<223> OTHER INFORMATION: Synthetic- IRAK4 primer seq

<400> SEQUENCE: 116
caagtttcta gtttaacttt ttcacaacca          30

<210> SEQ ID NO 117
<211> LENGTH: 22
<212> TYPE: DNA
<213> ORGANISM: Artificial Sequence
<220> FEATURE:
<223> OTHER INFORMATION: Synthetic- MAPRE1 F

<400> SEQUENCE: 117
ggtactcttg aaggcaaact gc          22

<210> SEQ ID NO 118
<211> LENGTH: 23
<212> TYPE: DNA
<213> ORGANISM: Artificial Sequence
<220> FEATURE:
<223> OTHER INFORMATION: Synthetic- MAPRE1 R

<400> SEQUENCE: 118
cgctgaatga atatctggaa cgc          23

<210> SEQ ID NO 119
<211> LENGTH: 30
<212> TYPE: DNA
<213> ORGANISM: Artificial Sequence
<220> FEATURE:
<223> OTHER INFORMATION: Synthetic- MAPRE1 primer seq

<400> SEQUENCE: 119
actgcatgaa acttgcttta taaatttagg                                           30

<210> SEQ ID NO 120
<211> LENGTH: 20
<212> TYPE: DNA
<213> ORGANISM: Artificial Sequence
<220> FEATURE:
<223> OTHER INFORMATION: Synthetic- MIP F

<400> SEQUENCE: 120
tcagccaacc attaccgtgt                                                       20

<210> SEQ ID NO 121
<211> LENGTH: 20
<212> TYPE: DNA
<213> ORGANISM: Artificial Sequence
<220> FEATURE:
<223> OTHER INFORMATION: Synthetic- MIP1R

<400> SEQUENCE: 121 taaagggac tgtccaccca                                                        20

<210> SEQ ID NO 122
<211> LENGTH: 26
<212> TYPE: DNA
<213> ORGANISM: Artificial Sequence
<220> FEATURE:
<223> OTHER INFORMATION: Synthetic- MIP primer seq

<400> SEQUENCE: 122
cattaccgtg ttgagtgcta ggtttc                                                26

<210> SEQ ID NO 123
<211> LENGTH: 20
<212> TYPE: DNA
<213> ORGANISM: Artificial Sequence
<220> FEATURE:
<223> OTHER INFORMATION: Synthetic- OMP F

<400> SEQUENCE: 123
ttgagaactg agtggggctg                                                       20

<210> SEQ ID NO 124
<211> LENGTH: 20
<212> TYPE: DNA
<213> ORGANISM: Artificial Sequence
<220> FEATURE:
<223> OTHER INFORMATION: Synthetic- OMP R

<400> SEQUENCE: 124
gcgtgtcatg aggttggtga                                                       20

<210> SEQ ID NO 125
<211> LENGTH: 20
<212> TYPE: DNA
<213> ORGANISM: Artificial Sequence
<220> FEATURE:
<223> OTHER INFORMATION: Synthetic- OMP primer seq

<400> SEQUENCE: 125
ttgagaactg agtggggctg                                                       20

<210> SEQ ID NO 126

```
-continued

<211> LENGTH: 20
<212> TYPE: DNA
<213> ORGANISM: Artificial Sequence
<220> FEATURE:
<223> OTHER INFORMATION: Synthetic- OPN1SW F

<400> SEQUENCE: 126
cccctaaccc cttttttcccc                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic- OPN1SW R

<400> SEQUENCE: 127
gttttgtggg gtgggaggat                                               20

<210> SEQ ID NO 128
<211> LENGTH: 25
<212> TYPE: DNA
<213> ORGANISM: Artificial Sequence
<220> FEATURE:
<223> OTHER INFORMATION: Synthetic- OPN1SW primer seq

<400> SEQUENCE: 128 ctaaccccctt tttccctgc agtac                                         25

<210> SEQ ID NO 129
<211> LENGTH: 20
<212> TYPE: DNA
<213> ORGANISM: Artificial Sequence
<220> FEATURE:
<223> OTHER INFORMATION: Synthetic- PRGN F

<400> SEQUENCE: 129
tgagctgggt ggccttaaca                                               20

<210> SEQ ID NO 130
<211> LENGTH: 21
<212> TYPE: DNA
<213> ORGANISM: Artificial Sequence
<220> FEATURE:
<223> OTHER INFORMATION: Synthetic- PRGN R

<400> SEQUENCE: 130
cattggcagg gccctttat c                                              21

<210> SEQ ID NO 131
<211> LENGTH: 20
<212> TYPE: DNA
<213> ORGANISM: Artificial Sequence
<220> FEATURE:
<223> OTHER INFORMATION: Synthetic- PRGN primer seq

<400> SEQUENCE: 131
ccagatggtc agttctgccc                                               20

<210> SEQ ID NO 132
<211> LENGTH: 20
<212> TYPE: DNA
<213> ORGANISM: Artificial Sequence
<220> FEATURE:
<223> OTHER INFORMATION: Synthetic- PRKAG3_sg1 F

<400> SEQUENCE: 132
```
atgtagggag actgaggcca                                                20

<210> SEQ ID NO 133
<211> LENGTH: 20
<212> TYPE: DNA
<213> ORGANISM: Artificial Sequence
<220> FEATURE:
<223> OTHER INFORMATION: Synthetic- PRKAG3_sg1 R

<400> SEQUENCE: 133
gcccattgga agcttgcaaa                                                20

<210> SEQ ID NO 134
<211> LENGTH: 25
<212> TYPE: DNA
<213> ORGANISM: Artificial Sequence
<220> FEATURE:
<223> OTHER INFORMATION: Synthetic- PRKAG3_sg1 primer seq

<400> SEQUENCE: 134
ttgggtccaa ctctgtgtta tggag                                          25

<210> SEQ ID NO 135
<211> LENGTH: 20
<212> TYPE: DNA
<213> ORGANISM: Artificial Sequence
<220> FEATURE:
<223> OTHER INFORMATION: Synthetic- STK3_sg1 F

<400> SEQUENCE: 135
acggcaaaac cctgtctcaa                                                20

<210> SEQ ID NO 136
<211> LENGTH: 25
<212> TYPE: DNA
<213> ORGANISM: Artificial Sequence
<220> FEATURE:
<223> OTHER INFORMATION: Synthetic- STK3_sg1 R

<400> SEQUENCE: 136
tccacagaaa actcatagta gactt                                          25

<210> SEQ ID NO 137
<211> LENGTH: 30
<212> TYPE: DNA
<213> ORGANISM: Artificial Sequence
<220> FEATURE:
<223> OTHER INFORMATION: Synthetic- STK3_sg1 primer seq

<400> SEQUENCE: 137
aaacaagggt aagcaaagaa ataaaatctc                                     30

<210> SEQ ID NO 138
<211> LENGTH: 20
<212> TYPE: DNA
<213> ORGANISM: Artificial Sequence
<220> FEATURE:
<223> OTHER INFORMATION: Synthetic- STK3_sg2 F

<400> SEQUENCE: 138
aagccatcct catctgcctt                                                20

<210> SEQ ID NO 139
<211> LENGTH: 21
<212> TYPE: DNA

```
<213> ORGANISM: Artificial Sequence
<220> FEATURE:
<223> OTHER INFORMATION: Synthetic- STK3_sg2 R

<400> SEQUENCE: 139
acacaaggaa tccggtcaag t                                      21

<210> SEQ ID NO 140
<211> LENGTH: 30
<212> TYPE: DNA
<213> ORGANISM: Artificial Sequence
<220> FEATURE:
<223> OTHER INFORMATION: Synthetic- STK3_sg2 primer seq

<400> SEQUENCE: 140
ggagaaaccc atctctacta aaaatacaaa                             30

<210> SEQ ID NO 141
<211> LENGTH: 24
<212> TYPE: DNA
<213> ORGANISM: Artificial Sequence
<220> FEATURE:
<223> OTHER INFORMATION: Synthetic- VEGFA F

<400> SEQUENCE: 141
gaagcaactc cagtcccaaa tatg                                   24

<210> SEQ ID NO 142
<211> LENGTH: 24
<212> TYPE: DNA
<213> ORGANISM: Artificial Sequence
<220> FEATURE:
<223> OTHER INFORMATION: Synthetic- VEGFA R

<400> SEQUENCE: 142
gttcacagcc tgaaaattac ccat                                   24

<210> SEQ ID NO 143
<211> LENGTH: 24
<212> TYPE: DNA
<213> ORGANISM: Artificial Sequence
<220> FEATURE:
<223> OTHER INFORMATION: Synthetic- VEGFA primer seq

<400> SEQUENCE: 143
gaagcaactc cagtcccaaa tatg                                   24

<210> SEQ ID NO 144
<211> LENGTH: 20
<212> TYPE: RNA
<213> ORGANISM: Artificial Sequence
<220> FEATURE:
<223> OTHER INFORMATION: Synthetic- Chr8q23_sg2

<400> SEQUENCE: 144
agucuacuau gaguuuucug                                        20

<210> SEQ ID NO 145
<211> LENGTH: 20
<212> TYPE: DNA
<213> ORGANISM: Artificial Sequence
<220> FEATURE:
<223> OTHER INFORMATION: Synthetic- MIP_OT1

<400> SEQUENCE: 145
agtggggtcc tcactgcact                                        20
```

<210> SEQ ID NO 146
<211> LENGTH: 20
<212> TYPE: DNA
<213> ORGANISM: Artificial Sequence
<220> FEATURE:
<223> OTHER INFORMATION: Synthetic- MIP_OT2

<400> SEQUENCE: 146
tgtggggcac tcactgcgct                                               20

<210> SEQ ID NO 147
<211> LENGTH: 20
<212> TYPE: DNA
<213> ORGANISM: Artificial Sequence
<220> FEATURE:
<223> OTHER INFORMATION: Synthetic- FAM163_OT1

<400> SEQUENCE: 147
ctgcagggcc cgctggagag                                               20

<210> SEQ ID NO 148
<211> LENGTH: 20
<212> TYPE: DNA
<213> ORGANISM: Artificial Sequence
<220> FEATURE:
<223> OTHER INFORMATION: Synthetic- FAM163_OT2

<400> SEQUENCE: 148
ctgcagggga cactggtgag                                               20

<210> SEQ ID NO 149
<211> LENGTH: 20
<212> TYPE: DNA
<213> ORGANISM: Artificial Sequence
<220> FEATURE:
<223> OTHER INFORMATION: Synthetic- OMP_OT1

<400> SEQUENCE: 149
aggctgtagc ccctgctgct                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic- OMP_OT2

<400> SEQUENCE: 150
gaactacagc cactgctgct                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic- FANCF_OT1

<400> SEQUENCE: 151
gctgcagaag ggattccaag                                               20

<210> SEQ ID NO 152
<211> LENGTH: 20
<212> TYPE: DNA
<213> ORGANISM: Artificial Sequence
<220> FEATURE:

<223> OTHER INFORMATION: synthetic- MAPRE_OT1

<400> SEQUENCE: 152
atctctgcag ataatccctg                                                     20

<210> SEQ ID NO 153
<211> LENGTH: 20
<212> TYPE: DNA
<213> ORGANISM: Artificial Sequence
<220> FEATURE:
<223> OTHER INFORMATION: Synthetic- OPN1SW_OT1

<400> SEQUENCE: 153
ttagaggcaa tgtggtactg                                                     20

<210> SEQ ID NO 154
<211> LENGTH: 20
<212> TYPE: DNA
<213> ORGANISM: Artificial Sequence
<220> FEATURE:
<223> OTHER INFORMATION: Synthetic- VEGFA_OT1

<400> SEQUENCE: 154
tgtgggtgag tgtgtgcgtg                                                     20

<210> SEQ ID NO 155
<211> LENGTH: 20
<212> TYPE: DNA
<213> ORGANISM: Artificial Sequence
<220> FEATURE:
<223> OTHER INFORMATION: Synthetic- MIP_OT1 F

<400> SEQUENCE: 155
ctcacagcaa ggtcgaccac                                                     20

<210> SEQ ID NO 156
<211> LENGTH: 20
<212> TYPE: DNA
<213> ORGANISM: Artificial Sequence
<220> FEATURE:
<223> OTHER INFORMATION: Synthetic- MIP_OT1 R

<400> SEQUENCE: 156
cacccctaca cactgccttt                                                     20

<210> SEQ ID NO 157
<211> LENGTH: 30
<212> TYPE: DNA
<213> ORGANISM: Artificial Sequence
<220> FEATURE:
<223> OTHER INFORMATION: Synthetic- MIP_OT1 primer seq

<400> SEQUENCE: 157
cattcgaaat cctatgctga gctttcatag                                          30

<210> SEQ ID NO 158
<211> LENGTH: 20
<212> TYPE: DNA
<213> ORGANISM: Artificial Sequence
<220> FEATURE:
<223> OTHER INFORMATION: Synthetic- MIP_OT2 F

<400> SEQUENCE: 158
cggctccagt gctctttctt                                                     20

```
<210> SEQ ID NO 159
<211> LENGTH: 20
<212> TYPE: DNA
<213> ORGANISM: Artificial Sequence
<220> FEATURE:
<223> OTHER INFORMATION: Synthetic- MIP_OT2 R

<400> SEQUENCE: 159
ggagggtacg caaggtttgg                                               20

<210> SEQ ID NO 160
<211> LENGTH: 22
<212> TYPE: DNA
<213> ORGANISM: Artificial Sequence
<220> FEATURE:
<223> OTHER INFORMATION: Synthetic- MIP_OT2 primer seq

<400> SEQUENCE: 160
gcctttctga ctcccatcct tc                                            22

<210> SEQ ID NO 161
<211> LENGTH: 20
<212> TYPE: DNA
<213> ORGANISM: Artificial Sequence
<220> FEATURE:
<223> OTHER INFORMATION: Synthetic- FAM163_OT1 F

<400> SEQUENCE: 161
gtggatagga gcatctgccc                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic- FAM163_OT1 R

<400> SEQUENCE: 162
gtgggagaag gaggtcatgc                                               20

<210> SEQ ID NO 163
<211> LENGTH: 23
<212> TYPE: DNA
<213> ORGANISM: Artificial Sequence
<220> FEATURE:
<223> OTHER INFORMATION: Synthetic- FAM163_OT1 primer seq

<400> SEQUENCE: 163
cctccccata tgcttggagt aag                                           23

<210> SEQ ID NO 164
<211> LENGTH: 20
<212> TYPE: DNA
<213> ORGANISM: Artificial Sequence
<220> FEATURE:
<223> OTHER INFORMATION: Synthetic- FAM163_OT2 F

<400> SEQUENCE: 164
gcccacattt gcactgactc                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic- FAM163_OT2 R
```

<400> SEQUENCE: 165
gatcatggtg atgtgcgcac                                               20

<210> SEQ ID NO 166
<211> LENGTH: 30
<212> TYPE: DNA
<213> ORGANISM: Artificial Sequence
<220> FEATURE:
<223> OTHER INFORMATION: Synthetic- FAM163_OT2 primer seq

<400> SEQUENCE: 166
agacaagaca ccacagcaat tccaattttg                                    30

<210> SEQ ID NO 167
<211> LENGTH: 20
<212> TYPE: DNA
<213> ORGANISM: Artificial Sequence
<220> FEATURE:
<223> OTHER INFORMATION: Synthetic- OMP_OT1 F

<400> SEQUENCE: 167
agatcctggg ggtctctgtg                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic- OMP_OT1 R

<400> SEQUENCE: 168
cgcctgctta tcatttgggc                                               20

<210> SEQ ID NO 169
<211> LENGTH: 30
<212> TYPE: DNA
<213> ORGANISM: Artificial Sequence
<220> FEATURE:
<223> OTHER INFORMATION: Synthetic- OMP_OT1 primer seq

<400> SEQUENCE: 169
gaactagaga cttatgagtg gttctaagat                                    30

<210> SEQ ID NO 170
<211> LENGTH: 20
<212> TYPE: DNA
<213> ORGANISM: Artificial Sequence
<220> FEATURE:
<223> OTHER INFORMATION: Synthetic- OMP_OT2 F

<400> SEQUENCE: 170
ttgcaacacc agggctttct                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic- OMP_OT2 R

<400> SEQUENCE: 171
cttcacaggc ttcagggagg                                               20

<210> SEQ ID NO 172
<211> LENGTH: 30

```
<212> TYPE: DNA
<213> ORGANISM: Artificial Sequence
<220> FEATURE:
<223> OTHER INFORMATION: Synthetic- OMP_OT2 primer seq

<400> SEQUENCE: 172
tagcatttcc ttctttagag gttgattatg                                   30

<210> SEQ ID NO 173
<211> LENGTH: 24
<212> TYPE: DNA
<213> ORGANISM: Artificial Sequence
<220> FEATURE:
<223> OTHER INFORMATION: Synthetic- FANCF_OT1 F

<400> SEQUENCE: 173
agtttcacat ccctgtctta cctc                                         24

<210> SEQ ID NO 174
<211> LENGTH: 24
<212> TYPE: DNA
<213> ORGANISM: Artificial Sequence
<220> FEATURE:
<223> OTHER INFORMATION: Synthetic- FANCF_OT1 R

<400> SEQUENCE: 174
agactcacaa catccatcag aaca                                         24

<210> SEQ ID NO 175
<211> LENGTH: 24
<212> TYPE: DNA
<213> ORGANISM: Artificial Sequence
<220> FEATURE:
<223> OTHER INFORMATION: Synthetic- FANCF_OT1 primer seq

<400> SEQUENCE: 175
agtttcacat ccctgtctta cctc                                         24

<210> SEQ ID NO 176
<211> LENGTH: 21
<212> TYPE: DNA
<213> ORGANISM: Artificial Sequence
<220> FEATURE:
<223> OTHER INFORMATION: Synthetic- MAPRE_OT1 F

<400> SEQUENCE: 176
acagtttgtg ggcttttggg t                                            21

<210> SEQ ID NO 177
<211> LENGTH: 20
<212> TYPE: DNA
<213> ORGANISM: Artificial Sequence
<220> FEATURE:
<223> OTHER INFORMATION: Synthetic- MAPRE_OT1 R

<400> SEQUENCE: 177
gcattctgcc ctgtttgtgg                                              20

<210> SEQ ID NO 178
<211> LENGTH: 24
<212> TYPE: DNA
<213> ORGANISM: Artificial Sequence
<220> FEATURE:
<223> OTHER INFORMATION: Synthetic- MAPRE_OT1 primer seq

<400> SEQUENCE: 178
```
cattttgagc aaggtcagaa ggac                                           24

<210> SEQ ID NO 179
<211> LENGTH: 20
<212> TYPE: DNA
<213> ORGANISM: Artificial Sequence
<220> FEATURE:
<223> OTHER INFORMATION: Synthetic- OPN1SW_OT1 F

<400> SEQUENCE: 179
tggccatagg aagcacagtc                                                20

<210> SEQ ID NO 180
<211> LENGTH: 20
<212> TYPE: DNA
<213> ORGANISM: Artificial Sequence
<220> FEATURE:
<223> OTHER INFORMATION: Synthetic- OPN1SW_OT1 R

<400> SEQUENCE: 180
atgatccccc tgtctctgct                                                20

<210> SEQ ID NO 181
<211> LENGTH: 24
<212> TYPE: DNA
<213> ORGANISM: Artificial Sequence
<220> FEATURE:
<223> OTHER INFORMATION: Synthetic- OPN1SW_OT1 primer seq

<400> SEQUENCE: 181
ctacctccct ctccttagct tctc                                           24

<210> SEQ ID NO 182
<211> LENGTH: 24
<212> TYPE: DNA
<213> ORGANISM: Artificial Sequence
<220> FEATURE:
<223> OTHER INFORMATION: Synthetic- VEGFA_OT1 F

<400> SEQUENCE: 182
agggacttga gtatctgcag tttt                                           24

<210> SEQ ID NO 183
<211> LENGTH: 24
<212> TYPE: DNA
<213> ORGANISM: Artificial Sequence
<220> FEATURE:
<223> OTHER INFORMATION: Synthetic- VEGFA_OT1 R

<400> SEQUENCE: 183
tgaagagata tctgcaccct catg                                           24

<210> SEQ ID NO 184
<211> LENGTH: 24
<212> TYPE: DNA
<213> ORGANISM: Artificial Sequence
<220> FEATURE:
<223> OTHER INFORMATION: Synthetic- VEGFA_OT1 primer seq

<400> SEQUENCE: 184
agggacttga gtatctgcag tttt                                           24

<210> SEQ ID NO 185
<211> LENGTH: 23
<212> TYPE: DNA
<213> ORGANISM: Artificial Sequence -continued

```
<220> FEATURE:
<223> OTHER INFORMATION: Synthetic- sgRNA_F

<400> SEQUENCE: 185
agagctagaa atagcaagtt aaa                                              23

<210> SEQ ID NO 186
<211> LENGTH: 16
<212> TYPE: DNA
<213> ORGANISM: Artificial Sequence
<220> FEATURE:
<223> OTHER INFORMATION: Synthetic- sgRNA_R

<400> SEQUENCE: 186
gactcggtgc cacttt                                                      16

<210> SEQ ID NO 187
<211> LENGTH: 20
<212> TYPE: RNA
<213> ORGANISM: Artificial Sequence
<220> FEATURE:
<223> OTHER INFORMATION: Synthetic- CRISPR ON V4 sgRNA variants

<400> SEQUENCE: 187
ucucccugag cuucagggag                                                  20
```

STABILIZED CRISPR COMPLEXES

CROSS-REFERENCE

This application is a continuation application of international application PCT/US2020/042681, filed on Jul. 17, 2020, which international application claims priority to U.S. provisional patent application No. 62/876,204 filed Jul. 19, 2019, U.S. provisional patent application No. 62/876,177 filed Jul. 19, 2019, U.S. provisional patent application No. 62/939,554 filed Nov. 22, 2019, U.S. provisional patent application No. 62/939,553 filed Nov. 22, 2019, International patent application no. PCT/US20/15127 filed Jan. 25, 2020 and U.S. provisional patent application No. 63/010,465 filed Apr. 15, 2020, which are herein incorporated by reference in their entireties.

SEQUENCE LISTING

A Sequence Listing accompanies this application and is submitted as an ASCII text file of the sequence listing named "174774.00073_SL_ST25.txt" which is 41,465 bytes in size and was created on Jun. 7, 2024. The sequence listing is electronically submitted and is incorporated herein by reference in its entirety.

BACKGROUND

CRISPR/Cas can be used in various medical, laboratory and other exploratory settings. The CRISPR/Cas system can be used as a gene editing tool in a plethora of different organisms to generate breaks at a target site and subsequently introduce mutations at the locus. Two main components can be needed for the gene editing process: an endonuclease-like Cas enzyme and a short RNA molecule to recognize a specific DNA target nucleic acid sequence. Instead of engineering a nuclease enzyme for every DNA target, the CRISPR/Cas system can rely on customized short RNA molecules to recruit the Cas enzyme to a different nucleic acid, e.g., DNA, target site. Examples of Cas enzymes include Cas9 and Cpf1. Synthetic guide RNAs, e.g., single guide RNAs (sgRNAs), used to form CRISPR complexes can be subject to degradation when not in complex with a Cas enzyme. Synthetic guide RNAs, e.g., single guide RNAs (sgRNAs), used to form CRISPR complexes can induce an immune response which can limit the application of currently available sgRNA/Cas nuclease complexes. CRISPR complexes can dissociate in vivo either partially or fully which can reduce efficiency and possibly cause off target cleavage events. Due to the instability of CRISPR complexes, they are often delivered encoded in a plasmid which relies on the transcription of the target cell to produce the encoded protein and guide sequence. There is a need for delivery of precise ratios of CRISPR Cas enzyme and guide RNA molecules that are consistent in any research context, such as the delivery of a pure reagent in a controlled dosing regimen. Additionally, there is a need for CRISPR complexes with enhanced stability for use in various settings requiring, for example, precise dosing of one or more exogenous CRISPR complexes with tunable activity.

SUMMARY

Disclosed herein is a CRISPR complex comprising a single guide RNA (sgRNA) cross-linked to a CRISPR effector protein at an unnatural nucleotide within the sgRNA, wherein the sgRNA comprises a crRNA region and a tracrRNA region, and wherein the unnatural nucleotide is outside a target binding region of the crRNA region. The unnatural nucleotide can comprise a uracil. The unnatural nucleotide can be at nucleotide position 49 of the sgRNA, wherein nucleotide position 1 is at a 5' end of the target binding region of the crRNA and nucleotide positions of the sgRNA are numbered consecutively from 5' to 3' from nucleotide position 1. The unnatural nucleotide can comprise a modification of a sugar. The unnatural nucleotide can comprise a modification of a base. The unnatural nucleotide can comprise a maleimide. The maleimide can covalently link to a cysteine on the CRISPR effector protein. The unnatural nucleotide can comprise pyridyl disulfide, alkoxyamine, NHS ester, diazarine, imidoester, haloacetyl group, hydrazide, aryl azide, isocyanate, dithiol phosphoramidite DTPA, 4-thio-UTP, 5-azido-UTP, 5-bromo-UTP, 8-azido-ATP, 5-APAS-UTP, or 8-N(3)AMP.

In some embodiments, the unnatural nucleotide can be in a stem loop of the tracrRNA region. A structure of the stem loop can be maintained relative to a structure of a stem loop of a sgRNA lacking the unnatural nucleotide. The unnatural nucleotide can be in a bulge of the tracrRNA region. A structure of the bulge can be maintained relative to a structure of a bulge of a sgRNA lacking the unnatural nucleotide. The unnatural nucleotide can be between stem loops of the tracrRNA region. The CRISPR complex can comprise nuclease activity.

In some embodiments, an off-target nuclease activity of the CRISPR complex is equal to or less than an off-target nuclease activity of a CRISPR complex comprising the CRISPR effector protein and the sgRNA that are not cross-linked. The unnatural nucleotide can be within 20 angstroms of a cysteine of the CRISPR effector protein. In some embodiments, the unnatural nucleotide can not be 4-thiouridine or a modified adenosine.

Further disclosed herein is a CRISPR complex comprising a single guide RNA (sgRNA) cross-linked to a CRISPR effector protein at a nucleotide at nucleotide position 49 of the sgRNA, wherein nucleotide position 1 is at a 5' end of the target binding region of the crRNA and nucleotide positions of the sgRNA are numbered consecutively from 5' to 3' from nucleotide position 1. The nucleotide at nucleotide position 49 can comprise a uracil. The CRISPR complex can comprise nuclease activity. In some embodiments, the CRISPR complex can comprise a single guide RNA (sgRNA) cross-linked to a CRISPR effector protein at an unnatural nucleotide within the sgRNA, wherein the CRISPR complex comprises nuclease activity.

Disclosed herein is a pharmaceutical formulation comprising the CRISPR complex and a pharmaceutically acceptable excipient. Further disclosed is a method comprising administering the pharmaceutical formulation to a subject.

Disclosed herein is a method comprising introducing the CRISPR complex into a cell. Also disclosed is a kit comprising the CRISPR complex and instructions.

Disclosed herein is a method of editing a nucleic acid molecule comprising contacting the CRISPR complex to a nucleic acid molecule. The CRISPR complex can comprise an off-target cleavage activity of less than 2% of cleavage events.

Disclosed here is a method of editing a target gene in a plurality of cells comprising administering the CRISPR complex to a plurality of cells comprising a target gene, thereby generating cells comprising edited target genes, wherein 99% of the cells comprising edited target genes remain viable after administration of the CRISPR complex. Cell viability can be measured by resazurin assay.

Disclosed herein is a method of producing a CRISPR complex comprising cross-linking a sgRNA comprising a crRNA region and a tracrRNA region to a CRISPR effector protein, wherein the cross-linking occurs at an unnatural nucleotide outside the crRNA region of the sgRNA, wherein nuclease activity of the CRISPR effector protein is maintained after the cross-linking. The unnatural nucleotide can comprise a uracil. The unnatural nucleotide can comprise a maleimide. The crosslinking can be between the uracil and a cysteine on the CRISPR effector protein. The uracil can comprise a 4-thio uridine. The crosslinking can be between the uracil and an amine group on the CRISPR effector protein. The uracil can comprise a 5-bromo uridine. The cross-linking can occur in solution, and a ratio of the sgRNA to the CRISPR effector protein in the solution can be at least 9:1. The crosslinking can comprise exposing the solution to UV light. The crosslinking can occur upon mixing of the sgRNA with the CRISPR effector protein.

Disclosed herein is a method comprising cross-linking a single guide RNA (sgRNA) comprising an unnatural nucleotide comprising a cross-linking agent to a CRISPR effector protein, wherein the cross-linking occurs at the unnatural nucleotide outside a target binding region of the sgRNA, thereby generating a cross-linked complex, wherein the cross-linked complex comprises nuclease activity.

Disclosed herein is a single guide RNA (sgRNA) comprising a crRNA region and a tracrRNA region and an unnatural nucleotide at nucleotide position 49, wherein nucleotide position 1 is at a 5' end of a target binding region of the crRNA region and nucleotide positions of the sgRNA are numbered consecutively from 5' to 3' from nucleotide position 1.

Disclosed herein is a single guide RNA (sgRNA) comprising a crRNA region and a tracrRNA region and a uracil at nucleotide position 49, wherein nucleotide position 1 is at a 5' end of a target binding region of the crRNA region and nucleotide positions of the sgRNA are numbered consecutively from 5' to 3' from nucleotide position 1.

Disclosed herein is a CRISPR complex comprising a single guide RNA (sgRNA) cross-linked to a CRISPR effector protein, wherein the sgRNA comprises a crRNA region, a tracrRNA region, and a sequence configured to modulate activity of the CRISPR complex. The sgRNA can be a CRISPR ON polynucleotide, CRISPR OFF polynucleotide, CRISPR ON/OFF polynucleotide, or CRISPR polynucleotide modified to decrease off-target editing. The sgRNA can comprise an unnatural nucleotide within the sgRNA, and sgRNA is cross-linked to the CRISPR effector protein at the unnatural nucleotide. The unnatural nucleotide can be outside a target binding region of the crRNA region. The unnatural nucleotide can be at nucleotide position 49 of the sgRNA, wherein nucleotide position 1 is at a 5' end of the target binding region of the crRNA and nucleotide positions of the sgRNA are numbered consecutively from 5' to 3' from nucleotide position 1. The unnatural nucleotide can comprise a modification of a sugar. The unnatural nucleotide can comprise a modification of a base. The unnatural nucleotide can comprise a maleimide. The maleimide can covalently link to a cysteine on the CRISPR effector protein. The unnatural nucleotide can comprise pyridyl disulfide, alkoxyamine, NHS ester, diazarine, imidoester, haloacetyl group, hydrazide, aryl azide, isocyanate, dithiol phosphoramidite DTPA, 4-thio-UTP, 5-azido-UTP, 5-bromo-UTP, 8-azido-ATP, 5-APAS-UTP, or 8-N(3)AMP. The unnatural nucleotide can be in a stem loop of the tracrRNA region. A structure of the stem loop can be maintained relative to a structure of a stem loop of a sgRNA lacking the unnatural nucleotide. The unnatural nucleotide can be in a bulge of the tracrRNA region. A structure of the bulge can be maintained relative to a structure of a bulge of a sgRNA lacking the unnatural nucleotide. The unnatural nucleotide can be between stem loops of the tracrRNA region. The CRISPR complex can comprise nuclease activity. An off-target nuclease activity of the CRISPR complex can be equal to or less than an off-target nuclease activity of a CRISPR complex comprising the CRISPR effector protein and the sgRNA that are not cross-linked. The unnatural nucleotide can be within 20 angstroms of a cysteine of the CRISPR effector protein. In some embodiments, the unnatural nucleotide may not be 4-thiouridine or a modified adenosine.

Disclosed herein is a polynucleotide comprising a modification, wherein the polynucleotide comprises: (i) a guide sequence configured to anneal to a target sequence in a target nucleic acid molecule (ii) a sequence configured to bind to a CRISPR effector protein and comprising the modification, and (iii) an unnatural nucleotide configured to cross-link to a CRISPR effector protein; wherein when the polynucleotide is complexed with a CRISPR effector protein, a first CRISPR complex is formed having a lower editing activity of an off-target nucleic acid molecule than a second CRISPR complex comprising the polynucleotide, without the modification, complexed with the CRISPR effector protein. The unnatural nucleotide can be at position 49. The modification can comprise a linker not comprising a canonical nucleotide base. The modification can comprise at least two linkers not comprising a canonical nucleotide base. The sequence of ii) can form, from 5' to 3', a tetraloop, a first stem loop, a second stem loop, and a third stem loop. In some instances, the polynucleotide does not comprise a fourth stem loop. In some instances, the polynucleotide does not comprise a stem loop at a 5' end of the polynucleotide. The linker can comprise a cleavable linker. The linker can comprise 3-(4,4'-Dimethoxytrityl)-1-(2-nitrophenyl)-propan-1-yl-[(2-cyanoethyl)-(N,N-diisopropyl)]-phosphoramidite. The linker can comprise a photolabile linker. The photolabile linker can be cleavable by ultraviolet radiation. The photolabile linker can be cleavable by visible light. The cleavable linker can comprise 3-(4,4'-Dimethoxytrityl)-1-(2-nitrophenyl)-propan-1-yl-[(2-cyanoethyl)-(N,N-diisopropyl)]-phosphoramidite. The cleavable linker can comprise 1-(7-(diethylamino)-2-oxo-2H-chromen-4-yl)propyl. The cleavable linker can comprise

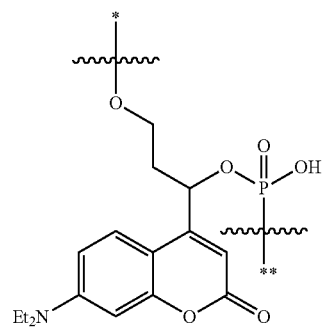

wherein * indicates a point of attachment to H, or a first nucleotide and ** indicates a point of attachment to OH, or a second nucleotide. The photolabile linker can comprise phosphoramidite. The photolabile linker can comprise coumarin. The modification can be at position 57 or position 74 of the polynucleotide, wherein position 1 is at a 5' end of the polynucleotide, and positions are counted from 5' to 3'. The modification can be at position 57 and position 74 of the polynucleotide. The modification can be in a loop. The modification can be in the first stem loop or the second stem loop. The modification can be in a loop of first stem loop or a loop of the second stem loop. The modification can be at one or both of positions 57 and 74, wherein position 1 is at a 5' end of the polynucleotide, and positions are counted from 5' to 3'. The modification can comprise a photo cleavable bond. In some instances the modification is not in a stem loop. The polynucleotide can comprise 2'-O-methyl analogs and 3'phosphorothioate inter nucleotide linkages at a first three 5' and 3' terminal RNA nucleotides. Editing activity can be measured as a percentage of off-target nucleic acid molecules that are edited. The editing activity of the off-target nucleic acid molecules by the first CRISPR complex can be lower that an editing activity of the second CRISPR complex with a p-value≤0.0001. The editing activity of the first CRISPR complex of the target nucleic acid molecule and an editing activity of the second CRISPR complex of the target nucleic acid molecule can be within 5%. The editing activity of the first CRISPR complex of the target nucleic acid molecule and the editing activity of the second CRISPR complex of the target nucleic acid molecule can be measured as a percentage of target nucleic acid molecules that are edited. Disclosed herein is a CRISPR complex comprising any of the aforementioned polynucleotides and a CRISPR enzyme. The CRISPR complex can comprises nuclease activity.

In another aspect, described herein, is a nucleotide or oligonucleotide comprising a linker of Formula (I):

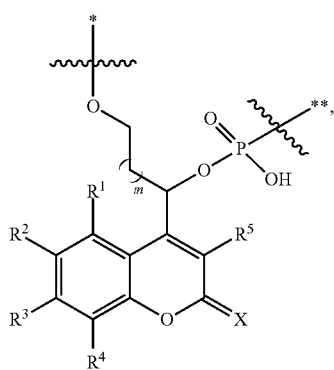

(I)

wherein: $R^1$, $R^2$, $R^3$, $R^4$, and $R^5$ are each independently selected from H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

m can be an integer selected from 1 to 10; X can be selected from O, S, =C(CN)2; * can indicate a point of attachment to H, or a pentose moiety; and ** can indicate a point of attachment to OH, or a phosphate group of a nucleotide. The linker of Formula (I) can be represented by Formula (I'):

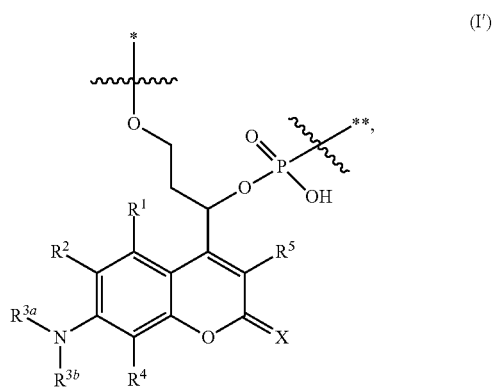

(I')

wherein: $R^1$, $R^2$, $R^{3a}$, $R^{3b}$, $R^4$, and $R^5$ are each independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, two or more of $R^2$, $R^{2a}$, $R^{3a}$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; X can be oxygen, S, or =C(CN)2. $R^1$, $R^2$, $R^4$, and $R^5$ can each independently be H or $C_{1-6}$ alkyl; and $R^{3a}$, and $R^{3b}$ can be $C_{1-6}$ alkyl. $R^1$, $R^2$, $R^4$, and $R^5$ can each be H; and $R^{3a}$, and $R^{3b}$ can each be ethyl.

In another aspect, provided herein is a compound comprising

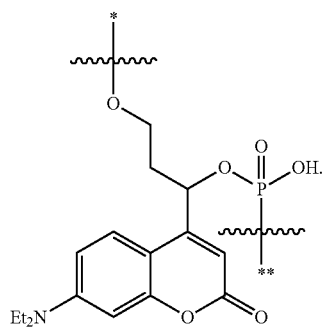

Disclosed herein is a polynucleotide comprising the aforementioned compound. The polynucleotide can further comprise a sequence configured to bind a CRISPR enzyme. The polynucleotide can further comprise a guide sequence configured to anneal to a target sequence in a target nucleic acid molecule. Disclosed herein is a CRISPR complex comprising a CRISPR enzyme and an aforementioned polynucleotide.

In another aspect, described herein, is a compound comprising Formula (I):

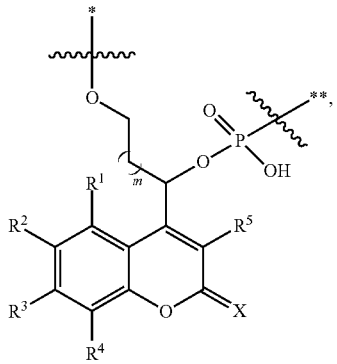

(I)

wherein: $R^1$, $R^2$, $R^3$, $R^4$, and $R^5$ are each independently selected from H alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

m can be an integer selected from 1 to 10; X can be selected from O, S, =C(CN)2; * can indicate a point of attachment to H, or a pentose moiety; and ** can indicate a point of attachment to OH, or a phosphate group of a nucleotide. The compound of Formula (I) can be represented by Formula (I'):

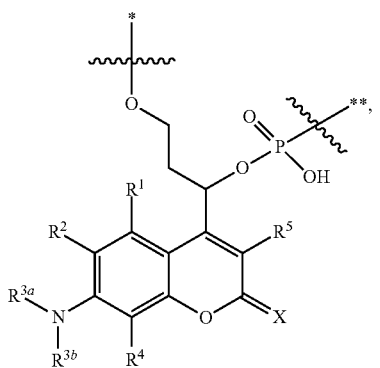

(I')

wherein: $R^1$, $R^2$, $R^{3a}$, $R^{3b}$, $R^4$, and $R^5$ are each independently selected from the group consisting of H, alkyl, substituted alkyl, alkoxy, alkenyl, alkynyl, haloalkyl, haloalkoxy, alkoxyalkyl, amino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl and optionally substituted heterocyclyl; alternatively, two or more of $R^2$, $R^{2a}$, $R^{3a}$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; X can be oxygen, S, or =C(CN)2. $R^1$, $R^2$, $R^4$, and $R^5$ can each independently be H or $C_{1-6}$ alkyl; and $R^{3a}$, and $R^{3b}$ can be $C_{1-6}$ alkyl. $R^1$, $R^2$, $R^4$, and $R^5$ can each be H; and $R^{3a}$, and $R^{3b}$ can each be ethyl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 61:
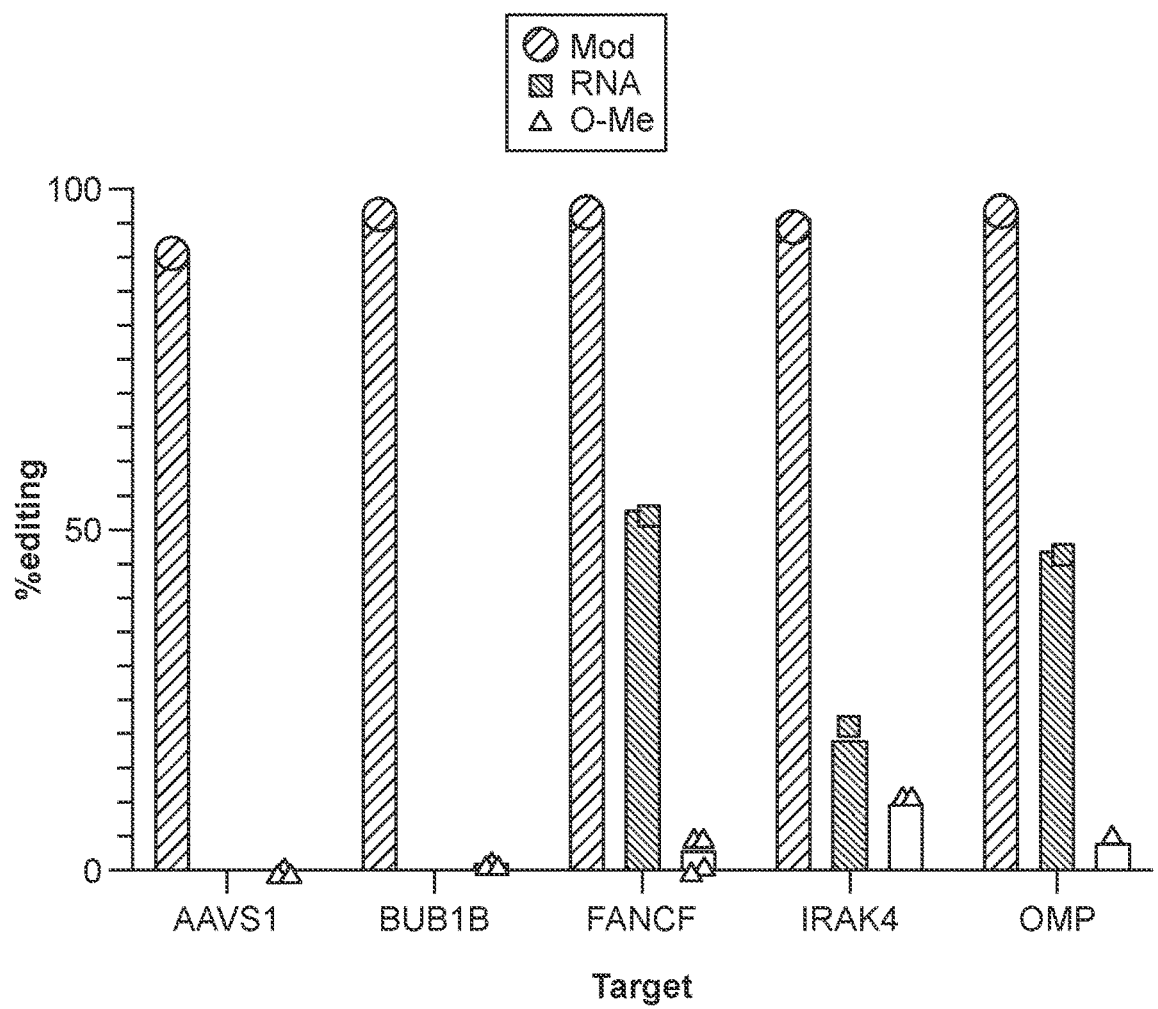

FIG. 61 shows a comparison of editing activity between standard sgRNA (Mod), CRISPR ON V1 (RNA) and CRISPR ON V2 (0-Me).

Figure 62:
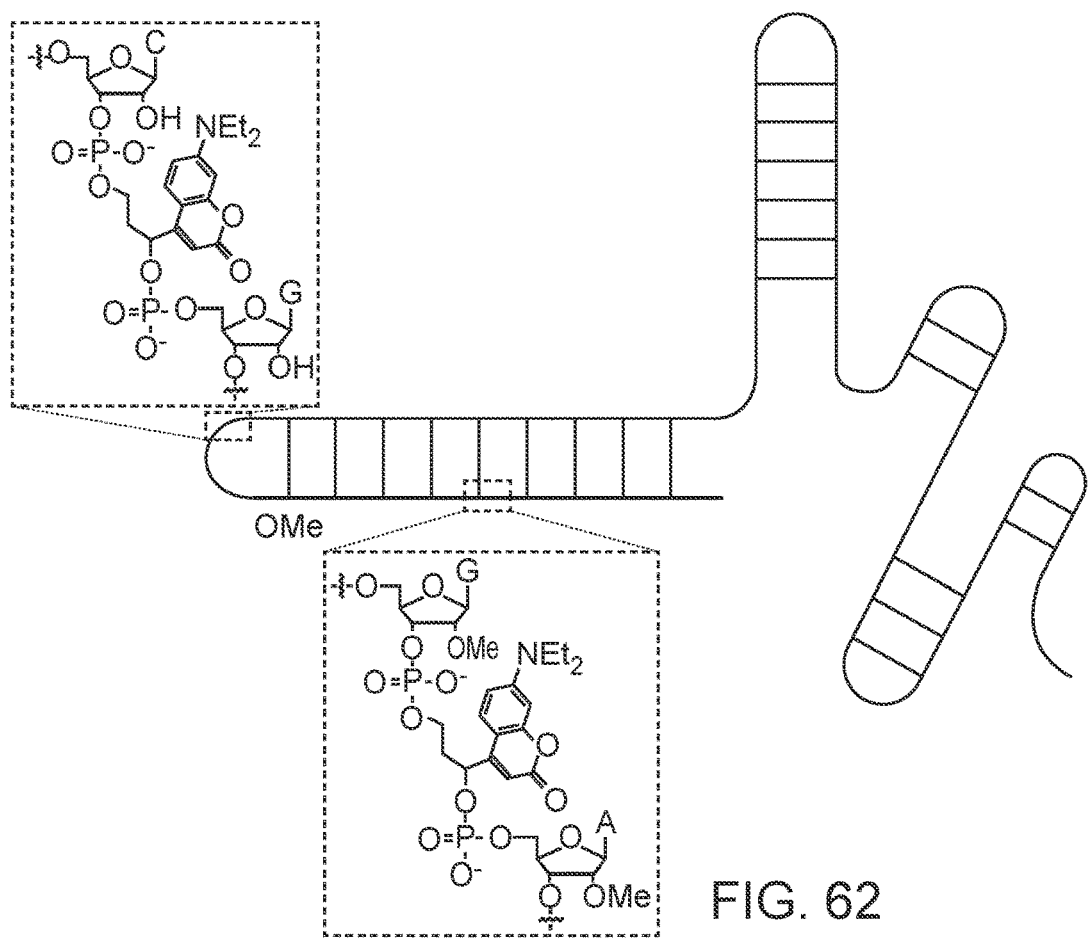

FIG. 62 shows the structure of CRISPR ON V3 sgRNA. CRISPR ON V3 is built upon CRISPR ON V2 but it incorporates photocleavable linkers in the middle of the protospacer backtrack (position 11) and immediately 5' of protospacer sequence (position 24).

Figure 63:
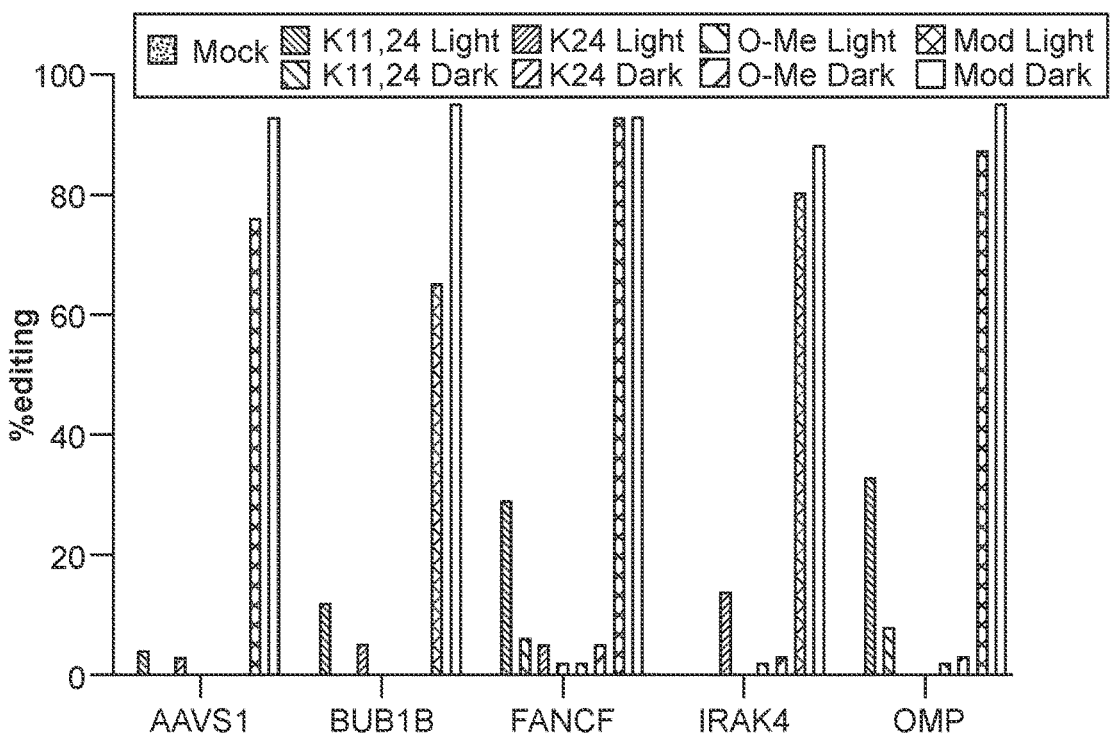

FIG. 63 shows editing using CRISPR ON V3 sgRNA (K11,24) targeting five unique loci in comparison to CRISPR ON V2 variant containing a single photocleavable linker at position 24 (K24), CRISPR ON V2 (0-Me) and standard sgRNA (Mod).

Figure 64:
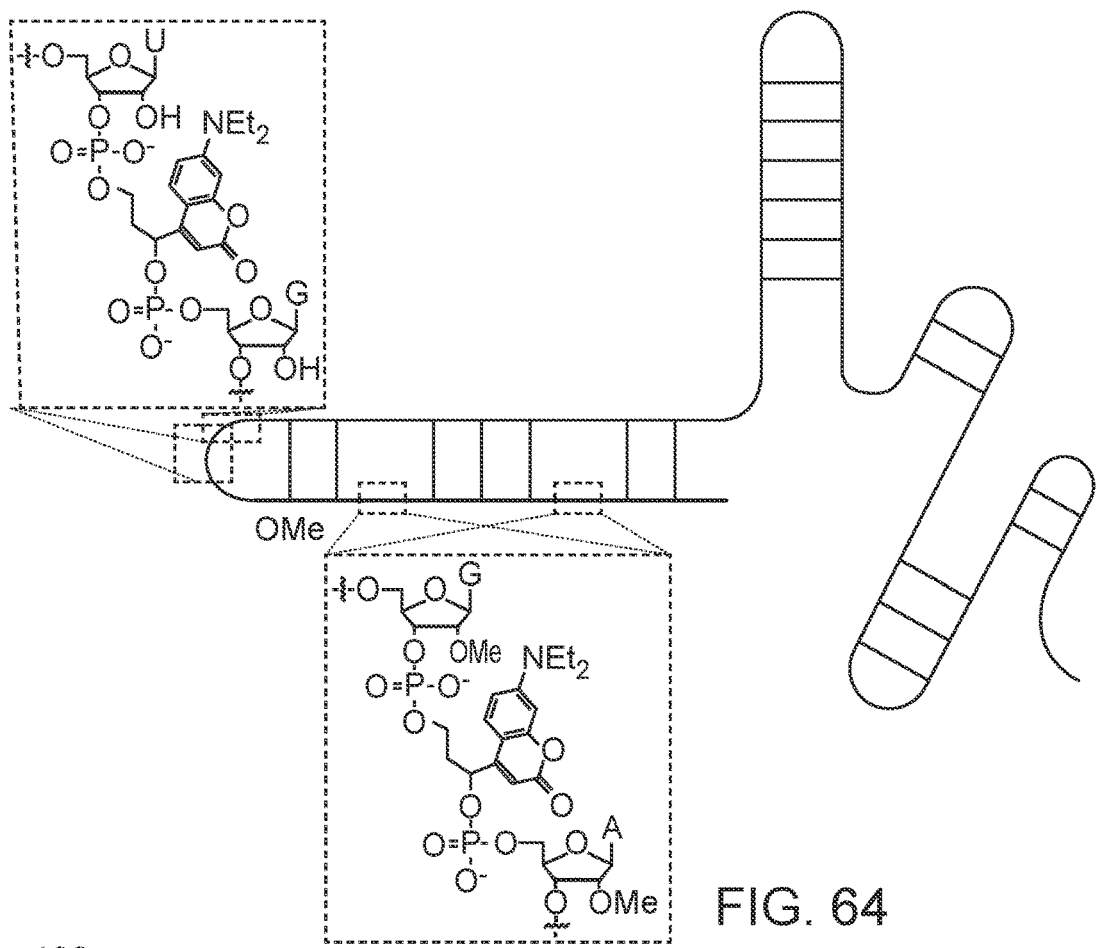

FIG. 64 shows the structure of CRISPR ON V4 sgRNA. CRISPR ON V4 builds on CRISPR ON V3 but introduces additional photocleavable linkers to ensure efficient displacement of the backtrack region by the DNA target. Photocleavable residues are placed at positions 23 and 24 to increase the probability of backtrack release from the sgRNA. Additional photocleavable residues are placed at position 6 and 14 to aid in dissociation.

Figure 65:
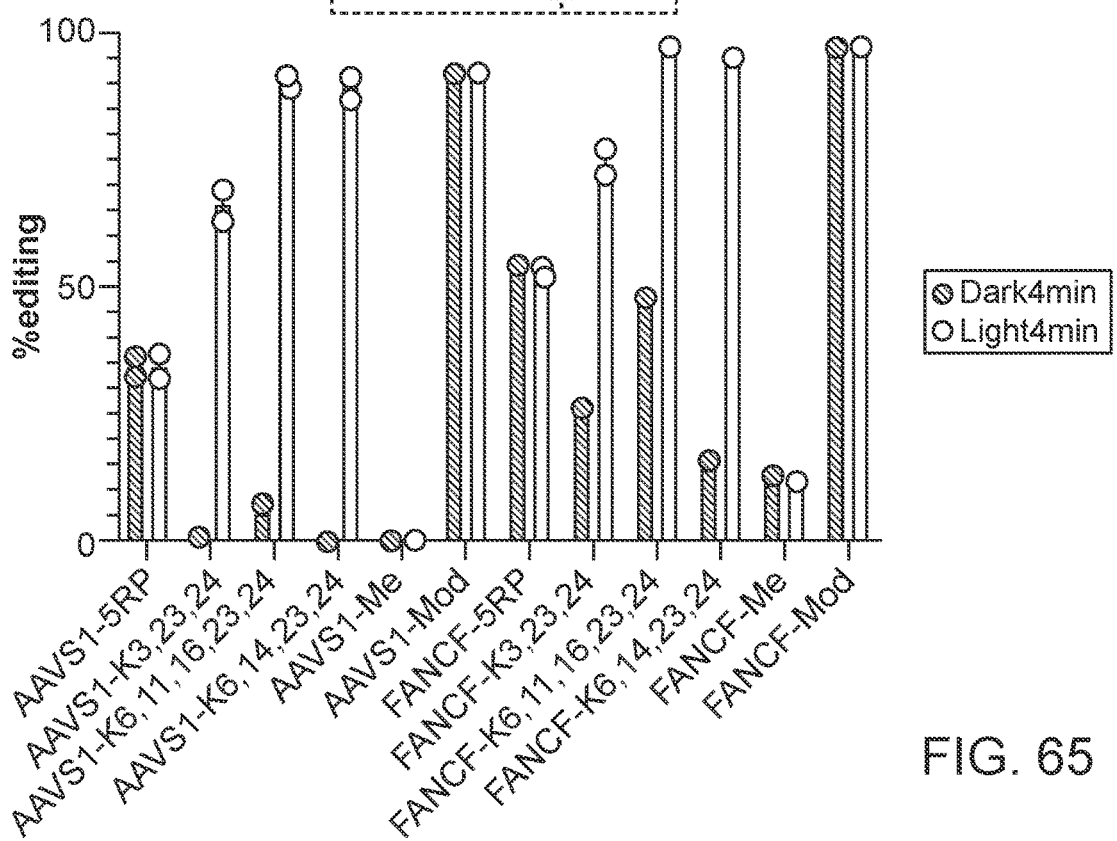

FIG. 65 shows editing using CRISPR ON V4 sgRNA variants in comparison to 5RP (comprising the additional sequence 5'-UCUCCCUGAGCUUCAGGGAG-3' at the 5' of the sgRNA), CRISPR ON V2 (Me) and standard sgRNA (Mod) at two loci. The CRISPR ON V4 sgRNAs variants included photocleavable linkers at nucleotides: 3, 23 and 24 (K3, 23, 24); 6, 11, 16, 23 and 24 (K6, 11, 16, 23, 24); 6, 14, 23 and 24 (K6, 14, 23, 24).

DETAILED DESCRIPTION

I. Overview

Disclosed herein is a polynucleotide (CRISPR polynucleotide) comprising a sequence designed to anneal to a target nucleic acid sequence and a sequence designed to bind a CRISPR effector protein, wherein the CRISPR polynucleotide comprises a cross-linker. The cross-linker can be in a hairpin region of the polynucleotide. In another aspect, provided herein is a CRISPR complex comprising the CRISPR polynucleotide and a CRISPR effector protein. The CRISPR polynucleotide can be designed to bind to the CRISPR effector protein, e.g., a Cas enzyme, to form the CRISPR complex. The Cas enzyme can be Cas9, Cas12a, Cas12b, etc. Also provided herein are methods for cross-linking the CRISPR polynucleotide to the CRISPR effector protein to form a cross-linked CRISPR complex. For example, the CRISPR polynucleotide can be covalently bonded to the Cas enzyme, e.g., through activation of the cross-linking reaction by exposure to a particular wavelength of light in the ultraviolet range or by the positioning of an unnatural nucleotide within the sgRNA which will form a covalent bond upon close proximity to a target amino acid side chain.

In another aspect, provided herein is a CRISPR complex comprising: a) a CRISPR polynucleotide comprising a sequence designed to anneal to a target nucleic acid sequence, a sequence designed to bind a CRISPR effector protein, with or without one or more elements that can be modulated to affect activity; and b) a CRISPR effector protein, wherein an equilibrium dissociation constant ($K_d$) for the CRISPR polynucleotide binding to the CRISPR effector protein is less than 8 pM.

In another aspect, the CRISPR polynucleotides can comprise (i) a sequence configured to covalently bind to a CRISPR effector protein, (ii) optionally, a guide sequence configured to anneal to a target sequence in a target molecule, and (iii) one or more elements that can be modulated to affect the activity of a CRISPR effector protein complexed with the CRISPR polynucleotide. A CRISPR effector protein complexed with the CRISPR polynucleotide can be considered to be "tunable." In some cases, the one or more elements can be modulated to increase the activity of a CRISPR effector protein complexed with the CRISPR polynucleotide (e.g., CRISPR "ON" complexes). In some cases, the one or more elements can be modulated to decrease the activity of a CRISPR effector protein complexed with the CRISPR polynucleotide (e.g., CRISPR "OFF" complexes). In some cases, a first element in the CRISPR polynucleotide can be modulated to increase the activity of a CRISPR effector protein complexed with the CRISPR polynucleotide and second element can be modulated to decrease the activity of a CRISPR effector protein complexed with the CRISPR polynucleotide (e.g., CRISPR "ON/OFF" complexes).

Also provided herein are complexes comprising a CRISPR effector protein crosslinked to a CRISPR polynucleotide (e.g., CRISPR ON complexes; CRISPR OFF complexes; or CRISPR ON/OFF complexes). In some cases, the cross-link can be at an unnatural nucleotide in the CRISPR polynucleotide. Methods of modulating the CRISPR polynucleotides are provided herein. Kits comprising the polynucleotides and, e.g., instructions, and optionally CRISPR effector protein, are provided. Furthermore, pharmaceutical formulations comprising the CRISPR polynucleotides and a pharmaceutically acceptable excipient are provided, as well as methods of administering the pharmaceutical formulations. Methods of introducing the CRISPR polynucleotides into a cell are also provided herein.

Methods and kits making use of the CRISPR polynucleotides and CRISPR complexes are provided herein. For example, provided herein are methods comprising contacting a target nucleic acid sequence with the CRISPR complex. In addition, provided herein is a pharmaceutical formulation comprising the CRISPR polynucleotide and/or the CRISPR complex and a pharmaceutically acceptable excipient. In another aspect, a method is provided comprising administering the pharmaceutical formulation to a subject. Moreover, provided herein is a method comprising introducing the CRISPR complex into a cell.

Kits comprising the CRISPR polynucleotide and/or CRISPR complex are also provided herein.

II. CRISPR Overview

Provided herein are CRISPR/Cas complexes with enhanced stability. Provided herein are CRISPR/Cas complexes with enhanced stability and tunable activity. CRISPR (clustered regularly interspaced short palindromic repeats) can be a family of DNA sequences found within the genomes of prokaryotes derived from DNA fragments from viruses previously encountered by the prokaryote. A CRISPR effector protein (e.g., a Cas nuclease) can bind to a CRISPR polynucleotide (e.g., RNA) derived from the DNA sequence, and also a target region: a (viral) DNA sequence complementary to the CRISPR polynucleotide sequence. Upon binding, the Cas nuclease can make a double strand cut in the target region of the target (viral)

DNA in order to inactivate it. The target region can comprise a "protospacer" and a "protospacer adjacent motif" (PAM), and both domains can be needed for a Cas enzyme mediated activity (e.g., cleavage). The target site can be adjacent to a PAM site for a nuclease, e.g., Cas9, C2c1, C2c3, or Cpf1. The Cas nuclease can be Cas9. The PAM site can be a short sequence recognized by the CRISPR effector protein and, in some cases, required for the Cas enzyme activity, e.g., the PAM site can be NGG. The sequence and number of nucleotides for the PAM site can differ depending on the type of the CRISPR effector protein, e.g., Cas enzyme. The protospacer can be referred to as a target site (or a genomic target site). The CRISPR polynucleotide can pair with (or hybridize) the opposite stand of the protospacer (binding site) to direct the Cas enzyme to the target region.

A. CRISPR Complex Overview

A CRISPR complex can be a non-naturally occurring or engineered DNA or RNA-targeting system comprising one or more DNA or RNA-targeting CRISPR effector proteins and one or more CRISPR polynucleotides. The one or more CRISPR polynucleotides can be any CRISPR polynucleotide provided herein. The target sequence can be a sequence to which a guide sequence of a CRISPR polynucleotide is designed to have complementarity, and "complementarity" can refer to the ability of a nucleic acid to form hydrogen bond(s) with another nucleic acid sequence by either traditional Watson-Crick base-pairing or other non-traditional types of base-paring. The CRISPR complex can interact with two nucleic acid strands that form a duplex structure, three or more strands forming a multi stranded complex, a single self-hybridizing strand, or any combination of these.

Upon binding of the CRISPR complex to the target sequence, sequences associated with the target sequence can be modified by the CRISPR effector protein. The CRISPR effector protein can be part of a fusion protein that can comprise one or more heterologous protein domains (e.g. about or more than about 1, 2, 3, 4, 5, 6, 7, 8, 9, 10, or more domains in addition to the CRISPR effector protein). In some examples, the functionality of the CRISPR complex is conferred by the heterologous protein domains.

In some cases, one or more elements of a CRISPR system can be derived from a type I, type II, or type III CRISPR system. In the CRISPR type II system, the CRISPR polynucleotide (e.g., guide RNA) can interact with Cas endonuclease and direct the nuclease activity of the Cas enzyme to a target region. The target region can comprise a "protospacer" and a "protospacer adjacent motif" (PAM), and both domains can be used for a Cas enzyme mediated activity (e.g., cleavage). The guide sequence can pair with (or hybridize) the opposite strand of the protospacer (binding site) to direct the Cas enzyme to the target region. The PAM site can refer to a short sequence recognized by the Cas enzyme and, in some cases, required for the Cas enzyme activity. The sequence and number of nucleotides for the PAM site can differ depending on the type of the Cas enzyme.

The CRISPR/Cas complex (CRISPR system) can be any one two classes. Class 1 can use a system of multiple Cas proteins to degrade foreign nucleic acids. Class 2 systems can use a single Cas protein for the same purpose. Class 1 can be divided into types I, III, and IV; class 2 can be divided into types II, V and VI. One or more elements of a CRISPR system can be derived from a type I, type II, or type III CRISPR/Cas system. In the CRISPR type II effector protein, the guide polynucleotide (e.g. RNA) can interact with the CRISPR effector protein (e.g., Cas) and direct the nuclease activity of the Cas enzyme to a target region. Type II Cas proteins include Cas9, Type V includes Cas12 (Cpf1), and Type VI includes Cas13 and Cas 14. The canonical target of Type II and Type V can be RNA whereas the canonical target of Type V can be DNA.

B. CRISPR Effector Protein

A CRISPR effector protein can comprise a Cas protein of, or derived from, a CRISPR/Cas type I, type II, or type III system, which can have an RNA-guided polynucleotide-binding or nuclease activity. Examples of suitable Cas proteins include CasX, Cas3, Cas4, Cas5, Cas5e (or CasD), Cas6, Cas6e, Cas6f, Cas7, Cas8a1, Cas8a2, Cas8b, Cas8c, Cas9 (also known as Csn1 and Csx12), Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cu1966, homologues thereof, and modified versions thereof. In some cases, a Cas protein can comprise a protein of or derived from a CRISPR/Cas type V or type VI system, such as Cpf1, C2c1, C2c2, homologues thereof, and modified versions thereof. In some cases, a CRISPR effector protein can be a catalytically dead or inactive Cas (dCas) protein. The Cas protein can be a Type II Cas9 from *Streptococcus pyogenes* (SpCas9), *Neisseria meningitidis* (NmCas9), *Methanococcus maripaludis, Corynebacterium diphtheriae, Corynebacterium efficiens, Corynebacterium glutamicum, Corynebacterium kroppenstedtii, Mycobacterium abscessus, Nocardia farcinica, Rhodococcus erythropolis, Rhodococcus jostii, Rhodococcus opacus, Acidothermus cellulolyticus, Arthrobacter chlorophenolicus, Kribbella lavida, Thermomonospora curvata, Bifidobacterium dentium, Bifidobacterium longum, Slackia heliotrinireducens, Persephonella marina, Bacteroides fragilis, Capnocytophaga ochracea, Flavobacterium psychrophilum, Akkermansia muciniphila, Roseiflexus castenholzii, Roseiflexus, Synechocystis, Elusimicrobium minutum, Fibrobacter succinogenes, Bacillus cereus, Listeria innocua, Lactobacillus casei, Lactobacillus rhamnosus, Lactobacillus salivarius, Streptococcus agalactiae, Streptococcus dysgalactiae, Streptococcus equi, Streptococcus gallolyticus, Streptococcus gordonii, Streptococcus mutans, Streptococcus thermophilus, Clostridium botulinum, Clostridium cellulolyticum, Finegoldia magna, Eubacterium rectale, Mycoplasma gallisepticum, Mycoplasma mobile, Mycoplasma penetrans, Mycoplasma synoviae, Streptobacillus moniliformis, Bradyrhizobium, Nitrobacter hamburgensis, Rhodopseudomonas palustris, Parvibaculum lavamentivorans, Dinoroseobacter shibae, Gluconacetobacter diazotrophicus, Azospirillum, Rhodospirillum rubrum, Acidovorax ebreus, Verminephrobacter eiseniae, Desulfovibrio salexigens, Campylobacter jejuni, Campylobacter lari, Helicobacter hepaticus, Wolinella succinogenes, Tolumonas auensis, Pseudoalteromonas atlantica, Shewanella pealeana, Legionella pneumophila, Actinobacillus succinogenes, Pasteurella multocida, Francisella novicida, Francisella tularensis,* or *Treponema denticola.*

The Cas protein can be a Type I Cas7 or Cas 1 from *Aeropyrum pernix, Desulfurococcus kamchatkensis, Ignicoccus hospitalis, Staphylothermus marinus, Hyperthermus butylicus, Metallosphaera sedula, Sulfolobus islandicus, Sulfolobus solfataricus, Sulfolobus tokodaii, Thermofilum pendens, Caldivirga maquilingensis, Pyrobaculum aerophilum, Pyrobaculum arsenaticum, Pyrobaculum calidifontis, Thermoproteus neutrophilus, Archaeoglobus fulgidus, Ferroglobus placidus, Haloarcula marismortui, Halomicrobium mukohataei, Halorhabdus utahensis, Halorubrum*

*lacusprofundi, Natronomonas pharaonis, Methanobrevibacter ruminantium, Methanobrevibacter smithii, Methanosphaera stadtmanae, Methanothermobacter thermautotrophicus, Methanocaldococcus fervens, Methanocaldococcus jannaschii, Methanocaldococcus vulcanius, Methanococcus aeolicus, Methanococcus maripaludis, Methanococcus vannielii, Methanocorpusculum labreanum, Methanospirillum hungatei, Methanosphaerula palustris, Methanosaeta thermophila, Methanococcoides burtonii, Methanosarcina acetivorans, Methanosarcina barkeri, Methanosarcina mazei, Pyrococcus abyssi, Pyrococcus furiosus, Pyrococcus horikoshii, Thermococcus gammatolerans, Thermococcus kodakarensis, Thermococcus sibiricus, Picrophilus torridus, Candidatus Korarchaeum cryptofilum, Nanoarchaeum equitans, Acidimicrobium ferrooxidans, Catenulispora acidiphila, Corynebacterium aurimucosum, Corynebacterium diphtheriae, Corynebacterium glutamicum, Corynebacterium jeikeium, Corynebacterium urealyticum, Nocardia farcinica, Rhodococcus erythropolis, Frankia alni, Frankia, Nakamurella multipartita, Rothia mucilaginosa, Xylanimonas cellulosilytica, Salinispora arenicola, Salinispora tropica, Actinosynnema mirum, Saccharomonospora viridis, Streptomyces avermitilis, Streptomyces griseus, Thermobifida fusca, Thermomonospora curvata, Bifidobacterium adolescentis, Bifidobacterium animalis, Bifidobacterium dentium, Gardnerella vaginalis, Eggerthella lenta, Rubrobacter xylanophilus, Aquifex aeolicus, Hydrogenobacter thermophilus, Hydrogenobaculum, Thermocrinis albus, Persephonella marina, Sulfurihydrogenibium azorense, Sulfurihydrogenibium, Bacteroides fragilis, Parabacteroides distasonis, Porphyromonas gingivalis, Spirosoma linguale, Rhodothermus marinus, Chlorobaculum tepidum, Chlorobium chlorochromatii, Chlorobium limicola, Chlorobium phaeobacteroides, Chlorobium phaeovibrioides, Pelodictyon luteolum, Pelodictyon phaeoclathratiforme, Chloroherpeton thalassium, Prosthecochloris aestuarii, Chloroflexus aggregans, Chloroflexus aurantiacus, Chloroflexus, Roseiflexus castenholzii, Roseiflexus, Herpetosiphon aurantiacus, Dehalococcoides, Sphaerobacter thermophilus, Thermomicrobium roseum, Cyanothece, Microcystis aeruginosa, Synechococcus, Synechocystis, Anabaena variabilis, Nostoc punctiforme, Nostoc, Deinococcus geothermalis, Thermus thermophilus, Dictyoglomus thermophilum, Dictyoglomus turgidum, Acidobacterium capsulatum, Alicyclobacillus acidocaldarius, Anoxybacillus flavithermus, Bacillus cytotoxicus, Bacillus clausii, Bacillus halodurans, Geobacillus, Lysinibacillus sphaericus, Exiguobacterium sibiricum, Listeria monocytogenes, Listeria seeligeri, Lactobacillus casei, Lactobacillus delbrueckii, Lactobacillus fermentum, Lactobacillus helveticus, Streptococcus equi, Streptococcus mutans, Streptococcus pyogenes, Alkaliphilus metalliredigens, Clostridium botulinum, Clostridium cellulolyticum, Clostridium difficile, Clostridium kluyveri, Clostridium novyi, Clostridium perfringens, Clostridium tetani, Clostridium thermocellum, Finegoldia magna, Symbiobacterium thermophilum, Eubacterium rectale, Heliobacterium modesticaldum, Candidatus Desulforudis audaxviator, Desulfitobacterium hafniense, Desulfotomaculum acetoxidans, Desulfotomaculum reducens, Pelotomaculum thermopropionicum, Syntrophomonas wolfei, Anaerocellum thermophilum, Acidaminococcus fermentans, Halothermothrix orenii, Carboxydothermus hydrogenoformans, Ammonifex degensii, Moorella thermoacetica, Thermoanaerobacter italicus Thermoanaerobacter pseudethanolicus, Thermoanaerobacter, Thermoanaerobacter tengcongensis, Caldicellulosiruptor saccharolyticus, Fusobacterium nucleatum, Leptotrichia buccalis, Thermodesulfovibrio yellowstonii, Nitrobacter winogradskyi, Methylobacterium nodulans, Methylobacterium, Dinoroseobacter shibae, Rhodobacter sphaeroides, Acetobacter pasteurianus, Acidiphilium cryptum, Gluconacetobacter diazotrophicus, Granulibacter bethesdensis, Azospirillum, Rhodospirillum centenum, Rhodospirillum rubrum, Zymomonas mobilis, Acidovorax citrulli, Acidovorax, Delftia acidovorans, Rhodoferax ferrireducens, Verminephrobacter eiseniae, Leptothrix cholodnii, Methylobacillus flagellatus, Chromobacterium violaceum, Laribacter hongkongensis, Neisseria gonorrhoeae, Nitrosomonas europaea, Nitrosomonas eutropha, Aromatoleum aromaticum, Thauera, Candidatus Accumulibacter phosphatis, Desulfatibacillum alkenivorans, Desulfobacterium autotrophicum, Desulfococcus oleovorans, Desulfotalea psychrophila, Desulfohalobium retbaense, Desulfovibrio desulfuricans, Desulfovibrio magneticus, Desulfovibrio vulgaris, Geobacter bemidjiensis, Geobacter lovleyi, Geobacter metallireducens, Geobacter, Geobacter sulfurreducens, Geobacter uraniireducens, Pelobacter carbinolicus, Pelobacter propionicus, Anaeromyxobacter dehalogenans, Anaeromyxobacter, Myxococcus xanthus, Haliangium ochraceum, Sorangium cellulosum, Syntrophus aciditrophicus, Syntrophobacter fumaroxidans, Campylobacter concisus, Campylobacter curvus, Campylobacter fetus, Campylobacter hominis, Sulfurospirillum deleyianum, Helicobacter pylori, Tolumonas auensis, Alteromonas macleodii, Teredinibacter turnerae, Psychromonas ingrahamii, Shewanella baltica, Shewanella oneidensis, Shewanella piezotolerans, Shewanella putrefaciens, Shewanella, Dichelobacter nodosus, Allochromatium vinosum, Nitrosococcus oceani, Alkalilimnicola ehrlichii, Thioalkalivibrio, Halothiobacillus neapolitanus, Citrobacter rodentium, Cronobacter sakazakii, Cronobacter turicensis, Dickeya dadantii, Dickeya zeae, Enterobacter, Erwinia pyrifoliae, Erwinia tasmaniensis, Escherichia coli, Escherichiafergusonii, Klebsiella pneumoniae, Klebsiella variicola, Pectobacterium atrosepticum, Pectobacterium wasabiae, Photorhabdus, Photorhabdus luminescens, Salmonella enterica, Shigella boydii, Shigella flexneri, Shigella sonnei, Xenorhabdus bovienii, Yersinia pestis, Yersinia pseudotuberculosis, Coxiella burnetii, Legionella pneumophila, Methylococcus capsulatus, Hahella chejuensis, Chromohalobacter salexigens, Marinomonas, Actinobacillus pleuropneumoniae, Actinobacillus succinogenes, Aggregatibacter actinomycetemcomitans, Aggregatibacter aphrophilus, Mannheimia succiniciproducens, Pasteurella multocida, Acinetobacter baumannii, Acinetobacter, Azotobacter vinelandii, Cellvibrio japonicus, Pseudomonas aeruginosa, Pseudomonas mendocina, Pseudomonas stutzeri, Vibrio fischeri, Photobacterium profundum, Vibrio cholerae, Vibrio harveyi, Vibrio parahaemolyticus, Xanthomonas, Xanthomonas axonopodis, Xanthomonas oryzae, Magnetococcus, Leptospira borgpetersenii, Leptospira interrogans, Fervidobacterium nodosum, Kosmotoga olearia, Petrotoga mobilis, Thermosipho africanus, Thermosipho melanesiensis, Thermotoga lettingae, Thermotoga maritima, Thermotoga neapolitana, Thermotoga petrophila, Thermotoga,* or *Thermobaculum terrenum.*

The Cas protein can be Type III Cas10 from *Desulfurococcus kamchatkensis, Ignicoccus hospitalis, Staphylothermus marinus, Hyperthermus butylicus, Metallosphaera sedula, Sulfolobus acidocaldarius, Sulfolobus islandicus, Sulfolobus solfataricus, Sulfolobus tokodaii, Thermofilum pendens, Caldivirga maquilingensis, Pyrobaculum aerophilum, Pyrobaculum arsenaticum, Pyrobaculum calidifontis, Pyrobaculum islandicum, Thermoproteus neutrophilus,*

*Archaeoglobus fulgidus, Natronomonas pharaonis, Methanobrevibacter ruminantium, Methanosphaera stadtmanae, Methanothermobacter thermautotrophicus, Methanocaldococcus fervens, Methanocaldococcus jannaschii, Methanocaldococcus, Methanocaldococcus vulcanius, Methanococcus aeolicus, Methanococcus vannielii, Methanospirillum hungatei, Methanosaeta thermophila, Methanosarcina acetivorans, Methanosarcina barkeri, Methanosarcina mazei, Methanopyrus kandleri, Pyrococcus furiosus, Pyrococcus horikoshii, Thermococcus onnurineus, Picrophilus torridus, Thermoplasma volcanium, Aciduliprofundum boonei, Candidatus Korarchaeum cryptofilum, Mycobacterium bovis, Mycobacterium tuberculosis, Frankia, Salinispora tropica, Saccharomonospora viridis, Saccharopolyspora erythraea, Thermobifida fusca, Rubrobacter xylanophilus, Aquifex aeolicus, Thermocrinis albus, Sulfurihydrogenibium azorense, Sulfurihydrogenibium, Porphyromonas gingivalis, Rhodothermus marinus, Chlorobaculum parvum, Chlorobium phaeobacteroides, Chlorobium phaeobacteroides, Pelodictyon phaeoclathratiforme, Chloroherpeton thalassium, Methylacidiphilum infernorum, Chloroflexus aggregans, Chloroflexus aurantiacus, Chloroflexus, Roseiflexus castenholzii, Roseiflexus, Herpetosiphon aurantiacus, Thermomicrobium roseum, Cyanothece, Microcystis aeruginosa, Synechococcus, Synechocystis, Anabaena variabilis, Nostoc punctiforme, Nostoc, Deinococcus geothermalis, Thermus thermophilus, Dictyoglomus thermophilum, Dictyoglomus turgidum, Candidatus Solibacter usitatus, Fibrobacter succinogenes, Alicyclobacillus acidocaldarius, Bacillus halodurans, Geobacillus, Staphylococcus epidermidis, Staphylococcus lugdunensis, Streptococcus sanguinis, Streptococcus thermophilus, Clostridium botulinum, Clostridium tetani, Clostridium thermocellum, Candidatus Desulforudis audaxviator, Desulfotomaculum acetoxidans, Desulfotomaculum reducens, Pelotomaculum thermopropionicum, Syntrophomonas wolfei, Anaerocellum thermophilum, Veillonella parvula, Halothermothrix orenii, Carboxydothermus hydrogenoformans, Ammonifex degensii, Thermoanaerobacter italicus, Thermoanaerobacter pseudethanolicus, Thermoanaerobacter, Thermoanaerobacter tengcongensis, Caldicellulosiruptor saccharolyticus, Ureaplasma parvum, Leptotrichia buccalis, Streptobacillus moniliformis, Thermodesulfovibrio yellowstonii, Pirellula staleyi, Rhodospirillum centenum, Rhodospirillum rubrum, Nitrosomonas europaea, Nitrosomonas eutropha, Candidatus Accumulibacter phosphatis, Desulfococcus oleovorans, Myxococcus xanthus, Haliangium ochraceum, Sorangium cellulosum, Syntrophus aciditrophicus, Syntrophobacter fumaroxidans, Arcobacter butzleri, Campylobacter fetus, Teredinibacter turnerae, Allochromatium vinosum, Halorhodospira halophila, Thioalkalivibrio, Dickeya dadantii, Pectobacterium carotovorum, Marinomonas, Mannheimia succiniciproducens, Vibrio vulnificus, Fervidobacterium nodosum, Kosmotoga olearia, Thermosipho africanus, Thermosipho melanesiensis, Thermotoga maritima, Thermotoga naphthophila, Thermotoga neapolitana, Thermotoga petrophila, Thermotoga,* or *Thermobaculum terrenum.*

Figure 3:
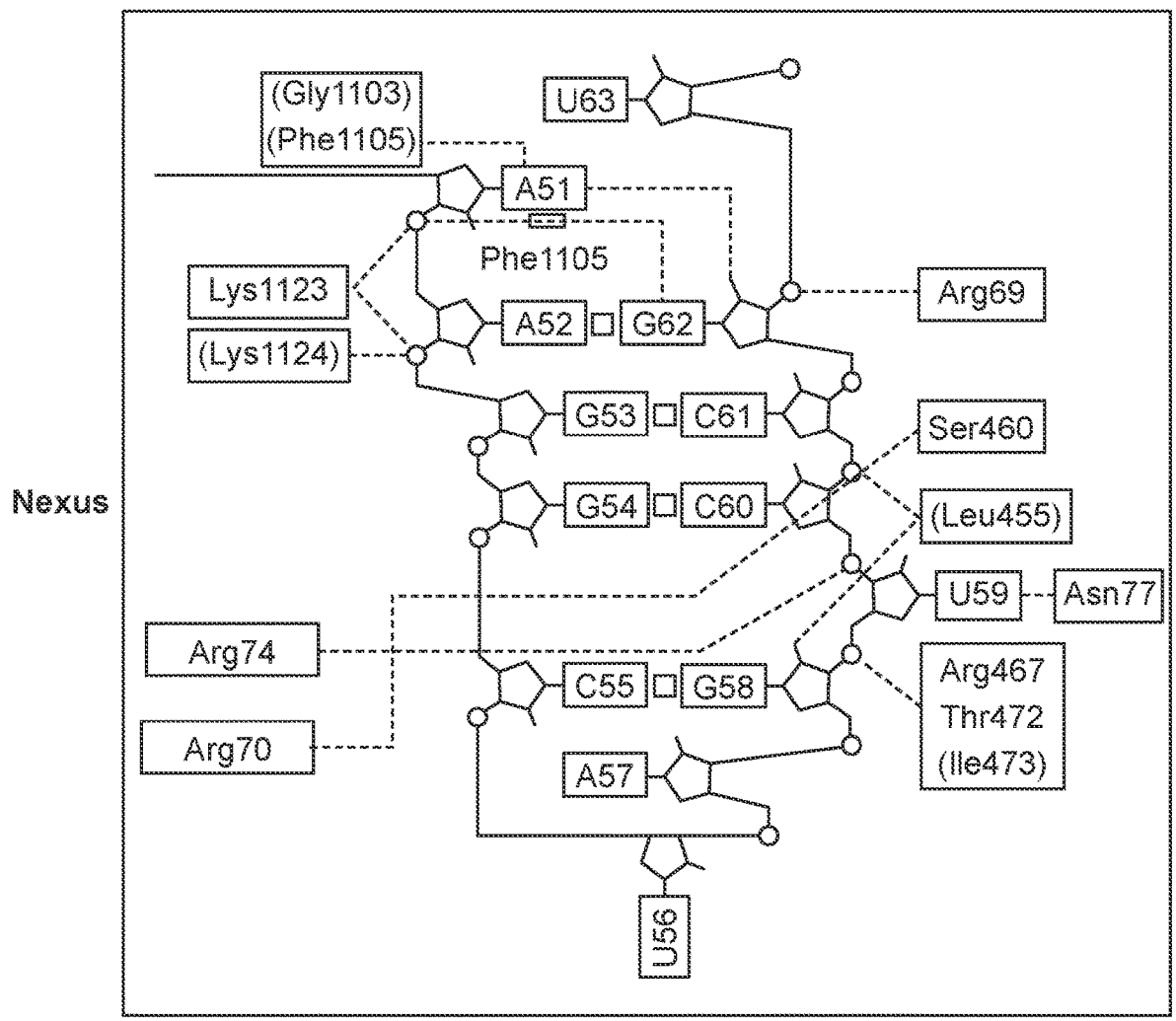
FIG. 3 shows a diagram of the interaction of bound sgRNA nucleotides within the nexus and adjacent amino acids of a Cas9 nuclease.
Figure 4:
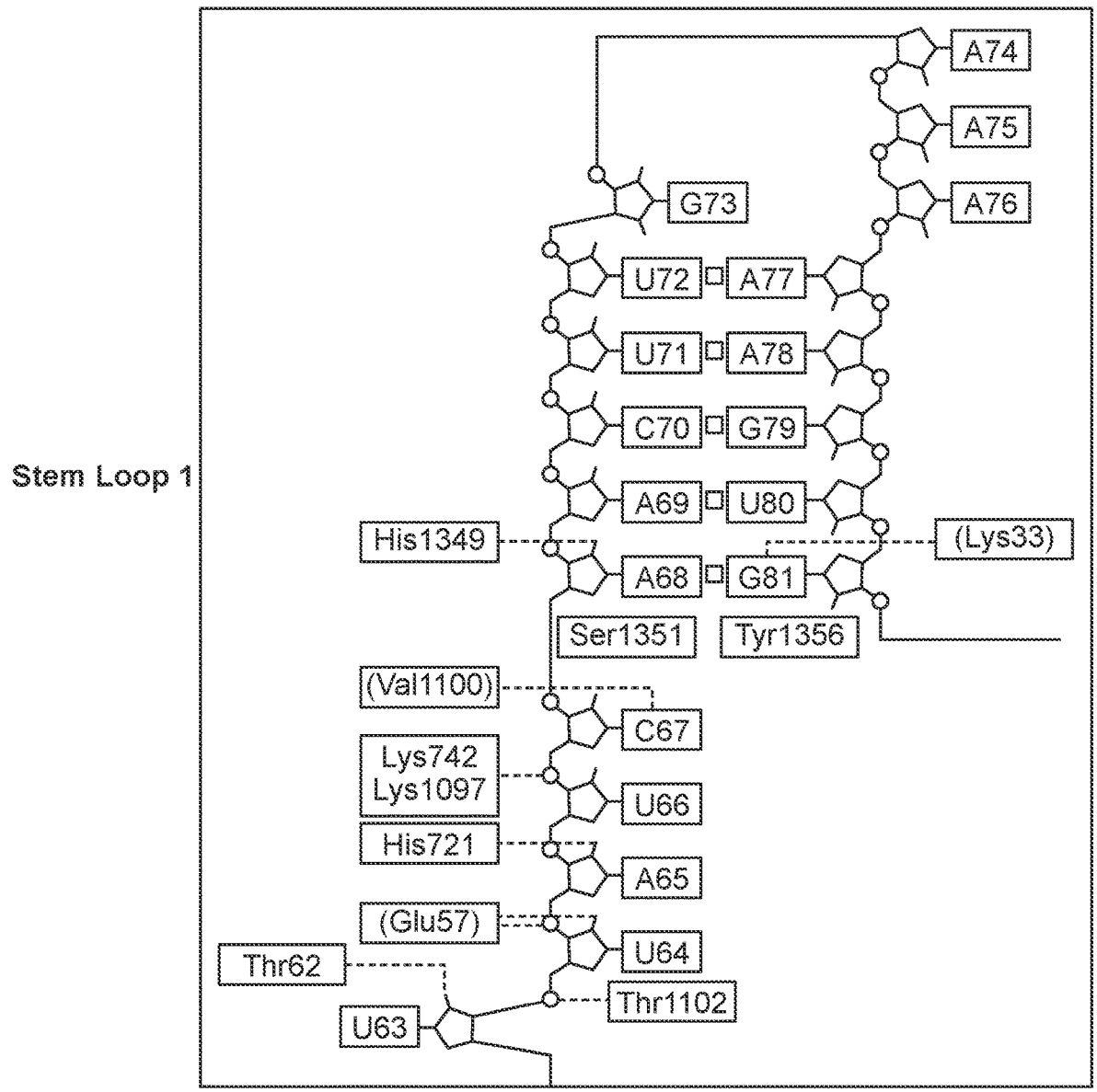
FIG. 4 shows a diagram of the interaction of bound sgRNA nucleotides within stem loop 1 and adjacent amino acids of a Cas9 nuclease.
Figure 5:
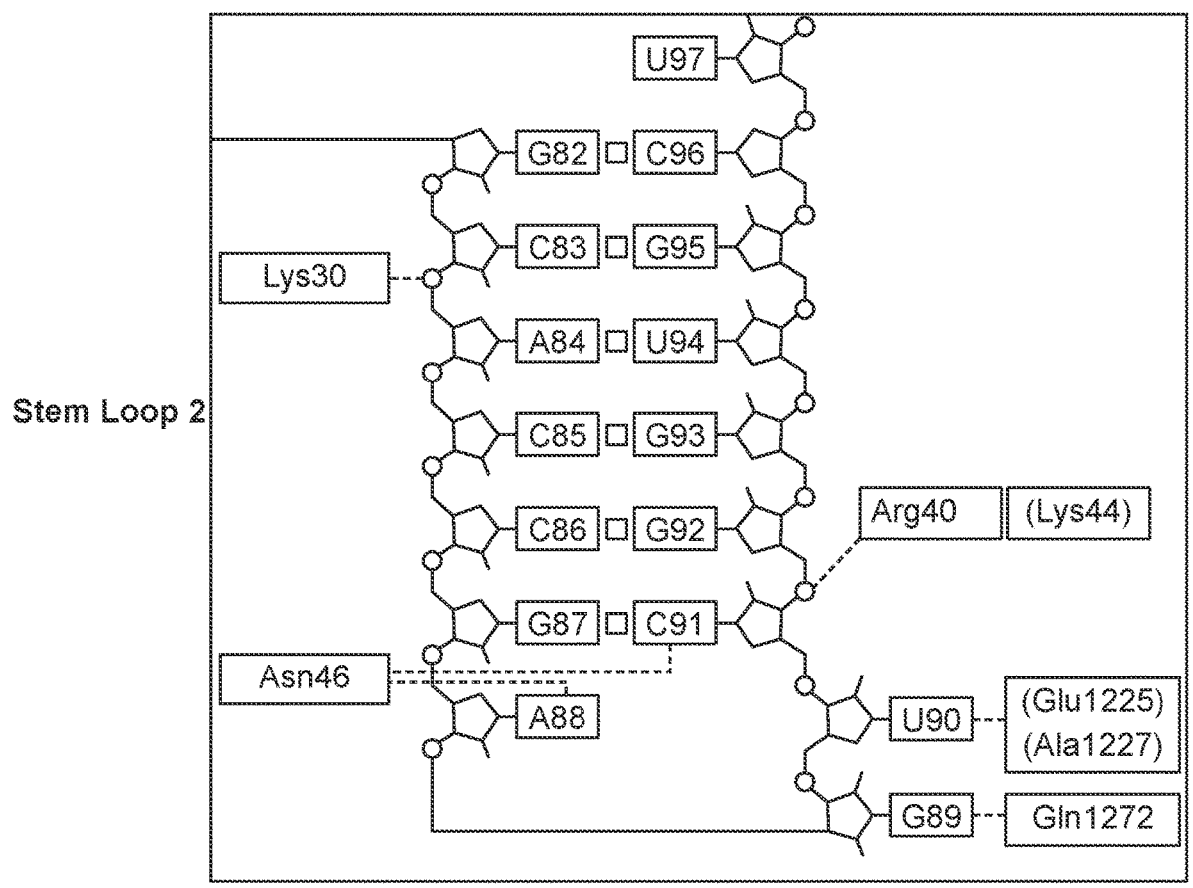
FIG. 5 shows a diagram of the interaction of bound sgRNA nucleotides within stem loop 2 and adjacent amino acids of a Cas9 nuclease.

The Cas protein can be Cas9. Cas9 can comprise an alpha helical lobe and a nuclease lobe. The alpha helical lobe can comprise three regions, a long a helix referred to as the bridge helix, a REC1 domain, and a REC2 domain. The nuclease lobe can comprise a RuvC domain, a HNH domain and a PAM-interacting domain. FIG. 3 highlights amino acids of different domains in close proximity with the nexus which can be cross-linking sites such as the REC1 domain (Ser460, Leu455, Arg467, Thr472, Ile 473), bridge helix (Arg69, Asn77, Arg74, Arg70), and PAM-interacting domain (Gly1103, Phe1105, Lys1123, Lys1124, Phe1105). FIG. 4 highlights amino acids of different domains in close proximity with stem loop 1 which can be cross-linking sites such as the RuvC domain (Lys33, Lys742, Lys1097, His721, Glu57), PAM-interacting domain (Ser1351, Tyr1356, His1349, Val1100, Thr1102), and bridge helix domain (Thr62). FIG. 5 highlights amino acids of different domains in close proximity with stem loop 2 which can be cross-linking sites such as the RuvC domain (Lys30, Asn46, Arg40, Lys44) and PAM-interacting domain (Glu1225, Ala1227, Gln1272).

Upon nucleic acid binding with a CRISPR polynucleotide (e.g., RNA) and a target DNA molecule the nuclease lobe can rotate ~100° relative to the alpha helical lobe. One or more crosslinking groups can be located so as to retain the full activity of the CRISPR effector protein, and the crosslinking method can permit retention of the full activity of the CRISPR effector protein (e.g., Cas nuclease).

C. Polynucleotides for Use in CRISPR Complexes

The CRISPR polynucleotide can comprise RNA, DNA-RNA hybrids, or derivatives thereof. The CRISPR polynucleotide can comprise nucleosides, which can comprise a base covalently attached to a sugar moiety, e.g., ribose or deoxyribose. The nucleosides can be ribonucleosides or deoxyribonucleosides. The nucleosides can comprise bases linked to amino acids or amino acid analogs, which can comprise free carboxyl groups, free amino groups, or protecting groups. The protecting groups can be a protecting group described, e.g., in P. G. M. Wuts and T. W. Greene, "Protective Groups in Organic Synthesis", 2nd Ed., Wiley-Interscience, New York, 1999. The CRISPR polynucleotides can comprise a canonical cyclic nucleotide, e.g., cAMP, cGMP, cCMP, cUMP, cIMP, cXMP, or cTMP. A canonical nucleotide base can be adenine, cytosine, uracil, guanine, or thymine. The nucleotide can comprise a nucleoside attached to a phosphate group or a phosphate analog.

The CRISPR polynucleotide can exist as one or more molecules of RNA, or DNA (e.g., in one or more vectors encoding said one or more molecules of RNA or protein). The CRISPR polynucleotides can be deoxyribonucleic acids (DNA), ribonucleic acids (RNA) and polymers thereof in either single-, double- or multi-stranded form. The CRISPR polynucleotide can comprise single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases.

The polynucleotide (CRISPR polynucleotide) sequence used in the CRISPR-Cas system can comprise a crRNA sequence and a tracrRNA sequence. In nature, crRNA and tracrRNA can exist as two separate RNA molecules. The term "tracrRNA" or "tracrRNA segment," can refer to a polynucleotide molecule or portion thereof that includes a protein-binding segment (e.g., the protein-binding segment is capable of interacting with a CRISPR-effector protein, such as a Cas9). The terms "guide RNA" and "gRNA" can encompass a single guide RNA (sgRNA), where the crRNA segment and the tracrRNA segment are located in the same RNA molecule.

In some cases, the gRNA can be a complex (e.g., via hydrogen bonds) of a CRISPR RNA (crRNA) segment and a trans-activating crRNA (tracrRNA) segment. The crRNA can comprise a hybridizing polynucleotide sequence and a tracrRNA-binding polynucleotide sequence. The hybridizing polynucleotide sequence can hybridize to a portion of a target nucleic acid (e.g., a selected exon). The hybridizing polynucleotide sequence of the crRNA can range from 17 to 23 nucleotides. The hybridizing polynucleotide sequence of the crRNA can be at least 17, 18, 19, 20, 21, 22, 23, or more nucleotides. The hybridizing polynucleotide sequence of the crRNA can be at most 23, 22, 21, 20, 19, 18, 17, or less nucleotides. In an example, the hybridizing polynucleotide sequence of the crRNA is 20 nucleotides. The hybridizing polynucleotide can be a guide sequence. The guide sequence can comprise sufficient complementarity with a target nucleic acid sequence to hybridize with the target nucleic acid sequence. The degree of complementarity, when optimally aligned using a suitable alignment algorithm, can be about or more than about 50%, 60%, 75%, 80%, 85%, 90%, 95%, 97.5%, or 99%. The degree of complementarity can be 100%. In some cases, the guide sequence e.g., can be about 5, 6, 7, 8, 9, 10, 11, 12, 13, 14, 15, 16, 17, 18, 19, 20, 25, 30, 40, 50, or more nucleotides in length. The guide sequence can be about 5 to about 40 nucleotides in length. The guide sequence can be designed in a way that reduces the likelihood that the guide sequence base pairs to itself or base pairs with another portion of the CRISPR polynucleotide. About or less than about 75%, 50%, 40%, 30%, 25%, 20%, 15%, 10%, 5%, 1%, or fewer of the nucleotides of the guide sequence can form a base-pair with another portion of the guide sequence or another portion of the CRISPR polynucleotide when the CRISPR polynucleotide is optimally folded.

In some cases, a single CRISPR polynucleotide is crosslinked to a single CRISPR effector protein. The single CRISPR polynucleotide can comprise a guide sequence and sequence that crosslinks to the CRISPR effector protein. The sequence that can crosslink the CRISPR effector protein can be a trans-activating RNA (tracrRNA). When a single CRISPR polynucleotide comprises a guide sequence and a tracrRNA, the single CRISPR polynucleotide can be referred to as a single guide RNA (or sgRNA).

In some cases, two CRISPR polynucleotides may be crosslinked to a single CRISPR effector protein. A first CRISPR polynucleotide can comprise a guide sequence, and a second CRISPR polynucleotide can comprise a tracrRNA and lack a guide sequence.

In some cases, the first CRISPR polynucleotide comprises a guide sequence and a first part of the sequence (which can be referred to as a tracr mate sequence) that forms the crRNA, and the second CRISPR polynucleotide comprises a second part of the sequence that forms the tracrRNA (which can be referred to as the tracr sequence). In some cases, the tracr sequence (or tracrRNA) hybridizes to the 'tracr mate' sequence within the crRNA thereby forming a double-stranded RNA duplex protein binding segment recognized by the CRISPR effector protein. A CRISPR polynucleotide comprising a guide sequence (also known as spacer sequence) but lacking sequence that can bind to the CRISPR effector protein can be referred to as a guide RNA (or gRNA). A CRISPR polynucleotide comprising a guide sequence and only part of a sequence that can bind to the CRISPR effector protein (e.g., a tracr mate sequence) (and lacks a tracr sequence) can also be referred to as a guide RNA (or gRNA) or crRNA.

A tracrRNA can hybridize to the 'tracr mate' sequence within the crRNA thereby forming a double-stranded RNA duplex protein binding segment recognized by the CRISPR effector protein. In some examples, the hybridization between the two produces a secondary structure, such as a hairpin. In some cases, the CRISPR polynucleotide sequence can comprise three, four, five, or more hairpins. The tracrRNA can comprise, or consist of, one or more hairpins and can be at least 10, 20, 30, 40, 50, 60, 70, 80, 90, or 100 nucleotides in length.

In some cases, a first CRISPR polynucleotide can be crRNA and a second CRISPR polynucleotide can be tracrRNA and the first CRISPR polynucleotide and second CRISPR polynucleotide can be two separate RNA molecules. In some cases, a single CRISPR polynucleotide can comprise (1) a guide sequence (or crRNA comprising a guide sequence) capable of hybridizing to a target sequence (e.g., a genomic target locus in a eukaryotic cell) and (2) a tracrRNA. In some cases, the first CRISPR polynucleotide can comprise (1) a guide sequence (or crRNA comprising a guide sequence) (e.g., capable of hybridizing to a target sequence in the eukaryotic cell); and (2) a tracr mate sequence (also known as direct repeat sequence), but lacking a tracrRNA sequence. The CRISPR effector protein can associate with a guide sequence capable of hybridizing to a target sequence and a tracr mate sequence (direct repeat sequence), without the requirement for a tracrRNA.

When the tracr and tracr mate sequences are in a single CRISPR polynucleotide, the tracr and tracr mate sequences can be covalently linked. The tracr and tracr mate sequence can be linked through a phosphodiester bond. The tracr and tracr mate can be covalently linked via a non-nucleotide loop comprising a moiety such as a spacer, attachment, bioconjugate, chromophore, reporter group, dye labeled RNA, or non-naturally occurring nucleotide analogue. The spacer can be a polyether (e.g., polyethylene glycol, polyalcohol, polypropylene glycol or mixtures of ethylene and propylene glycol), polyamine group (e.g., spennine, spermidine, or a polymeric derivative thereof), polyester (e.g., poly(ethyl acrylate)), polyphosphodiester, alkylene, and combinations thereof. The attachment can be a fluorescent label. The bioconjugate can be, e.g., a peptide, a glycoside, a lipid, a cholesterol, a phospholipid, a diacyl glycerol, a dialkyl glycerol, a fatty acid, a hydrocarbon, an enzyme substrate, a steroid, biotin, digoxigenin, a carbohydrate, or a polysaccharide. The chromophore, reporter group, or dye-labeled RNA can be a fluorescent dye, e.g., fluorescein or rhodamine, a chemiluminescent, an electrochemiluminescent, or a bioluminescent marker compound.

Overall, the crRNA can range from 35 to 45 nucleotides. The crRNA can be at least 35, 36, 37, 38, 39, 40, 41, 42, 43, 44, 45, or more nucleotides. The crRNA can be at most 45, 44, 43, 42, 41, 40, 39, or less nucleotides. The tracrRNA can range from 60 to 80 nucleotides. The tracrRNA can be at least 60, 61, 62, 63, 64, 66, 68, 70, 72, 74, 76, 78, 80, or more nucleotides. The tracrRNA can be at most 80, 79, 78, 77, 76, 74, 72, 70, 68, 66, 64, 62, 60, or less nucleotides. In an example, the tracrRNA can be 72 nucleotides. In another example, the hybridizing polynucleotide sequence of the crRNA is 20 nucleotides, the crRNA is 42 nucleotides, and the respective tracrRNA is 72 nucleotides. In another example, the hybridizing polynucleotide of the crRNA is 20 nucleotides, the crRNA is a total of 34 nucleotides, and respective tracrRNA is 66 nucleotides.

In some instances, the crRNA and tracrRNA are joined into a single guide RNA molecule called a sgRNA, or "single guide RNA." Each sgRNA can comprise a constant region from about 20 to about 30, about 30 to about 40, about 40 to about 50, about 50 to about 60, about 60 to about 70, about 70 to about 80, or about 80 to about 100 nucleotides in length. Each sgRNA can comprise at least 90, 91, 92, 93, 94, 95, 96, 97, 98, 99, 100, 101, 102, 103, 104, 105, 106, 107, 108, 109, or 110 nucleotides.

Alternatively, the gRNA can be a complex of three or more RNA chains. At least one RNA chain of the complex of three or more RNA chains can comprise a hybridizing polynucleotide sequence. At least one RNA chain of the complex of three or more RNA chains can comprise a CRISPR effector protein (e.g., Cas enzyme) binding sequence.

When the gRNA hybridizes to a target nucleic acid molecule, the hybridized portion of the gene can be a target region (or target locus) that comprises a protospacer (target site), a protospacer adjacent motif (PAM) that is recognized by the CRISPR effector protein (e.g., Cas enzyme), and the opposite strand of the protospacer (binding site). The opposite strand of the protospacer can be the gRNA-hybridizing genomic region (sequence). The gRNA-hybridizing sequence in the target nucleic acid sequence can range from 17 to 23 nucleotides. The gRNA-hybridizing sequence in the gene can be at least 17, 18, 19, 20, 21, 22, 23, or more nucleotides. The gRNA-hybridizing sequence in the gene can be at most 23, 22, 21, 20, 19, 18, 17, or less nucleotides.

The CRISPR effector protein (e.g., Cas protein) can be Cas9, wherein the tracrRNA can interact with the alpha-helical lobe and the nuclease lobe of Cas9 through four hairpin loops; two hairpin loops can interact with each lobe respectively. The crRNA can be designed to complementarily bind to a target nucleic acid (e.g., DNA) sequence. A full length sgRNA target DNA binding region can be 20 nucleotides for Cas9. For Cas9, PAM sequences can include 3'-NGG, 3'-NGGNG (SEQ ID NO: 1), 3'NNAGAAW (SEQ ID NO: 2), and 3'-ACAY (SEQ ID NO: 3) where N is any nucleotide, W is A or T, and Y is C or T.

In some cases, to increase the effectiveness of a CRISPR polynucleotide, e.g., gRNA or sgRNA, other secondary structures may be added to the CRISPR polynucleotide, e.g., gRNA or sgRNA to enhance the stability of the CRISPR polynucleotide. In some cases, the increased stability can improve nucleic acid editing.

III. Stabilized CRISPR Complexes

The present disclosure encompasses a CRISPR effector protein covalently bound to a sgRNA, which can be termed a "locked CRISPR complex." The present disclosure encompasses a CRISPR effector protein covalently bound to a separate crRNA and/or a tracrRNA. Also provided herein are CRISPR complexes in which sgRNA and the CRISPR effector protein have enhanced binding affinity. A CRISPR polynucleotide can comprise gRNA, sgRNA, crRNA, or tracrRNA. A CRISPR effector protein can be covalently bound (e.g., crosslinked) to any CRISPR polynucleotide described herein, e.g., a gRNA, sgRNA, crRNA, tracrRNA, a CRISPR ON polynucleotide, a CRISPR OFF polynucleotide, a CRISPR ON/OFF polynucleotide, or a CRISPR polynucleotide modified to decrease off-target editing.

The CRISPR-Cas system can be modified to both knock out specific genes as well as knock-in specific genes. CRISPR-mediated knockouts can be generated through the non-homologous end joining repair pathway of a cell. In this event, CRISPR-Cas can bind to a target nucleic acid (e.g., DNA) region complementary to the bound RNA and execute a double strand cut in the target nucleic acid (e.g., DNA) region. When designing the sgRNA, a unique 3-9 nucleotide PAM recognition region can be designed in the sgRNA near the target nucleic acid (e.g., DNA) for those that Cas nucleases which require a PAM recognition site. Not every Cas nuclease requires a PAM region; for instance, Cas 14a does not require a PAM region for identification.

Enhancing the stability of a sgRNA in complex with a CRISPR effector protein by at least one covalent bond can decrease the number of off-target cleavage events, lowering the cell toxicity as compared to a CRISPR complex that is not covalently bound. CRISPR effector proteins crosslinked to a sgRNA ("locked") can be used to reduce off target editing as compared to Cas9 complexed with a standard sgRNA. Off-target editing can be determined using ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv or deep-sequencing techniques as described in Tsai et al. "GUIDE-seq enables genome-wide profiling of off-target cleavage by CRISPR-Cas nucleases", Nature Biotechnology 33, 187-197 (2015).

Covalently locking the sgRNA to the CRISPR effector protein can decrease the probability that sgRNA will cause toxicity within a cell. Locking a sgRNA to a CRISPR effector protein can increase the accuracy of dosing, by allowing one to administer a single species of CRISPR complex with a guide RNA designed for a specific target. One can administer two or more locked CRISPR complexes with unique targets from one another for a complex therapy targeting multiple sites. Additionally, formulating a sgRNA sequence in complex with a CRISPR effector protein such that it cannot dissociate from the complexed state may grant greater protection from degradation both in formulation and after administration.

A. Modified CRISPR Polynucleotide

Disclosed herein is a CRISPR polynucleotide modified with at least one unnatural nucleotide for crosslinking and a sequence for modulating activity. The sequence for modifying activity can be a CRISPR ON polynucleotide sequence, and CRISPR OFF polynucleotide sequence, a CRISPR ON/OFF polynucleotide sequence, or a CRISPR nucleotide modified to lower off-target editing. The unnatural nucleotide can be located in the tracrRNA, the crRNA, or the guide sequence of the crRNA.

In some cases, the CRISPR polynucleotide can be modified to improve the CRISPR polynucleotide's resistance to nucleases, serum stability, target specificity, blood system circulation, tissue distribution, tissue penetration, cellular uptake, potency, and/or cell permeability. For example, certain CRISPR polynucleotide modifications can increase nuclease stability, and/or lower interferon induction, without significantly affecting activity of the CRISPR polynucleotide (e.g., sgRNA). The modified CRISPR polynucleotide can have improved stability in serum and/or cerebral spinal fluid compared to an unmodified CRISPR polynucleotide having the same sequence. The CRISPR polynucleotide (e.g., sgRNA) disclosed herein can comprise one or more modifications at various locations, including at a sugar moiety, a phosphodiester linkage, and/or a base. A modified CRISPR polynucleotide as described herein can include both a sgRNA and a separate crRNA and tracrRNA. A CRISPR polynucleotide can be bound to a CRISPR effector protein by hydrogen bonding interactions.

Provided herein are CRISPR polynucleotides that can be crosslinked to a CRISPR effector protein by one or more covalent bonds, forming a locked CRISPR complex. There can be 1 to 3, 3 to 6, 6 to 9, 9 to 12, 12 to 15, 15 to 18, 18 to 21, 21 to 24, 24 to 27, 27 to 30, 30 to 33, 33 to 36, 36 to 39, 39 to 42, 42 to 45, 45 to 48, 48 to 51, 51 to 54, 54 to 57, 57 to 60, 60 to 62, 62 to 65, 65 to 68, 68 to 71, 71 to 74, 74 to 77, 77 to 80, 80 to 83, 83 to 86, 86 to 89, 89 to 91, 91 to 94, 94 to 97, 97 to 100 covalent bonds between a CRISPR polynucleotide and a CRISPR effector protein. There can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 covalent bonds between a CRISPR polynucleotide and a CRISPR effector protein. There can be at most 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 covalent bonds between a CRISPR polynucleotide and a CRISPR effector protein. There can be about 1 to about 10, about 10 to about 30, about 30 to about 60, or about 60 to about 80 covalent bonds between a CRISPR polynucleotide and a CRISPR effector protein.

The CRISPR polynucleotide can comprise a backbone that comprises phosphoramide, phosphorothioate, phosphorodithioate, boranophosphate linkage, O-methylphosphoramidite linkages, and/or peptide nucleic acids to control the activity of a CRISPR complex as described herein. Individual nucleotides can be modified so as to add a cross linker to the CRISPR polynucleotide capable of forming a covalent bond with an adjacent amino acid in the CRISPR effector protein. The location of the one or more cross-linkers can be within the tracrRNA region of the CRISPR polynucleotide, e.g., as is diagramed in FIG. 1. The one or more cross linkers can be within a hairpin loop of the sgRNA. The cross-linking reactions can be in close proximity to the acceptor molecule in the CRISPR effector protein in order for a covalent bond to form. An embodiment comprises designing the functionalized nucleotide to be within 20, 19, 18, 17, 16, 15, 14, 13, 12, 11, 10, 9, 8, 7, 6, 5, 4, 3, 2, or 1 angstroms of the acceptor molecule of the CRISPR effector protein, e.g., an adjacent amino acid in the CRISPR effector protein, prior to initiation of the cross linking.

In some cases, the CRISPR polynucleotide (e.g., gRNA, sgRNA, crRNA, or tracrRNA) can comprise at least one crosslinker, at least two crosslinkers, at least five crosslinkers, at least twelve crosslinkers, at least fifteen crosslinkers, at least twenty crosslinkers, at least twenty-five crosslinkers, at least thirty crosslinkers, at least thirty-five crosslinkers, at least forty crosslinkers, at least fifty crosslinkers, at least fifty-five crosslinkers, at least sixty crosslinkers, at least sixty-five crosslinkers, at least seventy crosslinkers, at least seventy-five crosslinkers, or at least 80 crosslinkers. The CRISPR polynucleotide can comprise at most 100, 50, 25, 10, 9, 8, 7, 6, 5, 4, 3, 2, or 1 crosslinker. The CRISPR polynucleotide can comprise about 1 to about 10, about 10 to about 30, about 30 to about 60, or about 60 to about 80 crosslinkers.

Figure 2:
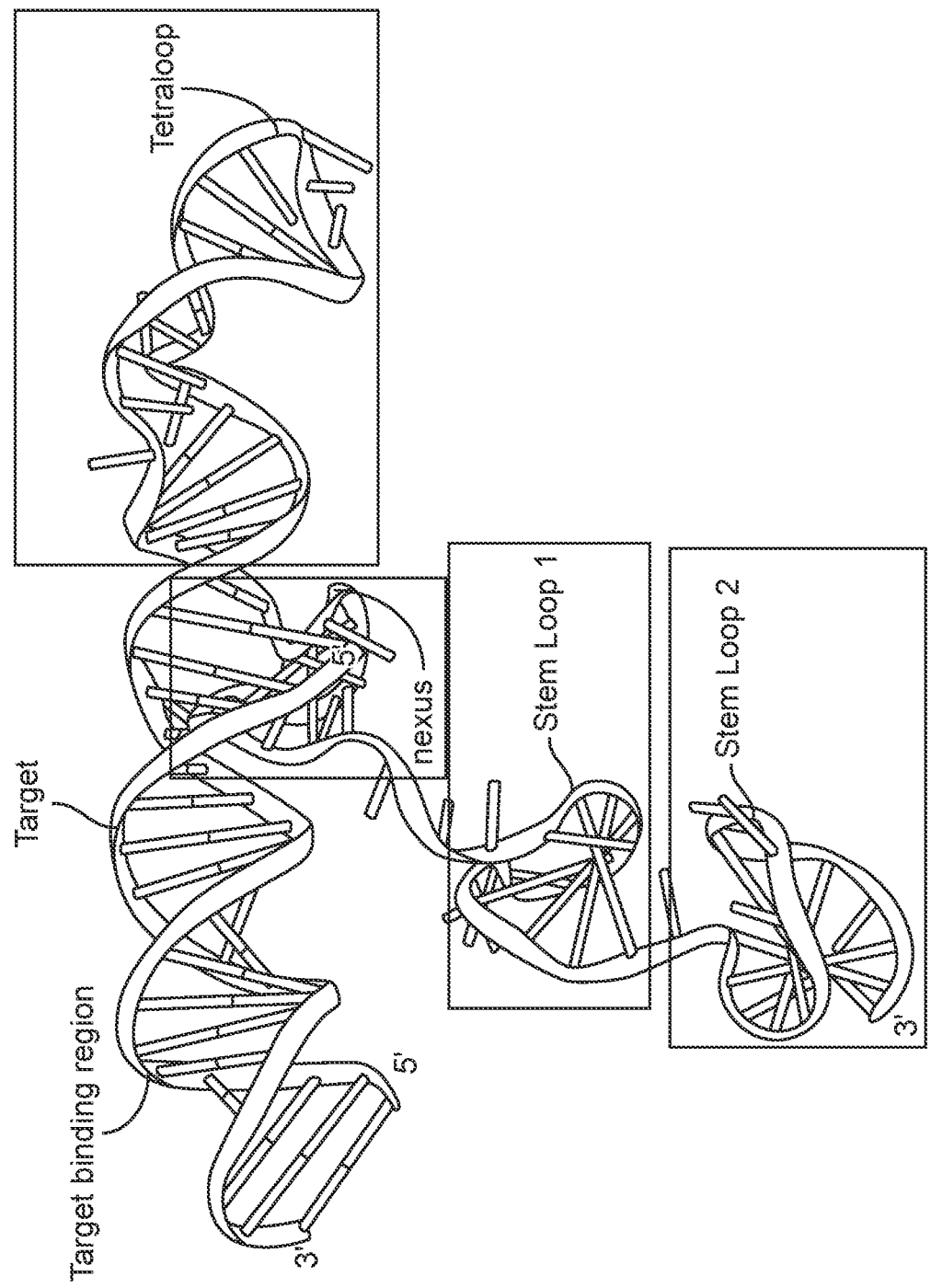
FIG. 2 shows a 3-D model of a sgRNA bound to a target sequence; the tetraloop and stem loops 1-3 are highlighted to relate the diagram to FIGS. 3-5 (images modified from Nishimasu, H., Ishitani, R., & Nureki, O. (2014). Crystal structure of *Streptococcus pyogenes* Cas9 in complex with guide RNA and target DNA. Cell. doi:10.2210/pdb4oo8/pdb).

Alternatively, or in combination, the position of the one or more cross linkers can be at any nucleotide of the tracrRNA sequence, or between any two nucleotides of the tracrRNA sequence, outside of the target binding crRNA region. One or more cross-linkers can be present in any stem region: nexus, stem loop 1, stem loop 2, or the tetraloop of the CRISPR polynucleotide (see, e.g., FIG. 2). The one or more cross-linker(s) can be in a hairpin loop or stem of nexus, stem loop 1, stem loop 2, or the tetraloop of the polynucleotide, or any combination thereof. The one or more cross-linker(s) can be present in one hairpin, two hairpins, three hairpins or four hairpins. A loop of a hairpin can comprise one crosslinker, two crosslinkers, three crosslinkers, four crosslinkers, five crosslinkers, six crosslinkers, etc. One, two, three, four, five or more crosslinkers can be in the bulge of the tetraloop.

Alternatively, or in combination with the above, one or more crosslinkers can be at nucleotide position 49 of the sgRNA, wherein nucleotide position 1 is at a 5' end of the target binding region of the crRNA and nucleotide positions of the sgRNA are numbered consecutively from 5' to 3' from nucleotide position 1.

One or more crosslinkers can be at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 of the sgRNA, wherein nucleotide position 1 is at a 5' end of the target binding region of the crRNA and nucleotide positions of the sgRNA are numbered consecutively from 5' to 3' from nucleotide position 1.

Figure 7A:
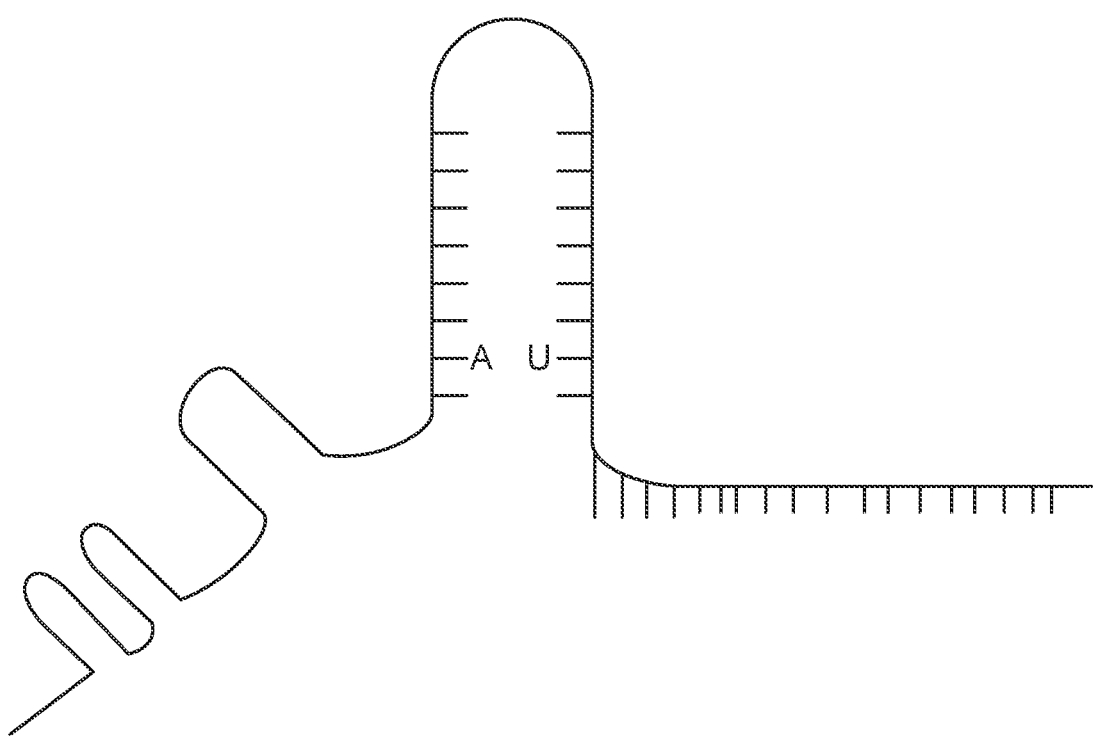
FIGS. 7A-7D show diagrams of a wild-type configuration of the sgRNA and three exemplary modifications to the sgRNA.
Figure 7B:
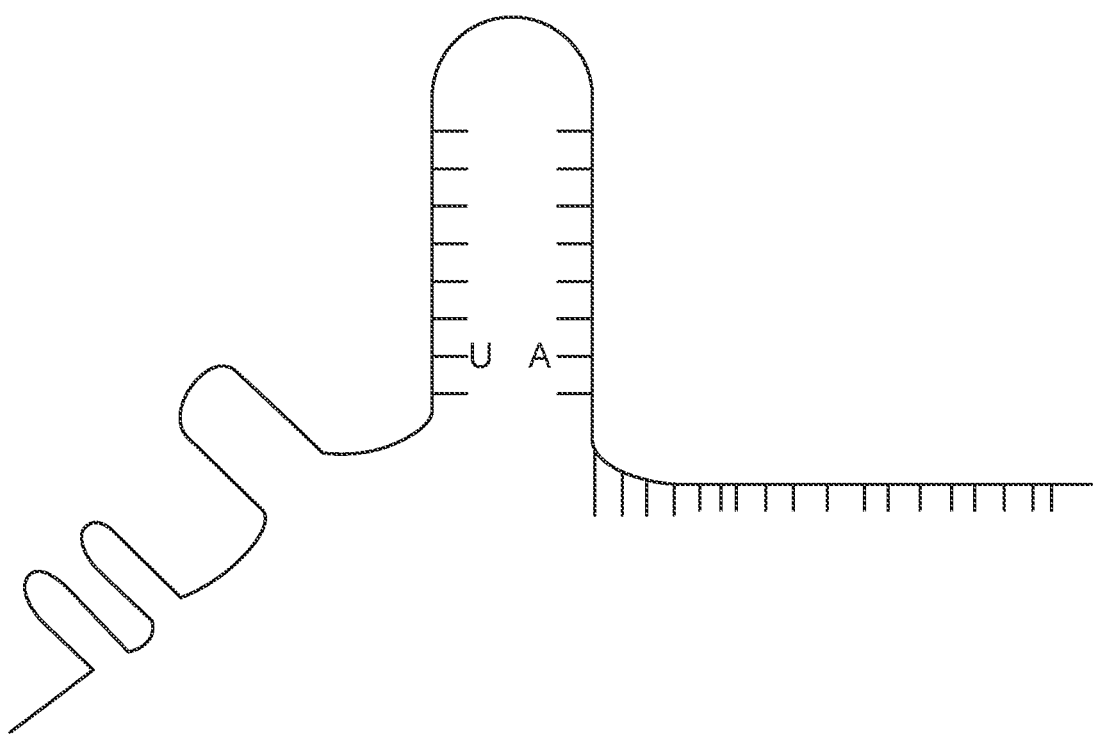
Figure 7C:
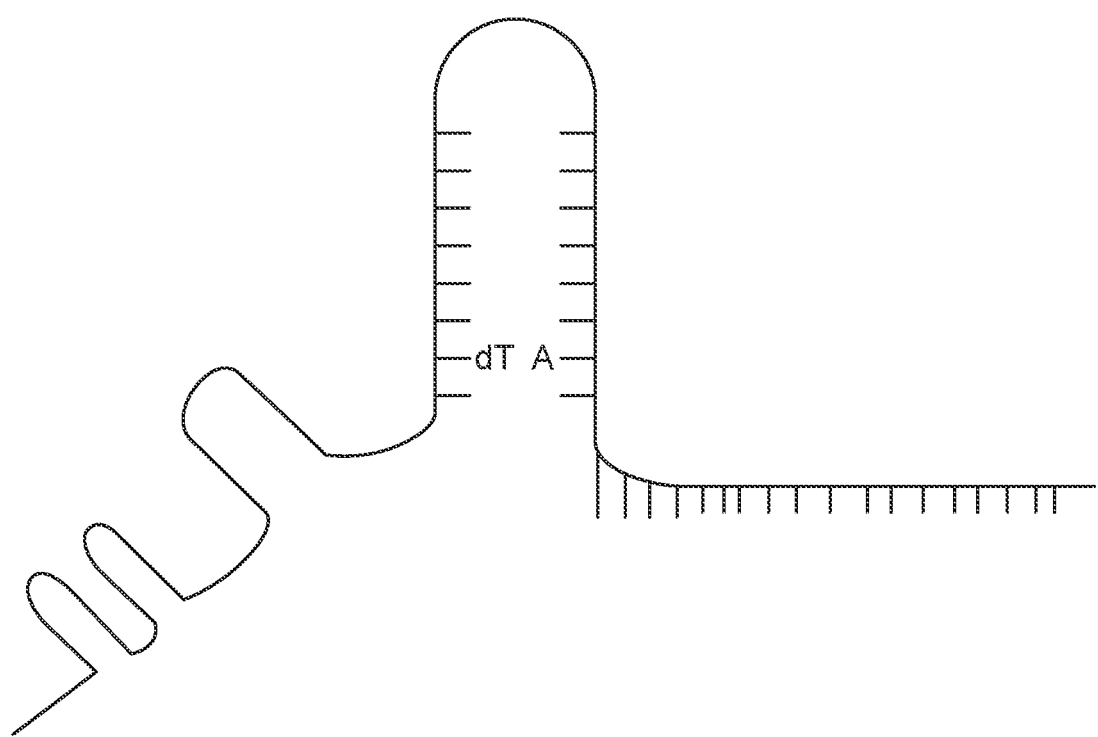
Figure 7D:
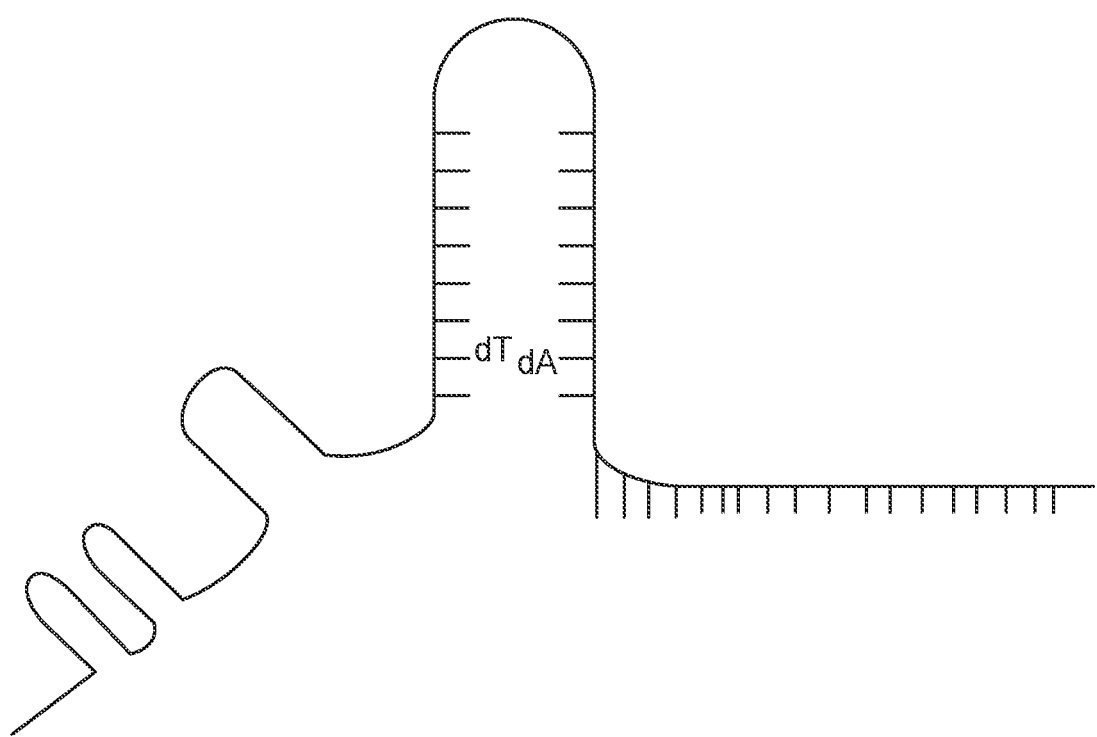

The one or more crosslinkers can be at any uracil residue of the sgRNA. The sgRNA can be modified such that hairpin structures of the sgRNA are maintained relative to a structure of a stem loop of an sgRNA lacking the crosslinker. The sgRNA can be modified by a nucleotide swap between complementary pairs of nucleotides within a hairpin structure. An exemplary swap can be a uracil-adenine swap at position 49 of the sgRNA, leaving position 22 with an adenine, as can be seen in FIG. 7B modified from the configuration seen in FIG. 7A. Alternatively, a deoxyuridine can replace the uridine at position 49 as can be seen in FIG. 7C. Alternatively, a deoxy-adenosine can replace the adenosine at position 22, as can be seen in FIG. 7D. As a final option, the uridine at position 50 can be substituted with a deoxyuridine.

Alternatively, or in combination with the above, the one or more crosslinkers can be in one hairpin stem, two hairpin stems, three hairpin stems, or four hairpin stems. A hairpin stem can comprise one crosslinker, two crosslinkers, three crosslinkers, four crosslinkers, five crosslinkers, six crosslinkers, seven crosslinkers, eight crosslinkers, etc. The one or more crosslinkers can be in un-base-paired nucleotides between stems. Alternatively, or in combination, one or more crosslinkers can be in one or more nucleotides between stem regions.

The one or more cross-linkers can be located on the backbone of the CRISPR polynucleotide (e.g., gRNA, sgRNA, crRNA, or tracrRNA), or can be included as cross-linker modified nucleotides. Nucleotide modifications can include (a) end modifications, including 5'end modifications or 3' end modifications; (b) nucleobase (or "base") modifications, including replacement or removal of bases; (c) sugar modifications, including modifications at the 2', 3' and/or 4' positions; and (d) backbone modifications, including modification or replacement of the phosphodiester linkages. The CRISPR polynucleotide can comprise a 2'fluoro-arabino nucleic acid, tricycle-DNA (tc-DNA), peptide nucleic acid, cyclohexene nucleic acid (CeNA), ethylene-bridged nucleic acid (ENA), a phosphodiamidate morpholino, (3-(4,4'-Dimethoxytrityl)-1-(2-nitrophenyl)-propan-1-yl-[(2-cyanoethyl)-(N,N-diisopropyl)]-phosphoramidite), or a combination thereof. The CRISPR polynucleotide (e.g., sgRNA) can comprise one or more non-naturally occurring nucleotides or nucleotide analogs, e.g., a nucleotide with phosphorothioate linkage, boranophosphate linkage, or bridged nucleic acids (BNA). The non-naturally occurring nucleotides or nucleotide analogs can be 2'-O-methyl analogs, 2'-deoxy analogs, 2-thiouridine analogs, N6-methyladenosine analogs, or 2'-fluoro analogs.

In some cases, the polynucleotide can comprise modified nucleotides and/or modified internucleotide linkages at the first 1, 2, 3, 4, 5, 6, 7, 8, 9, 10, 11 or 12 nucleotides at the 5' terminus. In some cases, the polynucleotide can comprise modified nucleotides and/or modified internucleotide linkages at 1, 2, 3, 4, 5, 6, 7, 8, 9, 10, 11 or 12 nucleotides at the 3' terminus. In some cases, the polynucleotide can comprise modified nucleotides and/or modified internucleotide linkages at the first 1, 2, 3, 4, 5, 6, 7, 8, 9, 10, 11 or 12 nucleotides at the 5' terminus or 1, 2, 3, 4, 5, 6, 7, 8, 9, 10, 11 or 12 nucleotides at the 3' terminus. In some cases, the polynucleotide can comprise modified nucleotides and/or modified internucleotide linkages at the first 1, 2, 3, 4, 5, 6, 7, 8, 9, 10, 11 or 12 nucleotides at the 5' terminus and the first 1, 2, 3, 4, 5, 6, 7, 8, 9, 10, 11 or 12 nucleotides at the 3' terminus. The modifications can be 2'-O-methyl analogs and/or 3' phosphorothioate internucleotide linkages.

The CRISPR polynucleotide can comprise one or more modified bases. The one or more modified bases can be 2-aminopurine, 5-bromo-uridine, pseudouridine (Ψ), N^methylpseudouridine (mel P), 5-methoxyuridine(5moU), inosine, or 7-methylguanosine.

In some cases, the 3' and 5' termini of a CRISPR polynucleotide can be substantially protected from nucleases e.g., by modifying the 3' or 5' linkages (e.g., U.S. Pat. No. 5,849,902 and WO 98/13526). For example, CRISPR polynucleotides can be made resistant by the inclusion of one or more "blocking groups." The one or more "blocking groups" can be a substituent (e.g., other than OH groups) that can be attached to polynucleotides or nucleomonomers, either as protecting groups or coupling groups for synthesis (e.g., FITC, propyl (CH2-CH2-CH3), glycol (—O—CH2-CH2-O—) phosphate (PO3 2-), hydrogen phosphonate, or phosphoramidite). The one or more blocking groups can be one or more "end blocking groups" or one or more "exonuclease blocking groups" that can protect the 5' and 3' termini of the CRISPR polynucleotide, including modified nucleotides and non-nucleotide exonuclease resistant structures.

The one or more end-blocking groups can be a cap structure (e.g., a 7-methylguanosine cap), inverted nucleomonomer, e.g., with 3'-3' or 5'-5' end inversions (see, e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. For example, the 3'-hydroxyl can be esterified to a nucleotide through a 3'→3' internucleotide linkage. For example, the alkyloxy radical can be methoxy, ethoxy, or isopropoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage.

The CRISPR polynucleotide can comprise one or more labels or tags. The one or more "labels" or "tags" can be a molecule that can be attached to another molecule, e.g., a CRISPR polynucleotide or a segment thereof, to provide a means by which the other molecule can be readily detected. The CRISPR polynucleotide can comprise a label, which can be fluorescent, luminescent, radioactive, enzymatically active, etc. The one or more labels can include fluorochromes, e.g. fluorescein isothiocyanate (FITC), rhodamine, Texas Red, phycoerythrin, allophycocyanin, 6-carboxyfluorescein(6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. 32P, 35S, 3H; etc. The one or more labels can be a two stage system, where the CRISPR polynucleotide is conjugated to biotin, haptens, etc. having a high affinity binding partner, e.g. avidin, specific antibodies, etc., where the binding partner is conjugated to a detectable label.

The CRISPR polynucleotide (e.g., sgRNA) can comprise one or more stem loops to which one or more stem-loop RNA binding proteins (RBPs) are capable of interacting. These stem loops can be positioned such that the interaction of the CRISPR polynucleotide (e.g., sgRNA) with the CRISPR effector protein (e.g., CRISPR enzyme) or binding of the CRISPR complex with a target DNA is not adversely affected. The one or more stem loops can lie outside the guide sequence of the CRISPR polynucleotide (e.g., the sgRNA). The one or more stem-loop RNA binding proteins can be, e.g., MS2, PP7, Qp, F2, GA, fr, JP501, M12, R17, BZ13, JP34, JP500, KU1, M11, MX1, TW18, VK, SP, F1, ID2, NL95, TW19, AP205, S1, S1m, 7s, or PRR1.

In some cases, the stem-loop RNA binding protein (RBP) can act as an adaptor protein (i.e., intermediary) that can bind both to the stem-loop RNA and to one or more other proteins or polypeptides, or one or more functional domains. The adaptor protein can recruit effector proteins or fusions that can comprise one or more functional domains. In some cases, the RNA binding protein can be a fusion protein with one or more functional domains.

1. Types of Modifications

In some cases, the CRISPR polynucleotide (e.g., gRNA, sgRNA, crRNA, or tracrRNA) can be modified to facilitate locking to a CRISPR effector protein. Modifications for locking a CRISPR polynucleotide (e.g., sgRNA) molecule to a CRISPR effector protein can include modifying nucleotides on the sgRNA with functional crosslinking groups.

Modified nucleotides can be introduced into a CRISPR polynucleotide (e.g., sgRNA). Suitable methods are, for example, synthesis methods using (automatic or semi-automatic) oligonucleotide synthesis devices, e.g., in a 3' to 5' direction. Such devices may comprise microarrays, polymerase cycling assembly (PCA), microchips, etc.

The CRISPR polynucleotide can comprise a sugar moiety. The sugar moieties can be natural, unmodified sugar, e.g., monosaccharide (e.g., pentose, e.g., ribose, deoxyribose), modified sugars, or sugar analogs. In some cases, the sugar moiety can have or more hydroxyl groups replaced with a halogen, a heteroatom, an aliphatic group, or the one or more hydroxyl groups can be functionalized as an ether, an amine, a thiol, or the like.

The CRISPR polynucleotide can comprise one or more modifications at a 2' position of a ribose. The one or more modifications at the 2' position of the ribose can be introduced, e.g., to reduce immunostimulation in a cellular context. The 2' moiety can be H, OR, R, halo, SH, SR, $H_2$, HR, $R_2$ or ON, wherein R is C1-C6 alkyl, alkenyl or alkynyl and halo is F, Cl, Br or I. Examples of sugar modifications include 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), azidotriphosphate (2'-azido-2'-deoxycytidine-5'-triphosphate, 2'-azido-2'-deoxyuridine-5'-triphosphate), and combinations thereof. The sugar-modified ribonucleotides can have the 2' OH group replaced by an H, alkoxy (or OR), R or alkyl, halogen, SH, SR, amino (such as $NH_2$, NHR, $NR_2$), or CN group, wherein R is lower alkyl, alkenyl, or alkynyl. The modification at the 2' position can be a methyl group.

The polynucleotide can comprise one or more nucleobase-modified ribonucleotides. The one or more modified ribonucleotides can contain a non-naturally occurring base (instead of a naturally occurring base), such as uridines or cytidines modified at the 5'-position, e.g., 5' (2-amino)propyl uridine or 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine.

The nucleobase-modified ribonucleotides can be m5C (5-methylcytidine), m5U (5-methyluridine), m6A (N6-methyladenosine), s2U (2-thiouridine), Um (2'-O-methyluridine), m1A (1-methyl adenosine), m2A (2-methyladenosine), Am (2-1-O-methyladenosine), ms2m6A (2-methylthio-N6-methyladenosine), i6A (N6-isopentenyl adenosine), ms2i6A (2-methylthio-N6isopentenyladenosine), io6A (N6-(cis-hydroxyisopentenyl) adenosine), ms2io6A (2-methylthio-N6-(cis-hydroxyisopentenyl)adenosine), g6A (N6-glycinylcarbamoyladenosine), t6A (N6-threonyl carbamoyladenosine), ms2t6A (2-methylthio-N6-threonyl carbamoyladenosine), m6t6A (N6-methyl-N6-threonylcarbamoyladenosine), hn6A(N6.-hydroxynorvalylcarbamoyl adenosine), ms2hn6A (2-methylthio-N6-hydroxynorvalyl carbamoyladenosine), Ar(p) (2'-O-ribosyladenosine(phosphate)), I (inosine), mi 1(1-methylinosine), m'1m (1,2'-O-dimethylinosine), m3C (3-methylcytidine), Cm (2T-0-methylcytidine), s2C (2-thiocytidine), ac4C (N4-acetylcytidine), f5C (5-fonnylcytidine), m5Cm (5,2-O-dimethylcytidine), ac4Cm (N4acetyl2TOmethylcytidine), k2C (lysidine), m1G (1-methylguanosine), m2G (N2-methylguanosine), m7G (7-methylguanosine), Gm (2'-0-methylguanosine), m22G (N2,N2-dimethylguanosine), m2Gm (N2,2'-0-dimethylguanosine), m22Gm (N2,N2,2'-0-trimethylguanosine), Gr(p) (2'-0-ribosylguanosine(phosphate)), yW (wybutosine), o2yW (peroxywybutosine), OHyW (hydroxywybutosine), OHyW* (undermodified hydroxywybutosine), imG (wyosine), mimG (methylguanosine), Q (queuosine), oQ (epoxyqueuosine), galQ (galtactosyl-queuosine), manQ (mannosyl-queuosine), preQo (7-cyano-7-deazaguanosine), preQi (7-aminomethyl-7-deazaguanosine), G (archaeosine), D (dihydrouridine), m5Um (5,2'-0-dimethyluridine), s4U (4-thiouridine), m5s2U (5-methyl-2-thiouridine), s2Um (2-thio-2'-O-methyluridine), acp3U (3-(3-amino-3-carboxypropyl)uridine), ho5U (5-hydroxyuridine), mo5U (5-methoxyuridine), cmo5U (uridine 5-oxyacetic acid), mcmo5U (uridine 5-oxyacetic acid methyl ester), chm5U (5-(carboxyhydroxymethyl)uridine)), mchm5U (5-(carboxyhydroxymethyl)uridine methyl ester), mcm5U (5-methoxycarbonyl methyluridine), mcm5Um (S-methoxycarbonylmethyl-2-O-methyluridine), mcm5s2U (5-methoxycarbonylmethyl-2-thiouridine), nm5s2U (5-aminomethyl-2-thiouridine), mnm5U (5-methylaminomethyluridine), mnm5s2U (5-methylaminomethyl-2-thiouridine), mnm5se2U (5-methylaminomethyl-2-selenouridine), ncm5U (5-carbamoylmethyl uridine), ncm5Um (5-carbamoylmethyl-2'-O-methyluridine), cmnm5U (5-carboxymethylaminomethyluridine), cnmm5Um (5-carboxymethylaminomethyl-2-L-Omethyluridine), cmnm5s2U (5-carboxymethylaminomethyl-2-thiouridine), m62A (N6,N6-dimethyladenosine), Tm (2'-O-methylinosine), m4C (N4-methylcytidine), m4Cm (N4,2-O-dimethylcytidine), hm5C (5-hydroxymethylcytidine), m3U (3-methyluridine), cm5U (5-carboxymethyluridine), m6Am (N6,T-0-dimethyladenosine), rn62Am (N6,N6,0-2-trimethyladenosine), m2'7G (N2,7-dimethylguanosine), m2'2'7G (N2,N2,7-trimethylguanosine), m3Um (3,2T-0-dimethyluridine), m5D (5-methyldihydrouridine), f5Cm (5-formyl-2'-0-methylcytidine), m1Gm (1,2'-0-dimethylguanosine), m'Am (1,2-0-dimethyl adenosine)irinomethyluridine), tm5s2U (S-taurinomethyl-2-thiouridine)), imG-14 (4-demethyl guanosine), imG2 (isoguanosine), or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(Ci-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxy cytosine, 5-(Ci-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, and combinations thereof.

The nucleobase-modified ribonucleotide can be Aminopurine, 2,6-Diaminopume (2-Amino-dA), 5-Bromo dU, deoxyuridine, Inverted dT, Inverted Dideoxy-T, dideoxy-C, 5-Methyl dC, Super (T), Super (G), 5-Nitroindole, 2'-O-Methyl RNA Bases, Hydroxymethyl dC, Iso dG, Iso dC, Fluoro C, Fluoro U, Fluoro A, Fluoro G, 2-MethoxyEthoxy MeC, 2-MethoxyEthoxy G, or 2-MethoxyEthoxyT.

a. Chemical Cross-Linkers for Locking

In some cases, the CRISPR effector protein can be modified to facilitate locking to a CRISPR polynucleotide (e.g., sgRNA). The CRISPR polynucleotide (e.g., sgRNA) can comprise one or more cross linkers. The one or more cross linkers can be a functional group that forms a covalent bond, e.g., between polymers, such as isocyanates. The one or more cross-linkers can be formaldehyde or glutaraldehyde. The cross-linking can involve bio conjugation. Bio conjugation crosslinking reagents can contain reactive groups that react with functional groups such as amines and sulfhydryls. Bio conjugation cross linkers can include sulfhydryl reactive groups such as maleimides, haloacetyls, aziridines, acryloyls, alkoxyamine, arylating agents, vinylsulfones, pyridyl disulfides, TNB-thiols, dithiol phosphoramidite DTPA etc. Bio conjugation cross linkers can also include amine reactive crosslinker reactive groups such as succinimidyl esters (NHS esters), sulfonyl chloride, aldehyde, carbodiimide, acyl azide, aryl azide, anhydride, fluorobenzene, carbonate, imidoester, epoxide, fluorophenyl ester, phosphoramidite, etc.

Further non-limiting examples of cross-linkers can be derived from the following compounds: thiol+thiol, thiol+maleimide, NHS ester+amine, carboxylic acid+NHS+amine, azide+phosphine (Staudinger ligation), carbonyl compound+amine, carbonyl compound+O-substituted hydroxylamines, diazirine+C-H/O—H, N—H, haloacetate+thiol, azide+alkyne, nitrone+alkyne, nitrile oxide+alkyne, tetrazine+alkene, 4-thiouridine, 5'-azideuridine, 5-bromouridine, 8-azidoadenosine, 5-((4-Azidophenacyl)thio)uridine.

The CRISPR polynucleotide (e.g., sgRNA) can be modified to comprise one or more unnatural nucleotides. An unnatural nucleotide can comprise a nucleotide which contains one or more modifications to the base, sugar, and/or phosphate moiety. The one or more modifications can comprise one or more chemical modifications. The one or more modifications can be, for example, of a 3'OH or 5'OH group, of the backbone, of the sugar component, and/or of the nucleotide base (e.g., purine or pyrimidine). The one or more modifications can include addition of one or more linker molecules for crosslinking. The one or more linker molecules can be configured to form covalent bonds with an amino acid. The one or more linker molecules can be configured to form non-covalent bonds with an amino acid. In one aspect, a modified base comprises a base other than adenine, guanine, cytosine, or thymine (in modified DNA), or a base other than adenine, guanine, cytosine or uracil (in modified RNA). In some embodiments, a modification is to a modified form of adenine, guanine, cytosine or thymine (in modified DNA) or a modified form of adenine, guanine, cytoside or uracil (in modified RNA). An unnatural nucleotide can be a nucleotide covalently modified at sugar, internucleotide phosphodiester bonds, purine or pyrimidine residues to comprise a functional group of a covalent linker. see, e.g., Sletten et al., Angew. Chem. Int. Ed. (2009) 48:6974-6998; Manoharan, M. Curr. Opin. Chem. Biol. (2004) 8: 570-9; Behlke et al., Polynucleotides (2008) 18: 305-19; Watts, et al., Drug. Discov. Today (2008) 13: 842-55; Shukla, et al., ChemMedChem (2010) 5: 328-49. An unnatural nucleotide can include a nucleotide modified, for example covalently modified, at a sugar, internucleotide phosphodiester bond, purine or pyrimidine residues to comprise a functional group. The covalent linker can be a chemical moiety selected from the group consisting of carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs. The chemical bonds can be based on carbamates, ethers, esters, amides, imines, amidines, aminotrizines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

Figure 6:
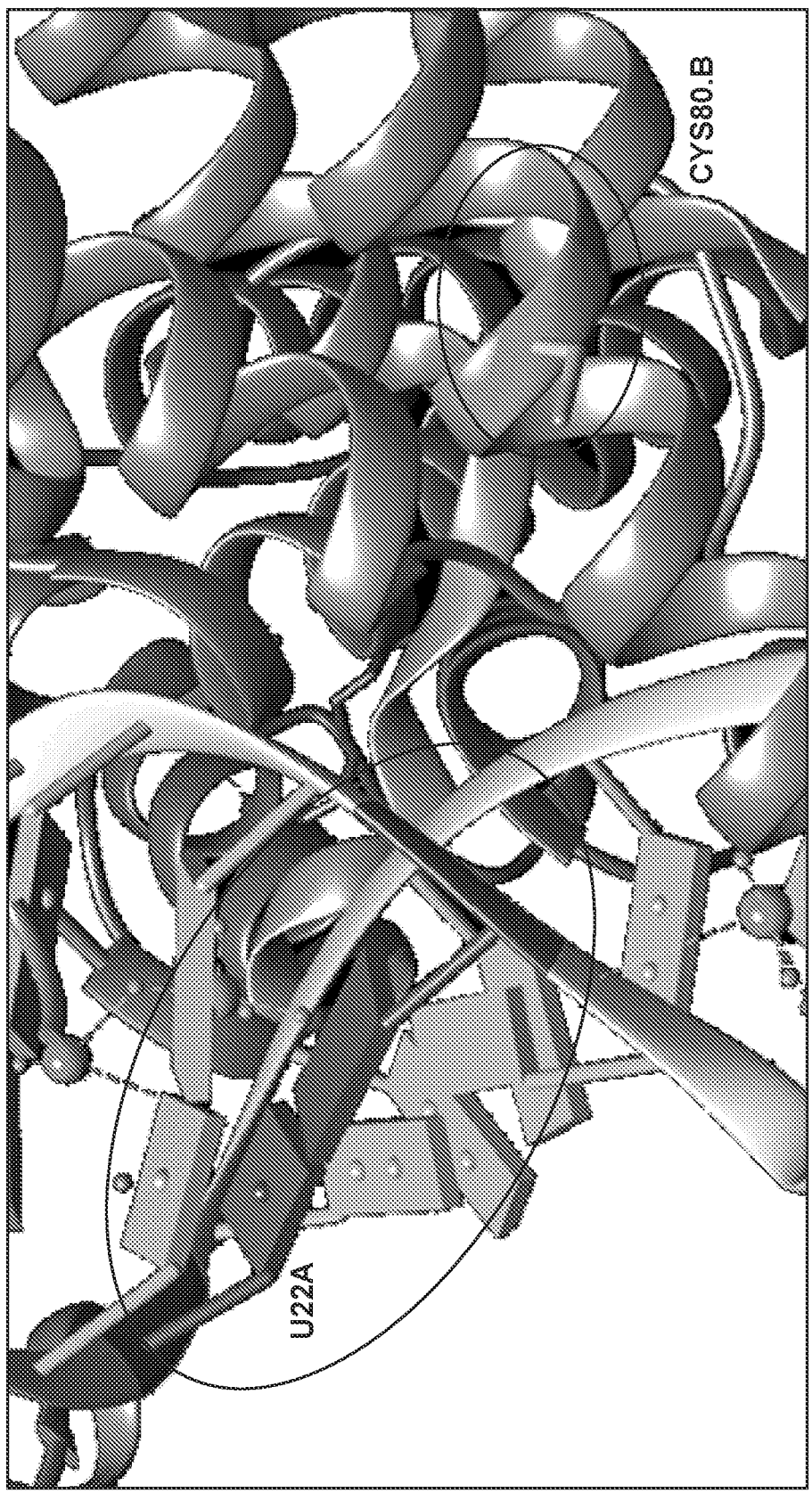
FIG. 6 shows a crystal structure showing exemplary RNA nucleotides to be modified and sites of crosslinking on the protein.

For example, unnatural nucleotides of the CRISPR polynucleotide (e.g., sgRNA) can comprise maleimides to crosslink to nearby cysteine amino acids in the CRISPR effector protein, forming a thioether bond. One technique for integrating unnatural nucleotides capable of crosslinking the CRISPR effector protein to the CRISPR polynucleotide (e.g., sgRNA) can involve modifying nucleotides of the CRISPR polynucleotide (e.g. sgRNA) with chemical groups that react with cysteines found in the CRISPR effector protein, such as maleimides. The unnatural nucleotides comprising maleimides can crosslink the CRISPR polynucleotide to the CRISPR effector protein by reacting with a thiol side chain of a Cysteine of the CRISPR effector protein. FIG. 6 shows a crystal structure of an exemplary location of an unnatural nucleotide to crosslink to an adjacent cysteine of a CRISPR effector protein comprising a Cas9 nuclease. Specifically, the structure shows an unnatural nucleotide, nucleotide position 22, (white circle on left) and an adjacent amino acid on the CRISPR effector protein, cysteine at position 80 of the CRISPR effector protein (white circle on right). As described above, sgRNA positions 22 and 49 can be modified with a uridine to adenine switch, as seen in FIG. 7B, leaving RNA nucleotide position 49 as a uracil (U49). An unnatural nucleotide at U49 can be integrated by modification of the sugar molecule of U49 to include crosslinking moieties that interact with Cys80 on SpCas9. Other positions of a sgRNA with a wild type tracr RNA sequence configured to complex with a Cas9 nuclease which could be modified with a uridine to adenine switch are U72/A77, U71/A78, and U94/A84. Uracil nucleotides at positions 77, 78 and 84 of the sgRNA can be modified with crosslinking groups described herein so as to form covalent bonds with adjacent amino acids of the Cas9 nuclease.

Figure 8:
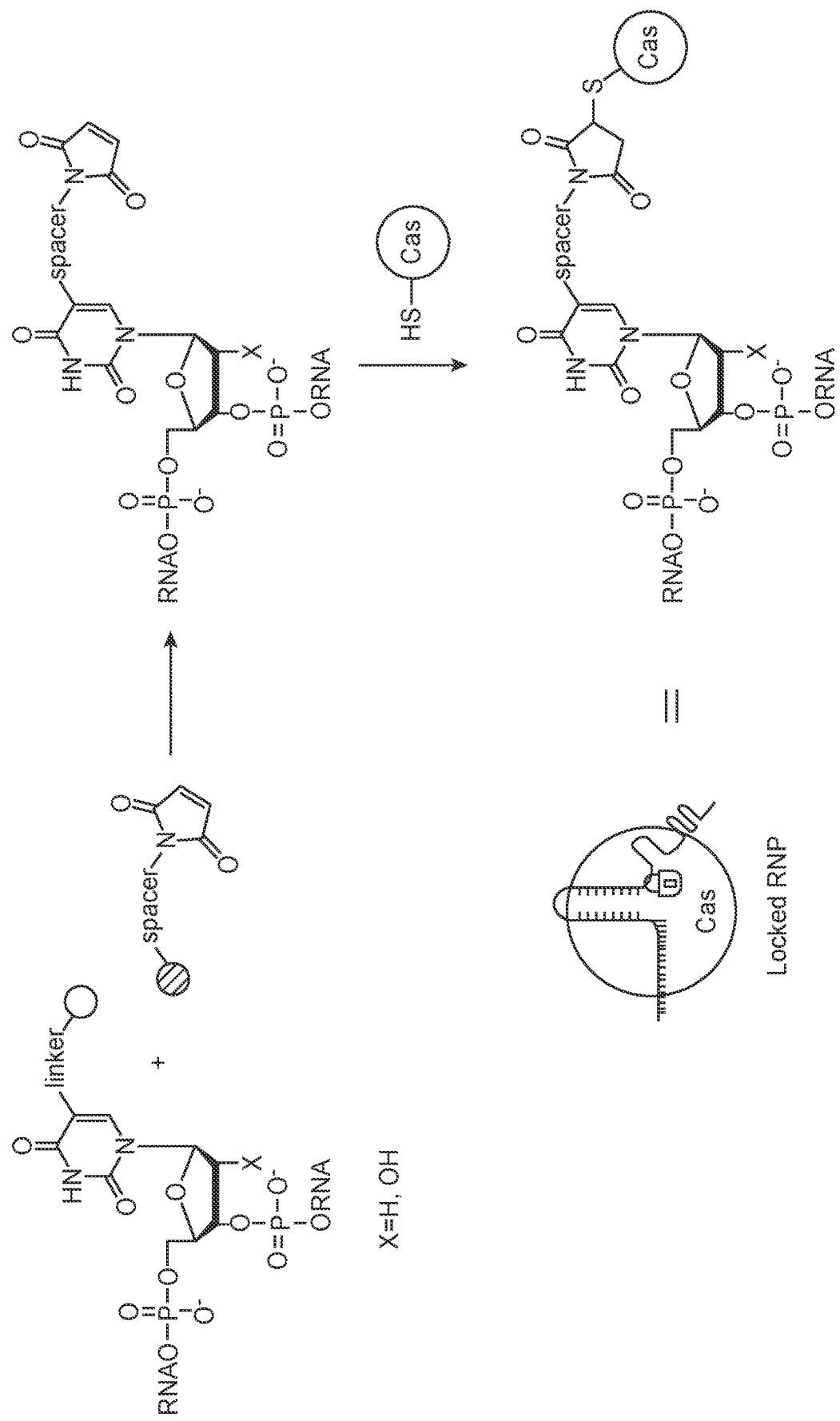
FIG. 8 shows a diagram outlining an example of how a maleimide can be added to a uracil nucleotide.

FIG. 8 outlines an exemplary method of modifying a nucleotide with a linker group. The phosphoramidite nucleotide is reacted with a nucleophile attached to a spacer and a maleimide group. The incoming nucleophile replaces the linker group of the phosphoramidite nucleotide, leaving a spacer attached to the maleimide. When in proximity to a cysteine with a thiol group, such as when complexed with a CRISPR effector protein, the maleimide can form a covalent thioether bond with the cysteine under physiological conditions.

One technique for crosslinking the CRISPR effector protein to the CRISPR polynucleotide (e.g., sgRNA) can involve modifying nucleotides of the CRISPR polynucleotide (e.g., sgRNA) to create unnatural nucleotides with chemical groups that react with primary amines found on the side chain of lysine in the CRISPR effector protein, such as NHS esters, epoxide, aldehyde, acyl azide, etc.

Figure 9:
FIG. 9 shows a crystal structure of a CRISPR complex wherein all uracil bases in the sgRNA are highlighted.

FIG. 9 shows a crystal structure of a CRISPR complex wherein the native Uracil nucleotides of a sgRNA are highlighted. The Uracil nucleotides are at positions 22, 23, 24, 25, 31, 37, 44, 45, 50, 56, 59, 63, 64, 66, 71, 72, 80, 90, and 94. These residues could be functionalized to form crosslinks with a CRISPR effector protein.

Figure 10:
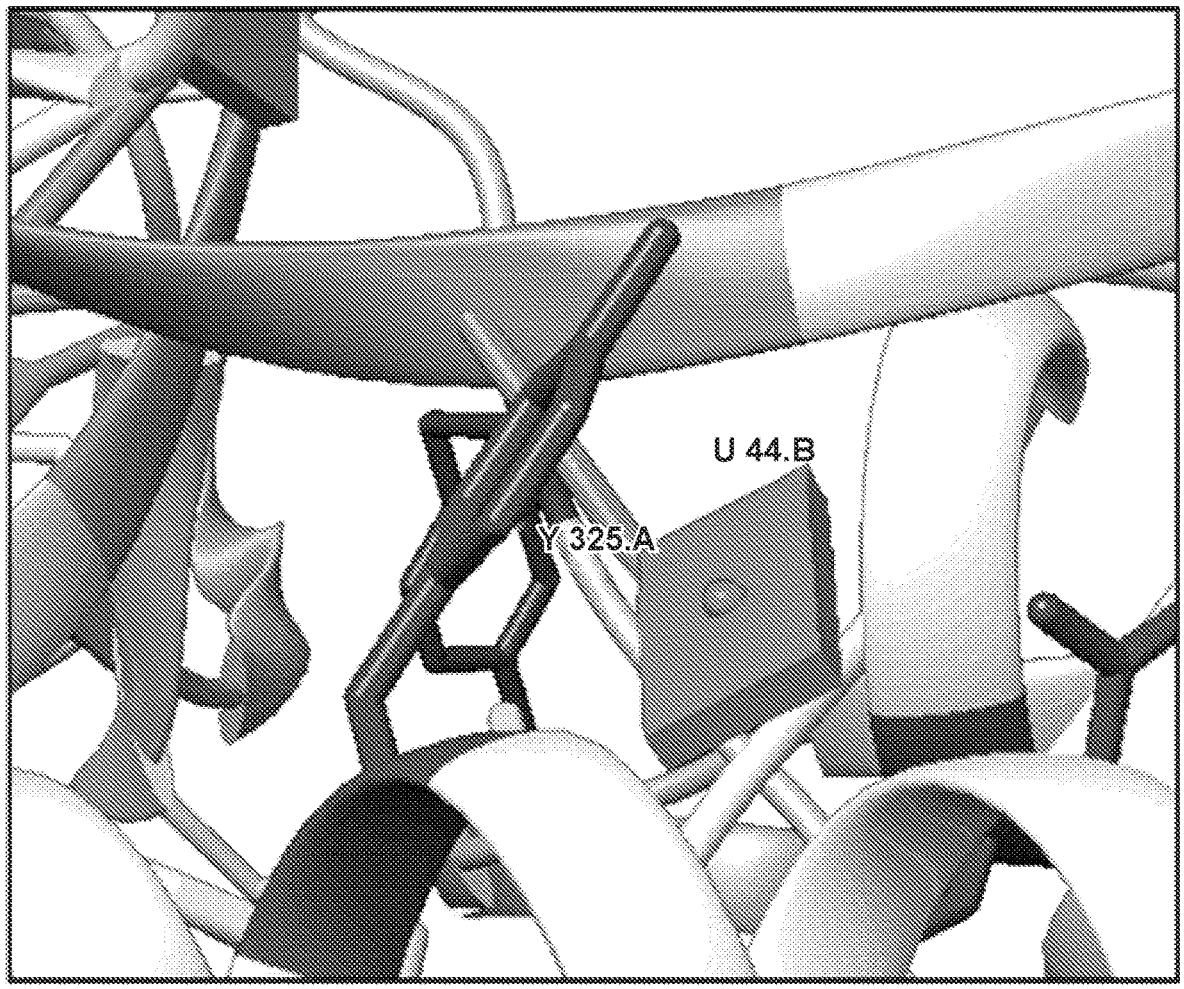
FIG. 10 shows a crystal structure of a CRISPR complex, focused on the spatial relationship between a uracil at position 44 of the sgRNA and an alpha helix comprising a tyrosine residue.

FIG. 10 shows a non-limiting example of a crystal structure of a CRISPR complex comprising a Cas9 nuclease. Position 44 of the sgRNA, a uracil, is highlighted as amenable to a modification due to its proximity to Tyrosine 325 of the CRISPR effector protein.

Figure 11:
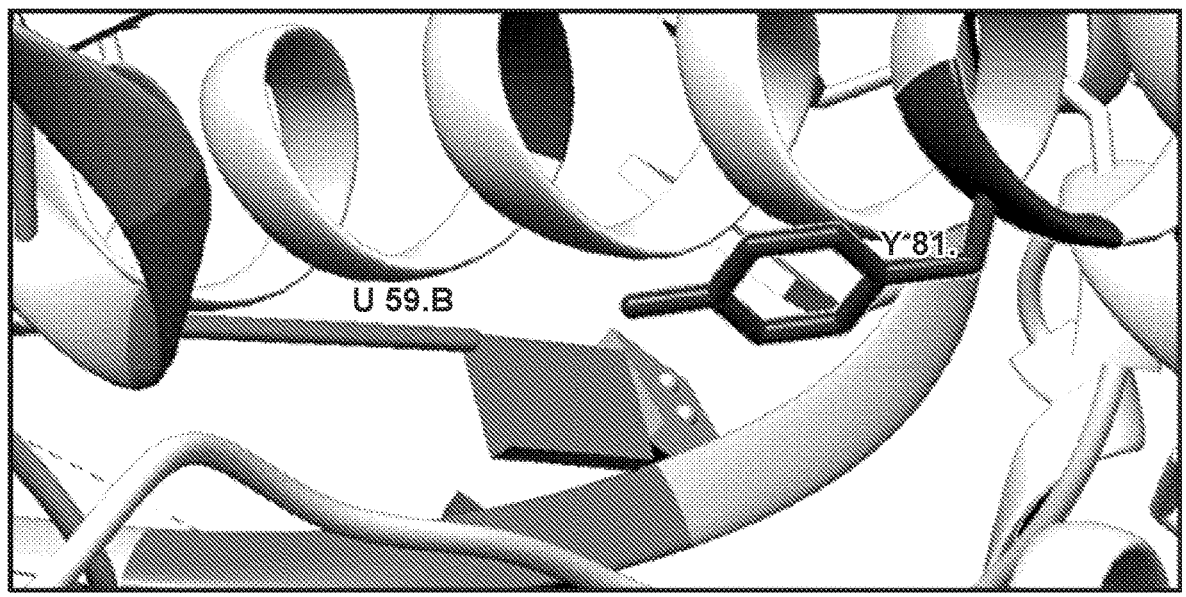
FIG. 11 shows a crystal structure of a CRISPR complex, focused on the spatial relationship between a uracil at position 59 to secondary structures of the CRISPR effector protein.

FIG. 11 shows a non-limiting example of a crystal structure of a CRISPR complex comprising a Cas9 nuclease. Position 59 of the sgRNA, a uracil, is highlighted as amenable to a modification due to its proximity to Tyrosine 81 of the CRISPR effector protein.

Figure 12:
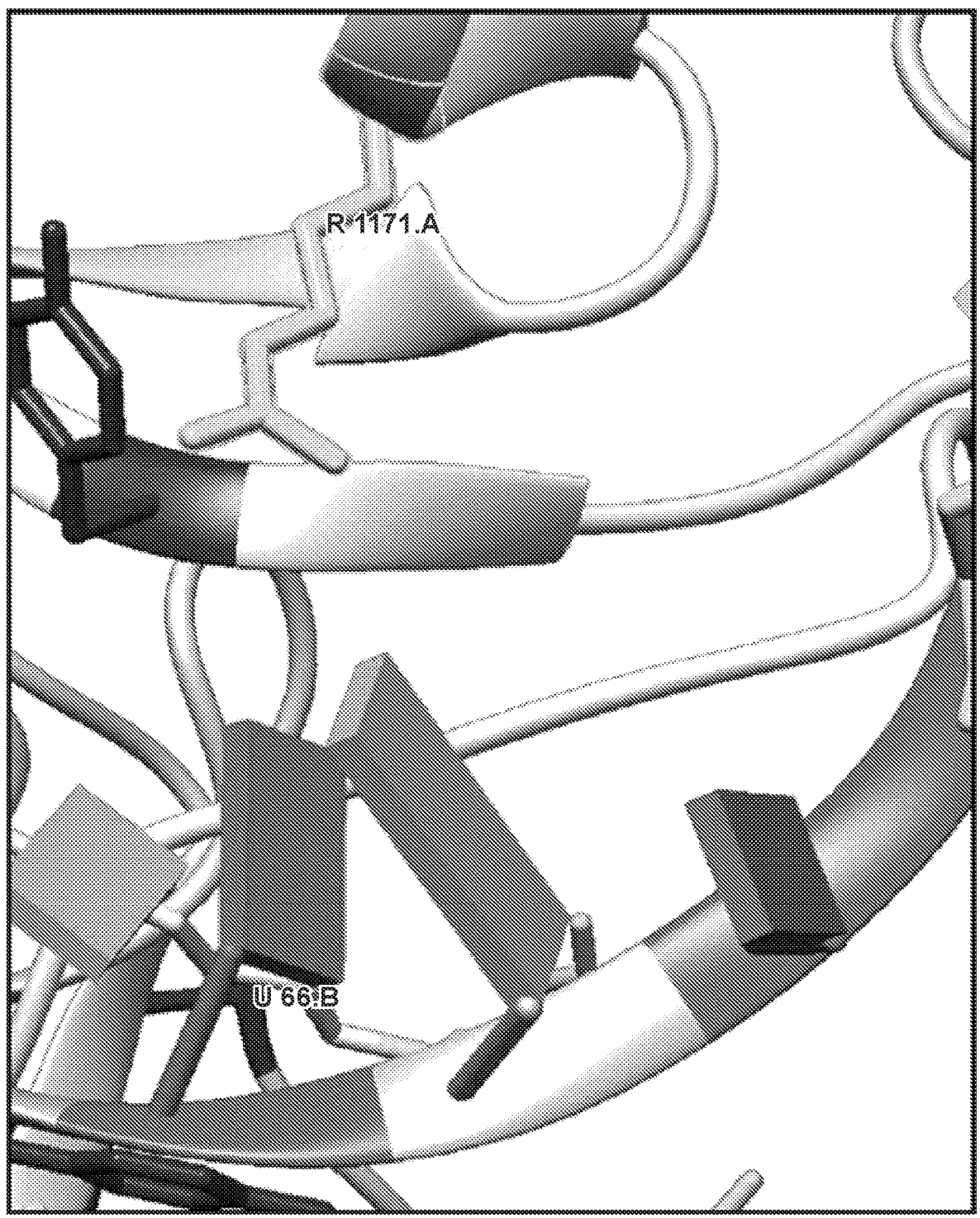
FIG. 12 shows a crystal structure of a CRISPR complex, focused on the spatial relationship between a uracil at position 66 to secondary structures of the CRISPR effector protein.

FIG. 12 shows a non-limiting example of a crystal structure of a CRISPR complex comprising a Cas9 nuclease. Position 66 of the sgRNA, a uracil, is highlighted as amenable to a modification due to its proximity to Arginine 1171 of the CRISPR effector protein.

Figure 13:
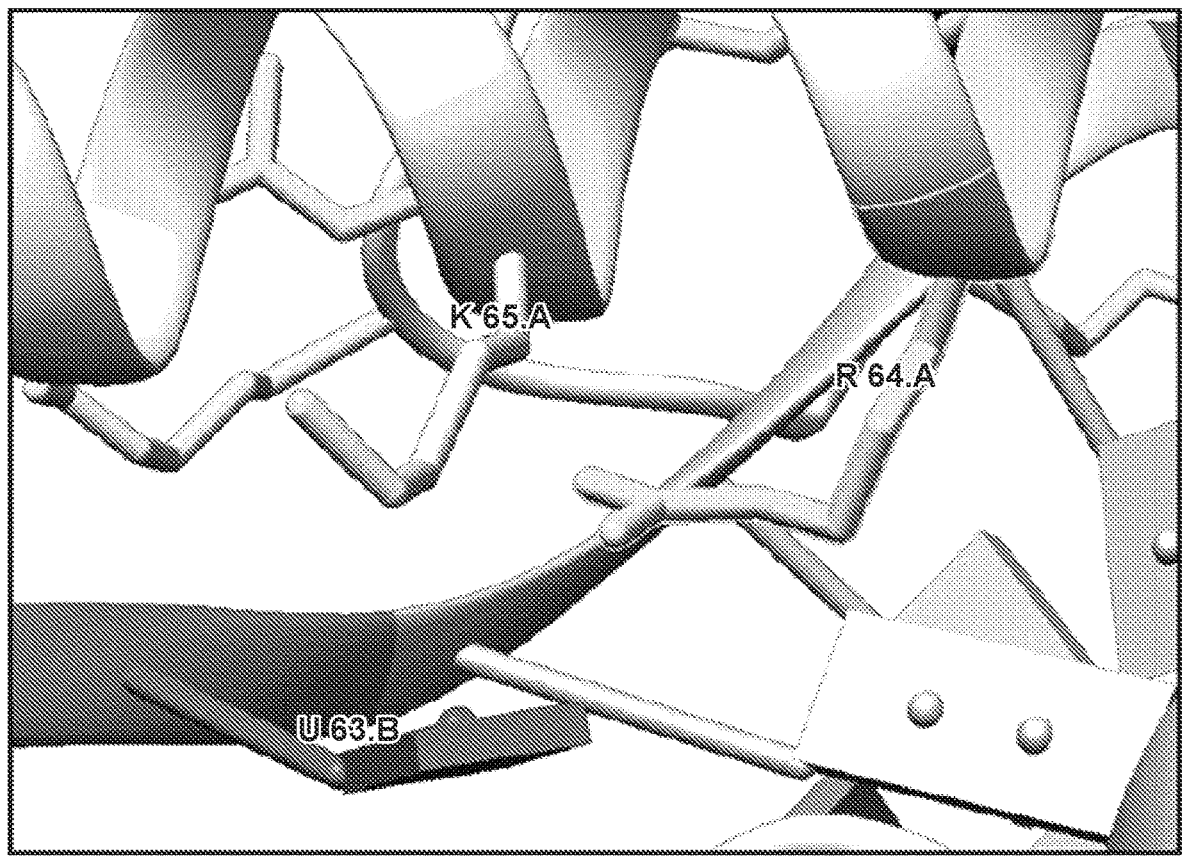
FIG. 13 shows a crystal structure of a CRISPR complex, focused on the spatial relationship between a uracil at position 63 to secondary structures of the CRISPR effector protein.
Figure 14:
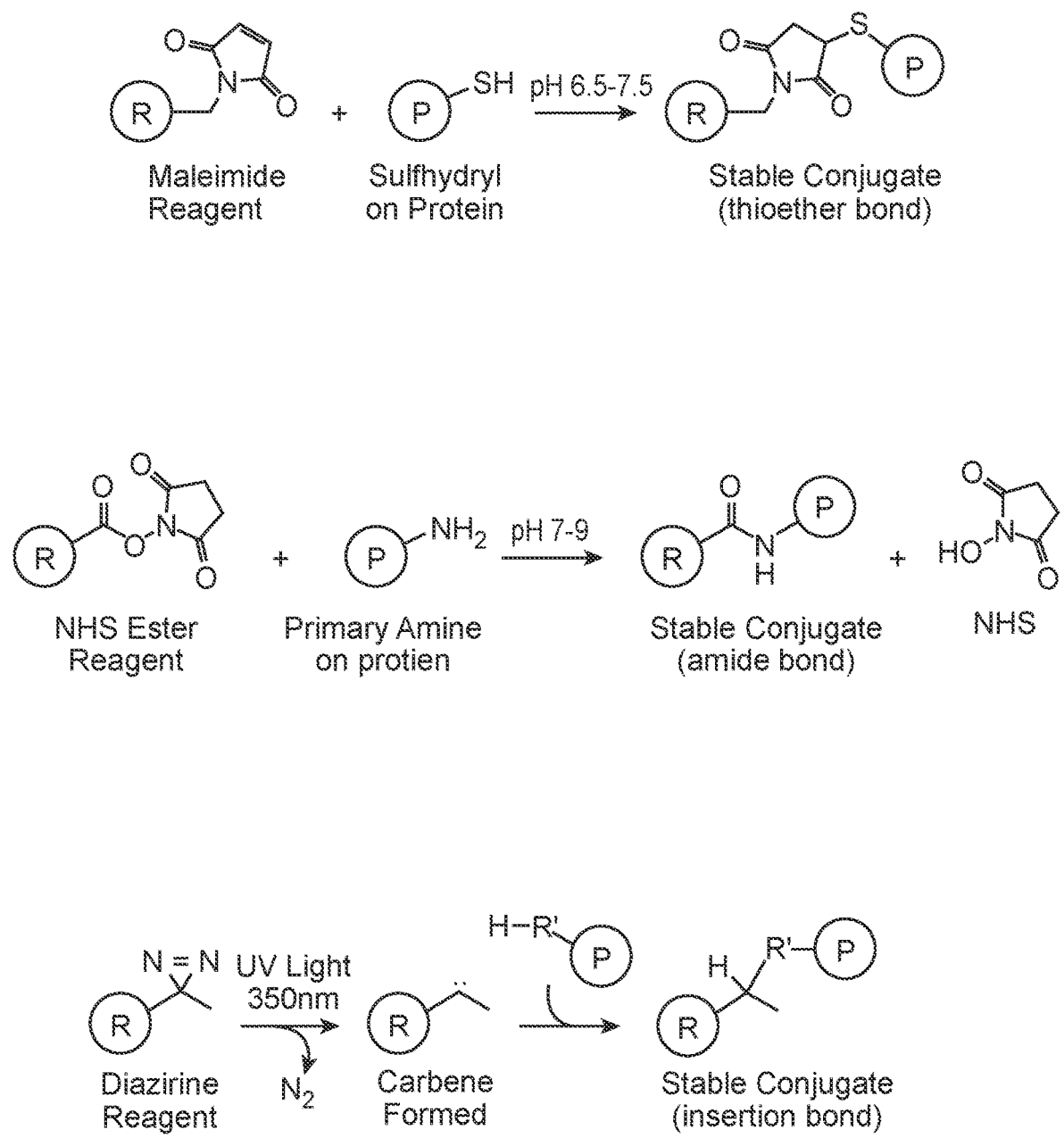
FIG. 14 shows three exemplary cross-linking reactions.

FIG. 13 shows a non-limiting example of a crystal structure of a CRISPR complex comprising a Cas9 nuclease. Position 63 of the sgRNA, a uracil, is highlighted as amenable to a diazirine modification due to its proximity to Arginine 64 and Lysine 65 of the CRISPR effector protein.

b. Photo Reactive Cross-Linkers for Locking

The CRISPR polynucleotides provided herein can comprise one or more photo labile linkers, e.g., aryl azides (phenyl azides) and diazirines. The one or more photo labile groups (linkers) can be used in photo-chemical crosslinking reactions that can use energy from light to be initiated. The one or more photo labile groups can be chemically inert compounds that become reactive when exposed to ultraviolet or visible light. The one or more photo labile groups incorporated into crosslinking compounds for use in bio conjugation techniques can be aryl azides, azido-methyl-coumarins, benzo-phenones, anthraquinones, diazo compounds, diazirines, and psoralen derivatives.

The CRISPR polynucleotides (e.g., sgRNA) can be modified with psoralen for crosslinking reactions with the CRISPR effector protein. Psoralen can react exclusively with RNA or DNA and can be used to label nucleic acids or to crosslink the CRISPR effector protein with the CRISPR polynucleotide. Nucleotides modified with photo labile groups that can be incorporated in to the CRISPR polynucleotide can include 4-thio-UTP, 5-azido-UPT, 5-bromo-UTP, 8 azido-ATP, -APAS-UTP, 8-N(3)AMP, 5-[N-(4-benzoyl-benzoyl)-3-aminoallyl]-deoxyuridine triphosphate (BP-dUTP, benzophenone modified), 5-[N-(4-azido-2,3,5,6-tetreafluorobenzoyl)-3-aminoallyl]-deoxy-uridine triphosphate (FAB-dUTP, perfluorinated aryl azide modified), 5-{N-[4-[3-(trifluoromethyl)-diazirin-3-yl] benzoyl]-3-aminoallyl}-deoxyuridine triphosphate (DB-dUTP, diazirine modified), and 5-[N-(p-azidobenzoyl)-3-aminoallyl]-deoxyuridine triphosphate (AB-dUTP, aryl azide modified).

Crosslinking can be by photo initiation. A light emitting device, producing wavelengths in and near the ultraviolet range, can be placed such that a solution carrying the CRISPR polynucleotide (e.g., sgRNA) bound to the CRISPR effector protein, e.g., by hydrogen bonding, can be exposed to the wavelength upon passing by the light emitting device. This exposure can lead to the photoinitiation of the photo labile group and the formation of a covalent bond linking the CRISPR polynucleotide (e.g., sgRNA) to the CRISPR effector protein as described above.

The wavelength of the light for photoinitiation can range from 220-465 nm. The intensity of light in the exposure protocol can be about 15, 20, 25, 35, 40, 50, 70, 90, 110, 120, 140, 160, 175, 190, 200, 220, 240, 260 280, 300, 320, 340, 360, 380, 400, 420, 440, 460, 480, 500, 520, 540, 560, 580, 600, 620, 650, 675, 700, 720, 745, 765, 790, 810, 830, 850, 870, 900, 920, 945, 965, 985, 1000, 1025, 1050, 1080, 1100, 1125, 1150, 1175, 1200, 1240, 1275, 1290, 1320, 1350, 1380, 1400, 1420, 1450, 1470, 1490, 1520, 1540, 1560, 1600, 1630, 1650, 1670, 1700, 1720 or 1750 mW/cm$^2$. The power wattage of the light used in the exposure protocol can be about 50, 70, 80, 90, 100, 120, 140, 160, 175, 190, 210, 230, 250, 270, 290, 310, 330, 250, 370, 390, 420, 450, 480, 500, 530, 550, 570, 600, 620, 650, 670, 700, 720, 750, 770, 800, 820, 850, 870, 900, 920, 950, 970, 1000, 1020, 1050, 1070, 1100, 1120, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400 4500, 4600, 4700, 4800, 4900, 5000, 5100, 5200, 5300, 5400, 5500, 5600, 5700, 5800, 5900, or 6000 W, as measured by an OAI 306 UV power meter.

The duration of exposure can be from 1 second to 30 minutes. The exposure protocol can comprise continuous exposure or pulsed exposure or both. The pulse exposure can be uniform or of varying durations. Exposure time to initiate crosslinking can be dependent upon the crosslinker chosen. For instance, upon exposure to UV light, diazirines can produce a reactive carbene with a half-life on the scale of nanoseconds. Aryl azides can form a reactive carbene upon exposure to UV light with a half-life on the scale of milliseconds. Exposure time can also be dependent on the distance from the available C—H group for reaction to the carbene.

The one or more photo labile groups used in crosslinking can be activated by a wavelength of light. The wavelength can provide excitation of the electron shell of the photo labile groups through a photon at a particular frequency. The reaction can occur upon excitation, which can lend flexibility to the crosslinking reaction with regard to the timing of the covalent bond formation. The one or more photo labile groups can be chosen to be activated by ultraviolet wavelengths.

Cross-linking can occur in vitro. Physiological conditions can be used to ensure the proper folding and attachment of the CRISPR effector protein to the CRISPR polynucleotide. Physiological conditions can include solutions with reagents, e.g., 20 mM Tris, pH 7.5, 100 mM KCl, 5 mM MgCl$_2$, 1 mM DTT and 5% (v/v) glycerol. Temperatures can be about 25° C. or 37° C.

To facilitate the formation of a CRISPR complex from individual CRISPR polynucleotides (e.g., sgRNA) and CRISPR effector proteins, a ratio (e.g., molar ratio) (CRISPR polynucleotide:CRISPR effector protein) provided can be about 0.001:1, 0.01:1, 0.1:1, 0.2:1, 0.3:1, 0.4:1, 0.5:1, 0.6:1, 0.7:1, 0.8:1, 0.9:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 25:1, 30:1, 40:1, 50:1, 60:1, 70:1, 80:1, 90:1, 100:1, and any variation in between. The ratio (e.g., molar ratio) (CRISPR polynucleotide:CRISPR effector protein) can be about 0.001:1 to about 0.01:1, about 0.01 to about 0.1:1, about 0.1:1 to about 1:1, about 1:1 to about 10:1, or about 10:1 to about 100:1, or about 100:1 to about 1000:1.

Cross linking can also occur in vivo, e.g., after a cell is contacted with a solution of CRISPR effector protein, unbound or bound to the CRISPR polynucleotide. In some cases, the CRISPR polynucleotide (e.g., sgRNA) and/or CRISPR effector protein (e.g., Cas9) can be expressed from a nucleic acid in the cell. The cell can be exposed to UV light in order to lock (e.g., covalently cross-link) the CRISPR polynucleotide (e.g., sgRNA) to the CRISPR effector protein (e.g., Cas9). The cell can be ectodermal (e.g., neurons and fibroblasts), mesodermal (e.g., cardiac muscle cells), endodermal (e.g., pancreatic cells), epithelial (e.g., lung and nasal passageways), neutrophils, eosinophils, basophils, lymphocytes, osteoclasts, endothelial cells, hematopoietic, red blood cells, etc. The cell can be derived from specific cell lines such as CHO cells (e.g., CHOK1); HEK293 cells; Caco2 cells; U2-OS cells; NIH 3T3 cells; NSO cells; SP2 cells; DG44 cells; K-562 cells, U-937 cells; MC5 cells; IMR90 cells; Jurkat cells; HepG2 cells; HeLa cells; HT-1080 cells; HCT-116 cells; Hu-h7 cells; Huvec cells; and Molt 4 cells. Examples of other cells applicable to the scope of the present disclosure can include stem cells, embryonic stem cells (ESCs) and induced pluripotent stem cells (iPSCs), MSC-1, K562, etc.

Timing of the cross linking can be dependent upon the crosslinking functional group chosen. In the case of a photo reactive cross linker, the exposure of the CRISPR effector protein/CRISPR polynucleotide complex to, e.g., light, can occur after the CRISPR effector protein and CRISPR polynucleotide are mixed in solution together.

The duration of exposure to the light, e.g., UV light, can be from 1 second to 30 minutes. The duration of exposure to the light, e.g., UV light, can be less than two seconds, less than five seconds, less than ten seconds, less than twenty seconds, less than 30 seconds, less than 45 seconds, less than 50 seconds, less than one minute, less than two minutes, less than five minutes, less than ten minutes, less than fifteen minutes, less than twenty minutes, less than 30 minutes, less than 45 minutes.

2. Modifications to Modulate CRISPR Activity

In some cases, e.g., to increase the effectiveness of a CRISPR polynucleotide, e.g., gRNA or sgRNA, one or more modifications can be added to the CRISPR polynucleotide, e.g., gRNA or sgRNA that lower the off-target editing activity of the CRISPR polynucleotide in complex with a CRISPR enzyme. The one or more modifications can be at various locations, including at a sugar moiety, a phosphodiester linkage, and/or a base. For example, the CRISPR polynucleotide can comprise a backbone that comprises phosphoramide, phosphorothioate, phosphorodithioate, boranophosphate linkage, O-methylphosphoramidite linkages, and/or peptide nucleic acids. The one or more can comprise a 2'fluoro-arabino nucleic acid, tricycle-DNA (tc-DNA), peptide nucleic acid, cyclohexene nucleic acid (CeNA), locked nucleic acid (LNA), a locked nucleic acid (LNA) nucleotide comprising a methylene bridge between the 2' and 4' carbons of the ribose ring, bridged nucleic acids (BNA), ethylene-bridged nucleic acid (ENA), a phosphodiamidate morpholino, or a combination thereof.

The CRISPR polynucleotide modified with at least one unnatural nucleotide to crosslink to a CRISPR effector protein may comprise a sequence configured to facilitate a cleavage property. The cleavage property of the CRISPR polynucleotide modified with at least one unnatural nucleotide to crosslink to a CRISPR effector protein can be altered by a cleavable element that can alter the propensity of cleavage of the CRISPR polynucleotide at the point of its incorporation, under appropriate conditions. A "cleavable element" can comprise natural nucleotides or one or more modified nucleotides. The cleavable element can be incorporated into the CRISPR polynucleotide (e.g., sgRNA) during nucleic acid synthesis.

Two or more cleavable elements in a CRISPR polynucleotide can have different cleavage characteristics, e.g., the two or more cleavable elements, when incorporated into a CRISPR polynucleotide (e.g., sgRNA), can be selectively cleaved in each other's presence by using different agents and/or reaction conditions.

As used herein, the terms "cleaving," "cleaved" and "cleavage" can all relate to the scission of the CRISPR polynucleotide (e.g., sgRNA) substantially at each point of occurrence of a cleavable element in the CRISPR polynucleotide (e.g., sgRNA).

The cleavage can be initiated by an agent. The agent can be, e.g., a chemical entity or physical force that causes the cleavage of a cleavable element. The agent can be a chemical or combination of chemicals, a biomolecule or combination of biomolecules, normal or coherent (laser) visible or ultraviolet (UV) light, heat or other forms of electromagnetic energy. In some cases, a combination of agents, e.g., two or more agents, can be used simultaneously or sequentially to cleave a CRISPR polynucleotide (e.g., sgRNA). By simultaneously is meant a CRISPR polynucleotide (e.g., sgRNA) can be exposed to the two or more agents at the same time, although the two or more agents can react with the CRISPR polynucleotide (e.g., sgRNA) one at a time. By sequentially it is meant that the CRISPR polynucleotide (e.g., sgRNA) can be contacted with one agent and then a second agent at a later time.

A CRISPR polynucleotide comprising one or more unnatural nucleotides to crosslink to a CRISPR effector protein can comprise more than one type of cleavable element. In some examples, the first cleavable element and the second cleavable element have the same cleavage characteristics. In some examples, the second cleavable element has different cleavage characteristics than the first cleavable element. For example, the first cleavable element can be a photocleavable linker and the second cleavable element can be susceptible to cleavage by a chemical nuclease. In another example, the first cleavable element can be susceptible to cleavage by a chemical nuclease, and the second cleavable element can be engineered to be photocleavable allowing orthogonal treatment regimens to be applied. In some cases, the same cleavable element can have more than one type of cleavage characteristic. The first and second cleavable element can be any cleavable element described herein.

A cleavable element (e.g., cleavable linker) can refer to an entity that can connect two or more constituents of a CRISPR polynucleotide (e.g., sgRNA or crRNA) that renders the CRISPR polynucleotide (e.g., sgRNA or crRNA) susceptible to cleavage under appropriate conditions. For instance, the appropriate conditions can be exposure to UV light. The cleavable linker can comprise one or more modified or unmodified nucleotides, which are susceptible to scission under the appropriate conditions.

The cleavable linker can comprise a modified internucleoside linkage. The modified internucleoside linkage can be an internucleotide linkage that has a phosphorus atom or those that do not have a phosphorus atom. Internucleoside linkages containing a phosphorus atom therein include, for example, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, P-ethyoxyphosphodiester, P-ethoxyphosphodiester, P-alkyloxyphosphotriester, methylphosphonate, thionophosphoramidates, thionoalkylphosphonates, thionoalkylphosphotriesters, selenophosphates and boranophosphates, and nonphosphorus containing linkages, e.g., acetals and amides, such as are known in the art, having normal 3'-5' linkages, 2'-5' linked analogs of these, and those having inverted polarity wherein one or more internucleotide linkages is a 3' to 3', 5' to 5' or 2' to 2' linkage. Polynucleotides having inverted polarity can comprise a single 3' to 3' linkage at the 3'-most internucleotide linkage i.e. a single inverted nucleoside residue which may be abasic (the nucleobase is missing or has a hydroxyl group in place thereof).

Non-phosphorus containing internucleoside linkages include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and CH2 component parts. Other modified internucleoside linkages that do not contain a phosphorus atom therein include, —CH2-NH—O—CH2-, —CH2-N(CH3)-O—CH2-(known as a methylene (methylimino)backbone), —CH2-O—N (CH3)-CH2-, —CH2-N(CH3)-N(CH3)-CH2- and —O—N (CH3)-CH2-CH2-.

The cleavable linker can be non-nucleotide in nature. A "non-nucleotide" can refer to any group or compound that can be incorporated into a polynucleotide chain in the place of one or more nucleotide units, including either sugar and/or phosphate substitutions. The group or compound can be abasic in that it does not contain a commonly recognized nucleotide base, such as adenosine, guanine, cytosine, uracil or thymine, for example at the C1 position of the sugar.

Non-nucleotidic linkers can be e.g. abasic residues (dSpacer), oligoethyleneglycol, such as triethyleneglycol (spacer 9) or hexaethylenegylcol (spacer 18), or alkane-diol, such as butanediol. The spacer units can be preferably linked by phosphodiester or phosphorothioate bonds. The linker units may appear just once in the molecule or may be incorporated several times, e.g. via phosphodiester, phosphorothioate, methylphosphonate, or amide linkages. Further preferred linkers are alkylamino linkers, such as C3, C6, C12 aminolinkers, and also alkylthiol linkers, such as C3 or C6 thiol linkers. In some examples, heterobifunctional and homobifunctional linking moieties may be used to conjugate peptides and proteins to nucleotides. Examples include 5'-Amino-Modifier C6 and 3'-Amino-Modifier C6 reagents.

a. CRISPR ON

Provided herein are CRISPR ON polynucleotides that can be covalently crosslinked to CRISPR effector proteins to form CRISPR ON complexes. A CRISPR ON polynucleotide can comprise (i) a guide sequence configured to anneal to a target sequence in a target molecule (ii) a sequence (e.g., a tracrRNA sequence) configured to bind to a CRISPR effector protein, and (iii) a first sequence element 5' of the guide sequence. The first sequence element 5' of the guide sequence can be referred to as a polynucleotide leader sequence. The first sequence element can comprise a secondary structure, e.g., a stem loop. The stem loop can comprise from about 3 base pairs (bp) to about 30 bp. The 5' end of the first sequence element can be annealed to the base in the sequence element immediately 5' to the guide sequence. In some cases, the 5' end of the first sequence element is annealed to the guide sequence. The CRISPR ON polynucleotide can further comprise a first cleavable element, e.g., a first non-naturally occurring cleavable element, e.g., a photolabile linker. The cleavable element can be positioned immediately 5' of the guide sequence. The cleavable element can be susceptible to cleavage by light, small molecule, or one or more cellular processes. The polynucleotide leader sequence can interfere with the ability of the guide sequence to anneal to a target sequence.

Figure 17:
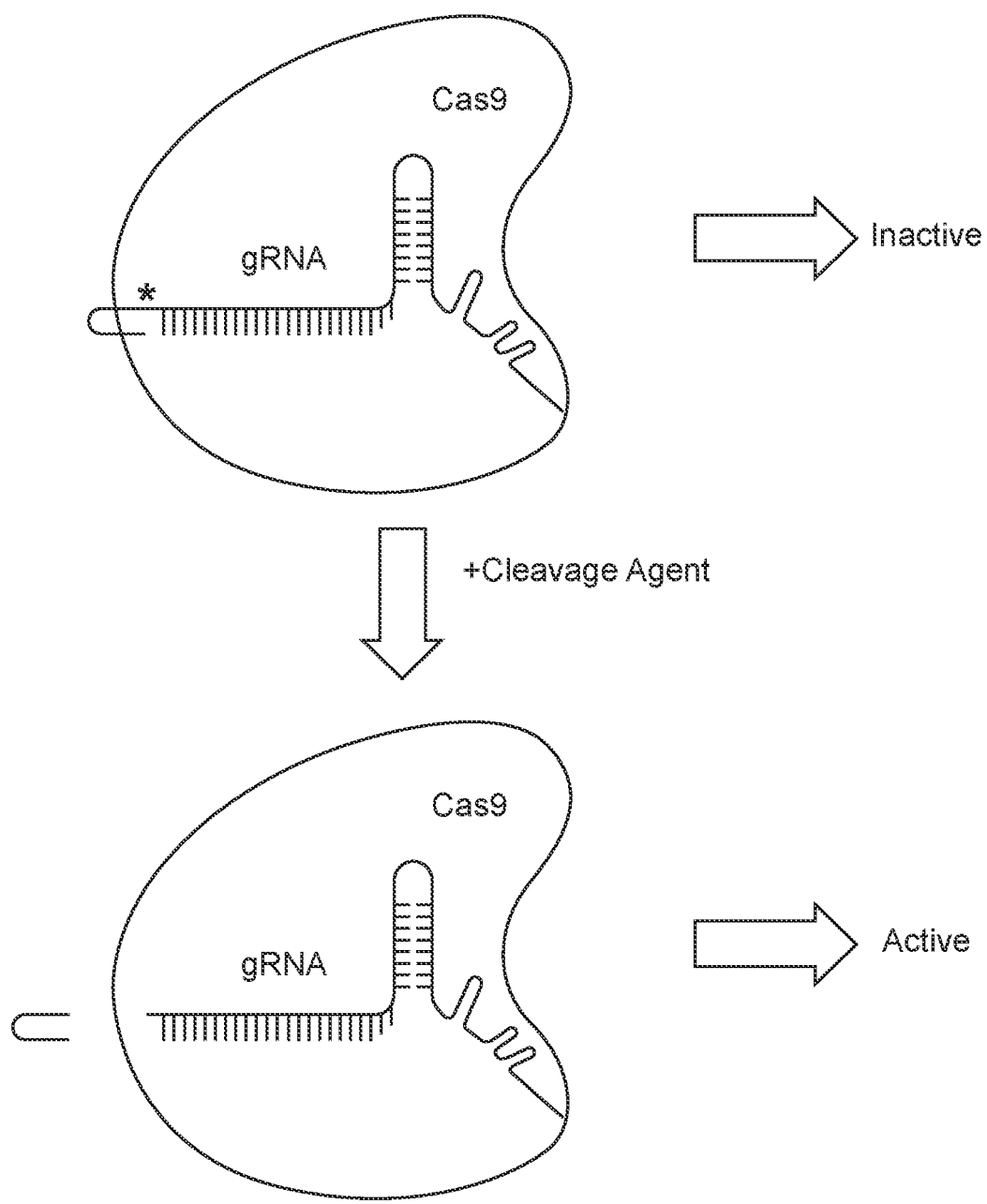
FIG. 17 shows an exemplary model of the activation of CRISPR-ON target cleavage activity. The inactive CRISPR complex comprises a CRISPR-ON single guide RNA (sgRNA) comprising an added stem-loop structure located at the 5' end of the canonical sgRNA complexed with a CRISPR effector protein, Cas9. The stem-loop structure can repress activity of the complex resulting in an inactive complex. Addition of cleavage agent can release the stem-loop structure, generating an active (ON) CRISPR complex that can allow genome editing to occur.

Complexes comprising a CRISPR effector protein and the crosslinked CRISPR ON polynucleotide (see e.g., FIG. 17A) can be assembled. A CRISPR complex comprising a crosslinked CRISPR ON polynucleotide with a first sequence element 5' of the guide sequence and a CRISPR effector protein can have a lower target specific activity than a CRISPR complex comprising a crosslinked CRISPR polynucleotide without the first sequence element; for example, the activity can be about 2-fold to about 100 fold lower. Provided herein are methods for the tunable targeting of a CRISPR complex to a target nucleic acid, e.g., DNA. The methods can comprise cleaving the cleavable element with a cleavage agent (see e.g., FIG. 17A), thereby releasing the first sequence element 5' of the guide sequence (see, e.g., FIG. 17C). For example, the cleavable element can be a photolabile linker, and the photolabile linker can be cleaved when exposed to light. Cleaving the cleavable linker can result in a CRISPR complex with higher target-specific cleavage activity than the CRISPR complex before the cleavage.

A CRISPR ON polynucleotide or CRISPR ON/OFF polynucleotide can comprise a first sequence element 5' of the guide sequence. The first sequence element 5' of the guide sequence can be referred to as a polynucleotide leader sequence. A CRISPR complex comprising a CRISPR polynucleotide with a polynucleotide leader sequence and a CRISPR effector protein crosslinked to the CRISPR polynucleotide can have a lower activity than a CRISPR complex comprising a CRISPR polynucleotide without the polynucleotide leader sequence. Removal of the polynucleotide leader sequence can result in a CRISPR complex with an increased activity (CRISPR ON).

i. Length of the Polynucleotide Leader Sequence

The polynucleotide leader sequence can range from about 1 nucleotide to about 50 nucleotides, e.g., about 5 nucleotides to about 30 nucleotides, about 10 nucleotides to about 20 nucleotides, about 15 nucleotides, or at least 4 nucleotides, 3 nucleotides to about 15 nucleotides, e.g., about 5 nucleotides to about 15 nucleotides, about 3 nucleotides to about 10 nucleotides, about 3 to about 15 nucleotides, or about 3 nucleotides to about 12 nucleotides, about 4 nucleotides to about 13 nucleotides, about 3 nucleotides to about 18 nucleotides, about 4 nucleotides to about 19 nucleotides, from 4 nucleotides to about 30 nucleotides, from 4 nucleotides to about 25 nucleotides, from 5 nucleotides to about 12 nucleotides, from 5 nucleotides to about at least 4 nucleotides, or 30 or fewer nucleotides in length.

ii. Composition of the Polynucleotide Leader Sequence

The polynucleotide leader sequence can comprise ribonucleotides and/or deoxyribonucleotides. The polynucleotide leader sequence can comprise non-canonical nucleotides or nucleotide analogues. The polynucleotide leader sequence can comprise any nucleotide or modified nucleotide or internucleotide linkage described herein. In some cases, the polynucleotide leader sequence can comprise any linker described herein.

iii. Secondary Structure in the Polynucleotide Leader Sequence

The polynucleotide leader sequence can form, or be designed to form, secondary structure. The secondary structure can be, e.g., a stem loop structure. The stem of the stem loop can comprise at least about 3 bp comprising complementary X and Y sequences (where X represents the sequence of one strand of the stem and Y represents the sequence of the other strand of the stem). The stem can comprise at least (or at most) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 base pairs. The stem can comprise a double stranded domain ranging from 1-20 bp, or from 2-5 bp, 2-9 bp, 3-10 bp, 4-9 bp, 5-10 bp, 5-20 bp, 6-20 bp, 7-20 bp, 8-20 bp etc. In some cases, the two strands of the stem can be covalently cross-linked.

The stem loop can comprise a single-stranded loop. The single-stranded loop can range from 1-50 bases, e.g., 3-5 bases, 3-7 bases, 4-10 bases, 5-20 bases, 6-25 bases, 3-25 bases, 3-30 bases, 4-30 bases, or 4-50 bases.

The 5' most base of the stem loop, or of the polynucleotide leader sequence, can anneal to a base in the polynucleotide leader sequence immediately 5' of the guide sequence. In some cases, the 5' most base of the polynucleotide leader sequence can anneal to a base 1-20 bases 3' of the 5' most base of the guide sequence, e.g., 2 bases, 3 bases, 4 bases, 5 bases, 6 bases, 7 bases, 8 bases, 9 bases, 10 bases, 11 bases, 12 bases, 15 bases, or 20 bases 3' of the 5' most base of the guide sequence. In some cases, the polynucleotide leader sequence does not comprise a base that base pairs to a base in the guide sequence.

The polynucleotide leader sequence can form a hairpin loop or stem-loop structure comprising one or more bulges (regions of single stranded sequence; these regions can correspond to positions comprising less than 100% sequence base-pairing in the secondary structure). The number, length, and/or position of the one or more bulges can vary and can affect the overall stability of the stem-loop structure.

The polynucleotide leader sequence can comprise 2, 3, 4, 5 or more bulges when optimally folded.

In some cases, the polynucleotide leader sequence can comprise non-polynucleotide moieties. The non-nucleotide moieties in the polynucleotide leader sequence can be biotin, antibodies, peptides, affinity, reporter or protein moieties (such as NHS esters or isothiocyanates), digoxigenin, enzymes such as alkaline phosphatase etc.

In some cases, the polynucleotide leader sequence lacks secondary structure. The polynucleotide leader sequence can comprise or consist of a single stranded contiguous stretch of nucleotides.

The melting temperature of a stem loop formed by the polynucleotide leader sequence can be about 25° C. to about 60° C., or about 30° C. to about 50° C., or about 40° C. to about 50° C.

iv. Activity Reduction by Polynucleotide Leader Sequence

A CRISPR complex comprising a CRISPR polynucleotide with a polynucleotide leader sequence and a CRISPR effector protein crosslinked to the CRISPR polynucleotide can have a lower activity than a CRISPR complex comprising a CRISPR polynucleotide without the polynucleotide leader sequence. In some cases, the activity is at least (or at most) 0.1-fold, 0.25 fold, 0.5 fold, 0.75 fold, 1 fold, 2 fold, 5 fold, 10 fold, 50 fold, 100 fold, or 1000 fold lower. In some cases, a CRISPR complex comprising a CRISPR polynucleotide with a polynucleotide leader sequence and a CRISPR effector protein has no activity. The activity can be, e.g., enzymatic activity or transcriptional activation activity. For example, when the CRISPR effector protein is a catalytically active Cas protein, the CRISPR complex can be unable to cleave target nucleic acid. In another example, when the CRISPR effector protein is a catalytically dead Cas protein fused to a transcription activation domain, the CRISPR complex can be unable to activate transcription of a target gene.

v. Removing the Polynucleotide Leader Sequence

The CRISPR polynucleotide can comprise one or more cleavable elements to permit release of the polynucleotide leader sequence. The one or more cleavable elements can be between the polynucleotide leader sequence and the guide sequence. In some cases, the one or more cleavable elements are within the polynucleotide leader sequence. In some cases, at least one cleavable element is within the polynucleotide leader sequence and at least one cleavable element is between the polynucleotide leader sequence and the guide sequence. In some cases, the one or more cleavable elements are positioned 5' of the guide sequence. The one or more cleavable elements can be at least, or at most, 2, 3, 4, 5, 6, 7, 8, 9 or 10 cleavable elements. In some cases, the one or more cleavable elements are positioned such that following cleavage, part of the polynucleotide leader sequence (e.g., 1 base, 2 bases, 5 bases, or 10 bases) remains covalently linked to the guide sequence. In some cases, the one or more cleavable elements are positioned such that following cleavage, none of the polynucleotide leader sequence remains covalently attached to the guide sequence.

The one or more cleavable elements can be any cleavable element described herein. The one or more cleavable elements can be the same type of cleavable element or different types of cleavable elements.

The CRISPR polynucleotide can be cleaved at the one or more cleavable elements while the CRISPR polynucleotide is not bound to a CRISPR effector protein. The CRISPR polynucleotide can be cleaved at the one or more cleavable elements while the CRISPR polynucleotide is crosslinked with a CRISPR effector protein. The CRISPR polynucleotide can be cleaved at the one or more cleavable elements while the CRISPR polynucleotide is crosslinked with a CRISPR effector protein and bound to a target sequence. In some cases, the polynucleotide leader sequence prevents the CRISPR polynucleotide from crosslinking with a CRISPR effector protein or reduces the ability of the CRISPR polynucleotide to crosslink to the CRISPR effector protein relative to a CRISPR polynucleotide that lacks the polynucleotide leader sequence; cleavage of the polynucleotide leader sequence from the CRISPR polynucleotide can increase the ability of the CRISPR polynucleotide to bind a CRISPR effector protein.

The CRISPR polynucleotide can be cleaved at the one or more cleavable elements in vitro. The CRISPR polynucleotide can be cleaved at the one or more cleavable elements while in a cell or organism, e.g., mouse, rabbit, goat, primate, e.g., chimpanzee, gorilla, or human.

The timing of the cleaving of the CRISPR polynucleotide at the one or more cleavable elements can vary. For example, the one or more cleavable elements can be cleaved immediately after the CRISPR polynucleotide is introduced into a cell or organism, or at least (or at most) 0.25, 0.5, 0.75, 1, 2, 3, 4, 5, 6, 7, 8, 9, 10, 11, 12, 13, 14, 15, 16, 17, 18, 19, 20, 21, 22, 23, 24, 48, 72, or 96 hours after introduction into a cell or organism.

A CRISPR polynucleotide can be exposed to a cleavage agent once. The CRISPR polynucleotide can be subjected to a cleavage agent more than once, e.g., 2 times, 3 times, 5 times, or 10 times. The CRISPR polynucleotide can be exposed to more than one type of cleavage agent, e.g., at least (or at most) 2, 3, 4, 5, 6, 7, 8, 9, or 10 cleavage agents.

A CRISPR polynucleotide can be exposed to a cleavage agent for varying durations. For example, a CRISPR polynucleotide can be exposed to a cleavage agent for 0.1 min, 0.5 min, 1 min, 2 min, 3 min, 4 min, 5 min, 10 min, 30 min, 60 min, 2 hr, 4 hr, 6 hr, 12 hr, 24 hr, 48 hr, 72 hr, or 96 hr.

In some cases, a sample comprises a plurality of CRISPR polynucleotides, and a cleavage agent can be used to cleave a certain percentage of the CRISPR polynucleotides. For example, a cleaving agent can be used to cleave at least (or at most) 5%, 10%, 15%, 20%, 25%, 30%, 35%, 40%, 45%, 50%, 55%, 60%, 65%, 70%, 75%, 80%, 85%, 90%, 95%, or 99% of the CRISPR polynucleotides in the sample. A dose of a cleaving agent can be used to cleave 100% of the CRISPR polynucleotides in the sample. The amount of cleavage can occur over at least (or at most) 1 min, 5 min, 10 min, 15 min, 30 min, 45 min, 1 hr, 2 hr, 6 hr, 12 hr, 24 hr, 48 hr, 72 hr, or 96 hr.

The release of the polynucleotide leader sequence can result in an increase in activity of a CRISPR effector protein (e.g., CRISPR enzyme, e.g., Cas9) bound to the CRISPR polynucleotide. In some cases, in a sample, release of the polynucleotide leader sequence results in at least a 0.1-fold, 0.25-fold, 0.5 fold, 0.75 fold, 1 fold, 2 fold, 5 fold, 10 fold, 50 fold, 100 fold, or 1000 fold increase in activity.

vi. Other Features

The CRISPR polynucleotide comprising a polynucleotide leader sequence can comprise a second set of one or more elements that can be subjected to a specific modification to generate a modified CRISPR polynucleotide that, when complexed with CRISPR effector protein, forms a second CRISPR complex with a lower target-specific cleavage activity. The second set of one or more elements can be a second set of one or more cleavable elements. For example, a CRISPR polynucleotide can comprise a polynucleotide leader sequence and a first set of one or more cleavable elements configured to permit release of the polynucleotide leader sequence and a second set of one or more cleavable elements configured to permit cleavage of the remaining CRISPR polynucleotide; this polynucleotide can be referred to as a CRISPR ON/OFF polynucleotide.

b. CRISPR OFF

Figure 18:
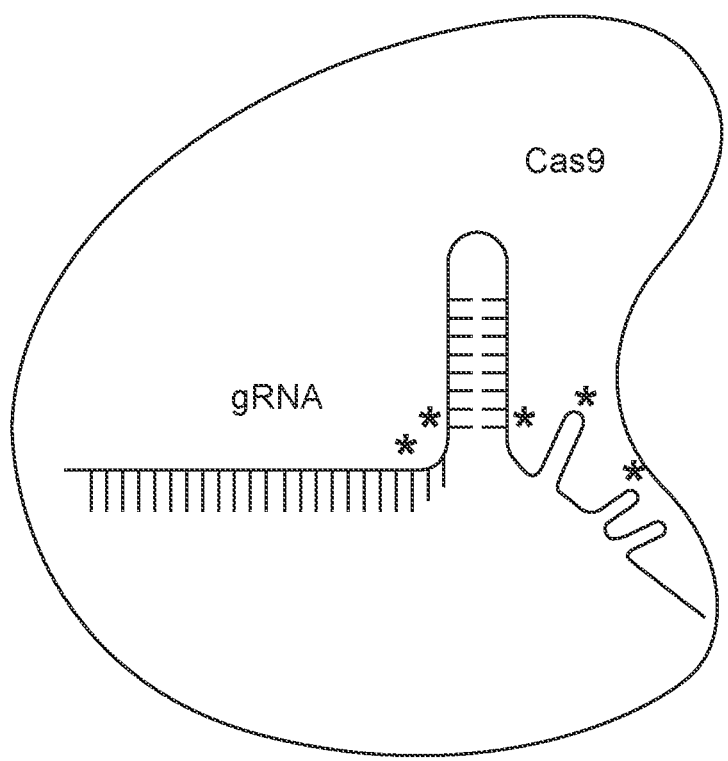
FIG. 18 shows exemplary positions of cleavable linkers in CRISPR-OFF sgRNA.

Provided herein are CRISPR OFF polynucleotides that can be crosslinked with CRISPR effector proteins to form CRISPR OFF complexes. A CRISPR OFF polynucleotide can comprise (i) a sequence (e.g., tracrRNA sequence) configured to bind a CRISPR effector protein and (ii) a cleavable linker. In some cases, the CRISPR OFF polynucleotide further comprises a guide sequence configured to anneal to a target sequence in a target molecule. The cleavable linker can be a non-naturally occurring cleavable linker. If the CRISPR OFF polynucleotide comprises the guide sequence, the cleavable linker can be positioned 3' of the 5' most base in the guide sequence (see, e.g., FIG. 18). The cleavable linker can be positioned within the sequence configured to crosslink the CRISPR effector protein (e.g., a tracrRNA sequence). In some cases, a base immediately 3' and/or immediately 5' of a cleavable linker is not annealed to another base in the CRISPR OFF polynucleotide. The cleavable linker can be a photolabile linker. The cleavable linker can be susceptible to cleavage by light, small molecule, or one or more cellular processes.

The off-target editing activity of a CRISPR effector protein complexed with a CRISPR OFF polynucleotide can be less than the off-target editing activity of a CRISPR effector protein complexed with a non-CRISPR-OFF polynucleotide, e.g., an sgRNA without one or more cleavable linkers. The off-target editing activity (e.g., as measured as described herein) can be reduced by a factor of: about 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60; at least 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60; or at most 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60. In some cases, the reduction occurs in the absence of exposure to a cleavage agent, e.g., UV light; in some cases, the reduction occurs after exposure to a cleavage agent. Complexes comprising a CRISPR effector protein complexed with a CRISPR OFF polynucleotide with a cleavable linker at positions 57 and/or 74 can have a lower off-target editing efficiency than a CRISPR effector protein complexed with an sgRNA without a cleavable linker. Complexes comprising a CRISPR effector protein complexed with a CRISPR OFF polynucleotide can have an on-target editing efficiency that is the same or is within 1%, 2%, 3%, 4%, or 5% of that of a CRISPR effector protein complexed with a non-CRISPR OFF polynucleotide. E.g., an sgRNA without a cleavable linker.

Complexes comprising a CRISPR effector protein crosslinked to the CRISPR OFF polynucleotide can be assembled. Provided herein are methods for the tunable targeting of a CRISPR complex to a target DNA. The methods can comprise cleaving the cleavable linker. Cleavage of the cleavable linker can result in a CRISPR complex with a lower target-specific cleavage activity than before the cleavage. In some cases, cleavage of the cleavable linker can cause the fragments of the CRISPR OFF polynucleotide generated by the cleaving, but not crosslinked to the CRISPR effector protein, to dissociate from the CRISPR effector protein. In some cases, cleavage of the cleavable linker renders a CRISPR complex inactive.

i. Position of the One or More Cleavable Elements

The one or more cleavable elements can be positioned 3' of the 5'-most base (or nucleotide) in the guide sequence or 5' of the 3' most base (or nucleotide) in the guide sequence. The one or more cleavable elements can be positioned about 1-30 bases 3' of the 5' end of the crRNA or guide sequence, e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases. The one or more cleavable elements can be positioned about 1-30 bases 3' from the 3' end of the crRNA sequence or guide sequence, e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases.

The one or more cleavable elements can be positioned in the sequence of the CRISPR polynucleotide, e.g., tracrRNA sequence, configured to bind to a CRISPR effector protein (e.g., Cas9). In some cases, the one or more cleavable elements can be 1-30 bases 3' of the 5' end of the tracr sequence, such as 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases. In some cases, the one or more cleavable elements can be 1-30 bases 5' of the 3' end of the tracr sequence, such as 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases.

In some examples, the one or more cleavable elements can be positioned immediately 5' or 3' of base (or nucleotide) 56 and/or nucleotide 73 in the CRISPR polynucleotide (e.g., sgRNA), wherein the 5'-most nucleotide of the guide sequence of the CRISPR polynucleotide (e.g., sgRNA) is nucleotide 1, or replace nucleotide 57 and/or nucleotide 74. In some examples, the one or more cleavable elements can be positioned immediately 5' or 3' of base (or nucleotide) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a CRISPR polynucleotide (e.g., sgRNA), wherein the 5'-most base (or nucleotide) of the guide sequence of the CRISPR polynucleotide (e.g., sgRNA) is base (or nucleotide) 1 or replace base 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a CRISPR polynucleotide (e.g., sgRNA).

ii. Impact of the One or More Cleavage Elements Before Exposure to a Cleavage Agent In some cases, a CRISPR polynucleotide (e.g., sgRNA) comprising the one or more cleavable elements and complexed with a CRISPR effector protein (e.g., Cas9) does not have a reduced activity relative to a CRISPR polynucleotide (e.g., sgRNA) without the one or more cleavable elements and complexed to a CRISPR effector protein (e.g., before exposing the CRISPR polynucleotide to a cleavage agent). In some cases, a CRISPR polynucleotide (e.g., sgRNA) comprising the one or more cleavable elements and complexed with a CRISPR effector protein (e.g., Cas9) does have a reduced activity relative to a CRISPR polynucleotide (e.g., sgRNA) without the one or more cleavable elements and complexed to a CRISPR effector protein (e.g., before exposing the CRISPR polynucleotide to a cleavage agent).

iii. Cleavage of the One or More Cleavable Elements

The one or more cleavable elements can be any cleavable element described herein. The one or more cleavable elements can be the same type of cleavable element or different types of cleavable elements. The one or more cleavable elements can be at least, or at most, 2, 3, 4, 5, 6, 7, 8, 9 or 10 cleavable elements.

The CRISPR polynucleotide (e.g., sgRNA) can be cleaved at the one or more cleavable elements while the CRISPR polynucleotide (e.g., sgRNA) is not bound to a CRISPR effector protein (e.g., Cas9). The CRISPR polynucleotide (e.g., sgRNA) can be cleaved at the one or more cleavable elements while the CRISPR polynucleotide (e.g., sgRNA) is complexed with a CRISPR effector protein (e.g., Cas9). The CRISPR polynucleotide (e.g., sgRNA) can be cleaved at the one or more cleavable elements while the CRISPR polynucleotide (e.g., sgRNA) is complexed with a CRISPR effector protein (e.g., Cas9) and bound to a target sequence. In some cases, following cleavage, one or more of the resulting fragments of the CRISPR polynucleotide (e.g., sgRNA) remains bound to the CRISPR effector protein (e.g., Cas9). In some cases, following cleavage, one or more (or all) of the resulting fragments of the CRISPR polynucleotide (e.g., sgRNA) no longer bind, or are no longer capable of binding to, a CRISPR effector protein (e.g., Cas9).

The CRISPR polynucleotide can be cleaved at the one or more cleavable elements in vitro. The CRISPR polynucleotide can be cleaved at the one or more cleavable elements in vivo. The CRISPR polynucleotide can be cleaved at the one or more cleavable elements while in a cell or organism, e.g., mouse, rabbit, goat, primate, e.g., chimpanzee, gorilla, or human.

The timing of the cleaving of the CRISPR polynucleotide (e.g., sgRNA) at the one or more cleavable elements can vary. For example, the one or more cleavable elements can be cleaved immediately after the CRISPR polynucleotide (e.g., sgRNA) is introduced into a cell or organism, or at least (or at most) 0.25, 0.5, 0.75, 1, 2, 3, 4, 5, 6, 7, 8, 9, 10, 11, 12, 13, 14, 15, 16, 17, 18, 19, 20, 21, 22, 23, 24, 48, 72, or 96 hours after introduction into a cell or organism.

A CRISPR polynucleotide (e.g., sgRNA) can be exposed to a cleavage agent once. A CRISPR polynucleotide (e.g., sgRNA) can be subjected to a cleavage agent more than once, e.g., 2 times, 3 times, 5 times, or 10 times. The CRISPR polynucleotide (e.g., sgRNA) can be exposed to more than one type of cleavage agent, e.g., at least (or at most) 2, 3, 4, 5, 6, 7, 8, 9, or 10 cleavage agents.

A CRISPR polynucleotide (e.g., sgRNA) can be exposed to a cleavage agent for varying durations. For example, a CRISPR polynucleotide (e.g., sgRNA) can be exposed to a cleavage agent for 0.1 min, 0.5 min, 1 min, 2 min, 3 min, 4 min, 5 min, 10 min, 30 min, 60 min, 2 hr, 4 hr, 6 hr, 12 hr, 24 hr, 48 hr, 72 hr, or 96 hr.

In some cases, a sample comprises a plurality of CRISPR polynucleotides (e.g., sgRNAs), and a cleavage agent can be used to cleave a certain percentage of the CRISPR polynucleotides (e.g., sgRNAs). For example, a cleaving agent can be used to cleave at least (or at most) 5%, 10%, 15%, 20%, 25%, 30%, 35%, 40%, 45%, 50%, 55%, 60%, 65%, 70%, 75%, 80%, 85%, 90%, 95%, or 99% of the CRISPR polynucleotides (e.g., sgRNAs) in the sample. A dose of a cleaving agent can be used to cleave 100% of the CRISPR polynucleotides (e.g., sgRNAs) in the sample. The amount of cleavage can occur over at least (or at most) 1 min, 5 min, 10 min, 15 min, 30 min, 45 min, 1 hr, 2 hr, 6 hr, 12 hr, 24 hr, 48 hr, 72 hr, or 96 hr.

Cleavage can result in a decrease in activity of a CRISPR effector protein (e.g., CRISPR enzyme, e.g., Cas9) bound to the CRISPR polynucleotide (e.g., sgRNA). In some cases, in a sample, exposure to one or more cleavage agents results in at least a 0.1-fold, 0.25-fold, 0.5 fold, 0.75 fold, 1 fold, 2 fold, 5 fold, 10 fold, 50 fold, 100 fold, or 1000 fold decrease in activity. In some cases, in a sample, exposure to one more cleavage agents results in complete loss of activity.

c. CRISPR ON/OFF

Provided herein are CRISPR "ON/OFF" polynucleotides that can be crosslinked with CRISPR effector proteins to form CRISPR "ON/OFF" complexes. A CRISPR ON/OFF polynucleotide can comprise a guide sequence configured to anneal to a target sequence in a target molecule, a sequence (e.g., a tracrRNA sequence) configured to crosslink to a CRISPR effector protein, and (a) a first element configured to be subjected to a first specific modification that generates a first modified polynucleotide that, when crosslinked with a CRISPR effector protein, forms a first CRISPR complex with higher target-specific cleavage activity than a CRISPR complex comprising the polynucleotide that has not had been subjected to the first specific modification, and (b) a second element configured to be subjected to a second specific modification to generate a second modified polynucleotide that, when crosslinked with CRISPR effector protein, forms a second CRISPR complex with a lower target-specific cleavage activity than the first CRISPR complex. A CRISPR ON/OFF polynucleotide can comprise features of CRISPR ON polynucleotides and CRISPR OFF polynucleotides described herein.

Complexes comprising a CRISPR effector protein crosslinked to the CRISPR ON/OFF polynucleotide can be assembled. Provided herein are methods for the tunable targeting of a CRISPR complex to a target DNA. The methods can comprise subjecting the first element of the CRISPR ON/OFF polynucleotide to a first specific modification, thereby generating the first modified polynucleotide that, when crosslinked with the CRISPR effector protein, forms the first CRISPR complex with higher target-specific cleavage activity than the CRISPR complex comprising the polynucleotide that has not had been subjected to the first specific modification. The methods can further comprise subjecting the second element to the second specific modification after the subjecting the first element to the first modification, thereby forming the second modified polynucleotide that, when crosslinked with CRISPR effector protein, forms a second CRISPR complex with a lower target-specific cleavage activity than the first CRISPR complex. In some cases, the second modification can cause portions of the CRISPR polynucleotide not crosslinked to the CRISPR effector protein to fragment and/or dissociate from the CRISPR effector protein.

d. CRISPR OFF Polynucleotides and Reduced Off-Target Editing

The CRISPR polynucleotide can comprise one or more modifications such that, when the polynucleotide is complexed with a CRISPR effector protein, (e.g., Cas9), to form a CRISPR complex, the CRISPR complex has a lower off-target cleavage activity than a CRISPR complex with a polynucleotide without the one or more modifications when not exposed to light. The one or more modifications can be one or more linkers described herein. The one or more modifications can be one or more cleavable linkers described herein. The one or more modifications can be one or more modifications at a 2' position of a ribose as described herein. The one or more modifications can be one or more cleavable elements. The one or more modifications can comprise 3-(4,4'-Dimethoxytrityl)-1-(2-nitrophenyl)-propan-1-yl-[(2-cyanoethyl)-(N,N-diisopropyl)]-phosphoramidite. The CRISPR OFF polynucleotide can further comprise 2'-O-methyl analogs and 3' phosphorothioate internucleotide linkages at the first three 5' and 3' terminal RNA nucleotides. A. Position of the one or more modifications The one or more modifications can be positioned 3' of the 5'-most base (or nucleotide) in the guide sequence or 5' of the 3' most base (or nucleotide) in the guide sequence. The one or more modifications can be positioned about 1-30 bases 3' of the 5' end of the crRNA or guide sequence, e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases. The one or more modifications can be positioned about 1-30 bases 3' from the 5' end of the crRNA sequence or guide sequence, e.g., 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases.

Figure 1:
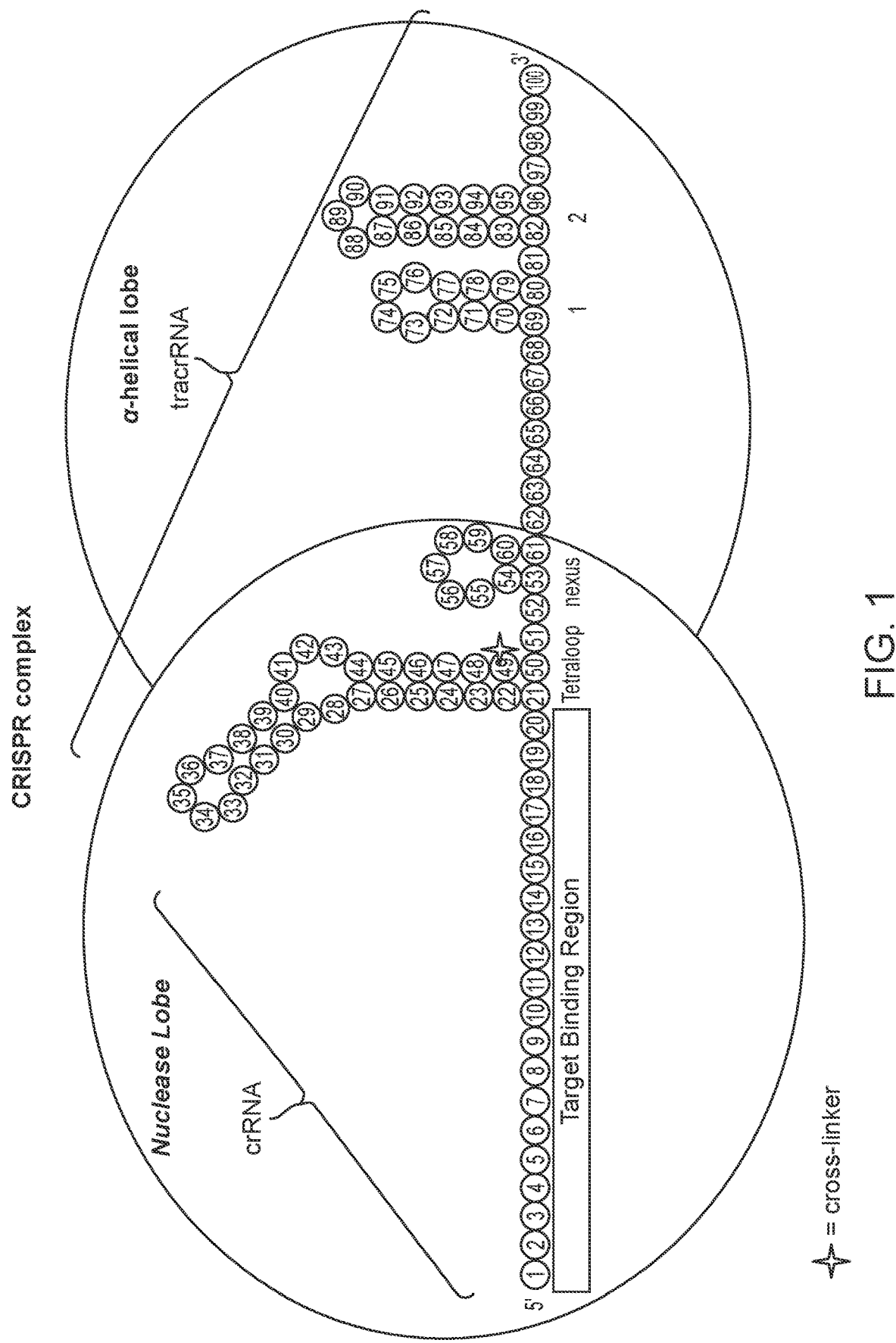
FIG. 1 shows a simplified diagram of a CRISPR complex wherein the polynucleotide is a single guide RNA (sgRNA). The star indicates an exemplary position of an unnatural nucleotide for cross-linking the polynucleotide to the Cas nuclease. The bar indicates the target binding region of the polynucleotide.

The one or more modifications can be positioned in the sequence of the CRISPR polynucleotide, e.g., tracrRNA sequence, configured to bind to a CRISPR effector protein (e.g., Cas9). In some cases, the one or more modifications can be in a tetraloop, nexus, stem loop 1, or stem loop 2 of the CRISPR polynucleotide shown in FIG. 1. In some cases the one or more modifications can be a loop of the tetraloop, a bulge of the tetraloop, a first stem of the tetraloop, a second stem of the tetraloop, in a loop structure of the nexus, in the stem of the nexus, in a loop structure of stem loop 1, in a stem of stem loop 1, in a loop structure of stem loop 2, or in a stem of stem loop 2; examples of the tetraloop, nexus, stem loop1, and stem loop 2 are illustrated in FIG. 1. In some cases, the one or more modifications does not include sequence 5' of the guide sequence configured to form a stem loop, e.g., with the guide sequence. In some cases, the one or more modifications can be 1-30 bases 3' of the 5' end of the tracr sequence, such as 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases. In some cases, the one or more modifications can be 1-30 bases 5' of the 3' end of the tracr sequence, such as 2 bases, 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, or 30 bases.

In some examples, the one or more modifications can be positioned immediately 5' or 3' of base (or nucleotide) 56 and/or nucleotide 73 in the CRISPR polynucleotide (e.g., sgRNA), wherein the 5'-most nucleotide of the guide sequence of the CRISPR polynucleotide (e.g., sgRNA) is nucleotide 1, or replace nucleotide 57 and/or nucleotide 74. In some examples, the one or more complex altering elements can be positioned immediately 5' or 3' of base (or nucleotide) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a CRISPR polynucleotide (e.g., sgRNA), wherein the 5'-most base (or nucleotide) of the guide sequence of the CRISPR polynucleotide (e.g., sgRNA) is base (or nucleotide) 1 or replace base 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a CRISPR polynucleotide (e.g., sgRNA).

B. Impact of the One or More Modifications

In some cases, a CRISPR polynucleotide (e.g., sgRNA) comprising the one or more modifications and complexed with a CRISPR effector protein (e.g., Cas9) does not have a reduced editing activity at a target sequence relative to a CRISPR polynucleotide (e.g., sgRNA) without the one or more modifications and complexed to a CRISPR effector protein (e.g., before exposing the CRISPR polynucleotide to a cleavage agent). In some cases, a CRISPR polynucleotide (e.g., sgRNA) comprising the one or more modifications and complexed with a CRISPR effector protein (e.g., Cas9) does have a reduced editing activity at a target sequence relative to a CRISPR polynucleotide (e.g., sgRNA) without the one or more complex altering elements and complexed to a CRISPR effector protein (e.g., before exposing the CRISPR polynucleotide to a cleavage agent). In some cases, editing activity at a target sequence is reduced about 1%, 2%, 3%, 4%, 5%, 6%, 7%, 8%, 9%, or 10% or at most 1%, 2%, or 3%, 4%, 5%, 6%, 7%, 8%, 9%, or 10% relative to a standard CRISPR complex.

In some cases, a CRISPR polynucleotide (e.g., sgRNA) comprising the one or more modifications and complexed with a CRISPR effector protein (e.g., Cas9) has a reduced editing activity at an off-target sequence relative to a CRISPR polynucleotide (e.g., sgRNA) without the one or more modifications and complexed to a CRISPR effector protein (e.g., before exposing the CRISPR polynucleotide to a cleavage agent). Editing activity at an off-target sequence can be described as off-target editing. Off-target editing can be editing at a sequence that is not exactly complementary to the guide sequence of the CRISPR polynucleotide. In some cases, the editing activity at an off-target sequence is reduced about, at least, or at most 5%, 10%, 15%, 20%, 25%, 30%, 40%, 50%, 60%, 70%, 80%, 90%, or 100%. In some cases, the off-target editing activity is 0%, 1%, 5%, 10%, 20%, 25%, 30%, 40%, 50%, 60%, 70%, 80%, 90%, or 95%. In some cases, the off-target editing activity is less than 1%, 5%, 10%, 15%, 20%, 25%, 30%, 40%, 50%, 60%, 70%, 80%, 90%, or 95%. In some cases, the off-target editing activity is 0%-5%, 5%-10%, 10%-25%, 25%-50%, 50%-75%, or 75%-95%.

The off-target editing activity of a CRISPR effector protein complexed with a CRISPR OFF polynucleotide without exposure to light can be less than the off-target editing activity of a CRISPR effector protein complexed with a non-CRISPR-OFF polynucleotide, e.g., an sgRNA modified only with 2'-O-methyl analogs and 3' phosphorothioate internucleotide linkages at the first three 5' and 3' terminal RNA nucleotides. The off-target editing activity of a CRISPR effector protein complexed with a CRISPR OFF polynucleotide when not cleaved (e.g., when not exposed to light) can be statistically lower, with a p-value≤0.05, ≤0.01, ≤0.005, ≤0.001, ≤0.0005, or ≤0.0001, than a CRISPR effector protein complexed with a non-CRISPR-OFF polynucleotide. The off-target editing activity (e.g., as measured as described herein) can be reduced by a factor of: about 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60; at least 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60; or at most 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60. In some cases, complexes comprising a CRISPR effector protein complexed with a CRISPR OFF polynucleotide with a modification at positions 57 and/or 74 can have a lower off-target editing efficiency than a CRISPR effector protein complexed with an sgRNA without a cleavable linker when not cleaved (e.g., when not exposed to light or another cleavage-inducing treatment). Complexes comprising a CRISPR effector protein complexed with a CRISPR OFF polynucleotide when not cleaved (e.g., when not exposed to light or another cleavage-inducing treatment) can have an on-target editing efficiency that is the same or is within 1%, 2%, 3%, 4%, or 5% of that of a CRISPR effector protein complexed with a non-CRISPR OFF polynucleotide, e.g., an sgRNA without a cleavable linker.

In some cases, the off-target editing activity is measured at one nucleic acid region. The off-target editing activity can be measured at more than one genomic region (e.g., gene). The off-target editing activity can be measured at 1, 2, 3, 4, 5, 6, 7, 8, 9, 10, 25, 50, 75, or 100 genomic regions (e.g., genes). The off-target editing activity can be measured at 1, 2, 3, 4, 5, 6, 7, 8, 9, 10, 25, 50, 75, 100, 1000, or 10,000 genomic regions (e.g., genes). The off-target editing activity can be measured at most 1, 2, 3, 4, 5, 6, 7, 8, 9, 10, 25, 50, 75, 100, 1000, or 10,000 genomic regions (e.g., genes).

The off-target editing activity can be measured by analyzing nucleic acid molecules from a cell contacted by CRISPR complex. The measurement can be made using nucleic acid molecules extracted from the cells, about, or at most 30 minutes, 1 hours, 2 hours, 5 hours, 10 hours, 12 hours, 24 hours, 36 hours, 48 hours, 60 hours, 72 hours, 4 days, 5 days, or 6 days after transfection. The CRISPR complex can be introduced into the cell by transformation. The nucleic acid molecules can be analyzed by, e.g., sequencing, PCR, mass spectrometry, southern blot, etc. The off-target editing can be visualized, e.g., by presenting data in, e.g., graph, e.g., scatterplot.

CRISPR complexes comprising a CRISPR polynucleotide can be used to reduce off-target editing as compared to Cas9 complexed with an sgRNA without a modification as described herein. Off-target editing can be determined using ICE (Inference of CRISPR Editing) to measure the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv or deep-sequencing techniques as described in Tsai et al. "GUIDE-seq enables genome-wide profiling of off-target cleavage by CRISPR-Cas nucleases", Nature Biotechnology 33, 187-197 (2015). Off target editing sites can have sequences that have a high percent sequence identity to the target sequence. The sequence identity can be less than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31% or 30%. Off target editing sites can have sequences that are close in proximity to a PAM region, for example mismatches between the guide RNA and DNA may be tolerated at the 5' end of the protospacer (distal to the PAM) to produce an off-target edit. Those of skill in the art readily understand how to determine sequence identity between two nucleic acids. For example, the sequence identity can be calculated after aligning the two sequences so that the sequence identity is at its highest level. Another way of calculating sequence identity can be performed by published algorithms. Optical alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/b12seq/b12.html), or by inspection.

e. Cleavable Elements

The one or more cleavable elements can be any cleavable element described herein.

i. Types of Cleavable Elements

The cleavage property of the CRISPR polynucleotide can be altered by a cleavable element that can alter the propensity of cleavage of the CRISPR polynucleotide at the point of its incorporation, under appropriate conditions. A "cleavable element" can comprise natural nucleotides or one or more modified nucleotides. The cleavable element can be incorporated into the CRISPR polynucleotide (e.g., sgRNA) during nucleic acid synthesis.

Two or more cleavable elements in a CRISPR polynucleotide can have different cleavage characteristics, e.g., the two or more cleavable elements, when incorporated into a CRISPR polynucleotide (e.g., sgRNA), can be selectively cleaved in each other's presence by using different agents and/or reaction conditions.

As used herein, the terms "cleaving," "cleaved" and "cleavage" can all relate to the scission of the CRISPR polynucleotide (e.g., sgRNA) substantially at each point of occurrence of a cleavable element in the CRISPR polynucleotide (e.g., sgRNA).

The cleavage can be initiated by an agent. The agent can be, e.g., a chemical entity or physical force that causes the cleavage of a cleavable element. The agent can be a chemical or combination of chemicals, a biomolecule or combination of biomolecules, normal or coherent (laser) visible or ultraviolet (UV) light, heat or other forms of electromagnetic energy. In some cases, a combination of agents, e.g., two or more agents, can be used simultaneously or sequentially to cleave a CRISPR polynucleotide (e.g., sgRNA). By simultaneously is meant a CRISPR polynucleotide (e.g., sgRNA) can be exposed to the two or more agents at the same time, although the two or more agents can react with the CRISPR polynucleotide (e.g., sgRNA) one at a time. By sequentially is meant that the CRISPR polynucleotide (e.g., sgRNA) can be contacted with one agent and then a second agent at a later time.

A CRISPR polynucleotide (e.g., sgRNA) can comprise more than one type of cleavable element. In some examples, the first cleavable element and the second cleavable element have the same cleavage characteristics. In some examples, the second cleavable element has different cleavage characteristics than the first cleavable element. For example, the first cleavable element can be a photocleavable linker and the second cleavable element can be susceptible to cleavage by a chemical nuclease. In another example, the first cleavable element can be susceptible to cleavage by a chemical nuclease, and the second cleavable element can be engineered to be photocleavable allowing orthogonal treatment regimens to be applied. In some cases, the same cleavable element can have more than one type of cleavage characteristic. The first and second cleavable element can be any cleavable element described herein.

A cleavable element (e.g., cleavable linker) can refer to an entity that can connect two or more constituents of a CRISPR polynucleotide (e.g., sgRNA) that renders the CRISPR polynucleotide (e.g., sgRNA) susceptible to cleavage under appropriate conditions. For instance, the appropriate conditions can be exposure to UV light. The cleavable linker can comprise one or more modified or unmodified nucleotides, which are susceptible to scission under the appropriate conditions.

The cleavable linker can comprise a modified internucleoside linkage. The modified internucleoside linkage can be an internucleotide linkage that has a phosphorus atom or those that do not have a phosphorus atom. Internucleoside linkages containing a phosphorus atom therein include, for example, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, P-ethyoxyphosphodiester, P-ethoxyphosphodiester, P-alkyloxyphosphotriester, methylphosphonate, thionophosphoramidates, thionoalkylphosphonates, thionoalkylphosphotriesters, selenophosphates and boranophosphates, and nonphosphorus containing linkages, e.g., acetals and amides, such as are known in the art, having normal 3'-5' linkages, 2'-5' linked analogs of these, and those having inverted polarity wherein one or more internucleotide linkages is a 3' to 3', 5' to 5' or 2' to 2' linkage. Polynucleotides having inverted polarity can comprise a single 3' to 3' linkage at the 3'-most internucleotide linkage i.e. a single inverted nucleoside residue which may be abasic (the nucleobase is missing or has a hydroxyl group in place thereof).

Non-phosphorus containing internucleoside linkages include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and CH2 component parts. Other modified internucleoside linkages that do not contain a phosphorus atom therein include, —CH2-NH—O—CH2-, —CH2-N(CH3)-O—CH2-(known as a methylene (methylimino)backbone), —CH2-O—N (CH3)-CH2-, —CH2-N(CH3)-N(CH3)-CH2- and —O—N (CH3)-CH2-CH2-.

The cleavable linker can be non-nucleotide in nature. A "non-nucleotide" can refer to any group or compound that can be incorporated into a polynucleotide chain in the place of one or more nucleotide units, including either sugar and/or phosphate substitutions. The group or compound can be abasic in that it does not contain a commonly recognized nucleotide base, such as adenosine, guanine, cytosine, uracil or thymine, for example at the C1 position of the sugar.

Non-nucleotidic linkers can be e.g. abasic residues (dSpacer), oligoethyleneglycol, such as triethyleneglycol (spacer 9) or hexaethylenegylcol (spacer 18), or alkane-diol, such as butanediol. The spacer units can be preferably linked by phosphodiester or phosphorothioate bonds. The linker units can appear just once in the molecule or can be incorporated several times, e.g. via phosphodiester, phosphorothioate, methylphosphonate, or amide linkages. Further preferred linkers are alkylamino linkers, such as C3, C6, C12 aminolinkers, and also alkylthiol linkers, such as C3 or C6 thiol linkers. In some examples, heterobifunctional and homobifunctional linking moieties can be used to conjugate peptides and proteins to nucleotides. Examples include 5'-Amino-Modifier C6 and 3'-Amino-Modifier C6 reagents.

ii. Methods of Cleaving Cleavable Elements

The cleavable element can be cleaved by any suitable method, including exposure to acid, base, nucleophile, electrophile, radical, metal, reducing or oxidizing agent, light, temperature, enzymes, small molecule, nucleic acid, protein, etc. In some examples, the cleavable element (e.g., cleavable linker) is susceptible to cleavage by a cellular process or byproduct thereof. The cellular process can involve enzyme, second messenger molecules, metabolites, proteins, and free radicals.

iii. Photolabile Groups

The cleavable element can be a photolabile group. The photolabile group can be introduced into the CRISPR polynucleotide by phosphoramidite chemistry. If a photolabile group is used to crosslink, the photolabile group can be the same or different from the photolabile cleavable element. If the photolabile group used to crosslink is different from the photolabile group used to cleave, a different wavelength can be used to activate cleavage than is used to activate crosslinking. Two or more photolabile elements in a CRISPR polynucleotide can have different activation characteristics, e.g., the two or more elements, when incorporated into a CRISPR polynucleotide can be selectively activated in each other's presence by using different agents and/or reaction conditions.

Selective reaction of PC-aminotag phosphoramidites with the free 5'—OH group of a growing oligonucleotide chain, followed by cleavage from the support and deprotection, can result in the introduction of a phosphodiester group linked to a primary aliphatic amino group through a photocleavable linker. This amino group can then be used to introduce a variety of photocleavable markers through a postsynthetic modification reaction with amine reactive reagents (Olejnik J et. al, Nucleic acids research. 1998; 26:3572-6. For example, a CRISPR polynucleotide can comprise a photocleavable aliphatic group linking two nucleotides (e.g., nucleotide 53 and nucleotide 54) in the CRISPR polynucleotide, and the CRISPR polynucleotide can be exposed to UV light, resulting in a break in the CRISPR polynucleotide (e.g., between nucleotide 53 and 54). In other examples, a photocleavable aminotag phosphoramidite can be positioned in a CRISPR polynucleotide between the polynucleotide leader sequence and the guide sequence, and UV light can be used to initiate cleavage at the photocleavable aminotag phosphoramidite, thereby separating the polynucleotide leader sequence. An example of a photocleavable linker that can be used to initiate cleavage of the CRISPR polynucleotide can be 3-(4,4'-Dimethoxytrityl)-1-(2-nitrophenyl)-propan-1-yl-[(2-cyanoethyl)-(N,N-diisopropyl)]-phosphoramidite. For example, a CRISPR polynucleotide can comprise a photocleavable aliphatic group linking two nucleotides (e.g., nucleotide 53 and nucleotide 54) in the CRISPR polynucleotide, and the CRISPR polynucleotide can be exposed to visible light, resulting in a break in the CRISPR polynucleotide (e.g., between nucleotide 53 and 54). In other examples, a photocleavable coumarin photolinker can be positioned in a CRISPR polynucleotide between the polynucleotide leader sequence and the guide sequence, and visible light can be used to initiate cleavage at the photocleavable coumarin photolinker, thereby separating the polynucleotide leader sequence. An example of a photocleavable linker that can be used to initiate cleavage of the CRISPR polynucleotide can be a coumarin linker. Other methods of introducing photocleavable linkers into polynucleotide sequences have been described, e.g., in US Patent Applications: US20080227742A1, US20100022761A1, U.S. Pat. No. 7,897,737B2, the contents of which have been referenced here in their entirety.

iv. Ribonuclease Based Cleavage

In some examples, the one or more cleavable elements comprise a cleavage site for an endoribonuclease, e.g., an endoribonuclease which cleaves RNA at or within a defined ribonucleotide sequence motif. For example, the cleavable element can comprise a cleavage site recognized by a sequence-specific endoribonuclease. The endoribonuclease can be naturally occurring or engineered. In some examples, the endoribonuclease can be specific for single stranded RNA, double stranded RNA or a nucleotide sequence formed by a DNA:RNA hybrid. In some examples, the sequence-specificity of the endoribonuclease can be engineered by fusion with oligonucleotides or by fusion with other protein domains. For example, a sequence specific endoribonuclease enzyme can be engineered by fusing two functionally independent domains, a RNase HI, that hydrolyzes RNA in DNA-RNA hybrids in processive and sequence-independent manner, and a zinc finger that recognizes a sequence in DNA-RNA hybrids. In another conjugation of an antisense oligodeoxynucleotide to ribonuclease H can result in sequence-specific cleavage. See e.g., Sulej et.al, Nucleic acids research. 2012; 40(22):11563-70 and Fukuma et. al, Bioconjugate chemistry. 2003; 14(2):295-301. In some cases, the cleavable element can be capable of recruiting RNase H1 to cleave double stranded regions of the CRISPR polynucleotide. (See, e.g., U.S. Pat. No. 5,849, 902).

The cleavable element can comprise a cleavage site recognized by a sequence-specific ssRNA endoribonuclease such as the excised IVS rRNA portion of the Tetrahymena thermophila as described, e.g., in Zaug et. al, Biochemistry 1988; 27, 25, 8924-8931. In other examples the cleavable element can comprise one or more cleavage sites recognized by sequence-specific ssRNA endoribonuclease Cas2 as described, e.g., in Beloglazova et.al, J Biol Chem. 2008; 283(29): 20361-20371. In other examples the cleavable element can comprise one or more preferred sites in dsRNA recognized by RNase Mini-III from Bacillus subtilis, e.g., as discussed in Glow et. al, Nucleic Acids Res. 2015; 43 (5) 2864-73. In other examples, Short oligonucleotides can be used as external guide sequences (EGSs) to direct site-specific cleavage of the CRISPR polynucleotide by human RNase P. For example, 13-mer EGSs targeted to the 2.1-kb surface antigen mRNA of hepatitis B virus (HBV) were capable of inducing cleavage of the HBV RNA by RNase P. (See Werner M et. al, RNA. 1998; 4(7):847-55. The endoribonuclease can be a member of the sequence or structure specific endoribonuclease Cas6 superfamily, e.g., Cas6A (e.g. Hong Li (2015), Structure, January 6; 23(1): 13-20). The endoribonuclease can be Csy4, also known as Cas6f. The ssRNA endoribonuclease can belong to the Cas13 family of CRISPR endoribonuclease or derivatives thereof. The endoribonuclease can be Cpf1 or a Cas5d enzyme, which can process pre-creRNA transcripts (Zetsche, B. et al. (2016), "Multiplex gene editing by CRISPR-Cpf1 using a single crRNA array", Nature Biotechnology (2016) doi: 10.1038/nbt.3737).

The cleavable element can be an element that is cleavable by ribozymes, e.g. the hammerhead ribozyme, Hepatitis delta virus ribozyme etc. The ribozymes can be naturally occurring or can be engineered to be a trans-acting ribozymes by separation into 'catalyst' and 'substrate' strands as discussed, e.g., in Levy et. al, RNA 2005. 11: 1555-1562. In some cases, two ribozymes can be used in concert to allow cleavage after a desired target sequence. In some cases, alternative artificial ribozyme-protein complexes that function in different cellular compartments can be designed by the use of localizing determinants for delivering a ribozyme to a specific subcellular site or for targeting a specific type of RNA as shown in Samarsky et. al, Proc Natl Acad Sci USA. 1999; 96(12): 6609-6614. In some cases, use of the ribozyme can involve binding of an exogenous small molecule for activity, e.g., glmS ribozyme.

In some examples, the activity of the ribozyme can be further tuned to be ligand-controlled by coupling with an aptamer. The aptamer can be chosen based on its ability to bind a ligand or otherwise "sense" a change in environment (such as pH, temperature, osmolarity, salt concentration, etc) in a manner directly coupled through an information transmission domain to loop I and/or loop II. The ligand can, for example, be a protein, nucleotide or small molecule ligand. The binding of the ligand to the aptamer can causes a change in the interaction of the information transmission domain with one or more of the loop, the stem or the catalytic core such that the ribozyme activity can be modulated dependent upon the presence or absence of the ligand as described, e.g., in U.S. Pat. No. 8,603,996B2.

Cleavage of the cleavable elements of the CRISPR polynucleotide (e.g., sgRNA) can be induced at a desired time independently; for example, a genetically-coded endoribonuclease can be activated within the host cells. A vector or plasmid encoding the endoribonuclease can be transfected into the cell at a desired time. One or more endoribonucleases can be under the control of one or more independent promoters. One or more of the promoters can be activated at desired times.

v. Antisense Oligonucleotides

The one or more cleavable elements of the CRISPR polynucleotide can be designed to allow the binding of an anti-sense oligonucleotide. The antisense oligonucleotide can be a single-stranded DNA (ssDNA) oligonucleotide. The ssDNA oligonucleotide can hybridize to single stranded RNA sequence in the CRISPR polynucleotide, and RNAse H can be used to cleave RNA of the DNA:RNA hybrid. With regard to the cleavable element (e.g., RNA loop of a stem loop in the CRISPR polynucleotide) to which the antisense oligonucleotide can bind, the cleavable element (e.g., loop of a stem loop) can be about 6 to about 40 nucleotides in length. The antisense oligonucleotide can be about 12 to about 16 nucleotides in length, or about 12 to about 25 nucleotides, or about 10 to about 30 nucleotides in length. The degree of complementarity between the antisense oligonucleotide and the cleavable element (e.g., loop of a stem loop) of the CRISPR polynucleotide can be at least 80%, 85%, 90%, 95%, 98%, 99%, or 100%. An antisense oligonucleotide whose sequence is fully or partially complementary to the cleavable element can be produced within the host cell or introduced into the host cell. Antisense oligonucleotides can be transfected into cells using polyethyleneimine (PEI) or other known transfection methods.

The one or more cleavable element of the CRISPR polynucleotide can comprise a miRNA responsive element. The length of the miRNA responsive element can be between about 15 to about 30 nucleotides, e.g., about 20 to about 25 nucleotides in length. The length of the miRNA can be about 20 to about 24 nucleotides, e.g., about 21 to about 23 nucleotides, e.g., about 22 nucleotides in length. The degree of sequence complementarity between the miRNA and the miRNA responsive element in the CRISPR polynucleotide can be at least 80%, 85%, 90%, 95%, 98%, 99%, or 100%.

The cleavable element can comprise a miRNA response element (MRE), and a miRNA that is capable of binding to the MRE can be produced within the host cell or introduced into the host cell. The miRNA can be present in the form of an miRISC complex which can target the MRE and cleave the first cleavable element.

vi. Site-Specific Chemical Nucleases

Specific cleavage of the CRISPR polynucleotide can be achieved by a chemical compound that has been designed to possess site-specific nuclease activity.

The chemical nuclease can be designed to have sequence-specific affinity to a CRISPR polynucleotide, e.g., CRISPR ON polynucleotide, CRISPR OFF polynucleotide, or CRISPR ON/OFF polynucleotide described herein. For example, RNA cleaving tris(2-aminobenzimidazoles) can be attached to DNA oligonucleotides or 2'-O-methyloligoribonucleotide via disulfide or amide bonds to form organocatalytic nucleases showing RNA substrate and site selectivity (see e.g., Gnaccarini et.al, J. Am. Chem. Soc., 2006, 128 (24), pp 8063-8067]. In other examples, the site-specificity of the chemical RNAse (e.g., 1,10-phenanthroline moiety, neocuprine Zn (II), neamine) for the CRISPR polynucleotide can be achieved through the use of peptide nucleic acids (PNA), e.g., polyamide nucleic acid.

The site-specificity of the chemical RNAse (e.g., diethylenetriamine moiety) for the CRISPR polynucleotide can be achieved by a combined use of anti-sense oligonucleotides, peptides proteins or PNAs. In some examples, RNA-binding proteins can be chemically converted to sequence-specific nucleases by covalent attachment to a coordination complex, such as 1,10-phenanthroline-copper complex. See e.g., Chen et.al, Sigman D S. Science. 1987; 237(4819): 1197-201. In another example, site-specific cleavage of CRISPR polynucleotide can be achieved by the conjugation of Bleomycin-Fe (II) with EDTA or an oligonucleotide to form an artificial nuclease with specificity for the CRISPR polynucleotide.

Examples of chemical nucleases include 1,10-phenanthrolinecopper (Sigman et al., 1993), ferrous-ethylenediaminetetraacetic acid (EDTA), macrocylic lanthanide complexes, metalloporphyrins, metallic complexes of salens, uranyl acetate, octahedral metal complexes of rhodium (III), benzene diazonium teetrafluoroborate, aliphatic monoamines-, diamines- and polyamines, aminoglycosides such as neomycin B and copper (II) aminoglycoside complexes etc. In some cases, the chemical nucleases can target the sugar moiety of nucleosides and catalyze oxidative cleavage by extracting a hydrogen atom from the sugar at the cleavage site.

vii. Photochemical Cleavage

In some examples, photocaging groups can be used to render further control on the activity of the agent used for the cleavage of the CRISPR polynucleotide. For example, photolysis of photoactivatable or "caged" probes can be used for controlling the release of site-specific chemical nucleases described in this disclosure. In another example, a photocaging group can be used to block cleavage by a ribonuclease or restriction enzyme of the CRISPR polynucleotide, until released by photolysis, e.g., as shown in Bohacova et.al, Biomol. Chem., 2018. 16, 1527. In another example, a photocaging group on one or more of the nucleotides in the CRISPR polynucleotide can be used to mask the recognition sequence for an anti-sense nucleotide, until release by photolysis, thereby initiating cleavage of the CRISPR polynucleotide. In another example, the photocaging group can be attached to the cleavage agent, such as the anti-sense oligonucleotide, which upon photolysis, becomes available for binding to the CRISPR polynucleotide and initiating the formation of a RISC complex. In another example, the photocaging group can be used to mask a 'miRNA response element' for cleavage of the CRISPR polynucleotide until release by photolysis. In other aspects, without limitation, photocaging groups can be used with orthogonal treatment regimens for the cleavage of multiple cleavage elements with different cleavage characteristics.

Photocaging groups can be used for 'tagging' the cleavage reaction, wherein the tag can be amenable for detection and/or quantification by one or more methods. For example, a 2-nitro-benzyl based photocleavable group can be labeled further with a dye that is released upon photolysis, and can be used as a detectable marker for the 'efficiency' of activation of the CRISPR ON polynucleotide or for the deactivation of the CRISPR OFF polynucleotide etc. In another example, the ribonuclease protein that binds to the cleavable element of CRISPR polynucleotide can be tagged upon initiation of the 'cleavage event' by the release of a 'fluorescent tag' from photocaged nucleotide that was incorporated into the cleavable element, wherein measurement of the fluorescent tag can be a surrogate marker for the cleavage of the CRISPR polynucleotide.

Examples of photocaging groups that can be synthetically incorporated into the CRISPR polynucleotide include ortho-nitrobenzyl based caging groups that can by linked to a heteroatom (usually O, S or N) as an ether, thioether, ester (including phosphate or thiophosphate esters), amine or similar functional group by methods known in the art. Examples of 2-nitrobenzyle based caging groups include α-carboxy-2-nitrobenzyl, 1-(2-nitrophenyl)ethyl, 4,5-dimethoxy-2-nitrobenzyl, 1-(4,5-dimethoxy-2-nitrophenyl)ethyl, 5-carboxymethoxy-2-nitrobenzyl, nitrophenyl etc. Other examples of photoremovable protecting groups, include benzyloxycarbonyl, 3-nitrophenyl, phenacyl, 3,5-dimethoxybenzoinyl, 2,4-dinitrobenzenesulphenyl, Ethedium Monoazide, Bimane Azide and their respective derivatives.

Photolabile linkers described herein can be represented as several mesomeric forms. Where a single structure is drawn, any of the relevant mesomeric forms are intended. The coumarin linkers described herein represented by a structural formula can be shown as any of the related mesomeric forms. Exemplary mesomeric structures are shown below for Formula (I):

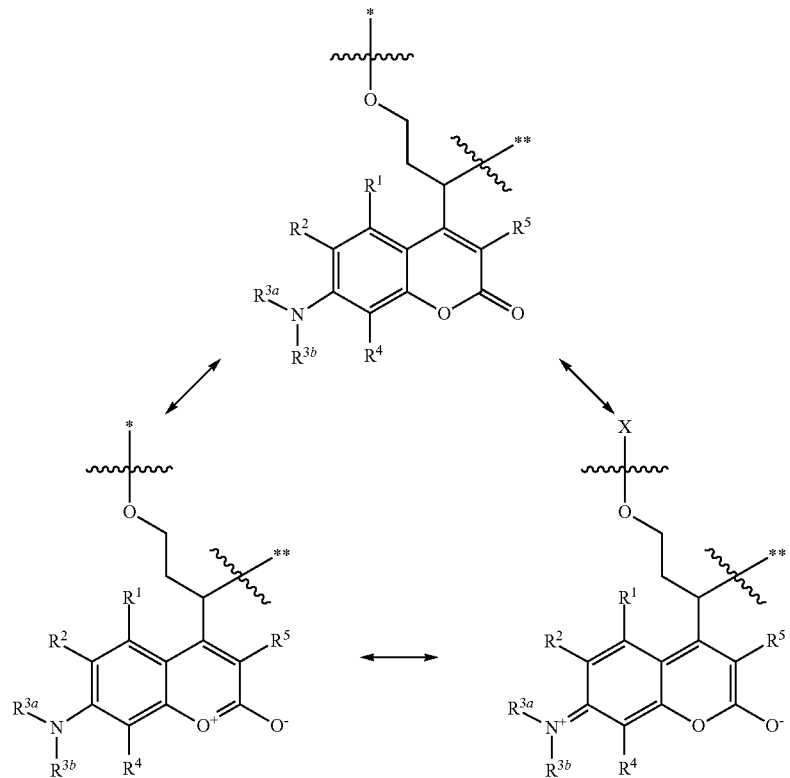

Photolabile protective groups can be attached to the hydroxy and phosphate or nucleobase in nucleosides and nucleotides. For example, photocaged derivatives of 2'-deoxy-5-(hydroxymethyl) uridine nucleoside, mono- and triphosphates protected by 2-nitrobenzyl-, 6-nitropiperonyl- and anthryl-9-methyl groups can be their enzymatically incorporated into the polynucleotide, e.g., as described in Bohacova et.al, Org. Biomol. Chem., 2018, 16, 152. Photocleavage can occur through a variety of mechanisms such as hydrogen bond abstraction from sugar ring, direct electron transfer from the base to the photo excited cleaver or singlet oxygen production by transfer of energy from the photocleavage and formation of adducts.

viii. Cleavage of Cleavable Element

The cleavable element(s) of the two or more (e.g., 2, 3, 4, 5, 6, 7, 8, 9 or 10) CRISPR polynucleotides can be cleaved by the same cleaving moiety. The cleavage of the two or more (e.g. 2, 3, 4, 5, 6, 7, 8, 9 or 10) different CRISPR polynucleotides can be induced by different external factors.

The cleavage inducing agent can be electromagnetic radiation. The cleavage inducing agent can be a particular wavelength of light in the visible spectrum. The cleavage element can be cleaved by UV light.

The wavelength of the light can range from 220-465 nm. The intensity of light in the exposure protocol can be about 5, 10, 15, 20, 25, 35, 40, 50, 70, 90, 110, 120, 140, 160, 175, 190, 200, 220, 240, 260 280, 300, 320, 340, 360, 380, 400, 420, 440, 460, 480, 500, 520, 540, 560, 580, 600, 620, 650, 675, 700, 720, 745, 765, 790, 810, 830, 850, 870, 900, 920, 945, 965, 985, 1000, 1025, 1050, 1080, 1100, 1125, 1150, 1175, 1200, 1240, 1275, 1290, 1320, 1350, 1380, 1400, 1420, 1450, 1470, 1490, 1520, 1540, 1560, 1600, 1630, 1650, 1670, 1700, 1720 or 1750 mW/cm². The intensity of light in the exposure protocol can range from about 70 mW/cm² to 100 mW/cm², 80 mW/cm² to 110 mW/cm², 90 mW/cm² to 120 mW/cm², 100 mW/cm² to 130 mW/cm², 110 mW/cm² to 140 mW/cm², 120 mW/cm² to 150 mW/cm², 130 mW/cm² to 160 mW/cm², 140 mW/cm² to 170 mW/cm², 150 mW/cm² to 180 mW/cm², 160 mW/cm² to 190 mW/cm², 170 mW/cm² to 200 mW/cm², 180 mW/cm² to 210 mW/cm², 190 mW/cm² to 220 mW/cm², 200 mW/cm² to 230 mW/cm², 210 mW/cm² to 240 mW/cm², 220 mW/cm² to 250 mW/cm², 230 mW/cm² to 260 mW/cm², 240 mW/cm² to 270 mW/cm², 250 mW/cm² to 280 mW/cm², 260 mW/cm² to 290 mW/cm², or 270 mW/cm² to 300 mW/cm². The wavelength of the light can range from about 320 nm to about 390 nm. The wavelength of the light can range from about 320 nm to 425 nm, 320 nm to 420 nm, 420 nm to 520 nm, 520 nm to 620 nm. 420 nm to 700 nm. The wavelength of light can be greater than about 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, or 700 nm. The wavelength of light can be less than about 700 nm, 690 nm, 680 nm, 670 nm, 660 nm, 650 nm, 640 nm, 630 nm, 620 nm, 610 nm, 600 nm, 590 nm, 580 nm, 570 nm, 560 nm, 550 nm, 540 nm, 530 nm, 520 nm, 510 nm, 500 nm, 490 nm, 480 nm, 470 nm, 460 nm, 450 nm, 440 nm, 430 nm, or 425 nm. The wavelength of light can range from about 420 nm to 430 nm, 430 nm to 440 nm, 440 nm to 450 nm, 450 nm to 460 nm, 460 nm, to 470 nm, 470 nm to 480 nm, 480 nm to 490 nm, 490 nm to 500 nm, 500 nm to 510 nm, 510 nm to 520 nm, 520 nm to 530 nm, 530 nm to 540 nm, 540 nm to 550 nm, 550 nm to 560 nm, 560 nm to 570 nm, 570 nm to 580 nm, 580 nm to 590 nm, 590 nm to 600 nm, 600 nm to 610 nm, 610 nm to 620 nm, 620 nm to 630 nm, 630 nm to 640 nm, 640 nm to 650 nm, 650 nm to 660 nm, 660 nm to 670 nm, 670 nm to 680 nm, 680 nm to 690 nm, or 690 nm to 700 nm. The power wattage of the light used in the exposure protocol can be about 50, 70, 80, 90, 100, 120, 140, 160, 175, 190, 210, 230, 250, 270, 290, 310, 330, 250, 370, 390, 420, 4450, 480, 500, 530, 550, 570, 600, 620, 650, 670, 700, 720, 750, 770, 800, 820, 850, 870, 900, 920, 950, 970, 1000, 1020, 1050, 1070, 1100, 1120, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400 4500, 4600, 4700, 4800, 4900, 5000, 5100, 5200, 5300, 5400, 5500, 5600, 5700, 5800, 5900, or 6000 W, as measured by an OAI 306 UV power meter.

The duration of exposure can be from 1 second to 30 minutes. The duration of exposure can be from 1 second to 30 seconds, 30 seconds to 60 seconds, 1 min to 5 min, 5 min to 10 min, 10 min to 20 min, 20 min to 30 min, 30 min to 40 min, 40 min to 50 min, or 50 min to 1 hr. The duration of exposure can be greater than about one hour, 50 min, 40 min, 30 min, 20 min, 10 min, 5 min, 1 min, 30 seconds, or one second. The duration of exposure can be less than about two seconds, 30 seconds, 1 min, 5 min, 10 min, 20 min, 30 min, 40 min, 50 min, or 1 hour. The exposure protocol can comprise continuous exposure or pulsed exposure or both. The pulse exposure can be uniform or of varying durations.

The light source can be a broad spectrum light that has been filtered through a bandpass filter. The bandpass filter can be a 345 nm bandpass filter. The bandpass filter can be a 420 nm long pass filter. The light source can be an ultraviolet (UV) light. The light source can be a LED. The LED can emit ultraviolet light. The LED can emit visible light. The LED can emit infrared light.

B. Modified CRISPR Effector Proteins for Locking

In some cases, CRISPR effector proteins are modified to facilitate locking to a CRISPR polynucleotide. The CRISPR polynucleotide can be modified to facilitate locking to a CRISPR effector protein. The CRISPR polynucleotide can comprise a CRISPR ON polynucleotide sequence, a CRISPR OFF polynucleotide sequence, a CRISPR ON/OFF polynucleotide sequence, or CRISPR polynucleotides comprising one or more modifications that, when complexed with a CRISPR enzyme, have reduced off-target editing activity, described herein. Both the CRISPR effector protein and the CRISPR polynucleotide can be modified to facilitate locking to a CRISPR effector protein. For example, the CRISPR effector protein can be modified with unnatural amino acids to facilitate cross linking to the CRISPR polynucleotide. In some cases, both the CRISPR polynucleotide (e.g., sgRNA) and the CRISPR effector protein are modified to facilitate locking. In some cases, only the CRISPR effector protein comprises a cross-linker, and the CRISPR polynucleotide does not comprise a cross-linker. In some cases, the CRISPR polynucleotide comprises a cross-linker and the CRISPR effector protein does not comprise a cross-linker.

As described below, the CRISPR effector protein can be modified either by the inclusion of one or more unnatural amino acids or by fusion (e.g., expression of a fusion) of the CRISPR effector protein with an amino acid sequence, such as a SNAP fusion protein, designed to facilitate binding to another molecule.

The CRISPR effector protein, e.g., Cas9, can comprise one or more mutations (and hence nucleic acid molecule(s) coding for same can have mutation(s)). The one or more mutations can be artificially introduced mutations and can be one or more mutations in a catalytic domain. Examples of catalytic domains with reference to a Cas9 enzyme can be RuvC I, RuvC II, RuvC III and HNH domains. The one or more mutations can render the one or more catalytic domains of Cas9 inactive. The one or more mutations can reduce the catalytic activity of Cas 9 0.1-fold, 0.25-fold, 0.5-fold, 0.75-fold, 1-fold, 2-fold, 5-fold, 10-fold, 50-fold, 100-fold, or 1000-fold. In some cases, the one or more mutations can increase the catalytic activity of Cas9 0.1-fold, 0.25-fold, 0.5-fold, 0.75-fold, 1-fold, 2-fold, 5-fold, 10-fold, 50-fold, 100-fold, or 1000-fold.

The CRISPR polynucleotide can be modified with a cell penetrating RNA aptamer. The cell penetrating RNA aptamer can improve the effective delivery of the CRISPR polynucleotide to a cell. The RNA aptamer can bind to a cell surface receptor and promote the entry of CRISPR polynucleotide into a cell. The cell penetrating aptamer can be designed to target a specific cell receptor in order to mediate cell-specific delivery.

1. Types of Modifications for Locking

CRISPR effector protein can be modified by the inclusion of unnatural amino acids. Unnatural amino acids include photo labile unnatural amino acids, e.g., photo labile unnatural amino acid cross linkers, e.g., p-azido-L-phenylalanine (AzF) or p-benzoyl-L-phenylalanine (BzF), can be used to form crosslinks in bio conjugation. Upon excitation at 350-360 nm, benzophenones, e.g., BzF, can preferentially react with otherwise inactivated carbon-hydrogen bonds on exposed functional groups located on the CRISPR polynucleotide. In some cases, benzophenones do not photo dissociate and their photo excited triplet state readily relaxes in the absence of a suitable carbon-hydrogen bond with which to react, thereby benzophenone can be a more forgiving reagent than other cross-linking reagents. AzF can generate reactive nitrenes upon exposure to ultraviolet light which can be used to link to the CRISPR polynucleotide.

The CRISPR effector protein can be fused to another protein, e.g., a SNAP protein. Configurations can involve the covalent attachment of a DNA repair template to the SNAP protein through a BG (O6-benzylguanine) linker as a method of keeping a DNA repair template close to the CRISPR complex and/or the attachment of the CRISPR polynucleotide, e.g., sgRNA, with a linker nucleotide sequence to attach to the SNAP protein through the use of a BG linker and a RNA aptamer as described below.

The CRISPR effector protein can be modified with a SNAP protein fusion to facilitate linking of the CRISPR polynucleotide (e.g., sgRNA) to the CRISPR effector protein. For example, a vector can be used to express a fusion protein comprising a CRISPR effector protein and a SNAP protein followed by an arm region. The arm region further comprises a series of amino acids configured for flexibility. The arm region can be further configured to link to a benzyl guanine modified polynucleotide. The SNAP protein region can be located at the N-terminus of the CRISPR effector protein. At the N-terminus of the SNAP protein can be the arm region. The CRISPR polynucleotide can be modified with a benzyl-guanine-binding RNA aptamer (as described, e.g., by Carrocci and Hoskins, Evolution and Characterization of a Benzylguanine-Binding RNA Aptamer, Chem Commun (Camb). 2016 Jan. 11; 52(3): 549-552. doi: 10.1039/c5cc07605f). Once the CRISPR polynucleotide is bound with a benzyl-guanine binding RNA aptamer, the CRISPR polynucleotide can be covalently bonded to the arm region of the fusion protein. The flexibility of the arm region can allow the CRISPR polynucleotide to complex with the CRISPR effector protein region of the fusion protein. Alternatively, the CRISPR polynucleotide can be complexed prior to attachment to the arm region of the fusion protein.

C. CRISPR Complexes with High Affinity Binding of CRISPR Effector Protein and Polynucleotide Provided herein is a CRISPR complex comprising (a) the polynucleotide comprising a sequence designed to anneal to a target nucleic acid sequence and a sequence designed to bind a CRISPR effector protein, and an activity modulating polynucleotide sequence (e.g. CRISPR ON, CRISPR OFF, or CRISPR ON/OFF, described herein); and (b) a CRISPR effector protein wherein an equilibrium dissociation constant ($K_d$) for the polynucleotide binding to the CRISPR effector protein is less than 8 pM (pM=picomolar). The equilibrium dissociation constant ($K_d$) can be less than 7 pM, 5 pM, 4 pM, 3 pM, 2 pM, 1 pM, 9 fM (fM=femtomolar), 8 fM, 7 fM, 6 fM, 5 fM, 4 fM, 3 fM, 2 fM, 1 fM, 9 aM (aM=attomolar), 8 aM, 7 aM, 6 aM, 5 aM, 4 aM, 3 aM, 2 aM, or 1 aM. The equilibrium dissociation constant ($K_d$) can be from about 1 pM to 8 pM, from about 1 fM to about 10 fM, or from about 1 aM to about 10 aM. The CRISPR effector protein can be covalently attached to the CRISPR polynucleotide. In some cases, the CRISPR effector protein is not covalently attached to the CRISPR polynucleotide.

IV. Methods of Using a Stabilized CRISPR Complex

Provided herein are methods of using stabilized (e.g., locked) CRISPR complexes described herein.

A. Administration to a Cell

An aspect of the present disclosure encompasses a method for administering a stabilized (e.g., locked) CRISPR complex to a cell. A stabilized CRISPR complex can comprise a CRISPR polynucleotide comprising an unnatural nucleotide to crosslink to a CRISPR effector protein and an activity modulating sequence (e.g. CRISPR ON, CRISPR OFF, or CRISPR ON/OFF, described herein). The method can comprise contacting the cell with a solution of stabilized (e.g., locked) CRISPR complex. Alternatively, or in combination, the method can comprise contacting a cell with a vector comprising CRISPR effector protein encoding regions and/or CRISPR polynucleotide encoding regions. Alternatively, or in combination non-viral mediated techniques can be used to introduce a CRISPR polynucleotide into a cell. Non-viral mediated techniques can include electroporation, calcium phosphate mediated transfer, nucleofection, sonoporation, heat shock, magnetofection, liposome mediated transfer, microinjection, microprojectile mediated transfer, nanoparticles, cationic polymer mediated transfer (e.g., DEAE-dextran, polyethylenimine, PEG, DMSO, etc.) or cell fusion.

Viral and non-viral mediated techniques can be used to introduce a CRISPR polynucleotide into a cell. The non-viral mediated techniques can be electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

The polynucleotide modified with at least one unnatural nucleotide for crosslinking comprising a CRISPR ON polynucleotide sequence, CRISPR OFF polynucleotide sequence, or CRISPR ON/OFF polynucleotide sequence, described herein and related vectors can be delivered to a cell naked (i.e. free from agents which promote transfection). The naked CRISPR polynucleotides can be delivered to the cell using routes of administration known in the art and described herein.

In some cases, the tunable modulation of the editing of a target gene in a target DNA in a host cell comprises the steps: (i) using viral or non-viral delivery methods or a combination thereof, described herein known in the art, to introduce into the host cell: (a) a CRISPR polynucleotide comprising an unnatural nucleotide to crosslink the CRISPR polynucleotide to a CRISPR effector protein, and a first and second cleavage elements, where the cleavage elements are susceptible to cleavage and where the nucleotide sequence of the guide sequence is fully or partially complementary to a target nucleic acid sequence, wherein the first cleavage element is position between a polynucleotide leader sequence and a 5' end of a guide sequence; and (b) a CRISPR effector protein (e.g., CRISPR enzyme, e.g., Cas9) with catalytic activity such that the CRISPR polynucleotide and the CRISPR enzyme form a CRISPR complex; and (ii) through exposure to UV light, inducing cleavage of the first sequence element in the polynucleotide, thereby releasing the polynucleotide leader sequence and activating higher target specific cleavage of the target gene by the CRISPR complex. Subsequently, the method can comprise (iii) inducing cleavage of the second sequence element, which can be located in scaffold sequence of the CRISPR polynucleotide, at a desired time through pulsed exposure to UV light, thereby cleaving the CRISPR polynucleotide and deactivating or lowering the target specific cleavage of the target gene by the CRISPR complex.

The cell can be ectodermal (e.g., neurons and fibroblasts), mesodermal (e.g., cardiac muscle cells), endodermal (e.g., pancreatic cells), epithelial (e.g., lung and nasal passageways), neutrophils, eosinophils, basophils, lymphocytes, osteoclasts, endothelial cells, hematopoietic, red blood cells, etc. The cell can be derived from specific cell lines such as CHO cells (e.g., CHOK1); HEK293 cells; Caco2 cells; U2-OS cells; NIH 3T3 cells; NSO cells; SP2 cells; DG44 cells; K-562 cells, U-937 cells; MC5 cells; IMR90 cells; Jurkat cells; HepG2 cells; HeLa cells; HT-1080 cells; HCT-116 cells; Hu-h7 cells; Huvec cells; and Molt 4 cells. Examples of other cells applicable to the scope of the present disclosure can include stem cells, embryonic stem cells (ESCs) and induced pluripotent stem cells (iPSCs), MSC-1, K562, etc.

In some cases, masks can be created to go over a cell culture. Mask can be created using a variety of techniques (laser cutting, 3D printing, photolithography, etc.) Masks can be designed to let light penetrate in a defined region. When used in conjunction with a CRISPR OFF complex comprising a photocleavable linker, editing in areas where the light (e.g., UV light or visible light) penetrates can be decreased, and editing in areas without exposure to light can be maintained. When used in conjunction with a CRISPR ON complex, editing in areas where the light (e.g., UV light) penetrates can be initiated.

Figure 30:
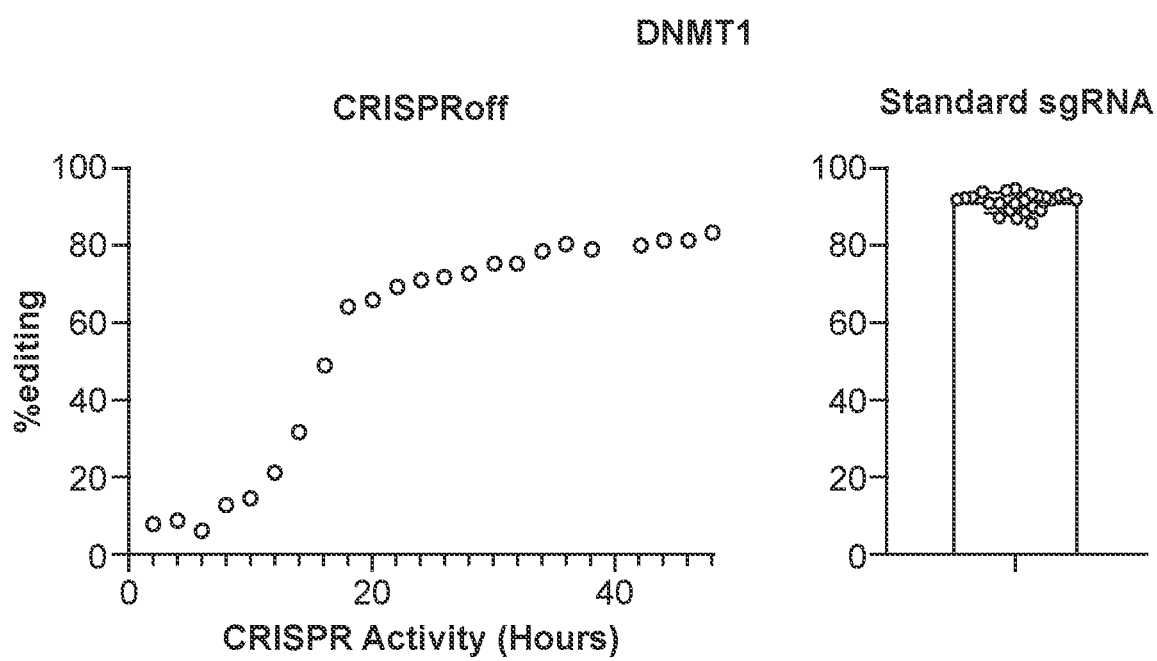
FIG. 30 shows time dependent editing activity of a CRISPR OFF complex targeting DNMT1 compared to a CRISPR complex comprising a standard sgRNA targeting DNMT1.
Figure 31:
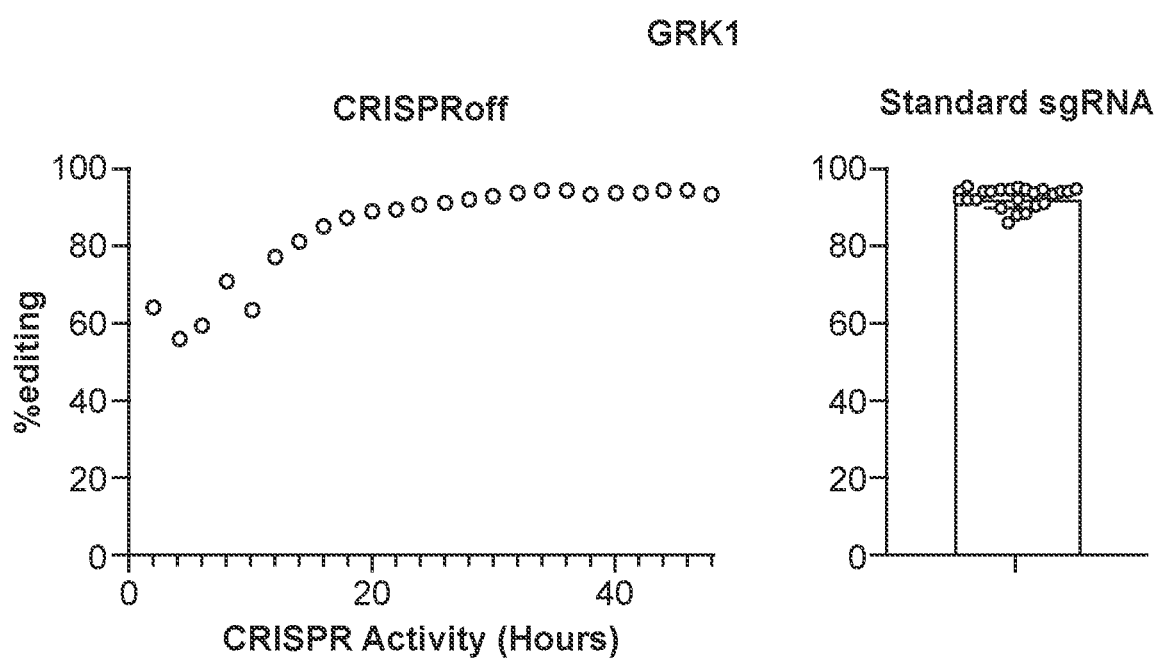
FIG. 31 shows time dependent editing activity of a CRISPR OFF complex targeting GRK1 compared to a CRISPR complex comprising a standard sgRNA targeting GRK1.
Figure 32:
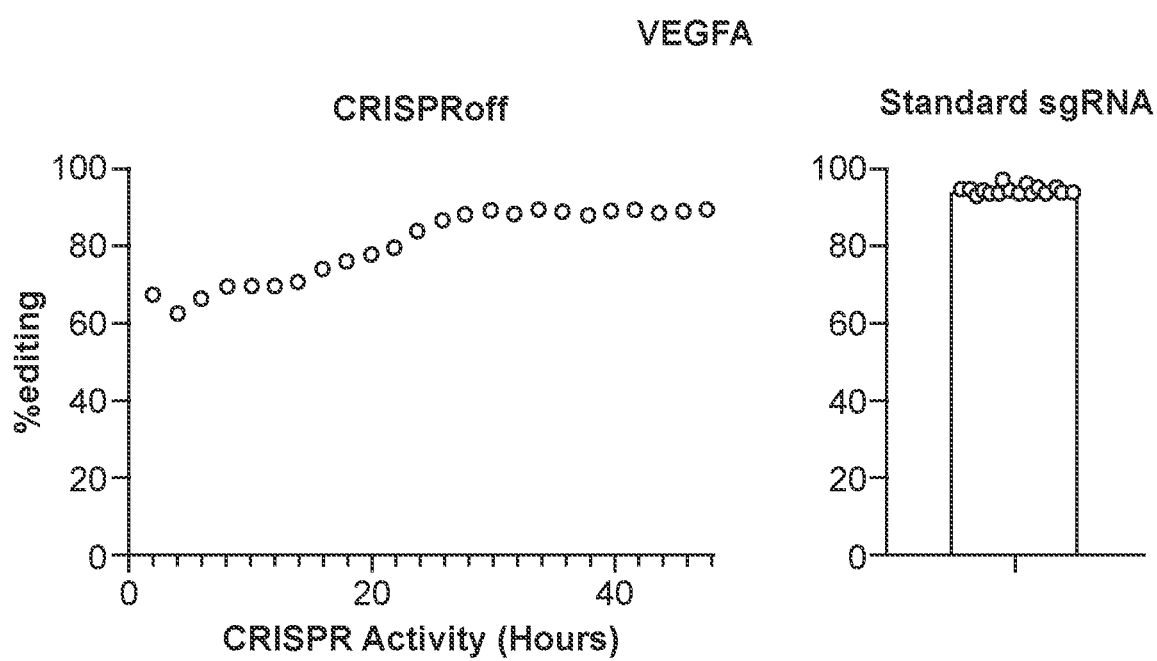
FIG. 32 shows time dependent editing activity of a CRISPR OFF complex targeting VEGFA compared to a CRISPR complex comprising a standard sgRNA targeting VEGFA.
Figure 33:
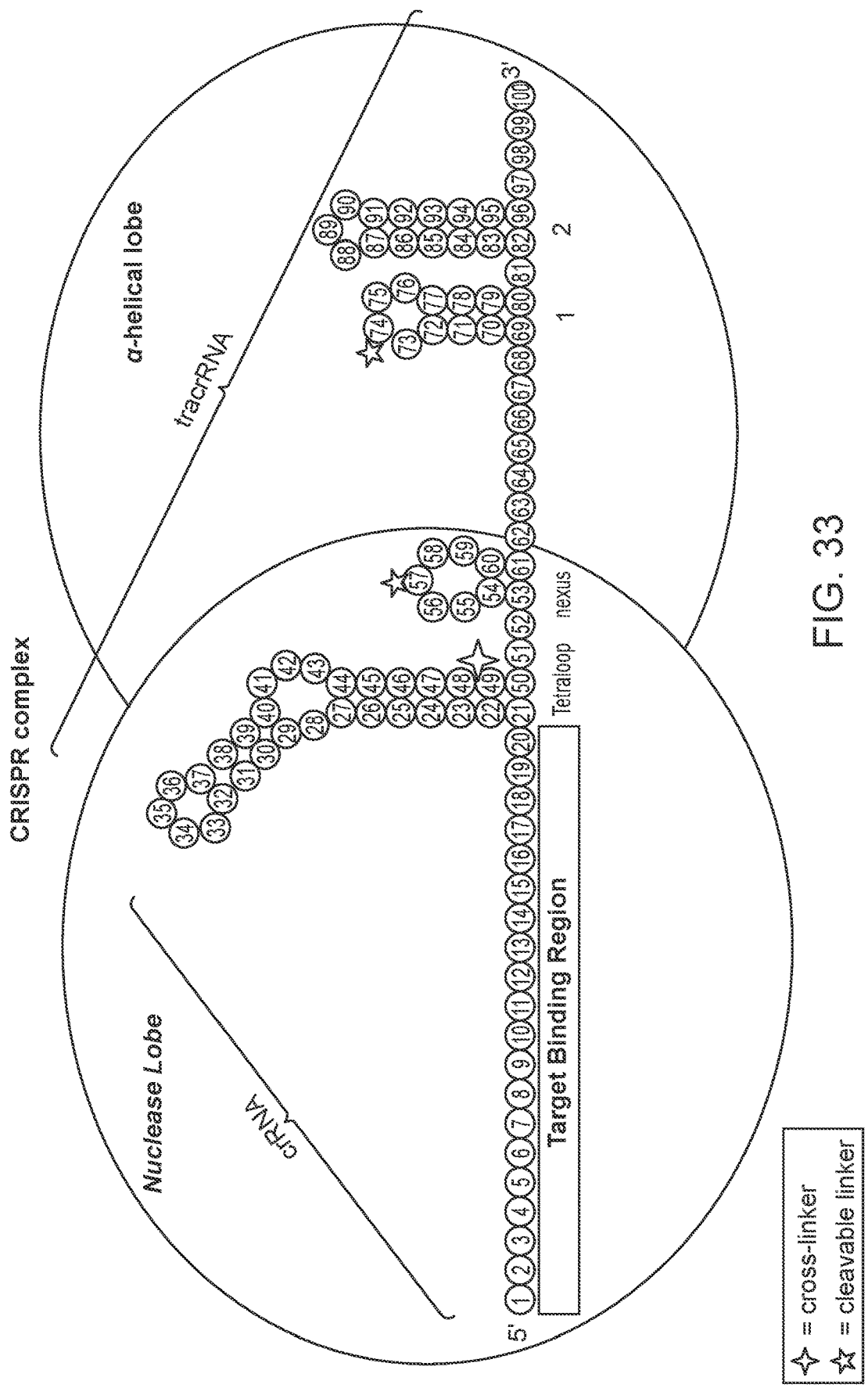
FIG. 33 shows a simplified diagram of a CRISPR complex wherein the polynucleotide is a single guide RNA (sgRNA). The four-pointed star indicates an exemplary position of an unnatural nucleotide for cross-linking the polynucleotide to the Cas nuclease. The five-pointed starts indicate exemplary positions of a cleavable linker. The bar indicates the target binding region of the polynucleotide.

In some cases, a CRISPR OFF complex activity can be time-dependent (e.g., as can be seen in Example 6, FIGS. 30-32). Cells can be exposed to a cleavage activator, such as UV light or visible light, at a time point prior to complete editing, resulting in a heterozygous clone. Alternatively, such a method can be used to target a diseased allele of a patient-derived cell line.

The stabilized (e.g., locked) CRISPR complex, with a dissociation constant near zero, can have an increased efficacy over current complexes in which the CRISPR polynucleotide can dissociate from the CRISPR effector protein prior to or during administration to a cell.

1. Multiple CRISPR Complexes

In some cases, a system comprises one or more CRISPR complexes provided herein. A first and second (or more) CRISPR complexes can be used in an in vitro or in vivo method. The CRISPR effector proteins in the first and second CRISPR complexes can be the same or different. In one example, an in vitro or in vivo system can comprise a plurality of CRISPR polynucleotides with different guide sequences and the same CRISPR effector protein (e.g, Cas9). In another example, an in vitro or in vivo system can comprise a CRISPR polynucleotide and a plurality of different CRISPR effector proteins (e.g., a mix of catalytically active and catalytically inactive CRISPR effector proteins).

Alternatively, or in combination, a host cell can comprise two or more (e.g., 2, 3, 4, 5, 6, 7, 8, 9, or 10) different locked CRISPR complexes, wherein the nucleotide sequences of the guide sequence of the different CRISPR complexes are independently fully or partially complementary to regions of two or more different target nucleic acids (e.g., DNA). The different CRISPR complexes can have different relative positions of one or more cleavage elements, or the same relative positions of the one or more cleavage elements.

B. Cleaving Target Nucleic Acid

An aspect of the present disclosure encompasses a method for cleaving a target nucleic acid. The method can comprise contacting a nucleic acid sequence with a stabilized (e.g., locked) CRISPR complex. A stabilized CRISPR complex can comprise a CRISPR polynucleotide comprising an unnatural nucleotide to crosslink to a CRISPR effector protein and an activity modulating sequence (e.g. CRISPR ON, CRISPR OFF, or CRISPR ON/OFF, described herein). A locked CRISPR complex, e.g., with crosslinking sites chosen so as to not interfere with the nuclease activity of the Cas nuclease or the binding efficiency of the crRNA region, can have an enhanced efficacy in the cleavage of a target nucleic acid. The polynucleotide can comprise a "protospacer" and a "protospacer adjacent motif (PAM)", and both domains can be needed for a CRISPR effector protein mediated activity (e.g., cleavage).

Each catalytic domain of the CRISPR effector protein can be active alternatively or in combination. Efficiency of each catalytic domain can be from 50% to 60%, 60% to 70%, 70% to 80%, 80% to 90%, or 90% to 99.9%.

After cleavage, DNA repair can occur by non-homologous end joining (NHEJ), microhomology mediated end joining (MMEJ, alternative nonhomologous end joining) or homology directed repair (HDR). A DNA template can be provided for HDR.

In some examples, the cleavage can lead to insertion and/or deletion ("indel") mutations or a frameshift by a nonhomologous end joining (NHEJ) process, leading to a target gene-specific knockout (KO). In some cases, CRISPR/Cas complex can be directed to the target genomic region by the specific gRNA (e.g., sgRNA) along with a co-administered, donor polynucleotide (single- or double-stranded). Following the cleavage of the target region, a homology-directed repair (HDR) process can use one or more of the donor polynucleotide as one or more templates for (a) repair of the cleaved target nucleotide sequence and (b) a transfer of genetic information from the donor polynucleotide to the target DNA. Depending on the nature of the genetic information, the HDR process can yield a target gene-specific KO or knock-in (KI). Examples of applications of the HDR-mediated gene KI include the addition (insert or replace) of nucleic acid material encoding for a protein, mRNA, small interfering RNA (siRNA), tag (e.g., 6×His), a reporter protein (e.g., a green fluorescent protein (GFP)), and a regulatory sequence to a gene (e.g., a promotor, polyadenylation signal).

For the HDR process, the donor polynucleotide can contain the desired edit, e.g., gene edit (sequence) to be copied, as well as additional nucleotide sequences on both ends (homology arms) that are homologous immediately upstream and downstream of the cleaved target site. In some cases, the efficiency of the HDR process can depend on the size of the gene edit and/or the size of the homology arms.

One or more CRISPR complexes can be provided to target one or more cleavage sites. For example, two CRISPR complexes can be provided to target two cleavage sites, ten CRISPR complexes can be provided to target ten cleavage sites, twenty CRISPR complexes can be provided to target twenty cleavage sites, etc. The number of different CRISPR polynucleotides (e.g., sgRNAs) that can be provided to a cell can be about 1, 2, 3, 4, 5, 6, 7, 8, 9, 10, 11, 12, 13, 14, 15, 25, 50, 100, or 1000, or to 3, 1 to 5, 1 to 10, 10 to 50, or 50 to 100.

CRISPR complexes described herein can induce one or more edits or mutations in a cell. The one or more edits or mutations can include the introduction, deletion, or substitution of one or more nucleotides at each target sequence of cells via CRISPR polynucleotides (e.g., the guides RNAs or sgRNAs). The one or more edits or mutations can be introduction, deletion, or substitution of about 1 to about 75 nucleotides at each target sequence of said cells. The one or more edits or mutations can be the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell. Target sequences can be genes and can include BUB1B, CAMK1, PRKAG3, STK3, CAMK1, Chr8q23, CEL, IRAK4, DNMT1, EMX1, FANCF, GRK1, PRGN, AAVS1, BUB1B, CXCR4, FAM163A, GAA, CRK1, IRAK4, MAPRE1, MIP, OMP, OPNISW, PRKAG3, STK3, and VEGFA (as can be seen in Examples 7, 8, 11, 12).

Multiple target sites can be targeted by sets of CRISPR complexes attached to different sgRNAs. Each gRNA in the set can be hybridizable to a region that is at most 170 bases apart from the hybridizable region of at least one other guide RNA from the set of guide RNAs. Each gRNA in the set of gRNAs that target the genomic region of interest can be hybridizable to a region that is about 10 to 200 bases (nucleotides) apart from the hybridizable region of the at least one other gRNA from the set of gRNAs. Each gRNA in the set of gRNAs can be hybridizable to a region that is at least 10, 15, 20, 25, 30, 25, 40, 45, 50, 60, 70, 80, 90, 100, 120, 140, 160, 180, 200 or more bases apart from the hybridizable region of the at least one other gRNA from the set of gRNAs. Each gRNA in the set of gRNAs can be hybridizable to a region that is at most 200, 180, 160, 140, 120, 100, 90, 80, 70, 60, 50, 45, 40, 35, 30, 25, 20, 15, 10, or less bases apart from the hybridizable region of the at least one other gRNA from the set of gRNAs. In an example, a minimum distance between a hybridizable region of a gRNA in the set of gRNAs is at least 30 bases apart from the hybridizable region of at least one other gRNA from the set of gRNAs. In another example, a maximum distance between a hybridizable region of a gRNA in the set of gRNAs is at most 150 bases apart from the hybridizable region of at least one other gRNA from the set of gRNAs.

In some cases, the CRISPR/Cas activity can be useful in any in vitro or in vivo application in which it is desirable to modify DNA in a site-specific (targeted) way, for example gene knock-out (KO), gene knock-in (KI), gene editing, gene tagging, etc., as used in, for example, gene therapy. Examples of gene therapy include treating a disease or as an antiviral, antipathogenic, or anticancer therapeutic; the production of genetically modified organisms in agriculture; the large scale production of proteins by cells for therapeutic, diagnostic, or research purposes; the induction of induced pluripotent stem cells (iPS cells or iPSCs); and the targeting of genes of pathogens for deletion or replacement.

C. Gene Regulation

An aspect of the present disclosure encompasses a method for regulating gene expression, or the transcription of a gene to mRNA, known as a knockdown method by targeting, to a gene, functional domains such as repressor domains and activator domains. A catalytically dead Cas nuclease linked to a transcription repressor (e.g., KRAB, DMT3A, and/or LSDT) and bound CRISPR polynucleotide (e.g., sgRNA) can bind to a complementary DNA region in a gene and block transcription. An embodiment of the method encompasses rendering a Cas nuclease catalytically dead upon photoinitiated crosslinking of the sgRNA to the Cas nuclease while maintaining the complementary binding activity of the sgRNA in the locked CRISPR complex to a target DNA sequence. In some cases, a catalytically dead CRISPR effector protein (e.g., Cas) can be fused to one or more transcriptional activators (e.g., VP64, p65, and/or RTa19), and a stabilized (e.g., locked) complex can be formed with a CRISPR polynucleotide (e.g., sgRNA). The stabilized (e.g., locked) complex can be delivered to a gene in a cell to upregulate transcription of the gene.

In some cases, the functional domain can be linked to a dead CRISPR effector protein (e.g., dead-CRISPR effector protein within a cell, a CRISPR complex can be formed.). The CRISPR ON polynucleotide comprising an unnatural nucleotide to crosslink with the CRISPR effector protein, can further comprises a polynucleotide leader sequence separated from a guide sequence by a photocleavable element. The cell can be exposed to UV radiation, resulting in cleavage of the cleavage element and release of the polynucleotide leader sequence. The CRISPR complex can then cleave target sequence. In some cases, a donor nucleic acid is also introduced into the cell, which can be used in homologous recombination at the cleavage site to introduce an edit to the nucleic acid.

The nucleic acid editing can target an endogenous regulatory control element (e.g., enhancer or silencer). The nucleic acid editing can target a promoter or promoter-proximal elements. These control elements can be located upstream or downstream of the transcriptional start site (TSS), starting from 200 bp from the TSS to 100 kb away. Targeting of known control elements can be used to activate or repress a gene of interest. A single control element can influence the transcription of multiple target genes. Targeting of a single control element can therefore be used to control the transcription of multiple genes simultaneously.

The one or more functional domains can be a nuclear localization sequence (NLS) or a nuclear export signal (NES).

The one or more functional domains can be a transcriptional activation domain. The transcriptional activation domain can be VP64, p65, MyoD1, HSF1, RTA, SET7/9, or a histone acetyltransferase. The CRISPR effector protein can be a dead Cas protein-fused with a domain with transcriptional activator or repressor activity. The dead Cas protein fused with a domain with transcriptional activator or repressor activity can be used to study the epistatic interactions between a given pair of genes in a specific tissue.

The one or more functional domains can have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

The one or more functional domains can be a transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase, or histone tail protease.

In some cases, the functional domain can be linked to a dead CRISPR effector protein (e.g., dead-Cas protein). The functional domain linked to the dead CRISPR effector protein (e.g., dead-Cas protein) can used to bind to and/or activate a promoter or enhancer. One or more CRISPR polynucleotides comprising a guide sequence that can anneal to the promoter or enhancer can also be provided to direct the binding of a CRISPR complex comprising a CRISPR effector protein (e.g., dead-Cas) to the promoter or enhancer. A CRISPR ON/OFF polynucleotide can be covalently crosslinked to a CRISPR effector protein, which can be a catalytically dead Cas9. The catalytically dead Cas9 can be fused to a transcription activation domain (e.g., VP64). The fusion, e.g., Cas9-VP64 fusion, and can be used to tunably modulate the expression of a target gene or a chromatin region. For example, the polynucleotide leader sequence of the CRISPR ON/OFF polynucleotide can prevent efficient localization of the CRISPR complex to target gene via the guide sequence. Cleavage of the polynucleotide leader sequence can result in efficient targeting of the CRISPR complex to the target sequence via the guide sequence, which can result in transcriptional activation. Subsequently, a second cleavage agent can be exposed to the CRISPR polynucleotide that results in cleavage of the CRISPR polynucleotide and reduces or inhibits the ability of the CRISPR complex (or CRISPR effector protein, if the cleaved CRISPR polynucleotide has dissociated from the CRISPR effector protein) to activate transcription of the gene.

Targeting of regions with either an activation or repression system described herein can be followed by readout of transcription of either a) a set of putative targets (e.g., a set of genes located in closest proximity to the control element) or b) whole-transcriptome readout by e.g. RNAseq or microarray.

In another example, CRISPR complexes provided herein can be used to study the epistatic interactions of two or more target genes in the host cell. A method can comprise of the steps: (i) using viral or non-viral delivery methods or a combination thereof, introducing into the host cell: (a) a CRISPR polynucleotide comprising first and second cleavage elements, where the cleavage elements are susceptible to cleavage and where the nucleotide sequence of the guide sequence is fully or partially complementary to a first target nucleic acid sequence; (b) a CRISPR effector protein (e.g., CRISPR) enzyme with catalytic activity, such that the CRISPR polynucleotide (e.g., sgRNA) and the CRISPR enzyme form a CRISPR complex; and (ii) at the desired time, inducing the cleavage of the first cleavage element in the CRISPR polynucleotide and activating higher target specific cleavage of the target gene by the CRISPR complex and then (iii) inducing cleavage of the second cleavage element at a desired time, thereby deactivating or lowering the target specific cleavage of the target gene by the CRISPR complex.

The method can further comprise (i) using viral or non-viral delivery methods or a combination thereof to introduce into the host cell: (a) a second CRISPR polynucleotide comprising of the first and second cleavage elements, where the cleavage elements are susceptible to cleavage and where the nucleotide sequence of the guide sequence is fully or partially complementary to a region of a second target sequence (e.g., in a target gene); (b) a CRISPR enzyme with catalytic activity, such that the second CRISPR polynucleotide (e.g., sgRNA) and the CRISPR enzyme form a second CRISPR complex; and (ii) at the desired time, inducing the cleavage of the first cleavage element in the second CRISPR polynucleotide and activating higher target specific cleavage of the target gene by the CRISPR complex and then (iii) inducing cleavage of the second cleavage element at a desired time, thereby deactivating or lowering the target specific cleavage of the target gene by the second CRISPR complex.

Furthermore, the cleavage of the first cleavage element in the first and second CRISPR complex can be under control of a tissue specific promoter, e.g., a muscle specific promoter. For example, expression of genetically engineered endoribonuclease Cas6a/Csy4 in the cell can be placed under the control of a tissue-specific promoter (e.g., muscle) promoter that can be activated at given times to induce cleavage of the first cleavage element. The second cleavage element in the first and second CRISPR complex can be inducibly cleaved at a desired time by exposure to a given sequence-specific small molecule. The CRISPR enzyme can be a dCas9-fused with a domain with transcriptional activator or repressor activity and can be used to study the epistatic interactions between a given pair of genes in a specific tissue.

In another example, CRISPR complexes described herein can be used to induce orthogonal transcription of two or more target genes in one or more target DNAs in a host cell. The term "orthogonal" can mean independent, i.e., the two or more target genes can be independently regulated or independently transcribed. The method can comprise the steps of using viral or non-viral delivery methods or a combination thereof for introducing into the host cell: (a) two or more different inducible CRISPR polynucleotides comprising of first and second cleavage elements, where the first and second sequence elements are susceptible to cleavage and where the nucleotide sequence of the guide sequence is fully or partially complementary to one or more target DNAs in the vicinity of the two or more different target genes; (b) a catalytically-inactive CRISPR enzyme linked to a transcriptional activator domain, such that the different inducible CRISPR polynucleotides and the CRISPR enzyme form different CRISPR complexes, wherein the CRISPR complexes comprise one or more effector domains; and (ii) at the desired times, inducing the cleavage of the first cleavage element in the first and second polynucleotide and thus coordinating the expression of the target genes. The target DNAs can be adjacent regions within a single gene or control element.

D. Pharmaceutical Formulation

The CRISPR polynucleotides and CRISPR complexes described herein can be used in vitro or in vivo to cause a change in a cell or an organism. The CRISPR polynucleotide and CRISPR effector protein can be introduced as a complex or they can form a complex within the cell. The CRISPR polynucleotide and/or CRISPR effector protein can be passively introduced to a cell or introduced through a vehicle. The CRISPR polynucleotide and the CRISPR effector protein can be present in a buffer at the time of introduction.

An aspect of the present disclosure encompasses a method for manufacturing stabilized (e.g., locked) CRISPR complexes for use in pharmaceutical formulations. CRISPR complexes can be prepared for delivery by, for example, liposomes and nanoparticle delivery. Alternatively, or in combination, vectors coding for CRISPR effector protein and/or CRISPR polynucleotide can be delivered to a patient by, for example, microinjection or other mechanical, physical, or viral methods. The CRISPR complexes and related vector constructs can be used in combination with one or more therapeutic, prophylactic, diagnostic, or imaging agents.

Pharmaceutical formulations can comprise one or more excipients to increase stability, enhance transfection to a cell, control release (such as from a carrier, e.g., nanoparticle), alter biodistribution, or alter translation of a vector encoding the CRISPR complex. Pharmaceutical formulations can comprise mixtures of the crosslinked CRISPR complex, water, co-solvents, buffer agents, and pH-adjusting agents. Co-solvent excipients can comprise oil, surfactants, emulsifiers, stabilizers, chelators, and preservatives. Stabilizers can include sugars and amino acids. Sugars can include sucrose and lactose. Amino acids can include glycine and monosodium glutamate. Preservatives can include phenol, phenoxyethanol and thimersosal.

The locked CRISPR complex an be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide, primary construct, or mRNA to specific tissues or cell types); (5) increase the translation of encoded protein in vivo; and/or (6) alter the release profile of encoded protein in vivo.

The excipients can be solvents, dispersion media, diluents, or other liquid vehicles, dispersion or suspension aids, surface active agents, isotonic agents, thickening or emulsifying agents, preservatives, and/or emulsifiers, preservatives, buffering agents, lubricating agents, and/or oils. The excipients can be lipidoids, liposomes, lipid nanoparticles, polymers, lipoplexes, core-shell nanoparticles, peptides, proteins, cells transfected with polynucleotide, primary construct, or Cas nuclease mRNA (e.g., for transplantation into a subject), hyaluronidase, nanoparticle mimics and combinations thereof.

Relative amounts CRISPR polynucleotide, CRISPR effector protein, or nucleic acid encoding either, and the pharmaceutically acceptable excipient, and/or any additional ingredients in a pharmaceutical composition can vary, depending upon the identity, size, and/or condition of the subject treated and further depending upon the route by which the composition is to be administered. The composition can comprise between 0.1% and 100%, e.g., between 0.5 and 50%, between 1-30%, between 5-80%, at least 80% (w/w) CRISPR polynucleotide, CRISPR effector protein, or nucleic acid encoding either.

The CRISPR polynucleotide sequence comprising at least one unnatural nucleotide for crosslinking and an activity modulating element such as a CRISPR ON polynucleotide, CRISPR OFF polynucleotide, or CRISPR ON/OFF polynucleotide, described herein can be formulated in pharmaceutical compositions comprising one or more pharmaceutically acceptable excipients. The pharmaceutical compositions can comprise one or more additional active substances, e.g., therapeutically and/or prophylactically active substances. General considerations in the formulation and/or manufacture of pharmaceutical compositions can be found, for example, in Remington: The Science and Practice of Pharmacy 2 ed., Lippincott Williams & Wilkins, 2005 (incorporated herein by reference in its entirety).

The synthesis of lipidoids has been extensively described and formulations containing these compounds are particularly suited for delivery of the modified CRISPR ON polynucleotide, CRISPR OFF polynucleotide, or CRISPR ON/OFF polynucleotide, described herein and primary constructs (see Mahon et al., Bioconjug Chem. 2010 21: 1448-1454; Schroeder et al., J Intern Med. 2010 267:9-21; Akinc et al, Nat Biotechnol. 2008 26:561-569; Love et al, Proc Natl Acad Sci USA. 2010 107: 1864-1869; Siegwart et al., Proc Natl Acad Sci USA. 2011 108: 12996-3001; all of which are incorporated herein in their entireties). Different ratios of lipidoids and other components including, but not limited to, disteroylphosphatidyl choline, cholesterol and PEG-DMG, can be used to optimize the formulation of the polynucleotide, primary construct, or Cas nuclease mRNA for delivery to different cell types including, but not limited to, hepatocytes, myeloid cells, muscle cells, etc.

The locked CRISPR complex can be formulated using one or more liposomes, lipoplexes, or lipid nanoparticles (LNP). The pharmaceutical compositions can include liposomes. The pharmaceutical compositions described herein can include liposomes such as those formed from the synthesis of stabilized plasmid-lipid particles (SPLP) or stabilized nucleic acid lipid particle (SNALP) that have been previously described and shown to be suitable for polynucleotide delivery in vitro and in vivo (see Wheeler et al. Gene Therapy. 1999 6:271-281; Zhang et al. Gene Therapy. 1999 6: 1438-1447; Jeffs et al. Pharm Res. 2005 22:362-372; Morrissey et al, Nat Biotechnol. 2005 2: 1002-1007). The CRISPR polynucleotides can be formulated in a lipid vesicle which can have crosslinks between functionalized lipid bilayers.

The locked CRISPR complex can be formulated in a lipid-polycation complex. The formation of the lipid-polycation complex can be accomplished by methods known in the art and/or as described in U.S. Pub. No. 20120178702, herein incorporated by reference in its entirety. The pharmaceutical composition can include at least one of the PEGylated lipids described in International Publication No. 2012099755, herein incorporated by reference.

The LNP formulation can be formulated by the methods described in International Publication Nos. WO2011 127255 or WO2008 103276, each of which is herein incorporated by reference in their entirety. The CRISPR polynucleotide can be encapsulated in LNP formulations as described in WO2011 127255 and/or WO2008103276; each of which is herein incorporated by reference in their entirety.

The locked CRISPR complex can be formulated as a solid lipid nanoparticle. A solid lipid nanoparticle (SLN) can be spherical with an average diameter between 10 to 1000 nm. SLN can possess a solid lipid core matrix that can solubilize lipophilic molecules and can be stabilized with surfactants and/or emulsifiers. The lipid nanoparticle can be a self-assembly lipid-polymer nanoparticle (see Zhang et al, ACS Nano, 2008, 2 (8), pp 1696-1702; herein incorporated by reference in its entirety).

The locked CRISPR complex, primary constructs, or the Cas nuclease mRNA can be encapsulated into a lipid nanoparticle or a rapidly eliminating lipid nanoparticle and the lipid nanoparticles or a rapidly eliminating lipid nanoparticle can then be encapsulated into a polymer, hydrogel and/or surgical sealant described herein and/or known in the art.

The locked CRISPR complex formulation for controlled release and/or targeted delivery can also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, The controlled release and/or targeted delivery formulation can comprise at least one degradable polyester which can contain polycationic side chains. The degradable polyester can be poly(serine ester), poly(L-lactide-co-L-lysine), poly(4-hydroxy-L-proline ester), and combinations thereof. The degradable polyesters can include a PEG conjugation to form a PEGylated polymer.

The locked CRISPR complex can be encapsulated in a therapeutic nanoparticle. The therapeutic nanoparticle can be formulated for sustained release. The period of time can include hours, days, weeks, months and years. As a non-limiting example, the sustained release nanoparticle can comprise a polymer and a therapeutic agent, e.g., CRISPR polynucleotides described herein (see International Pub No. 2010075072 and US Pub No. US20100216804 and US20110217377, each of which is herein incorporated by reference in their entirety. The therapeutic nanoparticles can be formulated to be target specific. The therapeutic nanoparticles can include a corticosteroid (see International Pub. No. WO2011084518).

The locked CRISPR complex can be encapsulated in, linked to and/or associated with synthetic nanocarriers. The synthetic nanocarriers can be formulated by the methods described in International Pub Nos. WO2010005740, WO2010030763. The synthetic nanocarriers can contain reactive groups to release the CRISPR polynucleotides, described herein (see International Pub. No. WO20120952552 and US Pub No. US20120171229, each of which is herein incorporated by reference in their entirety).

The synthetic nanocarriers can be formulated for targeted release. The synthetic nanocarrier can be formulated to release the CRISPR complex at a specified pH and/or after a desired time interval. The synthetic nanoparticle can be formulated to release the polynucleotides, primary constructs and/or Cas nuclease mRNA after 24 hours and/or at a pH of 4.5 (see International Pub. Nos. WO2010138193 and WO2010138194 and US Pub Nos. US20110020388 and US20110027217, each of which is herein incorporated by reference in their entireties).

The synthetic nanocarriers can be formulated for controlled and/or sustained release of the locked CRISPR complex described herein. The synthetic nanocarriers for sustained release can be formulated, e.g., as described herein and/or as described in International Pub No.

WO2010138192 and US Pub No. 20100303850, each of which is herein incorporated by reference in their entireties.

The locked CRISPR complex can be formulated with or in a polymeric compound. The polymer can include at least one polymer polyethenes, polyethylene glycol (PEG), poly (1-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, a biodegradable polymer, biodegradable block copolymer, biodegradable random copolymer, biodegradable polyester copolymer, biodegradable polyester block copolymer, biodegradable polyester block random copolymer, linear biodegradable copolymer, poly[a-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly (orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), acrylic polymers, amine-containing polymers or combinations thereof.

The locked CRISPR complex described herein can be conjugated with another compound. The CRISPR polynucleotide can also be formulated as a nanoparticle using a combination of polymers, lipids, and/or other biodegradable agents, e.g., calcium phosphate. Components can be combined in a core-shell, hybrid, and/or layer-by-layer architecture, to allow for fine-tuning of the nanoparticle so the delivery of the CRISPR polynucleotide can be enhanced (Wang et al, Nat Mater. 2006 5:791-796; Fuller et al, Biomaterials. 2008 29: 1526-1532; DeKoker et al, Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in its entirety).

The locked CRISPR complex can be formulated with peptides and/or proteins in order to increase transfection of cells by the locked CRISPR complex. The peptides can be cell penetrating peptides and proteins and peptides that enable intracellular delivery can be used to deliver pharmaceutical formulations.

The locked CRISPR complex can be transfected ex vivo into cells, and subsequently transplanted into a subject. Examples of such vectors include primary nucleic acid constructs or synthetic sequences encoding CRISPR effector proteins or related polypeptides. The pharmaceutical compositions can include red blood cells to deliver modified RNA to liver and myeloid cells, virosomes to deliver modified RNA in virus-like particles (VLPs), and electroporated cells e.g., from MAXCYTE® (Gaithersburg, MD) and from ERYTECH® (Lyon, France) to deliver modified RNA.

Cell-based formulations of the locked CRISPR complex disclosed herein or related vector constructs can be used to ensure cell transfection (e.g., in the cellular carrier), alter the biodistribution of the locked CRISPR complex (e.g., by targeting the cell carrier to specific tissues or cell types), and/or increase the translation of encoded protein.

The compositions can also be formulated for direct delivery to an organ or tissue by, e.g., direct soaking or bathing, via a catheter, by gels, powder, ointments, creams, gels, lotions, and/or drops, by using substrates such as fabric or biodegradable materials coated or impregnated with the compositions, and the like.

An aspect of the present disclosure encompasses a method for administering a pharmaceutical formulation to a patient. Unbound RNA can elicit an immune response by interferon gamma. A locked CRISPR complex can greatly lessen the likelihood of an unbound sgRNA in a pharmaceutical composition. Linked CRISPR complexes and related sequences/polypeptides can be administered by any route which results in a therapeutically effective outcome. These include enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. Compositions can be administered in a way which allows them to cross the blood-brain barrier, vascular barrier, or other epithelial barrier.

The pharmaceutical formulation can be administered to a subject in need thereof 4 times a day, 3 times a day, 2 times a day, daily, three times a week, two times a week, weekly, four times a month, 3 times a month, 2 times a month, monthly, 4 times a year, 3 times a year, 2 times a year, or annually. The administration can be for over a period of time, and the period of time can be at least or up to 1 week, at least or up to 1 month, at least or up to 1 year, at least or up to 10 years, or a lifetime of the subject.

E. Conditions

An aspect of the present disclosure encompasses the treatment of a disease condition with CRISPR complexes. Disease conditions can include cancer, neurological conditions, autoimmune disorders, etc. Treatment of a disease condition can comprise treatment of a diseased tissue. Treatment can comprise the treatment of cells with the CRISPR complex followed by injecting, grafting, or implanting the cells into a human patient.

The CRISPR ON polynucleotide, CRISPR OFF polynucleotide, or CRISPR ON/OFF polynucleotide, described herein can be used in a number of different scenarios in which delivery of a substance (the "payload") to a biological target is desired, for example delivery of detectable substances for detection of the target, or delivery of a therapeutic agent. The CRISPR polynucleotides and related vector constructs can be used in combination with one or more other therapeutic, prophylactic, diagnostic, or imaging agents.

The CRISPR ON polynucleotide, CRISPR OFF polynucleotide, or CRISPR ON/OFF polynucleotide, described herein and other primary constructs can be designed to include both a linker and a payload in any useful orientation. For example, a linker having two ends can be used to attach one end to the payload and the other end to the nucleobase, such as at the C-7 or C-8 positions of the deaza-adenosine or deaza-guanosine or to the N-3 or C-5 positions of cytosine or uracil. The payload can be a therapeutic agent such as a cytotoxin, radioactive ion, chemotherapeutic, or other therapeutic agent.

The CRISPR ON polynucleotide, CRISPR OFF polynucleotide, or CRISPR ON/OFF polynucleotide, described herein can be used to alter the phenotype of cells. The CRISPR polynucleotide or CRISPR effector protein encoding sequence can be used in therapeutics and/or clinical and research settings. The CRISPR ON polynucleotide, CRISPR OFF polynucleotide, or CRISPR ON/OFF polynucleotide, described herein and related vector constructs and the proteins translated from them described herein can be used as therapeutic or prophylactic agents. For example, a CRISPR polynucleotide or Cas nuclease mRNA described herein (e.g. a modified mRNA encoding a CRISPR-related polypeptide or effector protein) can be administered to a subject, and translated in vivo to direct the expression of a therapeutically relevant or prophylactic polypeptide in the subject.

The ability of a guide sequence (within a nucleic acid-targeting guide RNA or sgRNA) to direct sequence-specific binding of a nucleic acid-targeting complex to a target nucleic acid sequence can be assessed by any suitable assay. For example, the components of a nucleic acid-targeting CRISPR system sufficient to form a nucleic acid-targeting complex, including the guide sequence to be tested, can be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence. Cleavage of a target nucleic acid sequence can be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions.

Compositions provided herein can be used for treatment of any of a variety of diseases, disorders, and/or conditions, e.g., one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

In one aspect, the disease condition can be cardiovascular disease, diabetes, lung diseases, chronic obstructive pulmonary disease (COPD), asthma, idiopathic pulmonary fibrosis, chronic bronchitis, cystic fibrosis, coronary heart disease, cerebrovascular diseases, etc. In one aspect, the disease condition can be Alzheimer's disease, Amyotrophic lateral sclerosis (ALS), arteriovenous malformation, multiple sclerosis (MS), or Parkinson's disease. In another aspect, the disease condition can be psoriasis, Graves' disease, Guillain-Barre syndrome, hashimoto's thyroiditis, vasculitis, myasthenia gravis, chronic inflammatory demyelinating polyneuropathy, Type 1 diabetes mellitus, multiple sclerosis, systemic lupus, rheumatoid arthritis, etc.

In one aspect, the disease condition can be biliary tract cancer (e.g., adenocarcinoma), lung cancer (e.g., large cell carcinoma, non small cell carcinoma, squamous cell carcinoma, neoplasia, etc.), colorectal cancer, prostate cancer, endometrial cancer, ovarian cancer, hematopoietic cancer, leukemia, lymphatic cancer, renal cancer, breast cancer (e.g. carcinoma), esophageal cancer, pancreatic cancer, skin cancer (e.g. basal cell carcinoma, squamous cell carcinoma, malignant melanoma, etc.), soft tissue cancer (e.g. angiosarcoma, leimyosarcoma, liposarcoma, rhabdomyosarcoma, myxoma, malignant fibrous histiocytoma-pleomorphic sarcoma, etc.), testicular cancer (e.g., germinoma, seminoma, etc.), thyroid cancer (e.g., anaplastic carcinoma, follicular carcinoma, papillary carcinoma, Hurthle cell carcinoma, etc.), bladder cancer (e.g. transitional cell carcinoma), cervical cancer (e.g. adenocarcinoma), uterine cancer, peritoneal cancer, brain cancer, neuroblastoma, mesothelioma, cholangiocarcinoma, chondrosarcoma, leukemia (e.g. AML, CML, CMML, JMML, etc.), lymphoma (e.g. ALL, Burkitt's lymphoma, Hodgkin's lymphoma, Plasma cell myeloma, etc.), adrenal cortical cancer, anal cancer, aplastic anemia, bile duct cancer, bone cancer, bone metastasis, brain cancers, central nervous system (CNS) cancers, peripheral nervous system (PNS) cancers, cervical cancer, childhood Non-Hodgkin's lymphoma, pancreatic cancer (e.g. ductal adenocarcinoma, endocrine tumor, etc.), colon cancer (e.g. adenocarcinoma, adenoma, etc.), colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's lymphoma, Kaposi's sarcoma, kidney cancer, laryngeal and pharyngeal cancer, acute lymphocytic leukemia, acute myeloid leukemia, children's leukemia, chronic lymphocytic leukemia, chronic myeloid leukemia, liver cancer (e.g. hepatocellular carcinoma), lung carcinoid tumors, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, penile cancer, pituitary tumor, prostate cancer (e.g. adenocarcinoma), retinoblastoma, rhabdomyosarcoma, salivary gland cancer, sarcomas, melanoma skin cancer, nonmelanoma skin cancers, stomach cancer (e.g. adenocarcinoma, etc.), thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, Waldenstrom's macroglobulinemia, ganglia cancer (e.g. neuroblastoma), or a nerve sheath cancer.

F. Expression of CRISPR Effector Protein and CRISPR Polynucleotide

In some cases, one or more expression vectors for expressing CRISPR polynucleotide and CRISPR effector protein (e.g., CRISPR enzyme) can be transfected into a host cells. The expression vector comprising a DNA sequence coding for the CRISPR polynucleotide can be transfected into the host cell first and then an expression vector comprising a DNA sequence coding for the CRISPR effector protein (e.g., CRISPR enzyme) can be transfected into the host cell. The expression vector comprising a DNA sequence coding for the CRISPR effector protein (e.g., CRISPR enzyme) and an expression vector comprising a DNA sequence coding for the inducible CRISPR polynucleotide can be transfected simultaneously into the host cell. A single (type of) expression vector comprising a DNA sequence coding for the CRISPR effector protein (e.g., CRISPR enzyme) and a DNA sequence coding for the inducible CRISPR polynucleotide can be transfected into the host cell. The host cell can be a host cell which endogenously expresses the CRISPR effector protein (e.g., CRISPR enzyme). A messenger RNA encoding the CRISPR effector protein (e.g., CRISPR enzyme) can also be used with a CRISPR polynucleotide, e.g., a sgRNA for gene editing. When a vector is used, it can contain an inducible promoter. Conditional promoter(s) and/or inducible promoter(s) and/or tissue specific promoter(s) can be RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. In some cases, a transgene encoding a CRISPR effector protein (e.g., CRISPR enzyme) can be integrated into a genome of cell.

A transgene expressing the CRISPR effector protein (e.g., CRISPR enzyme) can be introduced in a cell. A CRISPR effector protein (e.g., CRISPR enzyme, e.g., Cas9) transgene can be introduced into an isolated cell. A CRISPR complex transgenic cell can be obtained by isolating cells from a transgenic organism. A CRISPR effector protein (e.g., CRISPR enzyme, e.g., Cas9) transgene can be delivered to a eukaryotic cell by means of vector (e.g., AAV, adenovirus, lentivirus) and/or particle and/or nanoparticle delivery, as also described herein.

In some cases, the CRISPR polynucleotide can be inducibly expressed. In some cases, the CRISPR effector protein (e.g., CRISPR enzyme) can be inducibly expressed. Inducing expression of the CRISPR polynucleotide and/or CRISPR effector protein (e.g., CRISPR enzyme) can result in formation of a CRISPR polynucleotide/CRISPR effector protein (e.g., CRISPR enzyme) complex that can be turned "on" at a desired time to target a target nucleic acid (e.g., target DNA) and to cleave that target nucleic acid (e.g., target DNA). The inducible complexes can be used to reduce off-target effects by limiting the active half-life of the complex or by achieving tissue-specific editing in model organisms or in human cells.

The inducible CRISPR polynucleotide and/or CRISPR effector protein (e.g., CRISPR enzyme) can be expressed within a host cell. The expression can be in any order.

V. CRISPR Polynucleotide Synthesis

The polynucleotide modified with an unnatural nucleotide for crosslinking further comprising a CRISPR ON polynucleotide sequence, CRISPR OFF polynucleotide sequence, CRISPR ON/OFF polynucleotide sequence, or CRISPR polynucleotides comprising one or more modifications that, when complexed with a CRISPR enzyme, have reduced off-target editing activity, described herein can be synthesized by any method known to one of ordinary skill in the art. The polynucleotide modified with an unnatural nucleotide for crosslinking further comprising a CRISPR ON polynucleotide, CRISPR OFF polynucleotide, or CRISPR ON/OFF polynucleotide, described herein can be chemically synthesized. The polynucleotide modified with an unnatural nucleotide for crosslinking further comprising a CRISPR ON polynucleotide, CRISPR OFF polynucleotide, or CRISPR ON/OFF polynucleotide, described herein can be synthesized using 2'-0-thionocarbamate-protected nucleoside phosphoramidites. Methods of synthesis of polynucleotides are described in, e.g., Dellinger et al., J. American Chemical Society 133, 11540-11556 (2011); Threlfall et al., Organic & Biomolecular Chemistry 10, 746-754 (2012); and Dellinger et al, J. American Chemical Society 125, 940-950 (2003). Any of the modifications described herein can be combined and incorporate a CRISPR ON polynucleotide, CRISPR OFF polynucleotide, or CRISPR ON/OFF polynucleotide described herein, for example, in the guide sequence and/or the sequence that binds a CRISPR effector protein (e.g., scaffold sequence). Alternatively, the CRISPR polynucleotides can be prepared by the phosphoramidite method described by Beaucage and Caruthers (Tetrahedron Lett., (1981) 22:1859-1862), or by the triester method according to Matteucci, et al., (J. Am. Chem. Soc, (1981) 103:3185), each of which is specifically incorporated herein by reference, or by other chemical methods using a commercial automated polynucleotide synthesizer.

The CRISPR polynucleotides can be chemically synthesized, e.g., according to the solid phase phosphoramidite triester method first described by Beaucage and Caruthers, Tetrahedron Lett. 22: 1859-1862 (1981), using an automated synthesizer, as described in Van Devanter et. al, Nucleic Acids Res. 12:6159-6168 (1984). Synthesis of the CRISPR polynucleotides can comprise introducing chemical modifications that employ special phosphoramidite reagents during solid phase synthesis.

A. sgRNA Linkage

A CRISPR polynucleotide that is a sgRNA can comprise a modified crRNA and tracrRNA sequence chemically linked or conjugated via a non-phosphodiester bond. The modified crRNA and tracrRNA sequence can be chemically linked or conjugated via a non-nucleotide loop. The modified crRNA and tracrRNA can be joined via a non-phosphodiester covalent linker. The covalent linker can be a chemical moiety selected from the group consisting of coumarin, carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

B. Cleavable Elements

The cleavable elements in the CRISPR polynucleotide herein can be provided with functional groups at each end that can be suitably protected or activated. The functional groups can be covalently attached via an ether, ester, carbamate, phosphate ester or amine linkage. For example, hexaethyleneglycol can be protected on one terminus with a photolabile protecting group (i.e., NVOC or MeNPOC) and activated on the other terminus with 2-cyanoethyl-N,N-diisopropylamino-chlorophosphite to form a phosphoramidite. Other methods of forming ether, carbamate or amine linkages are known to those of skill in the art and particular reagents and references can be found in such texts as March, Advanced Organic Chemistry, 4th Ed., Wiley-Interscience, New York, N.Y., 1992.

Methods of synthesizing the linkers described herein are well-known in the art. A non-limiting example of a method of synthesizing a linker of this application is provided below:

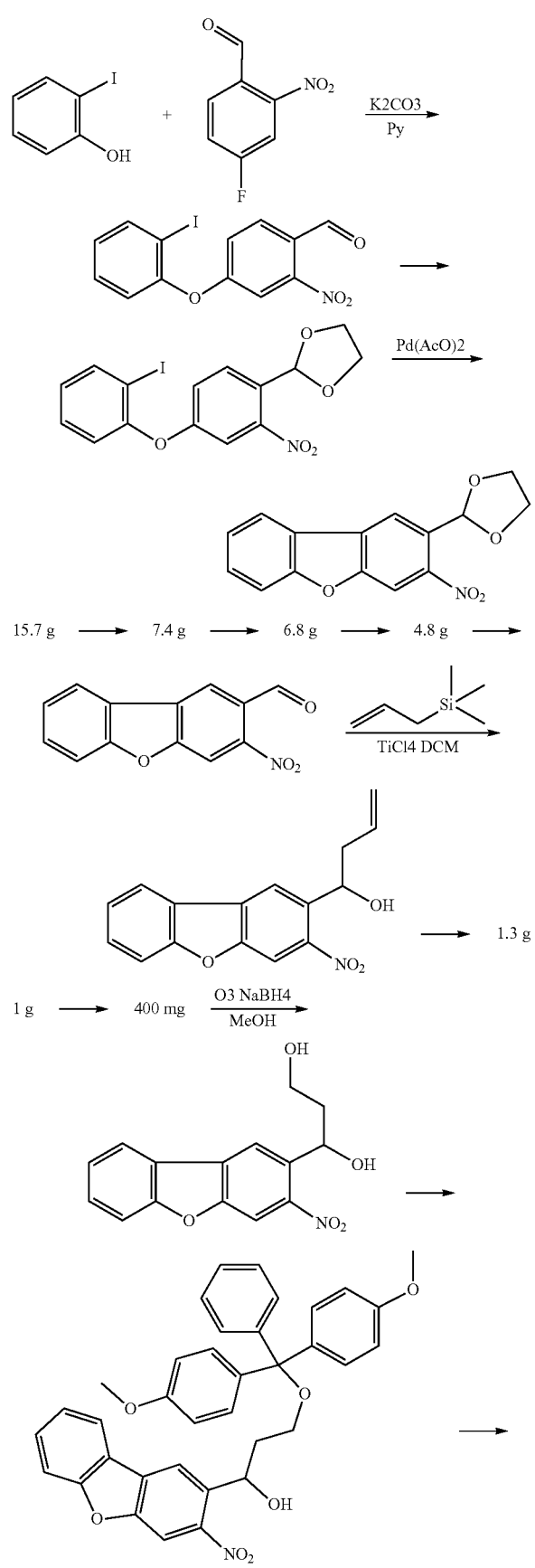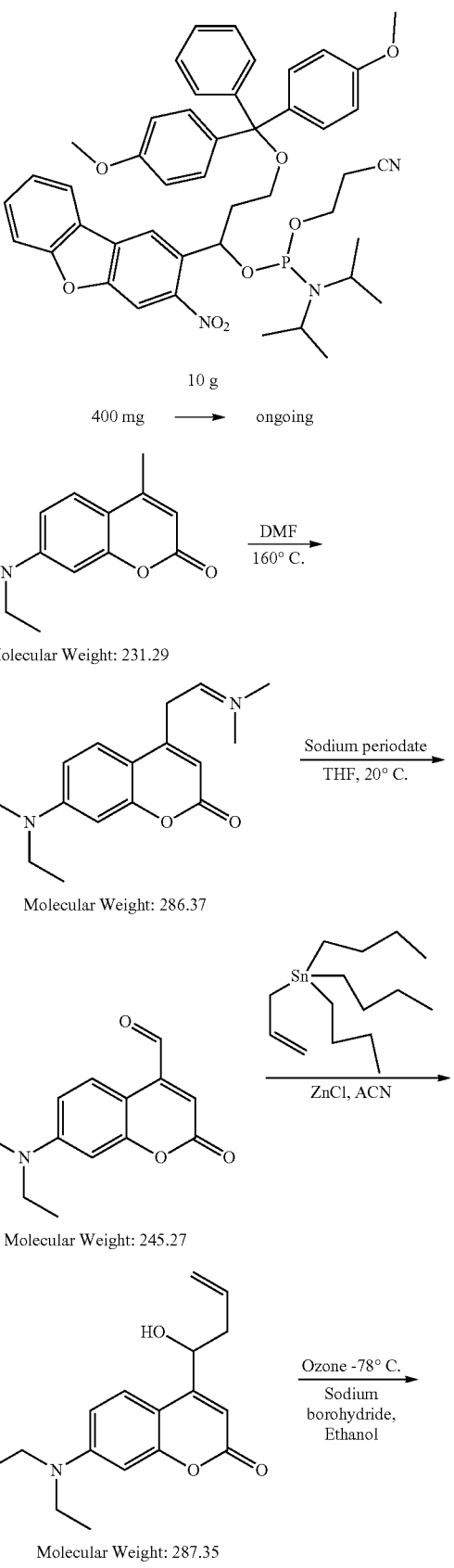

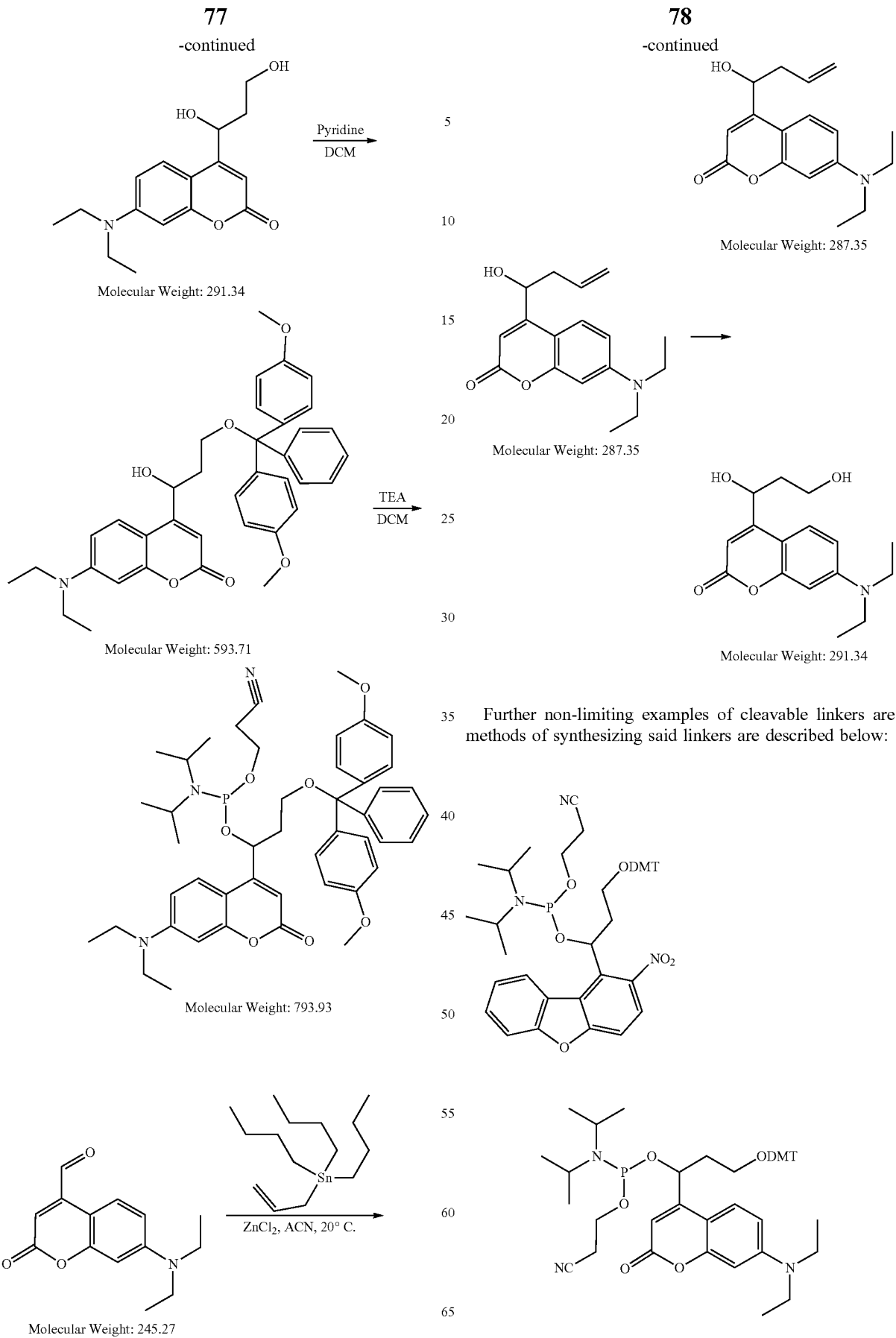
Further non-limiting examples of cleavable linkers are methods of synthesizing said linkers are described below:

79
-continued
80
-continued
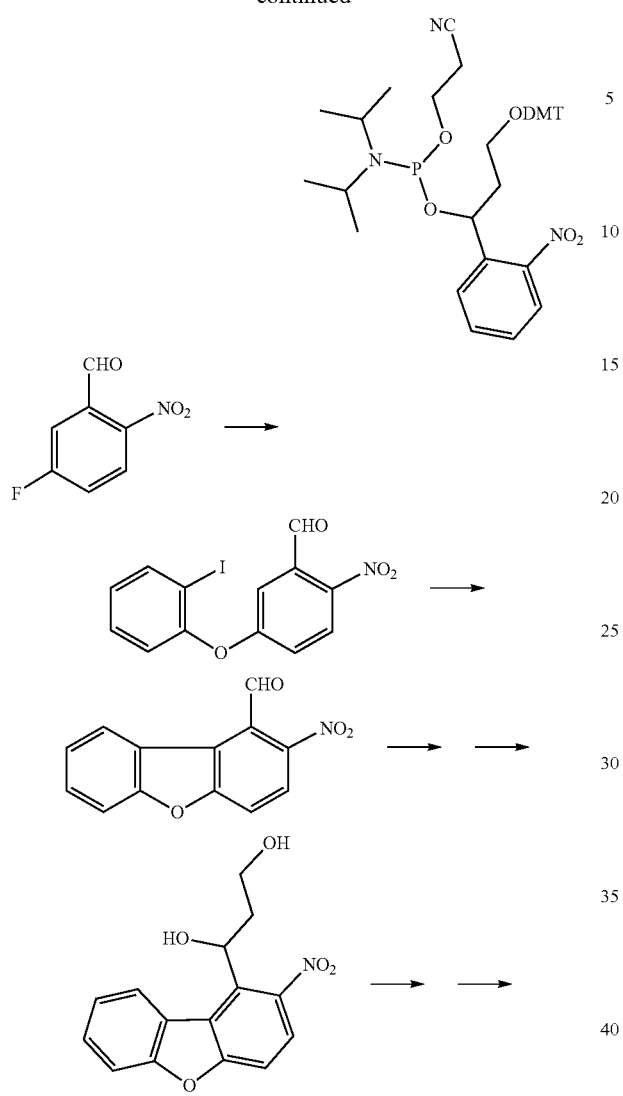
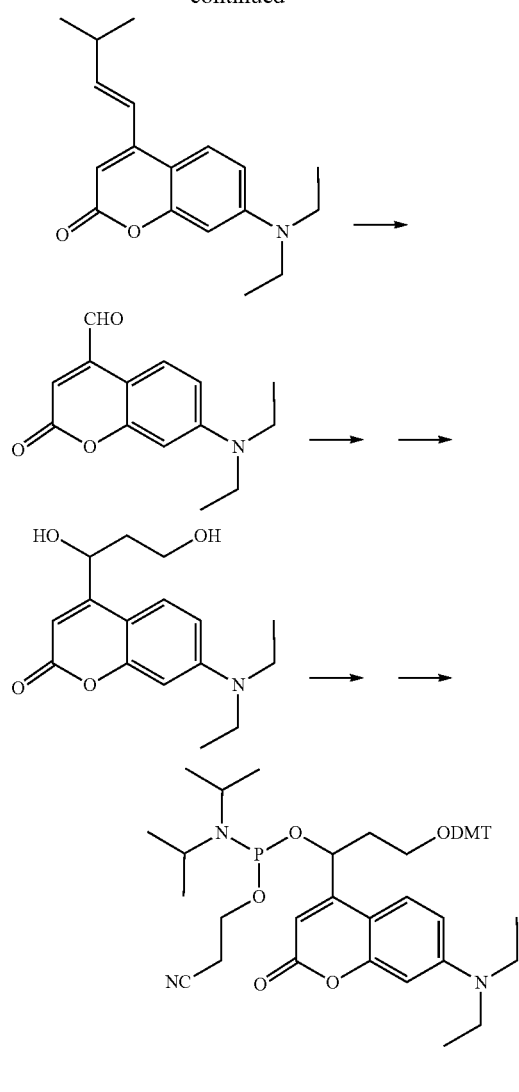
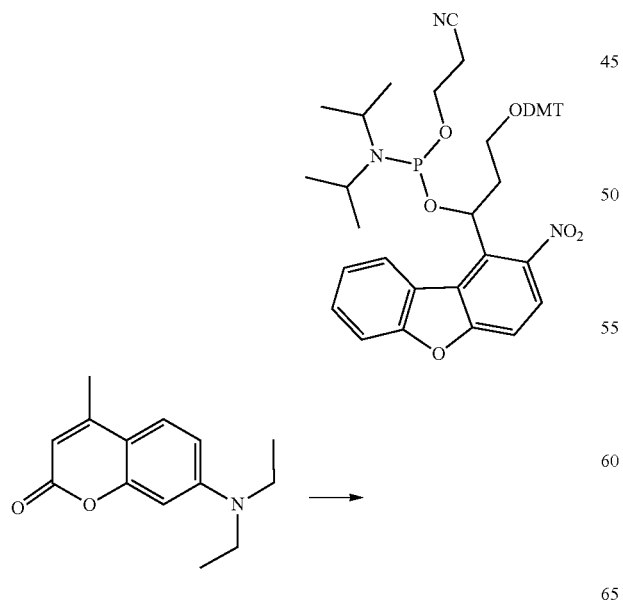

Non-limiting examples of cleavable linkers are methods of synthesizing said linkers are described below:

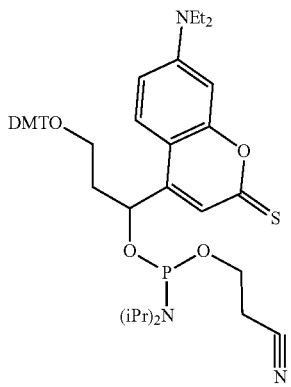

C. sgRNA Synthesis

The sgRNA comprising crRNA and tracrRNA can first be synthesized using a phosphoramidite synthetic protocol (Herdewijn, P., ed., Methods in Molecular Biology Col 288, Polynucleotide Synthesis. Methods and Applications, Humana Press, New Jersey (2012)). The sgRNA comprising crRNA and tracrRNA sequences can be functionalized to contain an appropriate functional group for ligation (see e.g., Hermanson, G. T., Bioconjugate Techniques, Academic Press (2013)). The functional group can be hydroxyl, amine, carboxylic acid, carboxylic acid halide, carboxylic acid active ester, aldehyde, carbonyl, chlorocarbonyl, coumarin, psoralen, diazirine, or azide. Once the modified tracr and the tracr mate sequences are functionalized, a covalent chemical bond or linkage can be formed between the two polynucleotides. The chemical bonds can be based on coumarin, carbamates, ethers, esters, amides, imines, amidines, aminotrizines, hydrozone, disulfides, thioethers, thioesters, phosphorothioates, phosphorodithioates, sulfonamides,

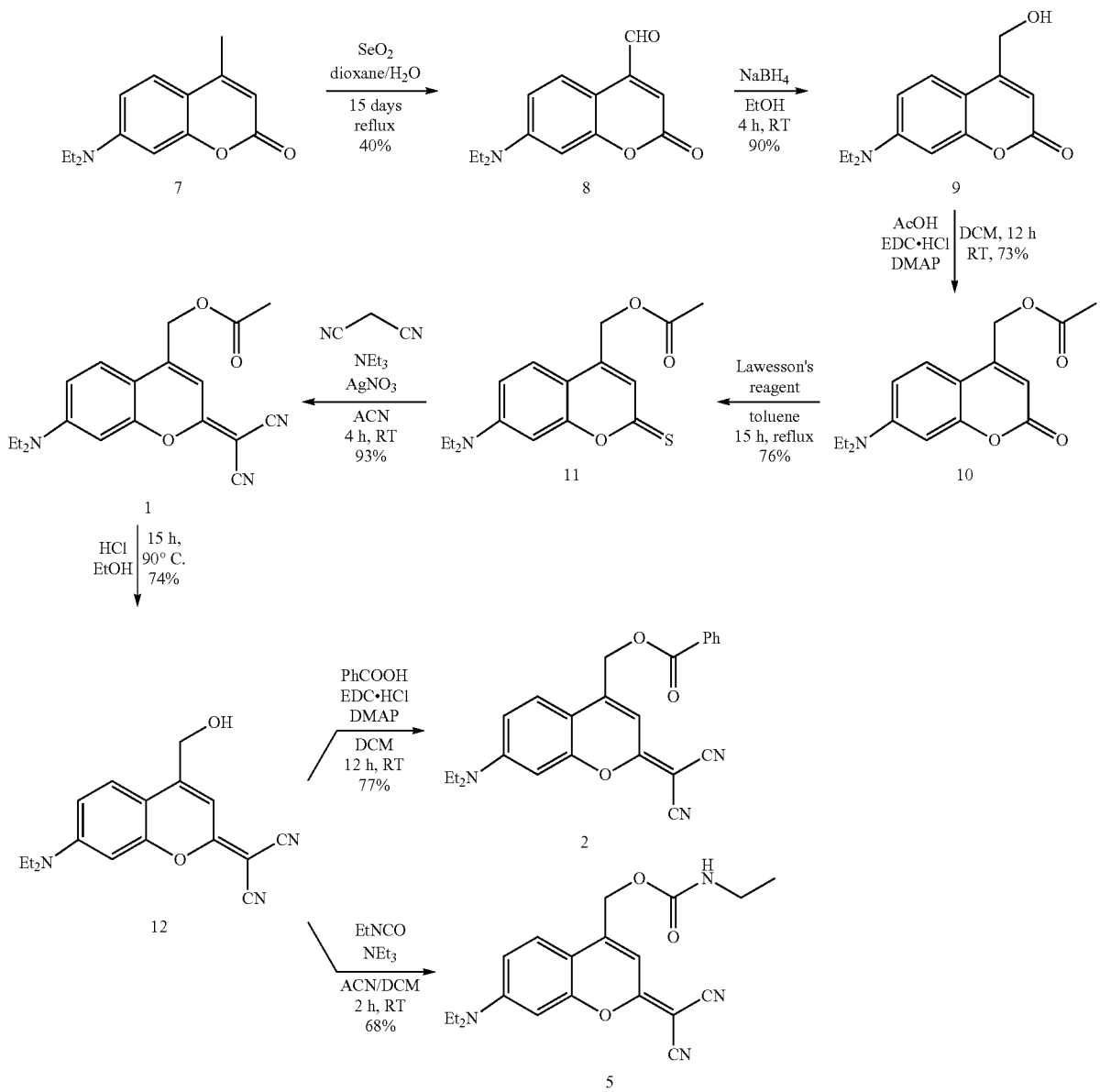

sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

The sgRNA comprising crRNA and tracrRNA sequence and can be chemically synthesized. The sgRNA can be synthesized together in the form of a fusion or synthesized separately and chemically linked. The chemical synthesis can use automated using solid-phase polynucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

The sgRNA can be covalently linked with various bioconjugation reactions, loops, bridges, and non-nucleotide links via modifications of sugar, internucleotide phosphodiester bonds, purine and pyrimidine residues. Sletten et al., Angew. Chem. Int. Ed. (2009) 48:6974-6998; Manoharan, M. Curr. Opin. Chem. Biol. (2004) 8: 570-9; Behlke et al., Polynucleotides (2008) 18: 305-19; Watts, et al., Drug. Discov. Today (2008) 13: 842-55; Shukla, et al., ChemMedChem (2010) 5: 328-49.

The sgRNA can be assembled using click chemistry. The crRNA tracrRNA and/or the sequence elements therein can be assembled by covalent linkage using a triazole linker. The sgRNA can be covalently linked by ligating a 5'-hexyne tracrRNA and a 3'-azide crRNA. Either or both of the 5'-hexyne tracrRNA and a 3'-azide crRNA can be protected with 2'-acetoxyethyl orthoester (2'-ACE) group, which can be subsequently removed using Dharmacon protocol (Scaringe et al., J. Am. Chem. Soc. (1998) 120: 11820-11821; Scaringe, Methods Enzymol. (2000) 317: 3-18).

VI. Kits

A kit can comprise one or more of the components described herein. The kit can comprise a CRISPR polynucleotide described herein. The kit can comprise a CRISPR effector protein (e.g., a CRISPR enzyme, e.g. Cas9) described herein. The kit can comprise a CRISPR complex described herein comprising a CRISPR polynucleotide described herein and a CRISPR effector protein described herein. The kit can comprise a linker, for example a cleavable linker. The kit can comprise a photocleavable linker. The kit can comprise instructions. The kit can comprise a cell or organism comprising a CRISPR polynucleotide, CRISPR effector protein, or CRISPR complex described herein.

The kit can comprise a genetic construct, e.g., vector system for expressing one or more CRISPR polynucleotides and/or one or more CRISPR effector proteins and instructions for using the kit. The kit can comprise a cell that comprises one or more genetic constructs (e.g., one or more vector systems) for expressing a CRISPR polynucleotide and/or CRISPR effector protein described herein.

The kit can comprise an excipient to generate a composition suitable for contacting a nucleic acid target with e.g., a CRISPR complex described herein. The composition can be suitable for contacting a nucleic acid target sequence within a genome. The composition can be suitable for delivering the composition (e.g., a CRISPR polynucleotide, e.g., a sgRNA, e.g., complexed with a CRISPR effector protein, e.g., a CRISPR enzyme, e.g. Cas9) to a cell. The composition can be suitable for delivering a CRISPR polynucleotide, e.g., a gRNA, or complexes thereof with CRISPR enzyme) to a subject. The excipient can be a pharmaceutically acceptable excipient.

The kit can comprise one or more reagents for use in cleaving one or more of the cleavable elements of the CRISPR polynucleotides described herein. The one or more reagents can be provided in any suitable container. The kit can comprise one or more reaction or storage buffers. The kit can comprise a reagent. The reagent can be provided in a form that is usable in a particular assay, or in a form that requires addition of one or more other components before use (e.g. in concentrate or lyophilized form). A reaction or storage buffer can be any buffer, e.g., sodium carbonate buffer, a sodium bicarbonate buffer, a borate buffer, a Tris buffer, a MOPS buffer, a HEPES buffer, or a combination thereof. The buffer can have a pH from about 7 to about 10.

The kit can comprise one or more polynucleotides corresponding to a guide sequence for insertion into a vector so as to operably link the guide sequence and a regulatory element. The kit can comprise a homologous recombination template polynucleotide.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-244 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A CRISPR complex comprising a guide RNA (gRNA) cross-linked to a CRISPR effector protein at a nucleotide within the gRNA, wherein the gRNA comprises a target binding region and a CRISPR effector protein binding region, and wherein the nucleotide is outside the target binding region of the gRNA.
2. The CRISPR complex of embodiment 1, wherein the nucleotide comprises a uracil.
3. The CRISPR complex of embodiment 1 or 2, wherein the gRNA is a single guide RNA (sgRNA) comprising a crRNA region comprising a target binding region and a tracrRNA region, and wherein the nucleotide is outside the target binding region of the crRNA region.
4. The CRISPR complex of embodiment 3, wherein the nucleotide is at nucleotide position 49 of the sgRNA, wherein nucleotide position 1 is at a 5' end of the target binding region of the crRNA and nucleotide positions of the sgRNA are numbered consecutively from 5' to 3' from nucleotide position 1.
5. The CRISPR complex of embodiment 3, wherein the nucleotide is at one or more nucleotide positions: 22, 23, 24, 25, 31, 37, 44, 49, 45, 50, 56, 59, 63, 64, 66, 71, 72, 77, 78, 80, 84, 90 or 94 of the sgRNA, wherein nucleotide position 1 is at a 5' end of the target binding region of the crRNA and nucleotide positions of the sgRNA are numbered consecutively from 5' to 3' from nucleotide position 1.
6. The CRISPR complex of any one of embodiments 1 to 5, wherein the nucleotide is an unnatural nucleotide.
7. The CRISPR complex of embodiment 6, wherein the unnatural nucleotide comprises a modification of a sugar.

8. The CRISPR complex of embodiment 6 or 7, wherein the unnatural nucleotide comprises a modification of a base.
9. The CRISPR complex of embodiment 6, wherein the unnatural nucleotide comprises a maleimide.
10. The CRISPR complex of embodiment 9, wherein the maleimide covalently links to a cysteine on the CRISPR effector protein.
11. The CRISPR complex of embodiment 6, wherein the gRNA is cross-linked to the CRISPR effector protein via a crosslinker, wherein the crosslinker comprises or is derived from pyridyl disulfide, alkoxyamine, NHS ester, diazarine, imidoester, haloacetyl group, hydrazide, aryl azide, isocyanate, dithiol phosphoramidite DTPA, 4-thio-UTP, 5-azido-UTP, 5-bromo-UTP, 8-azido-ATP, 5-APAS-UTP, or 8-N(3)AMP.
12. The CRISPR complex of embodiment 6, wherein the gRNA is cross-linked to the CRISPR effector protein via a crosslinker, wherein the crosslinker comprises disulfide, amide, imine, hydrazide, O-alkyl oxime, alkyl, amine, alcohol, triazole, isooxazoline, isoxazolidine, isoxazole or pyridazine.
13. The CRISPR complex of any one of embodiments 3 to 12, wherein the nucleotide is in a stem loop of the tracrRNA region.
14. The CRISPR complex of embodiment 13, wherein a structure of the stem loop is maintained relative to a structure of a stem loop of an sgRNA lacking the nucleotide.
15. The CRISPR complex of any one of embodiments 3 to 14, wherein the nucleotide is in a bulge of the tracrRNA region.
16. The CRISPR complex of embodiment 15, wherein a structure of the bulge is maintained relative to a structure of a bulge of an sgRNA lacking the nucleotide.
17. The CRISPR complex of any of embodiments 3 to 16, wherein the nucleotide is between stem loops of the tracrRNA region.
18. The CRISPR complex of any one of embodiments 1 to 17, wherein the CRISPR complex comprises nuclease activity.
19. The CRISPR complex of embodiment 18, wherein an off-target nuclease activity of the CRISPR complex is equal to or less than an off-target nuclease activity of a CRISPR complex comprising the CRISPR effector protein and the gRNA that are not cross-linked.
20. The CRISPR complex of any one of embodiments 1 to 19, wherein the nucleotide is within 20 angstroms of a cysteine of the CRISPR effector protein.
21. The CRISPR complex of any one of embodiments 1 to 20, wherein the nucleotide is not 4-thiouridine or a modified adenosine.
22. A CRISPR complex comprising a single guide RNA (sgRNA) cross-linked to a CRISPR effector protein at a nucleotide at nucleotide position 49 of the sgRNA, wherein the sgRNA comprises a crRNA region comprising a target binding region and a tracrRNA region, and wherein the nucleotide position 1 is at a 5' end of the target binding region of the crRNA and nucleotide positions of the sgRNA are numbered consecutively from 5' to 3' from nucleotide position 1.
23. The CRISPR complex of embodiment 22, wherein the nucleotide at nucleotide position 49 comprises a uracil.
24. The CRISPR complex of embodiment 22 or 23, wherein the CRISPR complex comprises nuclease activity.
25. The CRISPR complex of any one of embodiments 1 to 24, further comprising a sequence configured to modulate activity of the CRISPR complex.
26. The CRISPR complex of embodiment 25, wherein the gRNA comprises a CRISPR ON polynucleotide, a CRISPR OFF polynucleotide or a CRISPR ON/OFF polynucleotide comprising a cleavable linker.
27. The CRISPR complex of embodiment 26, wherein the CRISPR ON/OFF polynucleotide comprises a CRISPR ON polynucleotide and a CRISPR OFF polynucleotide.
28. The CRISPR complex of embodiment 26 or 27, wherein the CRISPR ON polynucleotide comprises a sequence element covalently linked to the 5' end of a guide sequence via a cleavable linker, wherein the guide sequence comprises a target binding region configured to anneal to a target sequence in a target nucleic acid molecule.
29. The CRISPR complex of embodiment 26 or 27, wherein the CRISPR ON polynucleotide comprises a sequence element covalently linked to the 5' end of a guide sequence, wherein the guide sequence comprises a target binding region configured to anneal to a target sequence in a target nucleic acid molecule.
30. The CRISPR complex of embodiment 29, wherein the sequence element is covalently linked to the 5' end of a guide sequence via a cleavable linker.
31. The CRISPR complex of embodiment 26 or 27, wherein the CRISPR ON polynucleotide comprises a sequence element comprising one or more cleavable linkers, wherein the sequence element is not covalently linked to the 5' end of a guide sequence via a cleavable linker, and wherein the guide sequence comprises a target binding region configured to anneal to a target sequence in a target nucleic acid molecule.
32. The CRISPR complex of any one of embodiments 28 to 31, wherein the sequence element comprises at least 15 nucleotides.
33. The CRISPR complex of any one of embodiments 28 to 31, wherein the sequence element comprises at least 20 nucleotides.
34. The CRISPR complex of any one of embodiments 28 to 33, wherein the sequence element comprises 24 nucleotides.
35. The CRISPR complex of any one of embodiments 31 to 34, wherein the sequence element comprises an RNA sequence.
36. The CRISPR complex of embodiment 35, wherein the RNA sequence comprises a modified RNA base.
37. The CRISPR complex of embodiment 36, wherein the modified RNA base is a 2'-O-Methyl RNA base.
38. The CRISPR complex of any one of embodiments 28 to 37, wherein the sequence element forms a stem loop comprising a loop.
39. The CRISPR complex of embodiment 38, wherein the loop comprises at least two nucleotides.
40. The CRISPR complex of embodiment 38 or 39, wherein the loop comprises at least three nucleotides.
41. The CRISPR complex of any one of embodiments 38 to 40, wherein the loop comprises four nucleotides.
42. The CRISPR complex of any one of embodiments 38 to 41, wherein the sequence element comprises a base-pair to the guide sequence.
43. The CRISPR complex of embodiment 42, wherein the sequence element comprises a base pair to the target binding region of the guide sequence.

44. The CRISPR complex of embodiment 43, wherein the sequence element base pairs with at least 10 nucleotides in the target binding region of the guide sequence.
45. The CRISPR complex of embodiment 43, wherein the sequence element base pairs with at least 15 nucleotides in the target binding region of the guide sequence.
46. The CRISPR complex of embodiment 43, wherein the sequence element base pairs with 20 nucleotides in the target binding region of the guide sequence.
47. The CRISPR complex of any one of embodiments 38 to 41, wherein the sequence element does not comprise a base-pair to the guide sequence.
48. The CRISPR complex of embodiment 47, wherein a 5'-most base of the sequence element anneals to a base in the sequence element immediately 5' of the guide sequence.
49. The CRISPR complex of any one of embodiments 28 to 48, further comprising one or more cleavable linkers in the sequence element.
50. The CRISPR complex of any one of embodiments 28 to 48, further comprising at least two cleavable linkers in the sequence element.
51. The CRISPR complex of any one of embodiments 28 to 48, further comprising at least three cleavable linkers in the sequence element.
52. The CRISPR complex of any one of embodiments 28 to 48, further comprising at least four cleavable linkers in the sequence element.
53. The CRISPR complex of any one of embodiments 28 to 48, further comprising at least five or more, seven or more, ten or more, fifteen or more, or twenty or more cleavable linkers in the sequence element.
54. The CRISPR complex of any one of embodiments 38 to 48, further comprising one or more cleavable linkers in the loop of the sequence element.
55. The CRISPR complex of any one of embodiments 38 to 48, further comprising two or more cleavable linkers in the loop of the sequence element.
56. The CRISPR complex of any one of embodiments 38 to 48, further comprising three cleavable linkers in the loop of the sequence element.
57. The CRISPR complex of any one of embodiments 38 to 48 or 54 to 56, further comprising one or more cleavable linkers at a nucleotide located in the middle positions of the sequence element.
58. The CRISPR complex of any one of embodiments 38 to 48 or 54 to 56, further comprising two or more cleavable linkers at a nucleotide located in the middle positions of the sequence element.
59. The CRISPR complex of any one of embodiments 38 to 48 or 54 to 56, further comprising three or more cleavable linkers at a nucleotide located in the middle positions of the sequence element.
60. The CRISPR complex of any one of embodiments 38 to 48 or 54 to 56, further comprising four or more cleavable linkers at a nucleotide located in the middle positions of the sequence element.
61. The CRISPR complex of embodiment 49, wherein the complex comprises a first cleavable linker at a position 24 in the sequence element and a second cleavable linker at a position 11 in the sequence element, wherein a nucleotide at a 5' end of the sequence element is nucleotide 1 and nucleotides are numbered in order from the 5' end of the sequence element to a 3' end of the sequence element.
62. The CRISPR complex of embodiment 49, wherein the complex comprises a first cleavable linker at a position 24 in the sequence element and one of more cleavable linker at a position of any one of: 5, 6, 10, 11, 14, 15, 16, 21, 22 or 23 in the sequence element, wherein a nucleotide at a 5' end of the sequence element is nucleotide 1 and nucleotides are numbered in order from the 5' end of the sequence element to a 3' end of the sequence element.
63. The CRISPR complex of embodiment 49, wherein the complex comprises a first cleavable linker at a position 24 in the sequence element and a second cleavable linker at a position 23 in the sequence element and one or more cleavable linker at a position of any one of: 5, 6, 10, 11, 14, 15 or 16 in the sequence element, wherein a nucleotide at a 5' end of the sequence element is nucleotide 1 and nucleotides are numbered in order from the 5' end of the sequence element to a 3' end of the sequence element.
64. The CRISPR complex of embodiment 49, wherein the complex comprises a cleavable linker at a position 24 in the sequence element and a first one or more cleavable linker at a position of any one of 21, 22 or 23 in the sequence element and a second one or more cleavable linker at a position of any one of: 5, 6, 10, 11, 14, 15 or 16 in the sequence element, wherein a nucleotide at a 5' end of the sequence element is nucleotide 1 and nucleotides are numbered in order from the 5' end of the sequence element to a 3' end of the sequence element.
65. The CRISPR complex of embodiment 49, wherein the complex comprises a first cleavable linker at a position 24 in the sequence element, a second cleavable linker at a position 23 in the sequence element and a third cleavable linker at a position 3 in the sequence element, wherein a nucleotide at a 5' end of the sequence element is nucleotide 1 and nucleotides are numbered in order from the 5' end of the sequence element to a 3' end of the sequence element.
66. The CRISPR complex of embodiment 49, wherein the complex comprises a first cleavable linker at a position 24 in the sequence element, a second cleavable linker at a position 23 in the sequence element and a third cleavable linker at a position 3 in the sequence element, wherein a nucleotide at a 5' end of the sequence element is nucleotide 1 and nucleotides are numbered in order from the 5' end of the sequence element to a 3' end of the sequence element.
67. The CRISPR complex of embodiment 49, wherein the complex comprises a first cleavable linker at a position 24 in the sequence element, a second cleavable linker at a position 23 in the sequence element, a third cleavable linker at a position 6 in the sequence element, a fourth cleavable linker at a position 16 in the sequence element and a fifth cleavable linker at a position 11 in the sequence element, wherein a nucleotide at a 5' end of the sequence element is nucleotide 1 and nucleotides are numbered in order from the 5' end of the sequence element to a 3' end of the sequence element.
68. The CRISPR complex of embodiment 49, wherein the complex comprises a first cleavable linker at a position 24 in the sequence element, a second cleavable linker at a position 23 in the sequence element, a third cleavable linker at a position 6 in the sequence element and a fourth cleavable linker at a position 14 in the sequence element, wherein a nucleotide at a 5' end of the sequence element is nucleotide 1 and nucleotides are numbered in order from the 5' end of the sequence element to a 3' end of the sequence element.

69. The CRISPR complex of any one of embodiments 61 to 68, wherein the sequence element is 24 nucleotides in length, the loop of the sequence element comprises nucleotides from positions 21 to 24 and nucleotides from positions 1 to 20 of the sequence element base pair to the target binding region of the guide sequence.

70. The CRISPR complex of embodiment 26 or 27, wherein the CRISPR OFF polynucleotide comprises a cleavable linker 3' of the 5' most nucleotide of a guide sequence, wherein the guide sequence comprises a target binding region configured to anneal to a target sequence in a target nucleic acid molecule.

71. The CRISPR complex of embodiment 70, wherein the cleavable linker is not at a 3' end of the polynucleotide, wherein the polynucleotide comprises the guide sequence and a sequence comprising a CRISPR effector protein binding region configured to bind to a CRISPR effector protein in order from a 5'end to a 3' end of the polynucleotide.

72. The CRISPR complex of any one of embodiments 26 to 71, wherein the cleavable linker is positioned immediately 3' of nucleotide 56 or 73 in the polynucleotide, wherein a nucleotide at a 5' end of the guide sequence is nucleotide 1 and nucleotides are numbered in order from the 5' end of the guide sequence to a 3' end of the polynucleotide.

73. The CRISPR complex of any one of embodiments 26 to 71, wherein the polynucleotide comprises a first cleavable linker and a second cleavable linker, wherein the first cleavable linker is positioned immediately 3' of nucleotide 56 and the second cleavable linker is positioned immediately 3' of nucleotide 73 in the polynucleotide, wherein a nucleotide at a 5' end of the guide sequence is nucleotide 1 and nucleotides are numbered in order from the 5' end of the guide sequence to a 3' end of the polynucleotide.

74. The CRISPR complex of any one of embodiments 26 to 73, wherein the polynucleotide comprises a tetraloop, a nexus, a stem loop 1 and a stem loop 2 from 5' to 3', wherein the cleavable linker is in a loop of the nexus or a loop of the stem loop 1.

75. The CRISPR complex of any one of embodiments 26 to 73, wherein the polynucleotide comprises a tetraloop, a nexus, a stem loop 1 and a stem loop 2 from 5' to 3', wherein the cleavable linker is in a loop of the nexus and a loop of the stem loop 1.

76. The CRISPR complex of any one of embodiments 26 to 75, wherein the cleavable linker is photolabile.

77. The CRISPR complex of embodiment 76, wherein the cleavable linker is cleaved by ultraviolet (UV) light.

78. The CRISPR complex of embodiment 77, wherein the cleavable linker is cleaved by light of wavelength in the range of 100 nm to 400 nm.

79. The CRISPR complex of embodiment 76, wherein the cleavable linker is cleaved by visible light.

80. The CRISPR complex of embodiment 76, wherein the cleavable linker is cleaved by light of wavelength 400 nm to 700 nm.

81. The CRISPR complex of embodiment 79, wherein the cleavable linker is cleaved by green light.

82. The CRISPR complex of embodiment 79, wherein the cleavable linker is cleaved by violet light.

83. The CRISPR complex of embodiment 79, wherein the cleavable linker is cleaved by blue light.

84. The CRISPR complex of embodiment 79, wherein the cleavable linker is cleaved by light of wavelength in the range of 490 nm to 570 nm.

85. The CRISPR complex of embodiment 79, wherein the cleavable linker is cleaved by light of wavelength in the range of 400 nm to 420 nm.

86. The CRISPR complex of embodiment 79, wherein the cleavable linker is cleaved by light of wavelength in the range of 420 nm to 430 nm.

87. The CRISPR complex of embodiment 79, wherein the cleavable linker is cleaved by light of wavelength in the range of 420 nm to 440 nm.

88. The CRISPR complex of embodiment 79, wherein the cleavable linker of the CRISPR ON polynucleotide is cleaved by green light.

89. The CRISPR complex of embodiment 79, wherein the cleavable linker of the CRISPR OFF polynucleotide is cleaved by violet light.

90. The CRISPR complex of embodiment 79, wherein the cleavable linker of the CRISPR OFF polynucleotide is cleaved by blue light.

91. The CRISPR complex of embodiment 79, wherein the cleavable linker of the CRISPR ON polynucleotide is cleaved by light of wavelength in the range of 490 nm to 570 nm.

92. The CRISPR complex of embodiment 79, wherein the cleavable linker of the CRISPR ON polynucleotide is cleaved by light of wavelength in the range of 420 nm to 430 nm.

93. The CRISPR complex of embodiment 79, wherein the cleavable linker of the CRISPR OFF polynucleotide is cleaved by light of wavelength in the range of 400 nm to 420 nm.

94. The CRISPR complex of embodiment 79, wherein the cleavable linker of the CRISPR OFF polynucleotide is cleaved by light of wavelength in the range of 420 nm to 430 nm.

95. The CRISPR complex of embodiment 79, wherein the cleavable linker of the CRISPR OFF polynucleotide is cleaved by light of wavelength in the range of 420 nm to 440 nm.

96. The CRISPR complex of embodiment 79, wherein the cleavable linker in the CRISPR ON polynucleotide of the CRISPR ON/OFF polynucleotide is cleaved by light of higher wavelength than the cleavable linker in the CRISPR OFF polynucleotide of the CRISPR ON/OFF polynucleotide.

97. The CRISPR complex of embodiment 96, wherein the cleavable linker of the CRISPR ON polynucleotide is cleaved by green light and the cleavable linker of the CRISPR OFF polynucleotide is cleaved by violet light.

98. The CRISPR complex of embodiment 96, wherein the cleavable linker of the CRISPR ON polynucleotide is cleaved by green light and the cleavable linker of the CRISPR OFF polynucleotide is cleaved by blue light.

99. The CRISPR complex of embodiment 96, wherein the cleavable linker of the CRISPR ON polynucleotide is cleaved by light of wavelength in the range of 490 nm to 570 nm and the cleavable linker of the CRISPR OFF polynucleotide is cleaved by light of wavelength in the range of 400 nm to 420 nm.

100. The CRISPR complex of embodiment 96, wherein the cleavable linker of the CRISPR ON polynucleotide is cleaved by light of wavelength in the range of 490 nm to 570 nm and the cleavable linker of the CRISPR OFF polynucleotide is cleaved by light of wavelength in the range of 420 nm to 430 nm.

101. The CRISPR complex of embodiment 96, wherein the cleavable linker of the CRISPR ON polynucleotide is cleaved by light of wavelength in the range of 490 nm to 570 nm and the cleavable linker of the CRISPR OFF polynucleotide is cleaved by light of wavelength in the range of 420 nm to 440 nm.

102. The CRISPR complex of any one of embodiments 26 to 101, wherein the cleavable linker is a phosphoramidite derivative.

103. The CRISPR complex of any one of embodiments 26 to 101, wherein the cleavable linker is a 3-(4,4'-Dimethoxytrityl)-1-(2-nitrophenyl)-propan-1-yl-[(2-cyanoethyl)-(N,N-diisopropyl)]-phosphoramidite derivative.

104. The CRISPR complex of any one of embodiments 26 to 101, wherein the cleavable linker is a 1-(7-(diethylamino)-2-oxo-2H-chromen-4-yl)-3-(4,4'-dimethoxytrityl)-propan-1-yl-[(2-cyanoethyl)-(N,N-diisopropyl)]-phosphoramidite derivative.

105. The CRISPR complex of any one of embodiments 26 to 101, wherein the cleavable linker comprises a phosphodiester.

106. The CRISPR complex of any one of embodiments 26 to 101, wherein the cleavable linker comprises a phosphomonoester.

107. The CRISPR complex of any one of embodiments 26 to 101, wherein the cleavable linker is a coumarin derivative.

108. The CRISPR complex of any one of embodiments 26 to 101, wherein the cleavable linker comprises a structure represented by the following formula:

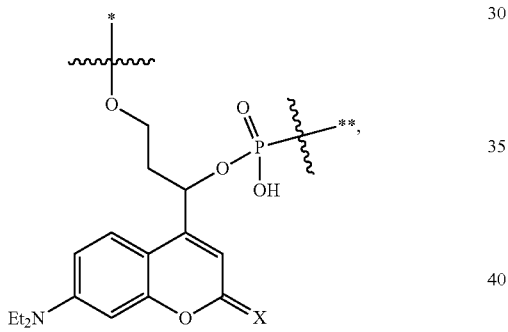

wherein:
X is O, S, or $CR^xR^y$, wherein $R^x$ and $R^y$ are independently selected from optionally substituted alkyl, optionally substituted alkenyl, optionally substituted alkynyl, optionally substituted heteroalkyl, halo, haloalkyl, alkoxy, alkoxyalkyl, haloalkoxy, amino, aminoalkyl, alkylamino, alkylaminoalkyl, hydroxy, hydroxyalkyl, C-carboxy, O-carboxy, acyl, thiol, alkylthio, thiolalkyl, C-amido, N-amido, ureido, nitro, cyano, sulfonyl, sulfo, sulfonate, sulfino, S-sulfonamido, N-sulfonamido, optionally substituted carbocyclyl, optionally substituted aryl, optionally substituted heteroaryl, and optionally substituted heterocyclyl; and
* indicates a point of attachment to H, or a first nucleotide; and
** indicates a point of attachment to OH, or a second nucleotide.

109. The CRISPR complex of embodiment 108, wherein X is oxygen.

110. The CRISPR complex of embodiment 108, wherein X is sulfur.

111. The CRISPR complex of embodiment 108, wherein X is =C(CN)2.

112. The CRISPR complex of any one of embodiments 26 to 101, wherein the cleavable linker comprises a structure represented by Formula (I):

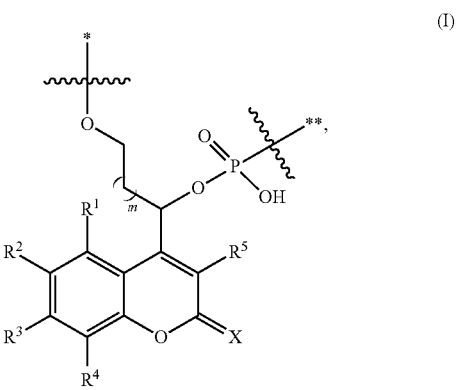

wherein:
$R^1$, $R^2$, $R^3$, $R^4$, and $R^5$ are each independently selected from H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;
alternatively, two or more of $R^1$, $R^2$, $R^3$, $R^4$ and $R^5$ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and
m is an integer selected from 1 to 10; and
X is O, S, or $CR^xR^y$, wherein $R^x$ and $R^y$ are independently selected from optionally substituted alkyl, optionally substituted alkenyl, optionally substituted alkynyl, optionally substituted heteroalkyl, halo, haloalkyl, alkoxy, alkoxyalkyl, haloalkoxy, amino, aminoalkyl, alkylamino, alkylaminoalkyl, hydroxy, hydroxyalkyl, C-carboxy, O-carboxy, acyl, thiol, alkylthio, thiolalkyl, C-amido, N-amido, ureido, nitro, cyano, sulfonyl, sulfo, sulfonate, sulfino, S-sulfonamido, N-sulfonamido, optionally substituted carbocyclyl, optionally substituted aryl, optionally substituted heteroaryl, and optionally substituted heterocyclyl,
with the proviso that, when X is O, and $R^3$ is dialkylamino, then m is an integer from 2 to 10; and
* indicates a point of attachment to H, or a first nucleotide; and
** indicates a point of attachment to OH, or a second nucleotide.

113. The CRISPR complex of embodiment 112, wherein X is oxygen.

114. The CRISPR complex of embodiment 112, wherein X is sulfur.
115. The CRISPR complex of embodiment 112, wherein X is =C(CN)2.
116. The CRISPR complex of embodiment 112, wherein the structure of Formula (I) is represented by Formula (I'):

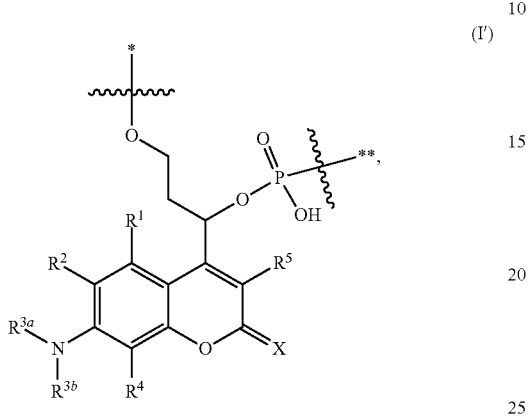

wherein:

R¹, R², R⁴, and R⁵ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

R³ᵃ and R³ᵇ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

alternatively, two or more of R¹, R², R³ᵃ, R³ᵇ and R⁴ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of R¹, R², R³ᵃ, R³ᵇ, R⁴, and R⁵ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and X is oxygen.

117. The CRISPR complex of embodiment 112, wherein the structure of Formula (I) is represented by Formula (I'):

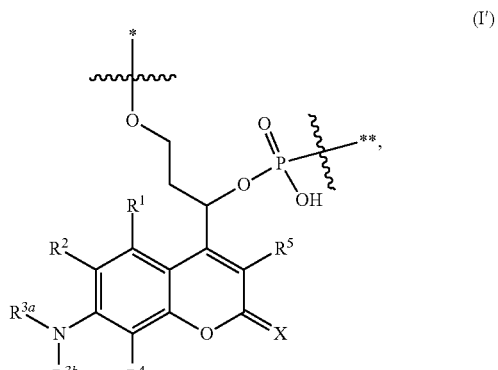

wherein:

R¹, R², R⁴, and R⁵ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

R³ᵃ and R³ᵇ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

alternatively, two or more of R¹, R², R³ᵃ, R³ᵇ and R⁴ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of R¹, R², R³ᵃ, R³ᵇ, R⁴, and R⁵ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and X is sulfur.

118. The CRISPR complex of embodiment 112, wherein the structure of Formula (I) is represented by Formula (I'):

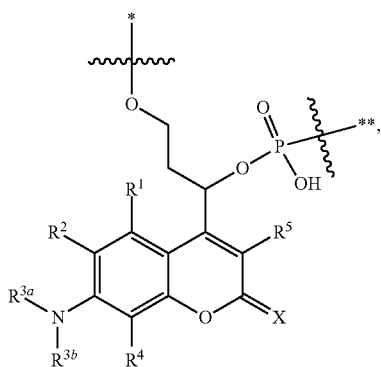

(I')

wherein:
$R^1$, $R^2$, $R^4$, and $R^5$ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
$R^{3a}$ and $R^{3b}$ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
alternatively, two or more of $R^1$, $R^2$, $R^{3a}$, $R^{3b}$ and $R^4$ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;
alternatively, two or more of $R^1$, $R^2$, $R^{3a}$, $R^{3b}$, $R^4$, and $R^5$ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and
X is =C(CN)2.

119. The CRISPR complex of any one of embodiments 116 to 118, wherein:
$R^1$, $R^2$, $R^4$, and $R^5$ are each independently H or $C_{1-6}$ alkyl; and
$R^{3a}$, and $R^{3b}$ are $C_{1-6}$ alkyl.

120. The CRISPR complex of any one of embodiments 116 to 118, wherein:
$R^1$, $R^2$, $R^4$, and $R^5$ are each H; and
$R^{3a}$, and $R^{3b}$ are each ethyl.

121. The CRISPR complex of any one of embodiments 1 to 120, wherein when the gRNA is complexed with a CRISPR effector protein, a first crosslinked CRISPR complex is formed having a lower editing activity of an off-target nucleic acid molecule than a second CRISPR complex comprising the gRNA not crosslinked with the CRISPR effector protein.

122. The CRISPR complex of embodiment 121, wherein the editing activity is measured as a percentage of off-target nucleic acid molecules that are edited.

123. The CRISPR complex of embodiment 121, wherein the editing activity is measured as a percentage of target nucleic acid molecules that are edited.

124. The CRISPR complex of any one of embodiments 121 to 123, wherein the editing activity of the off-target nucleic acid molecules by the first CRISPR complex is lower that an editing activity of the second CRISPR complex with a p-value≤0.0001.

125. The CRISPR complex of any one of embodiments 121 to 124, wherein an editing activity of the first CRISPR complex of the target nucleic acid molecule and an editing activity of the second CRISPR complex of the target nucleic acid molecule are within 5%.

126. The CRISPR complex of any one of embodiments 1 to 125, wherein the CRISPR effector protein is a type II CRISPR effector protein.

127. The CRISPR complex of embodiment 126, wherein the type II CRISPR effector protein is a Cas9 polypeptide.

128. The CRISPR complex of any one of embodiments 1 to 125, wherein the CRISPR effector protein is a type V CRISPR effector protein.

129. The CRISPR complex of embodiment 128, wherein the type V CRISPR effector protein is a Cas12a, a Cas12b, a Cas12c, a Cas12d, a Cas12e, a Cas12f, a Cas12g, a Cas12h or a Cas12i polypeptide.

130. The CRISPR complex of any one of embodiments 1 to 125, wherein the CRISPR effector protein is a type VI CRISPR effector protein.

131. The CRISPR complex of embodiment 130, wherein the type VI CRISPR effector protein is a Cas13a, a Cas13b, a Cas13c or a Cas13d polypeptide.

132. The CRISPR complex of any one of embodiments 1 to 125, wherein the CRISPR effector protein is Cas14a, a Cas14b, or a Cas14c polypeptide.

133. A single guide RNA (sgRNA) comprising a crRNA region and a tracrRNA region and a nucleotide at nucleotide position 49, wherein nucleotide position 1 is at a 5' end of a target binding region of the crRNA region and nucleotide positions of the sgRNA are numbered consecutively from 5' to 3' from nucleotide position 1.

134. A single guide RNA (sgRNA) comprising a crRNA region and a tracrRNA region and a uracil at nucleotide position 49, wherein nucleotide position 1 is at a 5' end of a target binding region of the crRNA region and nucleotide positions of the sgRNA are numbered consecutively from 5' to 3' from nucleotide position 1.

135. A polynucleotide comprising: (i) a guide sequence comprising a target binding region configured to anneal to a target sequence in a target nucleic acid molecule, (ii) a sequence comprising a CRISPR effector protein binding region configured to bind to a CRISPR effector protein, and (iii) a nucleotide configured to cross-link to a CRISPR effector protein, wherein the nucleotide is outside the target binding region of the guide sequence.

136. The polynucleotide of embodiment 135, wherein the nucleotide comprises a uracil.

137. The polynucleotide of embodiment 135 or 136, wherein the nucleotide is at nucleotide position 49 of the polynucleotide, wherein nucleotide position 1 is at a 5' end of the target binding region of the guide sequence and nucleotide positions of the polynucleotide are numbered consecutively from 5' to 3' from nucleotide position 1.

138. The polynucleotide of any one of embodiments 135 to 137, wherein the nucleotide is at one or more nucleotide positions: 22, 23, 24, 25, 31, 37, 44, 49, 45, 50, 56, 59, 63, 64, 66, 71, 72, 77, 78, 80, 84, 90, and 94 of the polynucleotide, wherein nucleotide position 1 is at a 5' end of the target binding region of the guide sequence and nucleotide positions of the polynucleotide are numbered consecutively from 5' to 3' from nucleotide position 1.

139. The polynucleotide of any one of embodiments 135 to 138, wherein the nucleotide is an unnatural nucleotide.

140. The polynucleotide of embodiment 139, wherein the unnatural nucleotide comprises a modification of a sugar.

141. The polynucleotide of embodiment 139 or 140, wherein the unnatural nucleotide comprises a modification of a base.

142. The polynucleotide of embodiment 139, wherein the unnatural nucleotide comprises a maleimide.

143. The polynucleotide of embodiment 142, wherein the maleimide covalently links to a cysteine on the CRISPR effector protein.

144. The polynucleotide of any one of embodiments 135 to 143, wherein the wherein the polynucleotide is cross-linked to the CRISPR effector protein via a crosslinker, wherein the crosslinker comprises or is derived from pyridyl disulfide, alkoxyamine, NHS ester, diazarine, imidoester, haloacetyl group, hydrazide, aryl azide, isocyanate, dithiol phosphoramidite DTPA, 4-thio-UTP, 5-azido-UTP, 5-bromo-UTP, 8-azido-ATP, 5-APAS-UTP, or 8-N(3)AMP.

145. The polynucleotide of any one of embodiments 135 to 143, wherein the wherein the polynucleotide is cross-linked to the CRISPR effector protein via a crosslinker, wherein the crosslinker comprises disulfide, amide, imine, hydrazide, O-alkyl oxime, alkyl, amine, alcohol, triazole, isooxazoline, isoxazolidine, isoxazole or pyridazine.

146. The polynucleotide of any one of embodiments 135 to 145, wherein the sequence of (ii) forms a tetraloop, a nexus, a first stem loop and a second stem loop from 5' to 3.

147. The polynucleotide of embodiment 135 or 145, wherein the polynucleotide does not comprise a third stem loop.

148. The polynucleotide of any one of embodiments 135 to 147, wherein the polynucleotide does not comprise a stem loop at a 5' end of the polynucleotide.

149. The polynucleotide of any one of embodiments 145 to 148, wherein the nucleotide is in a stem loop.

150. The polynucleotide of embodiment 149, wherein a structure of the stem loop is maintained relative to a structure of a stem loop of a polynucleotide lacking the nucleotide.

151. The polynucleotide of any one of embodiments 145 to 150, wherein the nucleotide is in the tetraloop.

152. The polynucleotide of embodiment 151, wherein a structure of the tetraloop is maintained relative to a structure of a tetraloop of a polynucleotide lacking the nucleotide.

153. The polynucleotide of embodiment 151 or 152, wherein the tetraloop comprises a bulge.

154. The polynucleotide of embodiment 153, wherein the nucleotide is in the bulge.

155. The polynucleotide of embodiment 154, wherein a structure of the bulge is maintained relative to a structure of a bulge of a polynucleotide lacking the nucleotide.

156. The polynucleotide of any one of embodiments 145 to 155, wherein the nucleotide is between stem loops.

157. The polynucleotide of any one of embodiments 135 to 156, wherein the nucleotide is within 20 angstroms of a cysteine of the CRISPR effector protein.

158. The polynucleotide of any one of embodiments 135 to 157, wherein the nucleotide is not 4-thiouridine or a modified adenosine.

159. The polynucleotide of any one of embodiments 135 to 158, wherein the polynucleotide comprises at least two nucleotides configured to cross-link to a CRISPR effector protein.

160. The polynucleotide of any one of embodiments 135 to 159, further comprising a sequence configured to modulate activity of the CRISPR effector protein.

161. The polynucleotide of embodiment 160, wherein the polynucleotide comprises a CRISPR ON polynucleotide, a CRISPR OFF polynucleotide or a CRISPR ON/OFF polynucleotide comprising a cleavable linker.

162. The polynucleotide of embodiment 161, wherein the CRISPR ON/OFF polynucleotide comprises a CRISPR ON polynucleotide and a CRISPR OFF polynucleotide.

163. The polynucleotide of embodiment 161 or 162, wherein the CRISPR ON polynucleotide comprises a sequence element covalently linked to the 5' end of the guide sequence via a cleavable linker.

164. The polynucleotide of embodiment 161 or 162, wherein the CRISPR ON polynucleotide comprises a sequence element covalently linked to the 5' end of a guide sequence, wherein the guide sequence comprises a target binding region configured to anneal to a target sequence in a target nucleic acid molecule.

165. The polynucleotide of embodiment 161 or 162, wherein the sequence element is covalently linked to the 5' end of a guide sequence via a cleavable linker.

166. The polynucleotide of embodiment 161 or 162, wherein the CRISPR ON polynucleotide comprises a sequence element comprising one or more cleavable linkers, wherein the sequence element is not covalently linked to the 5' end of a guide sequence via a cleavable linker, and wherein the guide sequence comprises a target binding region configured to anneal to a target sequence in a target nucleic acid molecule.

167. The polynucleotide of any one of embodiments 163 to 166, wherein the sequence element comprises at least 15 nucleotides.

168. The polynucleotide of any one of embodiments 163 to 166, wherein the sequence element comprises at least 20 nucleotides.

169. The polynucleotide of any one of embodiments 163 to 168, wherein the sequence element comprises 24 nucleotides.

170. The polynucleotide of any one of embodiments 163 to 169, wherein the sequence element comprises an RNA sequence.

171. The polynucleotide of embodiment 170, wherein the RNA sequence comprises a modified RNA base.

172. The polynucleotide of embodiment 171, wherein the modified RNA base is a 2'-O-Methyl RNA base.

173. The polynucleotide of any one of embodiments 163 to 172, wherein the sequence element forms a stem loop comprising a loop.
174. The polynucleotide of embodiment 173, wherein the loop comprises at least two nucleotides.
175. The polynucleotide of embodiment 173 or 174, wherein the loop comprises at least three nucleotides.
176. The polynucleotide of any one of embodiments 173 to 175, wherein the loop comprises four nucleotides.
177. The polynucleotide of any one of embodiments 173 to 176, wherein the sequence element comprises a base-pair to the guide sequence.
178. The polynucleotide of embodiment 177, wherein the sequence element comprises a base pair to the target binding region of the guide sequence.
179. The polynucleotide of embodiment 178, wherein the sequence element base pairs with at least 10 nucleotides in the target binding region of the guide sequence.
180. The polynucleotide of embodiment 178, wherein the sequence element base pairs with at least 15 nucleotides in the target binding region of the guide sequence.
181. The polynucleotide of embodiment 178, wherein the sequence element base pairs with 20 nucleotides in the target binding region of the guide sequence.
182. The polynucleotide of any one of embodiments 173 to 176, wherein the sequence element does not comprise a base-pair to the guide sequence.
183. The polynucleotide of embodiment 182, wherein a 5'-most base of the sequence element anneals to a base in the sequence element immediately 5' of the guide sequence.
184. The polynucleotide of any one of embodiments 163 to 183, further comprising one or more cleavable linkers in the sequence element.
185. The polynucleotide of any one of embodiments 163 to 183, further comprising at least two cleavable linkers in the sequence element.
186. The polynucleotide of any one of embodiments 163 to 183, further comprising at least three cleavable linkers in the sequence element.
187. The polynucleotide of any one of embodiments 163 to 183, further comprising at least four cleavable linkers in the sequence element.
188. The polynucleotide of any one of embodiments 163 to 183, further comprising at least five or more, seven or more, ten or more, fifteen or more, or twenty or more cleavable linkers in the sequence element.
189. The polynucleotide of any one of embodiments 173 to 183, further comprising one or more cleavable linkers in the loop of the sequence element.
190. The polynucleotide of any one of embodiments 173 to 183, further comprising two or more cleavable linkers in the loop of the sequence element.
191. The polynucleotide of any one of embodiments 173 to 183, further comprising three cleavable linkers in the loop of the sequence element.
192. The polynucleotide of any one of embodiments 173 to 183 or 189 to 191, further comprising one or more cleavable linkers at a nucleotide located in the middle positions of the sequence element.
193. The polynucleotide of any one of embodiments 173 to 183 or 189 to 191, further comprising two or more cleavable linkers at a nucleotide located in the middle positions of the sequence element.
194. The polynucleotide of any one of embodiments 173 to 183 or 189 to 191, further comprising three or more cleavable linkers at a nucleotide located in the middle positions of the sequence element.
195. The polynucleotide of any one of embodiments 173 to 183 or 189 to 191, further comprising four or more cleavable linkers at a nucleotide located in the middle positions of the sequence element.
196. The polynucleotide of embodiment 184, wherein the polynucleotide comprises a first cleavable linker at a position 24 in the sequence element and a second cleavable linker at a position 11 in the sequence element, wherein a nucleotide at a 5' end of the sequence element is nucleotide 1 and nucleotides are numbered in order from the 5' end of the sequence element to a 3' end of the sequence element.
197. The polynucleotide of embodiment 184, wherein the polynucleotide comprises a first cleavable linker at a position 24 in the sequence element and one of more cleavable linker at a position of any one of: 5, 6, 10, 11, 14, 15, 16, 21, 22 or 23 in the sequence element, wherein a nucleotide at a 5' end of the sequence element is nucleotide 1 and nucleotides are numbered in order from the 5' end of the sequence element to a 3' end of the sequence element.
198. The polynucleotide of embodiment 184, wherein the polynucleotide comprises a first cleavable linker at a position 24 in the sequence element and a second cleavable linker at a position 23 in the sequence element and one or more cleavable linker at a position of any one of: 5, 6, 10, 11, 14, 15 or 16 in the sequence element, wherein a nucleotide at a 5' end of the sequence element is nucleotide 1 and nucleotides are numbered in order from the 5' end of the sequence element to a 3' end of the sequence element.
199. The polynucleotide of embodiment 184, wherein the polynucleotide comprises a cleavable linker at a position 24 in the sequence element and a first one or more cleavable linker at a position of any one of 21, 22 or 23 in the sequence element and a second one or more cleavable linker at a position of any one of 5, 6, 10, 11, 14, 15 or 16 in the sequence element, wherein a nucleotide at a 5' end of the sequence element is nucleotide 1 and nucleotides are numbered in order from the 5' end of the sequence element to a 3' end of the sequence element.
200. The polynucleotide of embodiment 184, wherein the polynucleotide comprises a first cleavable linker at a position 24 in the sequence element, a second cleavable linker at a position 23 in the sequence element and a third cleavable linker at a position 3 in the sequence element, wherein a nucleotide at a 5' end of the sequence element is nucleotide 1 and nucleotides are numbered in order from the 5' end of the sequence element to a 3' end of the sequence element.
201. The polynucleotide of embodiment 184, wherein the polynucleotide comprises a first cleavable linker at a position 24 in the sequence element, a second cleavable linker at a position 23 in the sequence element and a third cleavable linker at a position 3 in the sequence element, wherein a nucleotide at a 5' end of the sequence element is nucleotide 1 and nucleotides are numbered in order from the 5' end of the sequence element to a 3' end of the sequence element.
202. The polynucleotide of embodiment 184, wherein the polynucleotide comprises a first cleavable linker at a position 24 in the sequence element, a second cleavable linker at a position 23 in the sequence element, a third cleavable linker at a position 6 in the sequence element, a fourth cleavable linker at a position 16 in the sequence element and a fifth cleavable linker at a position 11 in the sequence element, wherein a nucleotide at a 5' end of the sequence element is nucleotide 1 and nucleotides are numbered in order from the 5' end of the sequence element to a 3' end of the sequence element.

203. The polynucleotide of embodiment 184, wherein the polynucleotide comprises a first cleavable linker at a position 24 in the sequence element, a second cleavable linker at a position 23 in the sequence element, a third cleavable linker at a position 6 in the sequence element and a fourth cleavable linker at a position 14 in the sequence element, wherein a nucleotide at a 5' end of the sequence element is nucleotide 1 and nucleotides are numbered in order from the 5' end of the sequence element to a 3' end of the sequence element.

204. The polynucleotide of any one of embodiments 196 to 203, wherein the sequence element is 24 nucleotides in length, the loop of the sequence element comprises nucleotides from positions 21 to 24 and nucleotides from positions 1 to 20 of the sequence element base pair to the target binding region of the guide sequence.

205. A CRISPR ON polynucleotide comprising a sequence element covalently linked to the 5' end of the guide sequence via a cleavable linker.

206. A CRISPR ON polynucleotide comprising a sequence element covalently linked to the 5' end of a guide sequence, wherein the guide sequence comprises a target binding region configured to anneal to a target sequence in a target nucleic acid molecule.

207. The polynucleotide of embodiment 206, wherein the sequence element is covalently linked to the 5' end of a guide sequence via a cleavable linker.

208. A CRISPR ON polynucleotide comprising a sequence element comprising one or more cleavable linkers, wherein the sequence element is not covalently linked to the 5' end of a guide sequence via a cleavable linker, and wherein the guide sequence comprises a target binding region configured to anneal to a target sequence in a target nucleic acid molecule.

209. The polynucleotide of any one of embodiments 205 to 208, wherein the sequence element comprises an RNA sequence.

210. The polynucleotide of embodiment 209, wherein the RNA sequence comprises a modified RNA base.

211. A CRISPR ON polynucleotide comprising a sequence element covalently linked to a 5' end of a guide sequence via a cleavable linker, wherein the guide sequence comprises a target binding region configured to anneal to a target sequence in a target nucleic acid molecule and the sequence element comprises a modified RNA base.

212. The polynucleotide of embodiment 210 or 211, wherein the modified RNA base is a 2'-O-Methyl RNA base.

213. The polynucleotide of any one of embodiments 205 to 212, wherein the sequence element comprises at least 15 nucleotides.

214. The polynucleotide of any one of embodiments 205 to 213, wherein the sequence element comprises at least 20 nucleotides.

215. The polynucleotide of any one of embodiments 205 to 214, wherein the sequence element comprises 24 nucleotides.

216. The polynucleotide of any one of embodiments 205 to 215, wherein the sequence element forms a stem loop comprising a loop.

217. The polynucleotide of embodiment 216, wherein the loop comprises at least two nucleotides.

218. The polynucleotide of embodiment 216 or 217, wherein the loop comprises at least three nucleotides.

219. The polynucleotide of any one of embodiments 216 to 218, wherein the loop comprises four nucleotides.

220. The polynucleotide of any one of embodiments 216 to 219, wherein the sequence element comprises a base pair to the guide sequence.

221. The polynucleotide of embodiment 220, wherein the sequence element comprises a base pair to the target binding region of the guide sequence.

222. The polynucleotide of embodiment 221, wherein the sequence element base pairs with at least 10 nucleotides in the target binding region of the guide sequence.

223. The polynucleotide of embodiment 221, wherein the sequence element base pairs with at least 15 nucleotides in the target binding region of the guide sequence.

224. The polynucleotide of embodiment 221, wherein the sequence element base pairs with 20 nucleotides in the target binding region of the guide sequence.

225. The polynucleotide of any one of embodiments 216 to 219, wherein the sequence element does not comprise a base-pair to the guide sequence.

226. The polynucleotide of embodiment 225, wherein a 5'-most base of the sequence element anneals to a base in the sequence element immediately 5' of the guide sequence.

227. The polynucleotide of any one of embodiments 205 to 226, further comprising one or more cleavable linkers in the sequence element.

228. The polynucleotide of any one of embodiments 205 to 226, further comprising at least two cleavable linkers in the sequence element.

229. The polynucleotide of any one of embodiments 205 to 226, further comprising at least three cleavable linkers in the sequence element.

230. The polynucleotide of any one of embodiments 205 to 226, further comprising at least four cleavable linkers in the sequence element.

231. The polynucleotide of any one of embodiments 205 to 226, further comprising at least five or more, seven or more, ten or more, fifteen or more, or twenty or more cleavable linkers in the sequence element.

232. The polynucleotide of any one of embodiments 205 to 226, further comprising one or more cleavable linkers in the loop of the sequence element.

233. The polynucleotide of any one of embodiments 205 to 226, further comprising two or more cleavable linkers in the loop of the sequence element.

234. The polynucleotide of any one of embodiments 205 to 226, further comprising three cleavable linkers in the loop of the sequence element.

235. The polynucleotide of any one of embodiments 205 to 226 or 232 to 234, further comprising one or more cleavable linkers at a nucleotide located in the middle positions of the sequence element.

236. The polynucleotide of any one of embodiments 205 to 226 or 232 to 235, further comprising two or more cleavable linkers at a nucleotide located in the middle positions of the sequence element.

237. The polynucleotide of any one of embodiments 205 to 226 or 232 to 235, further comprising three or more cleavable linkers at a nucleotide located in the middle positions of the sequence element.
238. The polynucleotide of any one of embodiments 205 to 226 or 232 to 235, further comprising four or more cleavable linkers at a nucleotide located in the middle positions of the sequence element.
239. The polynucleotide of embodiment 227, wherein the polynucleotide comprises a first cleavable linker at a position 24 in the sequence element and a second cleavable linker at a position 11 in the sequence element, wherein a nucleotide at a 5' end of the sequence element is nucleotide 1 and nucleotides are numbered in order from the 5' end of the sequence element to a 3' end of the sequence element.
240. The polynucleotide of embodiment 227, wherein the polynucleotide comprises a first cleavable linker at a position 24 in the sequence element and one of more cleavable linker at a position of any one of: 5, 6, 10, 11, 14, 15, 16, 21, 22 or 23 in the sequence element, wherein a nucleotide at a 5' end of the sequence element is nucleotide 1 and nucleotides are numbered in order from the 5' end of the sequence element to a 3' end of the sequence element.
241. The polynucleotide of embodiment 227, wherein the polynucleotide comprises a first cleavable linker at a position 24 in the sequence element and a second cleavable linker at a position 23 in the sequence element and one or more cleavable linker at a position of any one of: 5, 6, 10, 11, 14, 15 or 16 in the sequence element, wherein a nucleotide at a 5' end of the sequence element is nucleotide 1 and nucleotides are numbered in order from the 5' end of the sequence element to a 3' end of the sequence element.
242. The polynucleotide of embodiment 227, wherein the polynucleotide comprises a cleavable linker at a position 24 in the sequence element and a first one or more cleavable linker at a position of any one of 21, 22 or 23 in the sequence element and a second one or more cleavable linker at a position of any one of 5, 6, 10, 11, 14, 15 or 16 in the sequence element, wherein a nucleotide at a 5' end of the sequence element is nucleotide 1 and nucleotides are numbered in order from the 5' end of the sequence element to a 3' end of the sequence element.
243. The polynucleotide of embodiment 227, wherein the polynucleotide comprises a first cleavable linker at a position 24 in the sequence element, a second cleavable linker at a position 23 in the sequence element and a third cleavable linker at a position 3 in the sequence element, wherein a nucleotide at a 5' end of the sequence element is nucleotide 1 and nucleotides are numbered in order from the 5' end of the sequence element to a 3' end of the sequence element.
244. The polynucleotide of embodiment 227, wherein the polynucleotide comprises a first cleavable linker at a position 24 in the sequence element, a second cleavable linker at a position 23 in the sequence element and a third cleavable linker at a position 3 in the sequence element, wherein a nucleotide at a 5' end of the sequence element is nucleotide 1 and nucleotides are numbered in order from the 5' end of the sequence element to a 3' end of the sequence element.
245. The polynucleotide of embodiment 227, wherein the polynucleotide comprises a first cleavable linker at a position 24 in the sequence element, a second cleavable linker at a position 23 in the sequence element, a third cleavable linker at a position 6 in the sequence element, a fourth cleavable linker at a position 16 in the sequence element and a fifth cleavable linker at a position 11 in the sequence element, wherein a nucleotide at a 5' end of the sequence element is nucleotide 1 and nucleotides are numbered in order from the 5' end of the sequence element to a 3' end of the sequence element.
246. The polynucleotide of embodiment 227, wherein the polynucleotide comprises a first cleavable linker at a position 24 in the sequence element, a second cleavable linker at a position 23 in the sequence element, a third cleavable linker at a position 6 in the sequence element and a fourth cleavable linker at a position 14 in the sequence element, wherein a nucleotide at a 5' end of the sequence element is nucleotide 1 and nucleotides are numbered in order from the 5' end of the sequence element to a 3' end of the sequence element.
247. The polynucleotide of any one of embodiments 239 to 246, wherein the sequence element is 24 nucleotides in length, the loop of the sequence element comprises nucleotides from positions 21 to 24 and nucleotides from positions 1 to 20 of the sequence element base pair to the target binding region of the guide sequence.
248. A CRISPR OFF polynucleotide comprising a cleavable linker 3' of the 5' most nucleotide of the guide sequence.
249. The polynucleotide of embodiment 248, wherein the cleavable linker is not at a 3' end of the polynucleotide.
250. The polynucleotide of any one of embodiments 161 to 249, wherein the cleavable linker is positioned in the CRISPR effector protein binding region.
251. The polynucleotide of any one of embodiments 161 to 250, wherein the cleavable linker is positioned immediately 3' of nucleotide 56 or 73 in the polynucleotide, wherein a nucleotide at a 5' end of the guide sequence is nucleotide 1, and nucleotides are numbered in order from the 5' end of the guide sequence to a 3' end of the polynucleotide.
252. The polynucleotide of any one of embodiments 161 to 251, wherein the polynucleotide comprises a first cleavable linker and a second cleavable linker, wherein the first cleavable linker is positioned immediately 3' of nucleotide 56 and the second cleavable linker is positioned immediately 3' of nucleotide 73 in the polynucleotide, wherein a nucleotide at a 5' end of the guide sequence is nucleotide 1 and nucleotides are numbered in order from the 5' end of the guide sequence to a 3' end of the polynucleotide.
253. The polynucleotide of any one of embodiments 161 to 252, wherein the polynucleotide comprises a tetraloop, a nexus, a stem loop 1 and a stem loop 2 from 5' to 3', wherein the cleavable linker is in a loop of the nexus or a loop of the stem loop 1.
254. The polynucleotide of any one of embodiments 161 to 252, wherein the polynucleotide comprises a tetraloop, a nexus, a stem loop 1 and a stem loop 2 from 5' to 3', wherein the cleavable linker is in a loop of the nexus and a loop of the stem loop 1.
255. A CRISPR ON/OFF polynucleotide comprising the CRISPR ON polynucleotide of any one of embodiments 205 to 247 and the CRISPR OFF polynucleotide of any one of embodiments 248 to 254.
256. The polynucleotide of any one of embodiments 161 to 255, wherein the cleavable linker is photolabile.
257. The polynucleotide of embodiment 256, wherein the cleavable linker is cleaved by ultraviolet (UV) light.

258. The polynucleotide of embodiment 257, wherein the cleavable linker is cleaved by light of wavelength in the range of 100 nm to 400 nm.
259. The polynucleotide of embodiment 256, wherein the cleavable linker is cleaved by visible light.
260. The polynucleotide of embodiment 256, wherein the cleavable linker is cleaved by light of wavelength 400 nm to 700 nm.
261. The polynucleotide of embodiment 259, wherein the cleavable linker is cleaved by green light.
262. The polynucleotide of embodiment 259, wherein the cleavable linker is cleaved by violet light.
263. The polynucleotide of embodiment 259, wherein the cleavable linker is cleaved by blue light.
264. The polynucleotide of embodiment 259, wherein the cleavable linker is cleaved by light of wavelength in the range of 490 nm to 570 nm.
265. The polynucleotide of embodiment 259, wherein the cleavable linker is cleaved by light of wavelength in the range of 400 nm to 420 nm.
266. The polynucleotide of embodiment 259, wherein the cleavable linker is cleaved by light of wavelength in the range of 420 nm to 430 nm.
267. The polynucleotide of embodiment 259, wherein the cleavable linker is cleaved by light of wavelength in the range of 420 nm to 440 nm.
268. The polynucleotide of embodiment 259, wherein the cleavable linker of the CRISPR ON polynucleotide is cleaved by green light.
269. The polynucleotide of embodiment 259, wherein the cleavable linker of the CRISPR OFF polynucleotide is cleaved by violet light.
270. The polynucleotide of embodiment 259, wherein the cleavable linker of the CRISPR OFF polynucleotide is cleaved by blue light.
271. The polynucleotide of embodiment 259, wherein the cleavable linker of the CRISPR ON polynucleotide is cleaved by light of wavelength in the range of 490 nm to 570 nm.
272. The polynucleotide of embodiment 259, wherein the cleavable linker of the CRISPR ON polynucleotide is cleaved by light of wavelength in the range of 420 nm to 430 nm.
273. The polynucleotide of embodiment 259, wherein the cleavable linker of the CRISPR OFF polynucleotide is cleaved by light of wavelength in the range of 400 nm to 420 nm.
274. The polynucleotide of embodiment 259, wherein the cleavable linker of the CRISPR OFF polynucleotide is cleaved by light of wavelength in the range of 420 nm to 430 nm.
275. The polynucleotide of embodiment 259, wherein the cleavable linker of the CRISPR OFF polynucleotide is cleaved by light of wavelength in the range of 420 nm to 440 nm.
276. The polynucleotide of embodiment 259, wherein the cleavable linker in the CRISPR ON polynucleotide of the CRISPR ON/OFF polynucleotide is cleaved by light of higher wavelength than the cleavable linker in the CRISPR OFF polynucleotide of the CRISPR ON/OFF polynucleotide.
277. The polynucleotide of embodiment 271, wherein the cleavable linker of the CRISPR ON polynucleotide is cleaved by light of wavelength in the range of 490 nm to 570 nm and the cleavable linker of the CRISPR OFF polynucleotide is cleaved by light of wavelength in the range of 400 nm to 420 nm.
278. The polynucleotide of embodiment 271, wherein the cleavable linker of the CRISPR ON polynucleotide is cleaved by light of wavelength in the range of 490 nm to 570 nm and the cleavable linker of the CRISPR OFF polynucleotide is cleaved by light of wavelength in the range of 420 nm to 430 nm.
279. The polynucleotide of embodiment 271, wherein the cleavable linker of the CRISPR ON polynucleotide is cleaved by light of wavelength in the range of 490 nm to 570 nm and the cleavable linker of the CRISPR OFF polynucleotide is cleaved by light of wavelength in the range of 420 nm to 440 nm.
280. The polynucleotide of embodiment 271, wherein the cleavable linker of the CRISPR ON polynucleotide is cleaved by green light and the cleavable linker of the CRISPR OFF polynucleotide is cleaved by violet light.
281. The polynucleotide of embodiment 271, wherein the cleavable linker of the CRISPR ON polynucleotide is cleaved by green light and the cleavable linker of the CRISPR OFF polynucleotide is cleaved by blue light.
282. The polynucleotide of any one of embodiments 161 to 281, wherein the cleavable linker is a phosphoramidite derivative.
283. The polynucleotide of any one of embodiments 161 to 281, wherein the cleavable linker is a 3-(4,4'-Dimethoxytrityl)-1-(2-nitrophenyl)-propan-1-yl-[(2-cyanoethyl)-(N,N-diisopropyl)]-phosphoramidite derivative.
284. The polynucleotide of any one of embodiments 161 to 281, wherein the cleavable linker is a 1-(7-(diethylamino)-2-oxo-2H-chromen-4-yl)-3-(4,4'-dimethoxytrityl)-propan-1-yl-[(2-cyanoethyl)-(N,N-diisopropyl)]-phosphoramidite derivative.
285. The polynucleotide of any one of embodiments 161 to 281, wherein the cleavable linker comprises a phosphodiester.
286. The polynucleotide of any one of embodiments 161 to 281, wherein the cleavable linker comprises a phosphomonoester.
287. The polynucleotide of any one of embodiments 161 to 281, wherein the cleavable linker is a coumarin derivative.
288. The polynucleotide of any one of embodiments 161 to 281, wherein the cleavable linker comprises a structure represented by the following formula:

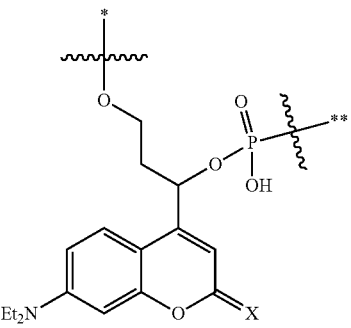

wherein:
X is O, S, or CR$^x$R$^y$, wherein R$^x$ and R$^y$ are independently selected from optionally substituted alkyl, optionally substituted alkenyl, optionally substituted alkynyl, optionally substituted heteroalkyl, halo, haloalkyl, alkoxy, alkoxyalkyl, haloalkoxy, amino, aminoalkyl, alkylamino, alkylaminoalkyl, hydroxy, hydroxyalkyl, C-carboxy, O-carboxy, acyl, thiol, alkylthio, thiolalkyl, C-amido, N-amido, ureido, nitro, cyano, sulfonyl, sulfo, sulfonate, sulfino, S-sulfonamido, N-sulfonamido, optionally substituted carbocyclyl, optionally substituted aryl, optionally substituted heteroaryl, and optionally substituted heterocyclyl; and
* indicates a point of attachment to H, or a first nucleotide; and
** indicates a point of attachment to OH, or a second nucleotide.

289. The polynucleotide of embodiment 288, wherein X is oxygen.

290. The polynucleotide of embodiment 288, wherein X is sulfur.

291. The polynucleotide of embodiment 288, wherein X is =C(CN)2.

292. The polynucleotide of any one of embodiments 161 to 281, wherein the cleavable linker comprises a structure represented by Formula (I):

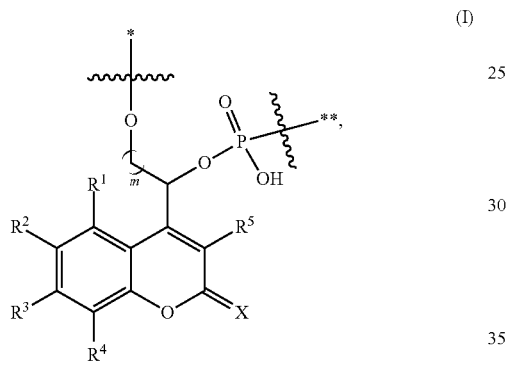

wherein:
$R^1$, $R^2$, $R^3$, $R^4$, and $R^5$ are each independently selected from H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl; alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;
alternatively, two or more of $R^1$, $R^2$, $R^3$, $R^4$, and $R^5$ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and
m is an integer selected from 1 to 10; and
X is O, S, or $CR^xR^y$, wherein $R^x$ and $R^y$ are independently selected from optionally substituted alkyl, optionally substituted alkenyl, optionally substituted alkynyl, optionally substituted heteroalkyl, halo, haloalkyl, alkoxy, alkoxyalkyl, haloalkoxy, amino, aminoalkyl, alkylamino, alkylaminoalkyl, hydroxy, hydroxyalkyl, C-carboxy, O-carboxy, acyl, thiol, alkylthio, thiolalkyl, C-amido, N-amido, ureido, nitro, cyano, sulfonyl, sulfo, sulfonate, sulfino, S-sulfonamido, N-sulfonamido, optionally substituted carbocyclyl, optionally substituted aryl, optionally substituted heteroaryl, and optionally substituted heterocyclyl,
with the proviso that, when X is O, and $R^3$ is dialkylamino, then m is an integer from 2 to 10; and
* indicates a point of attachment to H, or a first nucleotide; and
** indicates a point of attachment to OH, or a second nucleotide.

293. The polynucleotide of embodiment 292, wherein X is oxygen.

294. The polynucleotide of embodiment 292, wherein X is sulfur.

295. The polynucleotide of embodiment 292, wherein X is =C(CN)2.

296. The polynucleotide of embodiment 292, wherein the structure of Formula (I) is represented by Formula (I'):

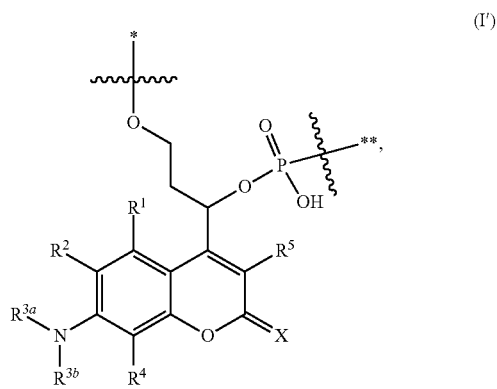

wherein:
$R^1$, $R^2$, $R^4$, and $R^5$ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
$R^{3a}$ and $R^{3b}$ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
alternatively, two or more of $R^1$, $R^2$, $R^{3a}$, $R^{3b}$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of R¹, R², R³ᵃ, R³ᵇ, R⁴, and R⁵ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and X is oxygen.

297. The polynucleotide of embodiment 292, wherein the structure of Formula (I) is represented by Formula (I'):

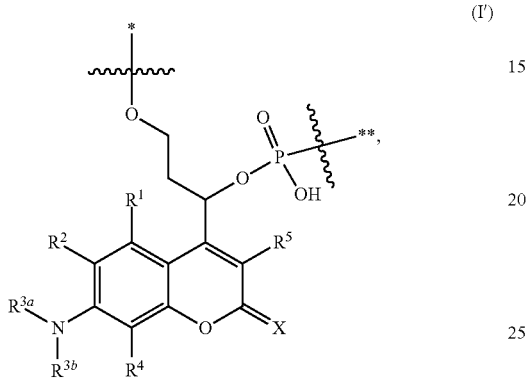

wherein:

R¹, R², R⁴, and R⁵ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

R³ᵃ and R³ᵇ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

alternatively, two or more of R¹, R², R³ᵃ, R³ᵇ, and R⁴, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of R¹, R², R³ᵃ, R³ᵇ, R⁴, and R⁵ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and X is sulfur.

298. The polynucleotide of embodiment 292, wherein the structure of Formula (I) is represented by Formula (I'):

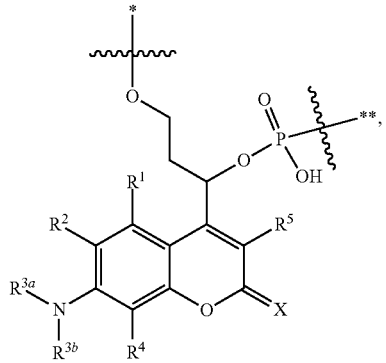

wherein:

R¹, R², R⁴, and R⁵ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

R³ᵃ and R³ᵇ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

alternatively, two or more of R¹, R², R³ᵃ, R³ᵇ and R⁴, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of R¹, R², R³ᵃ, R³ᵇ, R⁴, and R⁵ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and X is =C(CN)2.

299. The polynucleotide of any one of embodiments 296 to 298, wherein:

R¹, R², R⁴, and R⁵ are each independently H or $C_{1-6}$ alkyl; and

R³ᵃ, and R³ᵇ are $C_{1-6}$ alkyl.

300. The polynucleotide of any one of embodiments 296 to 299, wherein:

R¹, R², R⁴, and R⁵ are each H; and

R³ᵃ, and R³ᵇ are each ethyl.

301. The polynucleotide of any one of embodiments 135 to 300, wherein when the polynucleotide is complexed with a CRISPR effector protein, a first crosslinked CRISPR complex is formed having a lower editing activity of an off-target nucleic acid molecule than a second CRISPR complex comprising the polynucleotide not crosslinked with the CRISPR effector protein.
302. The polynucleotide of embodiment 301, wherein the editing activity is measured as a percentage of off-target nucleic acid molecules that are edited.
303. The polynucleotide of embodiment 301, wherein the editing activity is measured as a percentage of target nucleic acid molecules that are edited.
304. The polynucleotide of any one of embodiments 301 to 303, wherein the editing activity of the off-target nucleic acid molecules by the first CRISPR complex is lower that an editing activity of the second CRISPR complex with a p-value≤0.0001.
305. The polynucleotide of any one of embodiments 301 to 304, wherein an editing activity of the first CRISPR complex of the target nucleic acid molecule and an editing activity of the second CRISPR complex of the target nucleic acid molecule are within 5%.
306. A CRISPR complex comprising the polynucleotide of any one of embodiments 135 to 305 and a CRISPR effector protein.
307. The CRISPR complex of embodiment 306, wherein the CRISPR complex comprises nuclease activity.
308. A nucleotide or oligonucleotide or polynucleotide comprising a cleavable linker comprising a structure of Formula (I):

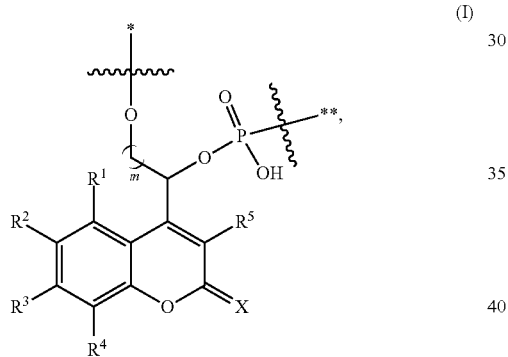

wherein:
$R^1$, $R^2$, $R^3$, $R^4$, and $R^5$ are each independently selected from H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;
alternatively, two or more of $R^1$, $R^2$, $R^3$, $R^4$, and $R^5$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and
m is an integer selected from 1 to 10; and X is O, S, or $CR^xR^y$, wherein $R^x$ and $R^y$ are independently selected from optionally substituted alkyl, optionally substituted alkenyl, optionally substituted alkynyl, optionally substituted heteroalkyl, halo, haloalkyl, alkoxy, alkoxyalkyl, haloalkoxy, amino, aminoalkyl, alkylamino, alkylaminoalkyl, hydroxy, hydroxyalkyl, C-carboxy, O-carboxy, acyl, thiol, alkylthio, thiolalkyl, C-amido, N-amido, ureido, nitro, cyano, sulfonyl, sulfo, sulfonate, sulfino, S-sulfonamido, N-sulfonamido, optionally substituted carbocyclyl, optionally substituted aryl, optionally substituted heteroaryl, and optionally substituted heterocyclyl,
with the proviso that, when X is O, and $R^3$ is dialkylamino, then m is an integer from 2 to 10; and
* indicates a point of attachment to H, or a first nucleotide; and
** indicates a point of attachment to OH, or a second nucleotide.
309. The nucleotide or oligonucleotide or polynucleotide of embodiment 308, wherein X is oxygen.
310. The nucleotide or oligonucleotide or polynucleotide of embodiment 308, wherein X is sulfur.
311. The nucleotide or oligonucleotide or polynucleotide of embodiment 308, wherein X is =C(CN)2.
312. The nucleotide or oligonucleotide or polynucleotide of embodiment 308, wherein the structure of Formula (I) is represented by Formula (I'):

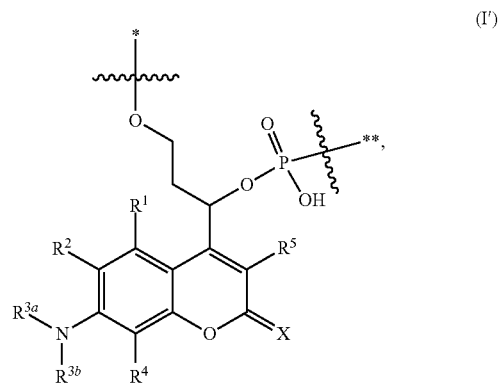

wherein:
$R^1$, $R^2$, $R^4$, and $R^5$ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
$R^{3a}$ and $R^{3b}$ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and
optionally substituted heterocyclyl;
alternatively, two or more of $R^1$, $R^2$, $R^{3a}$, $R^{3b}$ and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;
alternatively, two or more of $R^1$, $R^2$, $R^{3a}$, $R^{3b}$, $R^4$, and $R^5$ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and
X is oxygen.

313. The nucleotide or oligonucleotide or polynucleotide of embodiment 308, wherein the structure of Formula (I) is represented by Formula (I'):

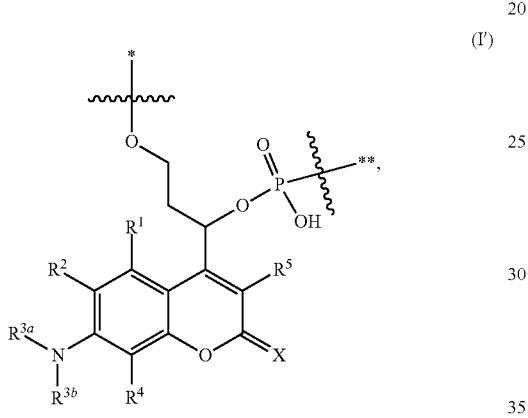

(I')

wherein:
$R^1$, $R^2$, $R^4$, and $R^5$ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
$R^{3a}$ and $R^{3b}$ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
alternatively, two or more of $R^1$, $R^2$, $R^{3a}$, $R^{3b}$ and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;
alternatively, two or more of $R^1$, $R^2$, $R^{3a}$, $R^{3b}$, $R^4$, and $R^5$ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and
X is sulfur.

314. The nucleotide or oligonucleotide or polynucleotide of embodiment 308, wherein the structure of Formula (I) is represented by Formula (I'):

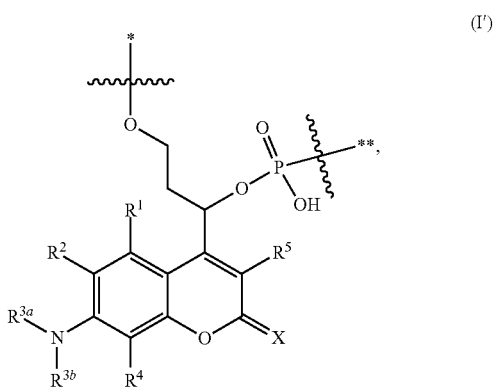

(I')

wherein:
$R^1$, $R^2$, $R^4$, and $R^5$ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
$R^{3a}$ and $R^{3b}$ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;
alternatively, two or more of $R^1$, $R^2$, $R^{3a}$, $R^{3b}$ and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;
alternatively, two or more of $R^1$, $R^2$, $R^{3a}$, $R^{3b}$, $R^4$, and $R^5$ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and
X is =C(CN)2.

315. The nucleotide or oligonucleotide or polynucleotide of any one of embodiments 312 to 314, wherein:
$R^1$, $R^2$, $R^4$, and $R^5$ are each independently H or $C_{1-6}$ alkyl; and
$R^{3a}$, and $R^{3b}$ are $C_{1-6}$ alkyl.

316. The nucleotide or oligonucleotide or polynucleotide of any one of embodiments 312 to 314, wherein:
$R^1$, $R^2$, $R^4$, and $R^5$ are each H; and
$R^{3a}$, and $R^{3b}$ are each ethyl.

317. A nucleotide or oligonucleotide or polynucleotide comprising a cleavable linker comprising a structure represented by the following formula:

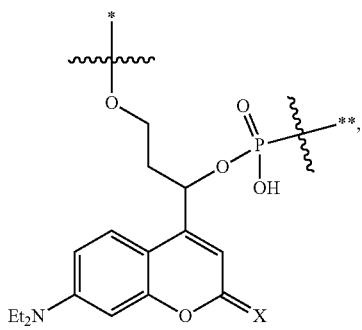

wherein:
X is O, S, or $CR^xR^y$, wherein $R^x$ and $R^y$ are independently selected from optionally substituted alkyl, optionally substituted alkenyl, optionally substituted alkynyl, optionally substituted heteroalkyl, halo, haloalkyl, alkoxy, alkoxyalkyl, haloalkoxy, amino, aminoalkyl, alkylamino, alkylaminoalkyl, hydroxy, hydroxyalkyl, C-carboxy, O-carboxy, acyl, thiol, alkylthio, thiolalkyl, C-amido, N-amido, ureido, nitro, cyano, sulfonyl, sulfo, sulfonate, sulfino, S-sulfonamido, N-sulfonamido, optionally substituted carbocyclyl, optionally substituted aryl, optionally substituted heteroaryl, and optionally substituted heterocyclyl; and
* indicates a point of attachment to H, or a first nucleotide; and
** indicates a point of attachment to OH, or a second nucleotide.

318. The nucleotide or oligonucleotide or polynucleotide of embodiment 317, wherein X is oxygen.
319. The nucleotide or oligonucleotide or polynucleotide of embodiment 317, wherein X is sulfur.
320. The nucleotide or oligonucleotide or polynucleotide of embodiment 317, wherein X is =C(CN)2.
321. The nucleotide or oligonucleotide or polynucleotide of any one of embodiments 308 to 320, wherein the nucleotide or oligonucleotide or polynucleotide further comprises a crosslinker.
322. The nucleotide or oligonucleotide or polynucleotide of embodiment 321, wherein the crosslinker comprises or is derived from pyridyl disulfide, alkoxyamine, NHS ester, diazarine, imidoester, haloacetyl group, hydrazide, aryl azide, isocyanate, dithiol phosphoramidite DTPA, 4-thio-UTP, 5-azido-UTP, 5-bromo-UTP, 8-azido-ATP, 5-APAS-UTP or 8-N(3)AMP.
323. The nucleotide or oligonucleotide or polynucleotide of embodiment 321, wherein the crosslinker comprises disulfide, amide, imine, hydrazide, O-alkyl oxime, alkyl, amine, alcohol, triazole, isooxazoline, isoxazolidine, isoxazole or pyridazine.
324. The nucleotide or oligonucleotide or polynucleotide of embodiment 321, wherein the crosslinker comprises or is derived from pyridyl disulfide, alkoxyamine, NHS ester, diazarine, imidoester, haloacetyl group, hydrazide, aryl azide, isocyanate, dithiol phosphoramidite DTPA, 4-thio-UTP, 5-azido-UTP, 5-bromo-UTP, 8-azido-ATP, 5-APAS-UTP or 8-N(3)AMP.
325. A nucleotide or oligonucleotide or polynucleotide comprising a crosslinker, wherein the crosslinker comprises disulfide, amide, imine, hydrazide, O-alkyl oxime, alkyl, amine, alcohol, triazole, isooxazoline, isoxazolidine, isoxazole or pyridazine.
326. A nucleotide or oligonucleotide or polynucleotide comprising a crosslinker, wherein the crosslinker comprises or is derived from pyridyl disulfide, alkoxyamine, NHS ester, diazarine, imidoester, haloacetyl group, hydrazide, aryl azide, isocyanate, dithiol phosphoramidite DTPA, 4-thio-UTP, 5-azido-UTP, 5-bromo-UTP, 8-azido-ATP, 5-APAS-UTP or 8-N(3) AMP.
327. A cell comprising one or more of: the CRISPR complex of any one of embodiments 1 to 125, 306 or 307, the sgRNA of embodiment 133 or 134 or the polynucleotide of any one of embodiments 135 to 305.
328. The cell of embodiment 323, wherein the cell is a stem cell.
329. The cell of embodiment 323, wherein the cell is an immune cell.
330. The cell of embodiment 328, wherein the stem cell is an induced pluripotent stem cell.
331. The cell of embodiment 329, wherein the immune cell is a T cell.
332. The cell of embodiment 329, wherein the immune cell is a natural killer cell (NK cell).
333. A compound comprising a structure represented by the following formula:

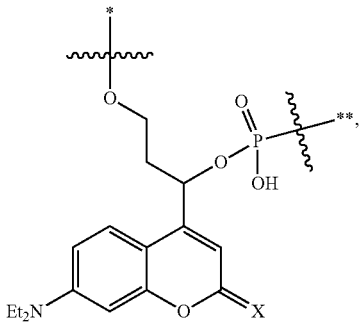

wherein:
X is O, S, or $CR^xR^y$, wherein $R^x$ and $R^y$ are independently selected from optionally substituted alkyl, optionally substituted alkenyl, optionally substituted alkynyl, optionally substituted heteroalkyl, halo, haloalkyl, alkoxy, alkoxyalkyl, haloalkoxy, amino, aminoalkyl, alkylamino, alkylaminoalkyl, hydroxy, hydroxyalkyl, C-carboxy, O-carboxy, acyl, thiol, alkylthio, thiolalkyl, C-amido, N-amido, ureido, nitro, cyano, sulfonyl, sulfo, sulfonate, sulfino, S-sulfonamido, N-sulfonamido, optionally substituted carbocyclyl, optionally substituted aryl, optionally substituted heteroaryl, and optionally substituted heterocyclyl; and
* indicates a point of attachment to H, or a first nucleotide; and
** indicates a point of attachment to OH, or a second nucleotide.

334. The compound of embodiment 333, wherein X is oxygen.

335. The compound of embodiment 333, wherein X is sulfur.

336. The compound of embodiment 333, wherein X is =C(CN)2.

337. A compound comprising a structure represented by Formula (I):

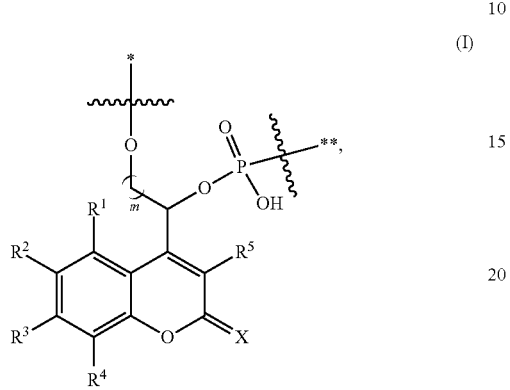

(I)

wherein:

$R^1$, $R^2$, $R^3$, $R^4$, and $R^5$ are each independently selected from H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

alternatively, two or more of $R^1$, $R^2$, $R^3$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of $R^1$, $R^2$, $R^3$, $R^4$, and $R^5$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and m is an integer selected from 1 to 10; and X is O, S, or $CR^xR^y$, wherein $R^x$ and $R^y$ are independently selected from optionally substituted alkyl, optionally substituted alkenyl, optionally substituted alkynyl, optionally substituted heteroalkyl, halo, haloalkyl, alkoxy, alkoxyalkyl, haloalkoxy, amino, aminoalkyl, alkylamino, alkylaminoalkyl, hydroxy, hydroxyalkyl, C-carboxy, O-carboxy, acyl, thiol, alkylthio, thiolalkyl, C-amido, N-amido, ureido, nitro, cyano, sulfonyl, sulfo, sulfonate, sulfino, S-sulfonamido, N-sulfonamido, optionally substituted carbocyclyl, optionally substituted aryl, optionally substituted heteroaryl, and optionally substituted heterocyclyl, with the proviso that, when X is O, and $R^3$ is dialkylamino, then m is an integer from 2 to 10; and

* indicates a point of attachment to H, or a first nucleotide; and

** indicates a point of attachment to OH, or a second nucleotide.

338. The compound of embodiment 337, wherein X is oxygen.

339. The compound of embodiment 337, wherein X is sulfur.

340. The compound of embodiment 337, wherein X is =C(CN)2.

341. The compound of embodiment 337, wherein the structure of Formula (I) is represented by Formula (I'):

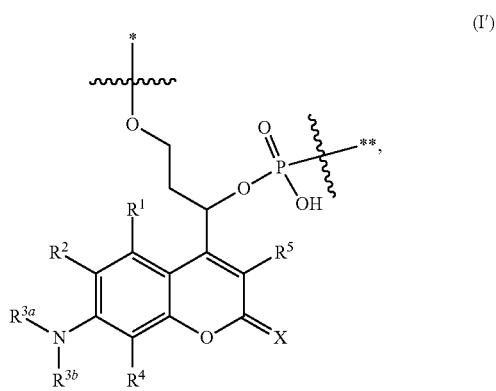

(I')

wherein:

$R^1$, $R^2$, $R^4$, and $R^5$ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

$R^{3a}$ and $R^{3b}$ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

alternatively, two or more of $R^1$, $R^2$, $R^{3a}$, $R^{3b}$, and $R^4$, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of $R^1$, $R^2$, $R^{3a}$, $R^{3b}$, $R^4$, and $R^5$ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and X is oxygen.

342. The compound of embodiment 337, wherein the structure of Formula (I) is represented by Formula (I'):

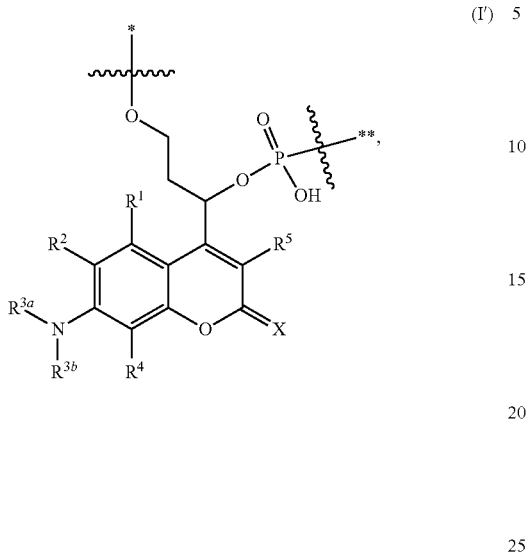

wherein:

R¹, R², R⁴, and R⁵ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

$R^{3a}$ and $R^{3b}$ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

alternatively, two or more of R¹, R², $R^{3a}$, $R^{3b}$, and R⁴, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of R¹, R², $R^{3a}$, $R^{3b}$, R⁴, and R⁵ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and X is sulfur.

343. The compound of embodiment 337, wherein the structure of Formula (I) is represented by Formula (I'):

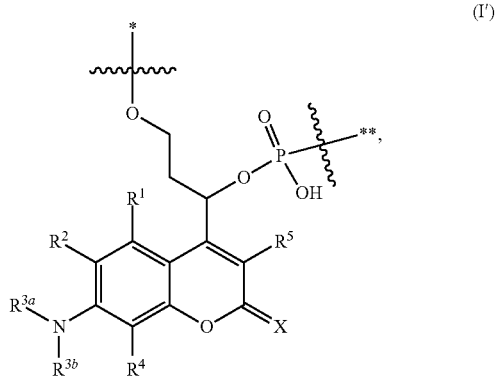

wherein:

R¹, R², R⁴, and R⁵ are each independently selected from the group consisting of H, alkyl, substituted alkyl, alkoxy, alkenyl, alkynyl, haloalkyl, haloalkoxy, alkoxyalkyl, amino, monoalkylamino, dialkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

$R^{3a}$ and $R^{3b}$ are independently selected from the group consisting of H, alkyl, substituted alkyl, alkoxy, alkenyl, alkynyl, haloalkyl, haloalkoxy, alkoxyalkyl, amino, alkylamino, aminoalkyl, halo, cyano, hydroxy, hydroxyalkyl, heteroalkyl, C-carboxy, O-carboxy, C-amido, N-amido, nitro, sulfonyl, sulfo, sulfino, sulfonate, S-sulfonamido, N-sulfonamido, optionally substituted carbocyclyl, optionally substituted aryl, optionally substituted heteroaryl, and optionally substituted heterocyclyl;

alternatively, two or more of R¹, R², $R^{3a}$, $R^{3b}$ and R⁴, together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle;

alternatively, two or more of R¹, R², $R^{3a}$, $R^{3b}$, R⁴, and R⁵ together with the atoms to which they are attached form a ring or ring system selected from optionally substituted 5- to 10-membered heteroaryl, optionally substituted 5- to 10-membered heterocyclyl, and optionally substituted $C_{5-10}$ carbocycle; and X is =C(CN)2.

344. A pharmaceutical formulation comprising one or more of: the CRISPR complex of any one of 1 to 132, 306 or 307, the sgRNA of embodiment 133 or 134, the polynucleotide of any one of embodiments 135 to 305, the cell of any one of embodiments 327 to 332 or the compound of any one of embodiments 333 to 343.

345. The pharmaceutical formulation of embodiment 344 further comprising a pharmaceutically acceptable excipient.

346. A method comprising administering the pharmaceutical formulation of embodiment 344 or 345 to a subject.

347. The method of embodiment 346, wherein the subject is a mammal.

348. The method of embodiment 347, wherein the mammal is a human.
349. A method comprising introducing one or more of: the CRISPR complex of any one of embodiments 1 to 132, 306 or 307, the sgRNA of embodiment 133 or 134 or the polynucleotide of any one of embodiments 135 to 305 into a cell.
350. The method of embodiment 349, wherein the cell is a stem cell.
351. The method of embodiment 349, wherein the cell is an immune cell.
352. The method of embodiment 350, wherein the stem cell is an induced pluripotent stem cell.
353. The method of embodiment 351, wherein the immune cell is a T cell.
354. The method of embodiment 351, wherein the immune cell is a natural killer cell (NK cell).
355. A method of editing a nucleic acid molecule comprising contacting the CRISPR complex of any one of embodiments 1 to 132, 306 or 307 with a nucleic acid molecule.
356. The method of embodiment 355, wherein the CRISPR complex comprises an off-target cleavage activity of less than 2% of cleavage events.
357. A method of editing a nucleic acid molecule comprising contacting the nucleic acid molecule with a CRISPR effector protein and one or more of: the sgRNA of embodiment 133 or 134 or the polynucleotide of any one of embodiments 135 to 305.
358. A method of editing a target gene in one or more cells comprising administering the CRISPR complex of any one of embodiments 1 to 132, 306 or 307 to the one or more cells comprising a target gene, thereby generating one or more cells comprising edited target genes.
359. A method of editing a target gene in one or more cells comprising administering a CRISPR effector protein or a polynucleotide encoding a CRISPR effector protein and one or more of: the sgRNA of embodiment 133 or 134 or the polynucleotide of any one of embodiments 135 to 305 to the one or more cells comprising a target gene, thereby generating one or more cells comprising edited target genes, wherein 99% of the cells comprising edited target genes remain viable after administration.
360. The method of embodiment 358 or 359, wherein 99% of the cells comprising edited target genes remain viable after administration.
361. The method of embodiment 360, further comprising measuring cell viability by a resazurin assay.
362. A method of producing a CRISPR complex comprising cross-linking a guide RNA (gRNA) wherein the cross-linking occurs at a nucleotide outside a target binding region of the gRNA, and wherein nuclease activity of the CRISPR effector protein is maintained after the cross-linking.
363. The method of embodiment 362, wherein the cross-linking occurs in a solution, and wherein a ratio of the gRNA to the CRISPR effector protein in the solution is at least 9:1.
364. The method of embodiment 363, wherein the cross-linking comprises exposing the solution to ultraviolet (UV) light.
365. The method of any one of embodiments 362 to 364, wherein the crosslinking occurs upon mixing of the gRNA with the CRISPR effector protein.
366. A method of cleaving the polynucleotide of any one of embodiments 205 to 305 comprising exposing the polynucleotide to a cleavage agent thereby cleaving the cleavable linker.
367. A method comprising:
introducing a CRISPR effector protein and the polynucleotide of any one of embodiments 205 to 305; and
exposing the polynucleotide to a cleavage agent thereby cleaving the cleavable linker.
368. The method of embodiment 366 or 367, wherein the polynucleotide is complexed with a CRISPR effector protein.
369. The method of any one of embodiments 366 to 368, wherein the cleavage agent is ultraviolet (UV) light.
370. The method of embodiment 369, wherein the cleavage agent is light of wavelength in the range of 100 nm to 400 nm.
371. The method of any one of embodiments 366 to 368, wherein the cleavage agent is visible light.
372. The method of any one of embodiments 366 to 368, wherein the cleavage agent is light of wavelength 400 nm to 700 nm.
373. The method of any one of embodiments 366 to 368, wherein the cleavage agent is green light.
374. The method of any one of embodiments 366 to 368, wherein the cleavage agent is violet light.
375. The method of any one of embodiments 366 to 368, wherein the cleavage agent is blue light.
376. The method of any one of embodiments 366 to 368, wherein the cleavage agent is light of wavelength in the range of 490 nm to 570 nm.
377. The method of any one of embodiments 366 to 368, wherein the cleavage agent is light of wavelength in the range of 400 nm to 420 nm.
378. The method of any one of embodiments 366 to 368, wherein the cleavage agent is light of wavelength in the range of 420 nm to 430 nm.
379. The method of any one of embodiments 366 to 368, wherein the cleavage agent is light of wavelength in the range of 420 nm to 440 nm.
380. The method of any one of embodiments 366 to 374, wherein the exposing increases a target-specific cleavage activity of a CRISPR effector protein complexed with the polynucleotide.
381. The method of any one of embodiments 366 to 376, wherein the polynucleotide is not in a cell.
382. The method of any one of embodiments 366 to 376, wherein the polynucleotide is in a cell.
383. The method of embodiment 382, wherein the cell is a stem cell.
384. The method of embodiment 382, wherein the cell is an immune cell.
385. The method of embodiment 383, wherein the stem cell is an induced pluripotent stem cell.
386. The method of embodiment 384, wherein the immune cell is a T cell.
387. The method of embodiment 384, wherein the immune cell is a natural killer cell (NK cell).
388. A system comprising one or more of: the CRISPR complex of any one of 1 to 132, 306 or 307, the sgRNA of embodiment 133 or 134, the polynucleotide of any one of embodiments 135 to 305, the cell of any one of embodiments 327 to 332, the compound of any one of embodiments 333 to 343 or the pharmaceutical formulation of embodiment 344 or 345.

389. A kit comprising one or more of: the CRISPR complex of any one of 1 to 132, 306 or 307, the sgRNA of embodiment 133 or 134, the polynucleotide of any one of embodiments 135 to 305, the cell of any one of embodiments 327 to 332, the compound of any one of embodiments 333 to 343, the pharmaceutical formulation of embodiment 344 or 345 or the system of embodiment 388.

390. The kit of embodiment 389 further comprising instructions for carrying out methods of any one of embodiments 346 to 387.

EXAMPLES

Example 1: Modified Polynucleotide with Cross-Linker Positioned in a Tetraloop Initial studies create a modified polynucleotide wherein the specific nucleotide at position 22 and position 49 are switched. As can be seen in FIG. 1, the nucleotide is located at the base of the tetraloop. Further, the nucleotides at this position are converted to deoxyribonucleic acids. This conversion has minimal effects to polynucleotide or ribonucleoprotein activity FIG. 2. Alternatively, the uracil molecule at position 50 can be converted to deoxythymidine.

Polynucleotides are next further modified by substituting the deoxynucleotide at either position 49 or 50 with an analog containing a reactive linker compound. To this reactive linker, a maleimide is covalently attached through known chemistry. Additionally, this maleimide compound can contain a variable length spacer. Modified polynucleotides are then mixed with Cas9 to form ribonucleoproteins. Ribonucleoproteins will undergo a cross-linking reaction under physiological conditions.

Figure 16:
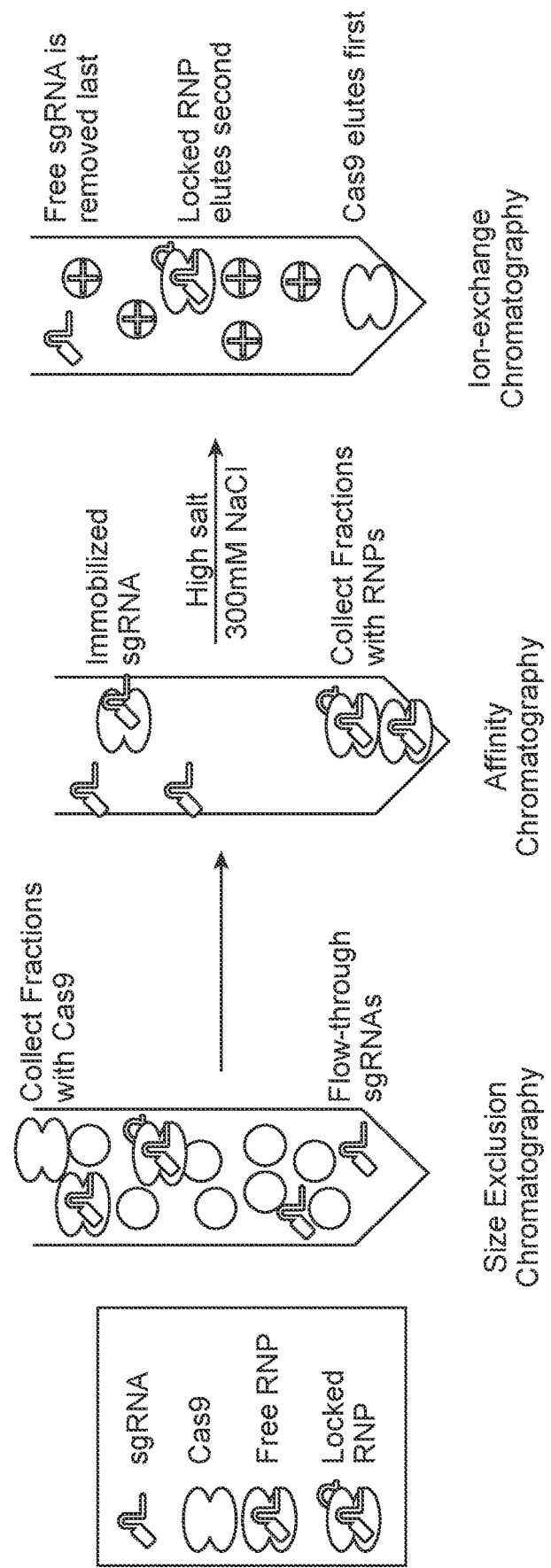
FIG. 16 shows an exemplary diagram of the purification of a locked CRISPR complex.

Cross-linked ribonucleoproteins (Locked RNPs) are next purified from individual free components and non-specific cross-linked species. Mixed solutions are first purified using size exclusion chromatography to separate free polynucleotides. Collected fractions are next passed through an affinity chromatography column with immobilized sgRNAs to separate free polypeptides from formed RNPs. Finally, purified RNPs are passed through a cation exchange column in high salt conditions (e.g., 300 mM NaCl) to isolate locked RNPs (as can be seen in FIG. 16). High salt conditions will cause dissociation of RNPs into component species Cas9 and sgRNA. Due to the covalently bond nature of locked RNPs, these species will stay together and can be purified accordingly.

Purified locked RNPs are transfected into immortalized cell lines to assay their capability to form double strand breaks within human cells. Polynucleotides to target specific regions of the genome are synthesized and formed into locked RNPs. Following transfection, Sanger sequencing is performed on transfected pool and resulting genomic data is analyzed by Inference of CRISPR Edits (ICE) software to detect the presence of indel mutations.

To test the specificity of the locked RNP complex, locked RNPs will be formed containing a specific polynucleotide sequence and purified. To this purification, a 10-fold excess of polynucleotide targeting a separate genomic region will be added and allowed to mix. This mixture is then transfected into cells. Editing at both loci is analyzed and shows that CRISPR induced editing only occurs at the locus targeted by locked RNPs.

Figure 15:
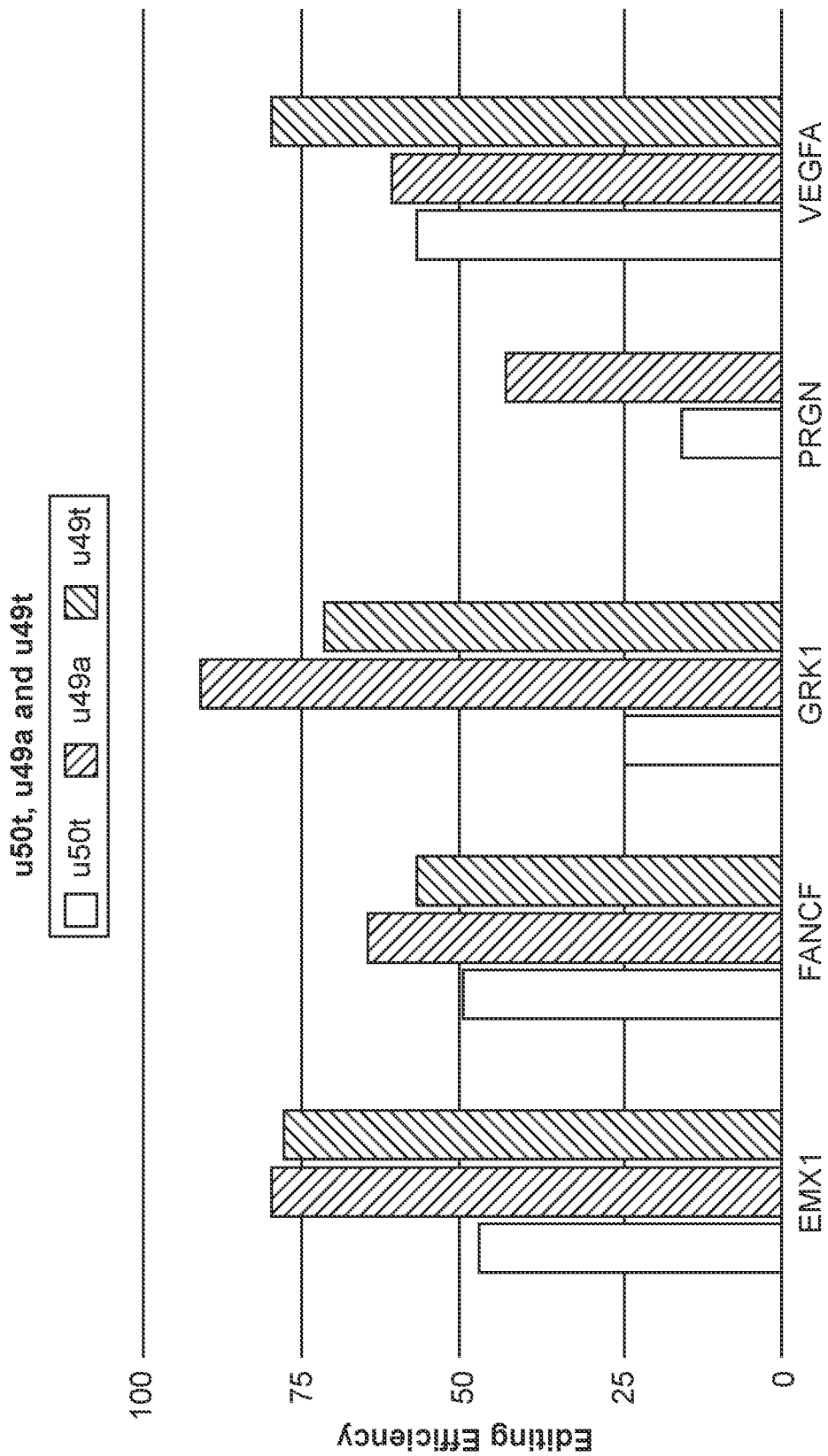
FIG. 15 shows results of an experiment wherein locked CRISPR complexes are used to cleave a gene sequence. The X axis indicates the gene targeted by the guide sequence, the Y axis indicates the percent of DNA sequences containing the targeted gene that was cleaved.

Example 2: Characterization of Target DNA Cutting Efficiency of CRISPR Complexes with sgRNA Modified to Allow Cross-Linking Cas9 nuclease (NLS-Cas9-NLS from Aldevron; PDB: 4oo8) was introduced into HEK 293 cells with 3 distinct sgRNAs comprising different modifications designed to be used in a locked CRISPR Complex. For each modification, a sgRNA was produced to target one of five DNA targets. Fifteen different sgRNAs were tested with a Cas9 nuclease, each introduced into a respective culture of HEK293 cells. FIG. 15 shows a schematic of genome editing efficiency with fifteen different sgRNAs targeting EMX1, FANCF, GRK1, PRGN, and VEGFA. The first modification of the sgRNA ("u50t") replaces the uracil nucleotide at position 50 with a thymidine DNA nucleotide. The second modification of the sgRNA ("u49a") flips the nucleotide positions U22 and A49, preserving the stem loop structure while allowing further functional modifications. The third modification of the sgRNA ("u49t") further builds upon u49a but replaces the new U49 with a deoxythymidine. Each modification was combined with each of the five target binding regions to target each of the five targets. The five DNA target regions were: EMX1 (GAGTCCGAGCAGAAGAAGAA) (SEQ ID NO: 4); FANCF (GCTGCAGAAGGGATTCCATG) (SEQ ID NO: 5); GRK1 (GCCGTCAAAGCTGCCTCGGG) (SEQ ID NO: 33); PRGN (CAGATGCCTGCTCAGTGTTG) (SEQ ID NO: 6); and VEGFA (GGTGAGTGAGTGTGTGCGTG) (SEQ ID NO: 7).

Genomic DNA was harvested from all samples and analyzed for presence of insertions and deletions using ICE (Inference of CRISPR Editing). ICE measured the amount of gene editing by analyzing Sanger sequencing traces and mapping level of sequence breakdown to indel formation frequencies, as described in Hsiau et al., "Inference of CRISPR Edits from Sanger Trace Data", 2019 bioRxiv. The graph in FIG. 15 represents editing efficiency. Samples were amplified using PCR and submitted for sequencing. After sequencing the number of sequences which are wild-type or edited following amplification were analyzed by ICE. Editing is expressed by percentage of sequences that are not wildtype. Most modified guide sgRNAs were able to induce gene editing across the five targets with the exception of the loss of editing seen using the u50t guide at the PGRN gene locus.

Example 3: Generation and Functional Characterization of Modified Polynucleotide with Photocleavable Linker Four sgRNAs were synthesized. The sequences representing a part of the sgRNAs are provided below. Modification on the sgRNAs includes 2'-O-methyl analogs and 3' phosphorothioate internucleotide linkages at the first three 5' and 3' terminal RNA nucleotides. "Control":

```
"Control":
                                       (SEQ ID NO: 8)
NNNNNNNNNNNNNNNNNNNNNGUUUUAGAGCUAGAAAUAGCAAGUUAAAA
UAAGGCUAGUCCGUUAUCAACUUGAAAAAGUGGCACCGAGUCGGUGCUU
UU
```

-continued

"No 2nd":

(SEQ ID NO: 9)
GAAANNNNNNNNNNNNNNNNNNNNNGUUUUAGAGCUAGAAAUAGCAAGUU
AAAAUAAGGCUAGUCCGUUAUCAACUUGAAAAAGUGGCACCGAGUCGGU
GCUUUU

"3 bp Stem":

(SEQ ID NO: 10)
UGAGAAAUCANNNNNNNNNNNNNNNNNNNNGUUUUAGAGCUAGAAAUAG
CAAGUUAAAAUAAGGCUAGUCCGUUAUCAACUUGAAAAAGUGGCACCGA
GUCGGUGCUUUU

"6 bp Stem":

(SEQ ID NO: 11)
CACUGAGAAAUCAGUGNNNNNNNNNNNNNNNNNNNGUUUUAGAGCUAG
AAAUAGCAAGUUAAAAUAAGGCUAGUCCGUUAUCAACUUGAAAAAGUGG
CACCGAGUCGGUGCUUUU

The first sgRNA ("Control" or "Mods") is a sgRNA lacked a polynucleotide leader sequence 5' of the guide sequence. The second sgRNA ("No 2nd" or "No Secondary") had a polynucleotide leader sequence 5' of the guide sequence that was designed to not form a stem loop, followed by a photocleavable linker, 3-(4,4'-Dimethoxytrityl)-1-(2-nitrophenyl)-propan-1-yl-[(2-cyanoethyl)-(N,N-diisopropyl)]-phosphoramidite (www.glenresearch.com/data/ProductInfo.php?item=10-4920) inserted between the 3' end of the polynucleotide leader sequence and 5' of the guide sequence. Two additional sgRNAs were synthesized with an added polynucleotide leader sequence designed to form a stem loop before the 5' base of the guide sequence, followed by a 3-(4,4'-Dimethoxytrityl)-1-(2-nitrophenyl)-propan-1-yl-[(2-cyanoethyl)-(N,N-diisopropyl)]-phosphoramidite (http://www.glenresearch.com/data/ProductInfo.php?item=10-4920) photocleavable linker inserted between the 3' end of the added polynucleotide leader sequence and the 5' base of the guide sequence. The third sgRNA ("3 bp Stem") had a polynucleotide leader sequence designed to form a 3 bp stem loop and the fourth sgRNA ("6 bp Stem") had polynucleotide leader sequence designed to form a 6 bp stem loop. The four types of sgRNA were then exposed to the UVA light (320-390 nm) using conditions known to be sufficient for photocleaving sgRNA in vitro.

Figure 19:
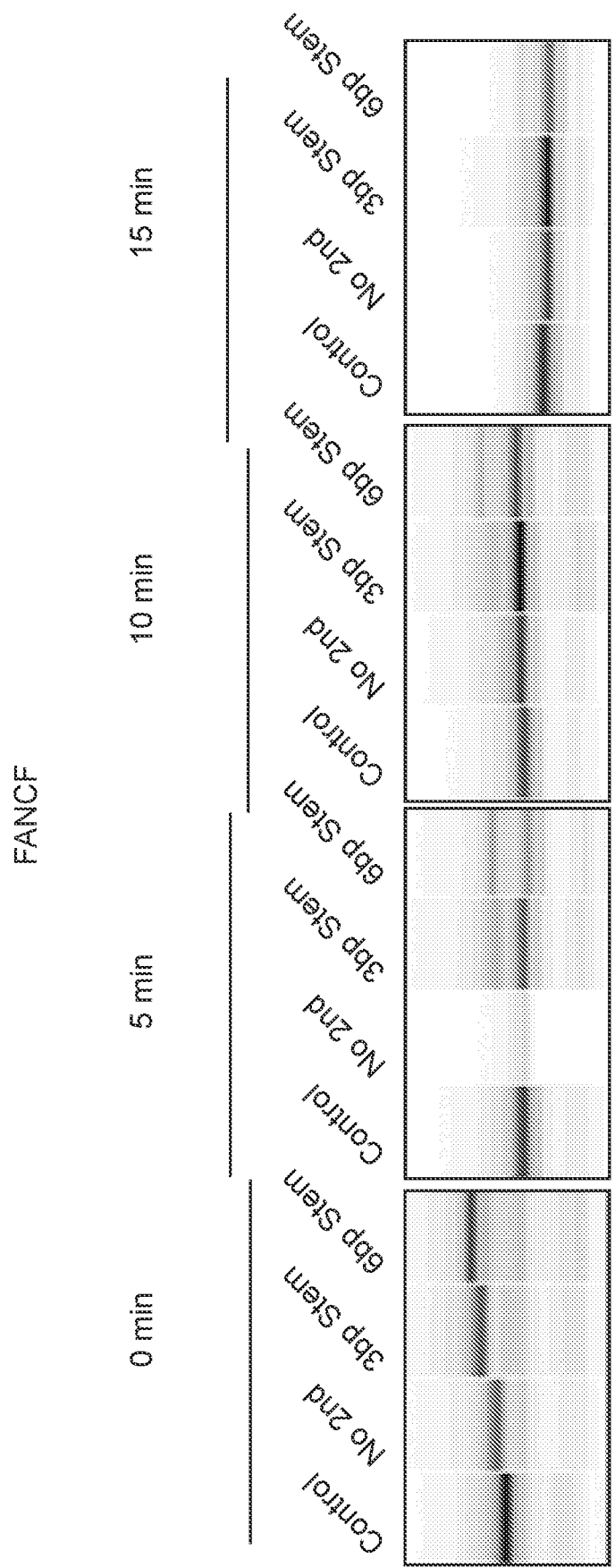
FIG. 19 shows the efficacy of cleavage of activatable CRISPR-ON sgRNA variants. CRISPR-ON sgRNAs comprising a 5' stem-loop element separated from guide sequence by a UV-susceptible cleavable linker were exposed to UV light for 0, 5, 10, or 15 minutes. Following 15 minutes of exposure, the sgRNAs displayed a banding pattern consistent with cleavage of the sequence 5' of the guide sequence. The "Control" lane is a sgRNA lacking any additional sequence 5' of the guide sequence, and the "No 2nd" condition uses a sgRNA with a non-stem forming 5' addition to the guide sequence. The "3 bp stem" and the "6 bp stem" conditions use sgRNAs designed to have stem regions of 3 and 6 bp length at the 5' end of the guide sequence, respectively.

FIG. 19 is a gel image run on a fragment analyzer using the small RNA analysis kit from Advanced Analytical, depicting the four sgRNA after exposure to UV light for 0 minutes, 5 minutes, 10 minutes, or 15 minutes. All images from a set time point were run on the same gel in adjacent lanes i.e. all 10 minute samples were run next to each other. Samples from different time points were run on different gels to allow testing of multiple sgRNA target sites. Comparison between conditions was primarily based on qualitative observation. After 5 minutes of exposure to UV light the second, third, and fourth sgRNAs showed a banding pattern consistent with cleavage of the polynucleotide leader sequence. The banding patterns after 10 minutes and 15 minutes of exposure were also consistent with cleavage of the polynucleotide leader sequence from the second, third, and fourth sgRNAs.

Figure 20:
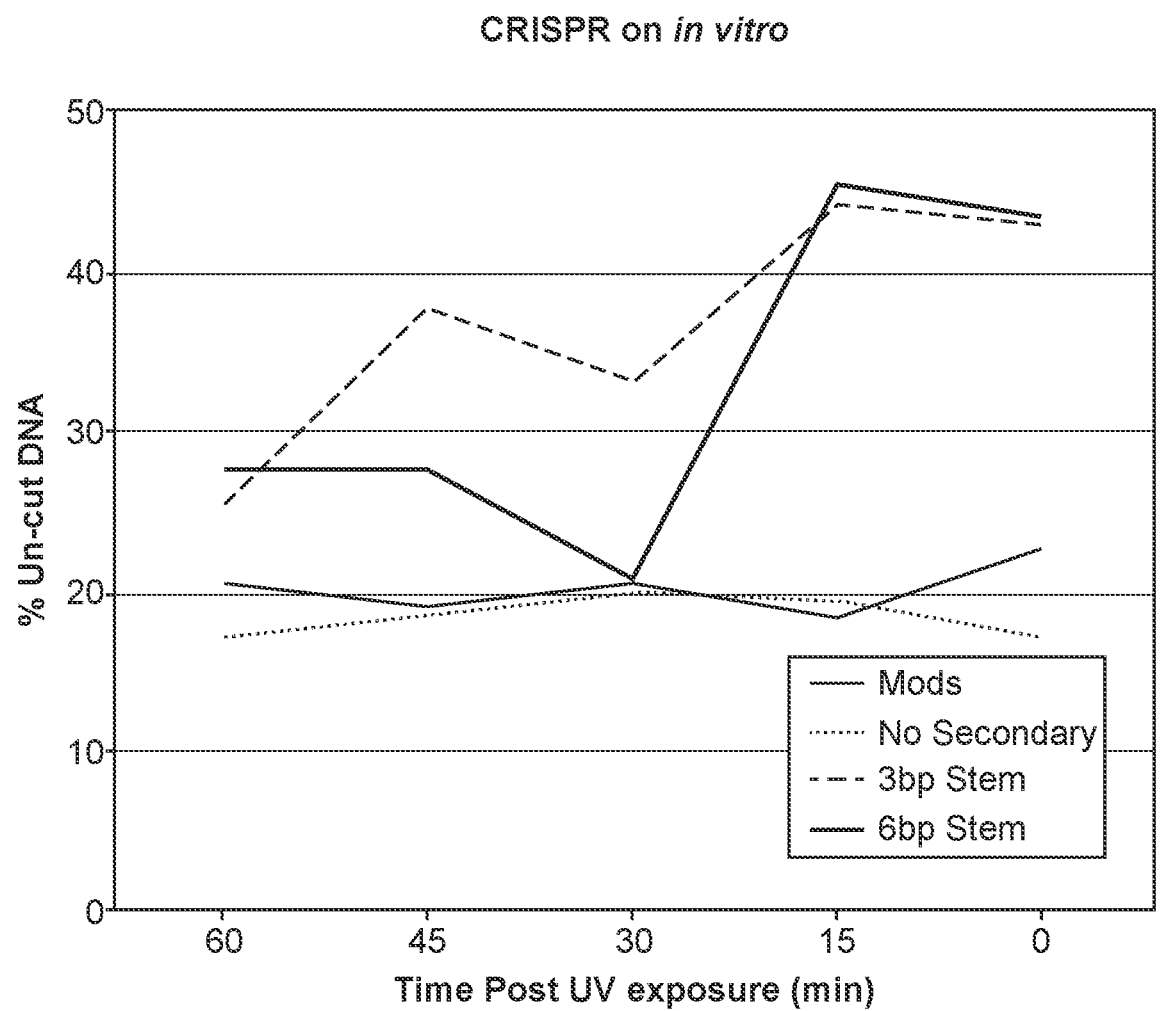
FIG. 20 shows the efficacy of in vitro CRISPR-ON sgRNA activation of target DNA cleavage. CRISPR-ON sgRNAs with 5' cleavable stem-loop were incubated with target DNA (human FANCF) for one hour and exposed to cleavage agent, UVA light (320-390 nm) at regular intervals. "Mods" is a sgRNA modified to include 2'-O-methyl analogs and 3' phosphorothioate internucleotide linkages at the first three 5' and 3' terminal RNA nucleotides, and lacking any 5' addition of bases to the guide sequence. Standard modification on sgRNAs includes. The "No Secondary" condition uses a sgRNA with a non-stem forming 5' addition to the guide sequence. The "3 bp stem" and the "6 bp stem" conditions use sgRNAs with sequences at the 5' end of the sgRNA designed to form stem regions of 3 and 6 bp, respectively.

Example 4: Characterization of Target DNA Cutting Efficiency Upon sgRNA Activation As described above, the four sgRNAs were complexed with spCas9 and incubated with target DNA for an appropriate duration in vitro. The four sgRNAs were then each exposed to UV light (320-390 nm) at 175 mW/cm2 for the indicated periodic intervals, shown in FIG. 20. UV-mediated cleavage of the sgRNAs with designed stems ("3 bp Stem" and "6 bp Stem") served to activate the CRISPR complex resulting in the cutting of the target specific DNA. The target DNA was then run on a fragment analyzer to demonstrate CRISPR-mediated cutting. FIG. 20 shows an example of sgRNA-Cas9 CRISPR complex incubated with target DNA (FANCF) and exposed to the cleavage agent at regular intervals. At 0 minutes post exposure, the third and fourth sgRNAs ("3 bp Stem" and "6 bp Stem") showed decreased cutting efficiency compared to the first and second sgRNAs. After 15 min of exposure to the cleavage agent, the activated sgRNAs registered an increase in cutting efficiency of target DNA. Measurement of the ratio of uncut to cut DNA showed a decrease from ~45% at 15 minutes exposure to ~20% at 30 minutes of exposure for "6 bp Stem." In comparison, the first sgRNA lacking 5' polynucleotide leader sequence ("Mods") or a 5' secondary structure ("No Secondary") did not exhibit activation with cleavage agent, as measured by ratio of uncut to cut DNA. "Mods" is a modified synthetic sgRNA with 2'-O-methyl analogs and 3' phosphorothioate internucleotide linkages at the first three 5' and 3' terminal RNA nucleotides, lacking any 5' addition of bases to the guide sequence, and the "No Secondary" condition uses an sgRNA with a non-stem forming 5' addition to the guide sequence. The "3 bp Stem" and the "6 bp Stem" conditions use sgRNAs with regions designed to form stems of 3 and 6 bp length at the 5' end of the sgRNA, respectively.

Example 5: Generation and Characterization of Deactivatable sgRNA

Six sgRNAs were synthesized. The sequences representing a part of the sgRNAs are provided below. Modification on sgRNAs includes 2'-O-methyl analogs and 3' phosphorothioate internucleotide linkages at the first three 5' and 3' terminal RNA nucleotides.

Control:

Control:

(SEQ ID NO: 12)
NNNNNNNNNNNNNNNNNNNNNNGUUUUAGAGCUAGAAAUAGCAAGUUAAAA
UAAGGCUAGUCCGUUAUCAACUUGAAAAAGUGGCACCGAGUCGGUGCUU
UU

21

(SEQ ID NO: 13)
NNNNNNNNNNNNNNNNNNNNNN*UUUUAGAGCUAGAAAUAGCAAGUUAAAA
UAAGGCUAGUCCGUUAUCAACUUGAAAAAGUGGCACCGAGUCGGUGCUU
UU

24

(SEQ ID NO: 14)
NNNNNNNNNNNNNNNNNNNNNGUU*UAGAGCUAGAAAUAGCAAGUUAAAA
UAAGGCUAGUCCGUUAUCAACUUGAAAAAGUGGCACCGAGUCGGUGCUU
UU

50

(SEQ ID NO: 15)
NNNNNNNNNNNNNNNNNNNNNNGUUUUAGAGCUAGAAAUAGCAAGUUAAAA
*AAGGCUAGUCCGUUAUCAACUUGAAAAAGUGGCACCGAGUCGGUGCUU
UU

57

(SEQ ID NO: 16)
NNNNNNNNNNNNNNNNNNNNNNGUUUUAGAGCUAGAAAUAGCAAGUUAAAA
UAAGGCU*GUCCGUUAUCAACUUGAAAAAGUGGCACCGAGUCGGUGCUU
UU

74

(SEQ ID NO: 17)
NNNNNNNNNNNNNNNNNNNNNNGUUUUAGAGCUAGAAAUAGCAAGUUAAAA
UAAGGCUAGUCCGUUAUCAACUUG*AAAAGUGGCACCGAGUCGGUGCUU
UU

Figure 21:
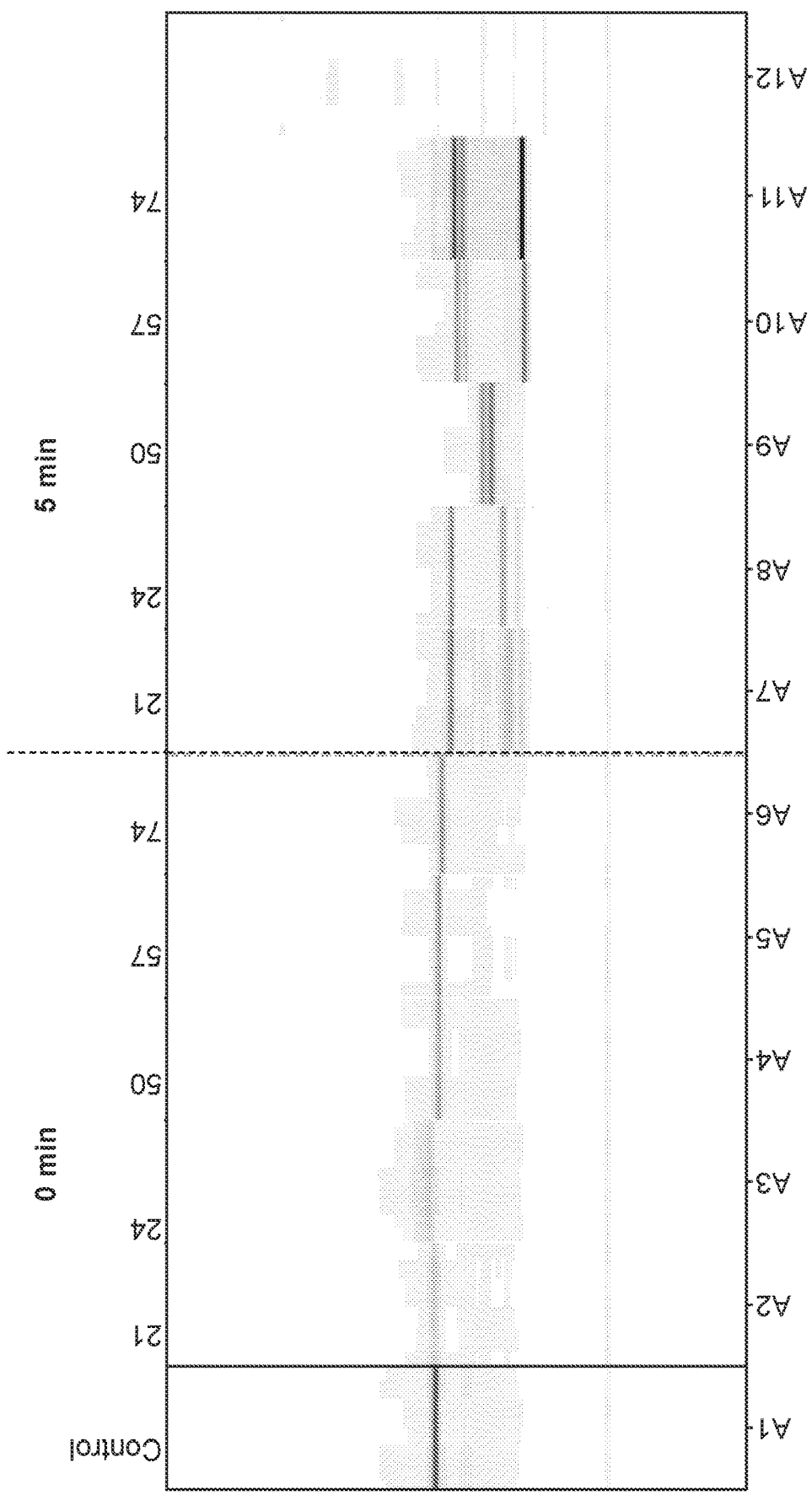
FIG. 21 shows the efficacy of cleavage of deactivatable CRISPR-OFF sgRNA variants. sgRNAs with five different cleavage points were subjected to cleavage agent (UV light) for 0 (left) or 5 (right) minutes.

The first sgRNA ("Control") did not comprise a photocleavable element. The second, third, fourth and fifth sgRNAs had photocleavable bonds at positions 21, 24, 50, 57 and 74 from the 5' end of the sgRNA. Five of the sgRNAs were then exposed to UV light for 5 minutes. FIG. 21 is an image of a gel depicting the five sgRNAs after exposure to UV light, run using fragment analyzer from Advanced Analytical. All samples were run with small RNA kit according to manufacturer protocol. After 5 minutes of exposure to UV light, all five sgRNAs showed a banding pattern consistent with cleavage at the respective positions of the photocleavable bond.

Example 6: Rapid Generation of Genome Edited Cell Lines

Figure 22:
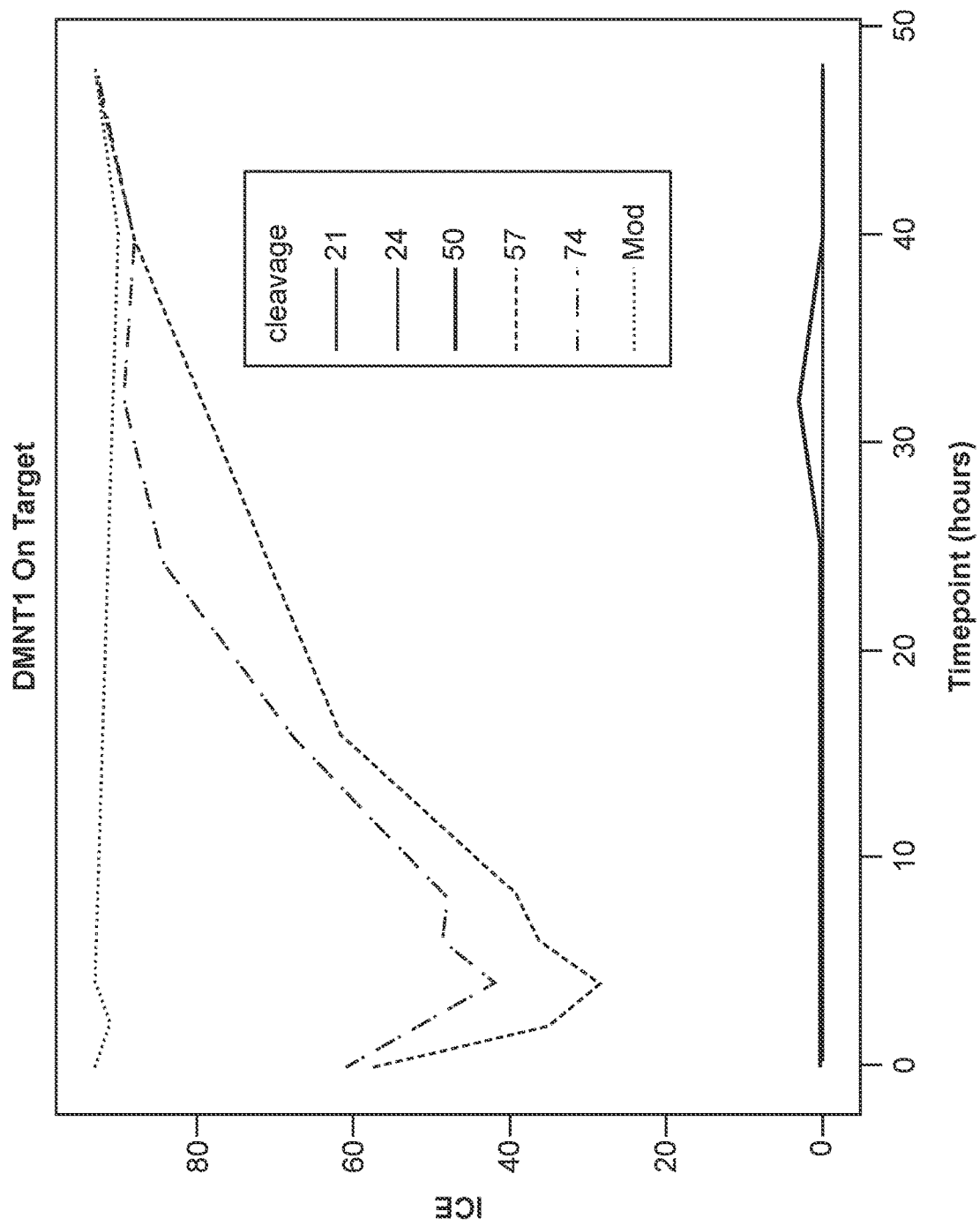
FIG. 22 shows a schematic of time-dependent CRISPR-OFF deactivation of genome editing efficiency in cells. Cells transfected with deactivatable sgRNA variants were treated with UV light at time points after RNP delivery and were allowed 48 total hours post RNP delivery to edit, repair, and recover. After 48 hours genomic DNA was harvested from all samples and analyzed for the presence of indels. Two CRISPR-OFF sgRNAs (57 and 74) displayed a time dependent increase of genome editing activity.

HEK 293T cells expressing Cas9 were transfected with sgRNAs comprising photocleavable linkers and subjected to cleavage agent. FIG. 22 shows a schematic of programmable genome editing efficiency with six different sgRNAs targeting DNMT1. The first sgRNA ("Mod") lacked a photocleavable site. The second, third, fourth and fifth sgRNAs had photocleavable bond at positions 21, 24, 50, 57 and 74 from 5' end of the sgRNA (b21, b24, b50, b57, and b74, respectively). sgRNA:Cas9 mixture [9:1 ratio] was introduced into the cells. The cells were exposed to the cleavage agent every two hours for 48 hours. Each sample was kept in the dark until the designated time point, then exposed once to UV light to induce cleavage. Cells were then left in dark until 48 hours post transfection. All samples were harvested 48 hours post transfection. After 48 hours post-transfection, genomic DNA was harvested from all samples and analyzed for presence of insertions and deletions using ICE (Inference of CRISPR Editing). ICE measured the amount of gene editing by analyzing Sanger sequencing traces and mapping level of sequence breakdown to indel formation frequencies, as described in Hsiau et al., "Inference of CRISPR Edits from Sanger Trace Data", 2019 bioRxiv. The graph in FIG. 22 represents editing efficiency. Samples were amplified using PCR and submitted for sequencing. After sequencing the number of sequences which are wild-type or edited following amplification were analyzed by ICE. Editing is expressed by percentage of sequences that are not wildtype. sgRNAs with photocleavable bonds at positions 57 and 74 display time dependent deactivation of genome editing efficiency.

Example 7: Generation of Edited HEK 293 Cell Lines

HEK 293 cells were transfected with Cas9 and sgRNAs comprising photocleavable (PC) linkers and were subjected to UV light to cleave the linker. Cas9 was complexed with 12 different sgRNAs comprising phosphoramidite (3-(4,4'-Dimethoxytrityl)-1-(2-nitrophenyl)-propan-1-yl-[(2-cyanoethyl)-(N,N-diisopropyl)]-phosphoramidite) incorporated at positions 57 and 74 CRISPR OFF with target binding regions targeting BUB1B

```
BUB1B
                                        (SEQ ID NO: 18)
(AGTGAAGCCATGTCCCTGGA),

CAMK1
                                        (SEQ ID NO: 19)
(sg1: TGCCAGGATCACCTCCGAGA),

PRKAG3
                                        (SEQ ID NO: 20)
(sg1- AGCAAGAAAACAGCAGCTCA;

(SEQ ID NO: 21)
sg2- AGCAAGAAAACAGCAGCUCA),

STK3
                                        (SEQ ID NO: 22)
(sg1- TCCTGAAGATCTGATTCAAC;

(SEQ ID NO: 23)
sg2- AAAGCAATACACAAGGAATC;

(SEQ ID NO: 24)
sg3- CCATAATGCAGCAATGTGAC;

(SEQ ID NO: 25)
sg4- UUUAAUUGCGACAACUUGAC,

IRAK4
                                        (SEQ ID NO: 26)
(GTCCTGTCTTTGTCACAGAA), and Chr8q23
                                        (SEQ ID NO: 27)
(sg1- AGTCTACTATGAGTTTTCTG;

(SEQ ID NO: 28)
sg2- TTATAGTTACGATGTTTGAT;

(SEQ ID NO: 29)
sg3- AAGCCTCAAATTAGGAGAAA) to produce 12
``` experimental populations. Cas9 was also complexed with 12 different sgRNAs without photocleavable linkers (standard) with the target binding regions described above. To form each of the 24 complex solutions, 10 pmol of Cas9 protein was mixed with 30 pmol of sgRNA. Each solution was diluted to 20 µL using transfection buffer and allowed to mix for 15 minutes at room temperature. HEK293 cells were harvested using TrypLE for 5 minutes at room temperature to singularize the cells. The populations were counted to determine the appropriate number of cells followed by centrifugation at 100×g for 3 minutes. The resulting pellets were then resuspended in nucleofection buffer at a concentration of 200,000 cells per 5 µL. The cell suspension as then added to the precomplexed Cas9 sgRNA solution and transfected. Each experimental population was split into two wells to form paired replicates of control and treatment cells. Four hours after transfection, treatment cells were exposed to UV light for one minute and 15 seconds (with a bandpass filter to limit wavelengths to those greater than 345 nm). The cells were subsequently returned to the incubator. 48 hours post transfection, control and treatment samples were harvested and genomic DNA was extracted. Genomic DNA was subjected to PCR using Amplitaq and primers specific to on-target and off-target loci. Sequencing data was analyzed using ICE for the presence of edits. ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv. Editing is expressed by percentage of sequences that are not wildtype.

Figure 23:
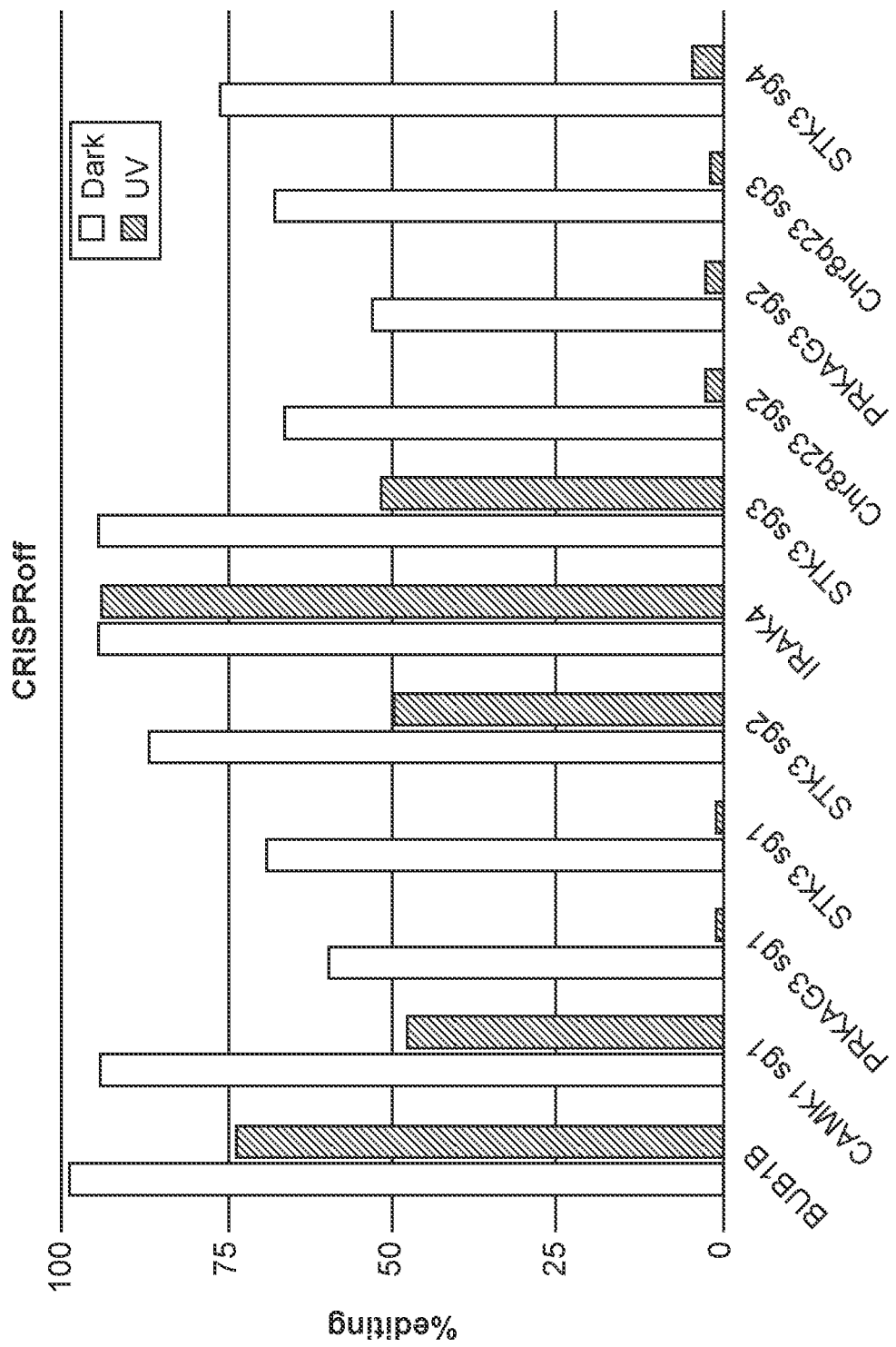
FIG. 23 shows results of an experiment wherein CRISPR OFF complexes are used to cleave a gene sequence. The X axis indicates the gene targeted by the guide sequence as well as the version of the guide sequence, and the Y axis indicates the percent of DNA sequences containing the targeted genes that were edited.

FIG. 23 shows a graph of the editing efficiency of Cas9 with the 12 different CRISPR OFF sgRNAs. The grey bars indicate the editing efficiency of the Cas9 in complex with the CRISPR OFF sgRNA without UV light exposure. The black bars indicate the editing efficiency of the Cas9 in complex with CRISPR OFF sgRNA after UV light exposure.

Figure 24:
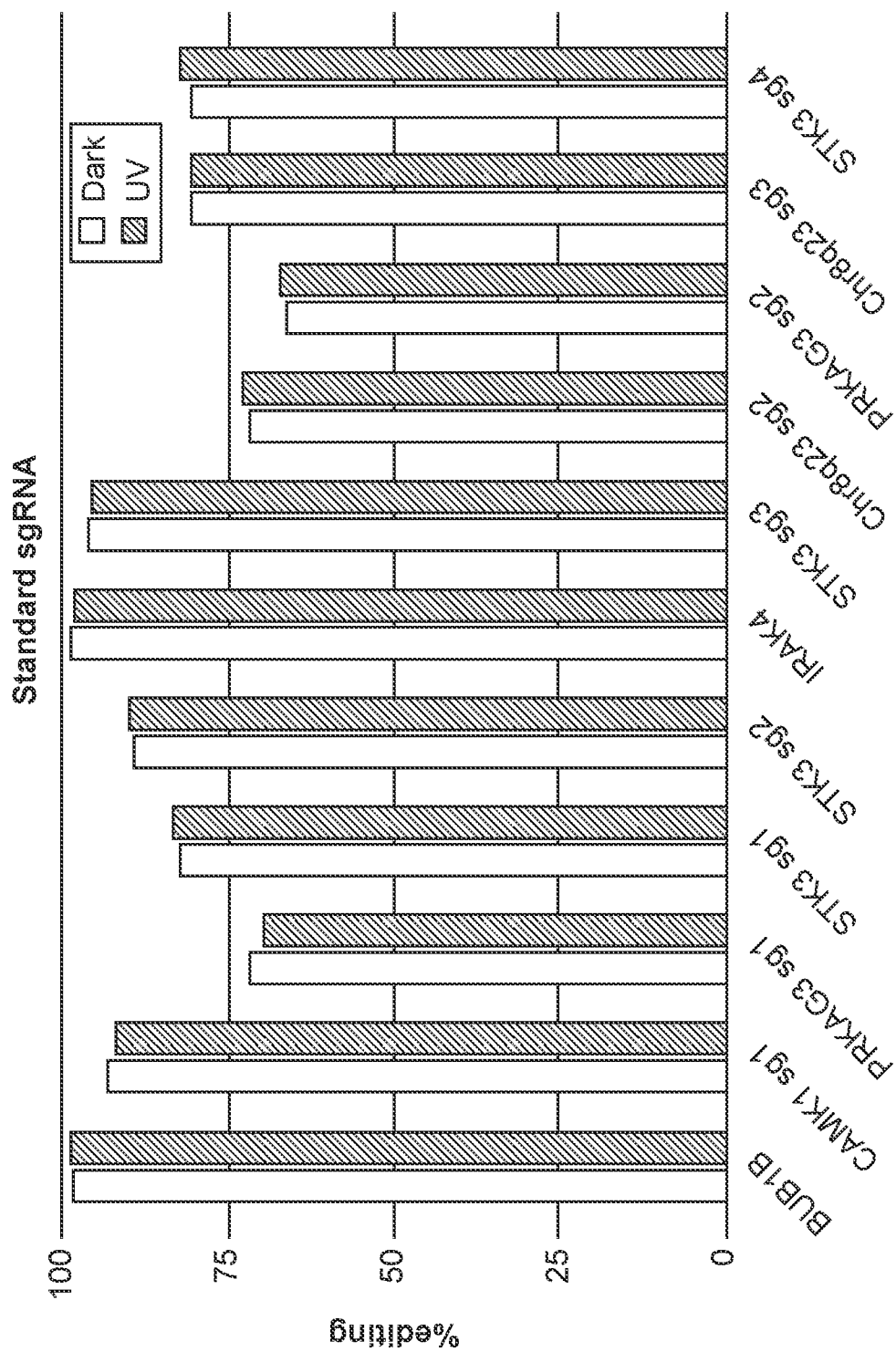
FIG. 24 shows results of an experiment ran as a control for the experiment corresponding to FIG. 23, wherein CRISPR complexes comprising a standard sgRNA are used to cleave a gene sequence. The X axis indicates the gene targeted by the guide sequence as well as the version of the guide sequence, and the Y axis indicates the percent of DNA sequences containing the targeted genes that were edited.

FIG. 24 shows the editing efficiency of Cas9 with 12 different standard sgRNAs without a photocleavable linker, with the same target binding region as the sgRNAs in FIG. 23. The grey bars indicate the editing efficiency of the Cas9 in complex with the standard sgRNA without UV light exposure. The black bars indicate the editing efficiency of the Cas9 in complex with standard sgRNA after UV light exposure.

Example 8: Generation of Edited U2OS Cell Lines

U2OS cells were transfected with Cas 9 and sgRNAs comprising photocleavable linkers and were subjected to UV light to cleave the linker. Cas9 was complexed with six different sgRNAs comprising phosphoramidite (3-(4,4'-Dimethoxytrityl)-1-(2-nitrophenyl)-propan-1-yl-[(2-cyanoethyl)-(N,N-diisopropyl)]-phosphoramidite) incorporated at positions 57 and 74 (CRISPR OFF) with target binding regions targeting

```
DNMT1
                                      (SEQ ID NO: 30)
(GGAGTGAGGGAAACGGCCCC),

EMX1
                                      (SEQ ID NO: 4)
(GAGTCCGAGCAGAAGAAGAA),

FANCF
                                      (SEQ ID NO: 32)
(GCTGCAGAAGGGATTCCATG),

GRKI
                                      (SEQ ID NO: 33)
(GCCGTCAAAGCTGCCTCGGG),

PRGN
                                      (SEQ ID NO: 6)
(CAGATGCCTGCTCAGTGTTG), and VEGFA
                                      (SEQ ID NO: 7)
(GGTGAGTGAGTGTGTGCGTG)
to produce six experimental
``` populations. Cas9 was also complexed with six different sgRNAs without photocleavable linkers (standard) with the target binding regions described above. To form each of the 12 complex solutions, 10 pmol of Cas9 protein was mixed with 30 pmol of sgRNA. Each solution was diluted to 20 µL using transfection buffer and allowed to mix for 15 minutes at room temperature. U2OS cells were harvested using TrypLE for 5 minutes at room temperature to singularize the cells. The populations were counted to determine the appropriate number of cells followed by centrifugation at 100×g for 3 minutes. The resulting pellets were then resuspended in nucleofection buffer at a concentration of 200,000 cells per 5 µL. The cell suspension was then added to the precomplexed Cas9 sgRNA solution and transfected. Each experimental population was split into two wells to form paired replicates of control and treatment cells. Four hours after transfection, treatment cells were exposed to UV light for one minute and 15 seconds (with a bandpass filter to limit wavelengths to those greater than 345 nm). The cells were subsequently returned to the incubator. 48 hours post transfection, control and treatment samples were harvested and genomic DNA was extracted. Genomic DNA was subjected to PCR using Amplitaq and primers specific to on-target and off-target loci. Sequencing data was analyzed using ICE for the presence of edits. ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv. Editing is expressed by percentage of sequences that are not wildtype.

Figure 25:
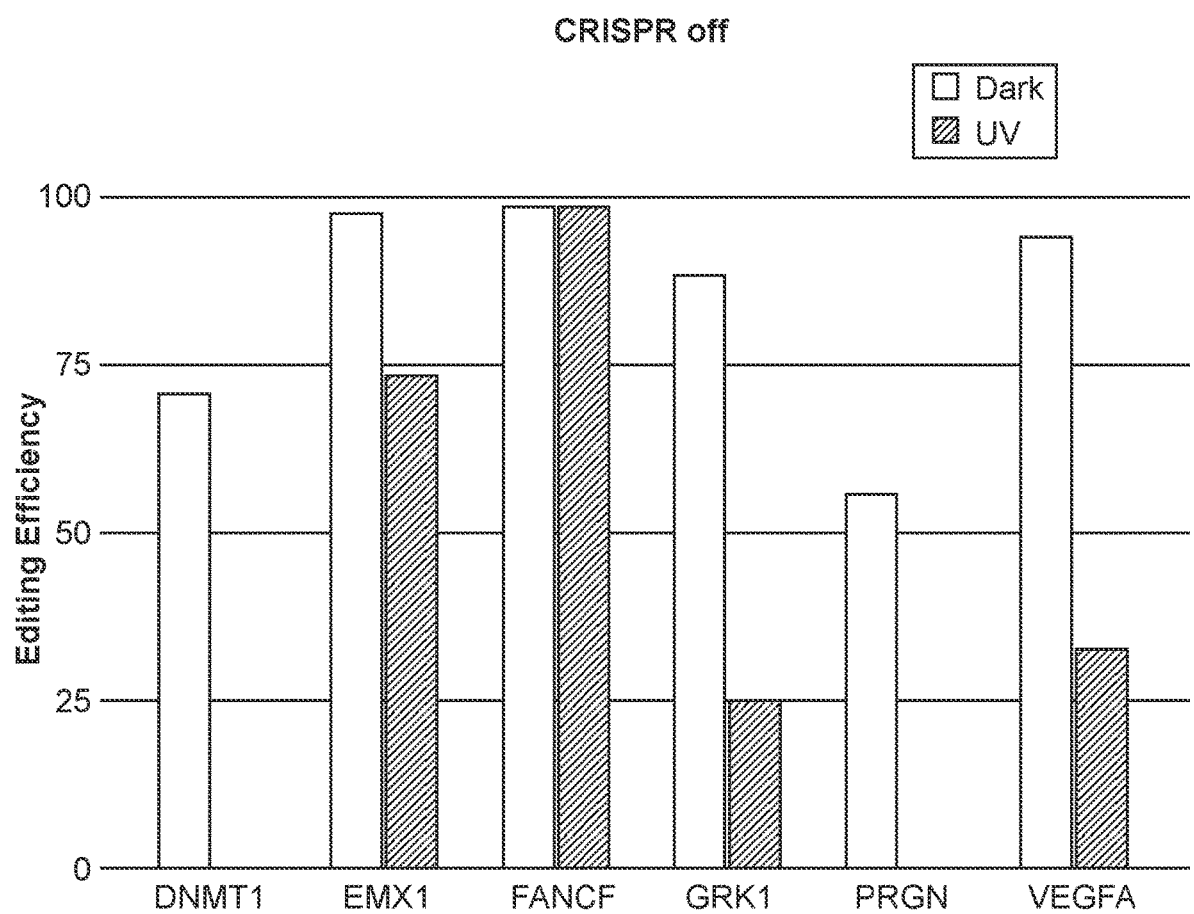
FIG. 25 shows results of an experiment wherein CRISPR OFF complexes are used to cleave a gene sequence. The X axis indicates the gene targeted by the guide sequence as well as the version of the guide sequence, and the Y axis indicates the percent of DNA sequences containing the targeted genes that were edited.

FIG. 25 shows a graph of the editing efficiency of Cas9 with the six different CRISPR OFF sgRNAs. The grey bars indicate the editing efficiency of the Cas9 in complex with the CRISPR OFF sgRNA without UV light exposure. The black bars indicate the editing efficiency of the Cas9 in complex with CRISPR OFF sgRNA after UV light exposure.

Figure 26:
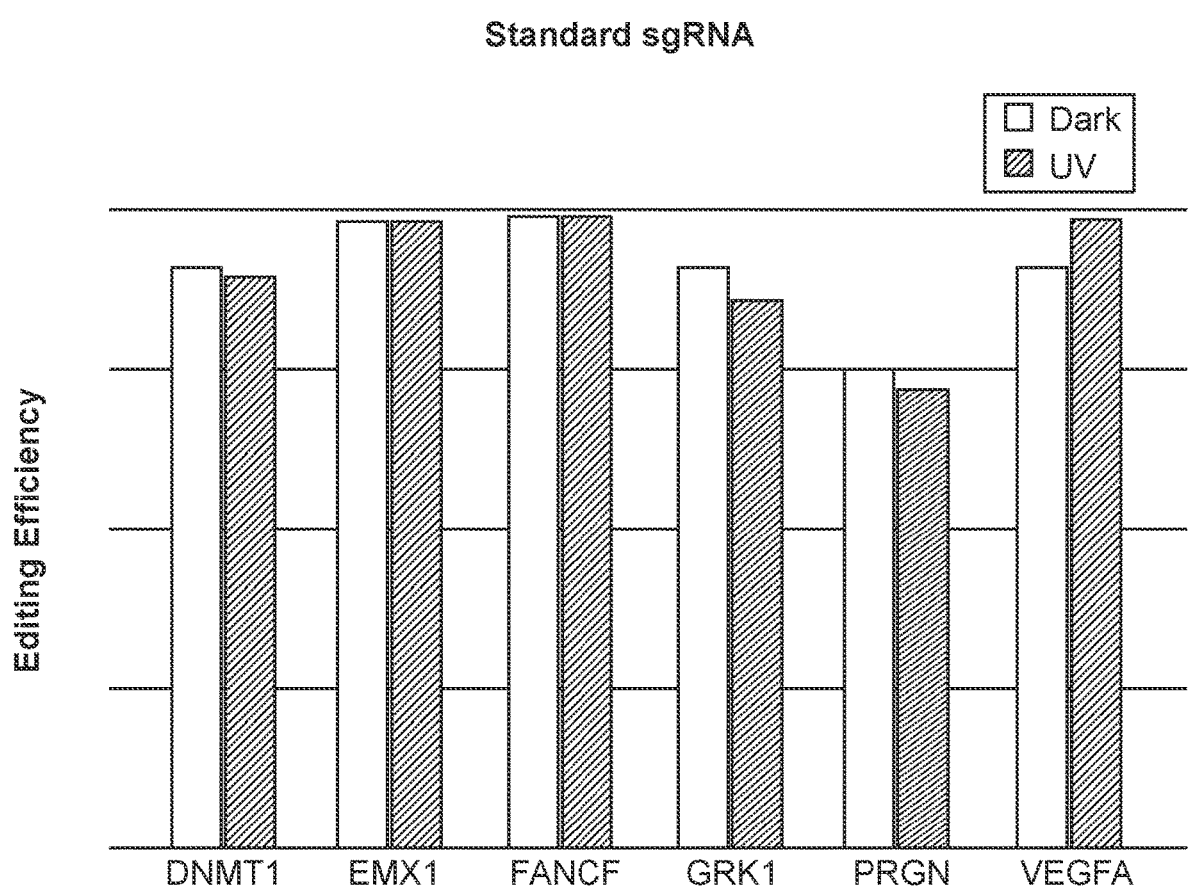
FIG. 26 shows results of an experiment ran as a control for the experiment corresponding to FIG. 25, wherein CRISPR complexes comprising a standard sgRNA are used to cleave a gene sequence. The X axis indicates the gene targeted by the guide sequence as well as the version of the guide sequence, and the Y axis indicates the percent of DNA sequences containing the targeted genes that were edited.

FIG. 26 shows the editing efficiency of Cas9 with six different standard sgRNAs without a photocleavable linker, with the same target binding region as the sgRNAs in FIG. 25. The grey bars indicate the editing efficiency of the Cas9 in complex with the standard sgRNA without UV light exposure. The black bars indicate the editing efficiency of the Cas9 in complex with standard sgRNA after UV light exposure.

Example 9: Analysis of Off-Target Editing by CRISPR-OFF Cas9 Complexes in HEK293T Cells without Exposure to UV Light FIG. 29 includes graphs depicting the percentage of editing at the off-target sites known to have a high degree of off-target editing for the sgRNAs targeting DNMT1, FANCF, and VEGFA described above.

The sequences used are as follows, where * indicates the location of a linker (3-(4,4'-Dimethoxytrityl)-1-(2-nitrophenyl)-propan-1-yl-[(2-cyanoethyl)-(N,N-diisopropyl)]-phosphoramidite):

```
DNMT1
On-target sgRNA:
                                      (SEQ ID NO: 36)
GGAGTGAGGGAAACGGCCCCGTTTTAGAGCTAGAAATAGCAAGTTAAAA
TAAGGCTAGTCCGTTATCAACTTGAAAAAGTGGCACCGAGTCGGTGCTT
TT On-target CRISPR OFF:
                                      (SEQ ID NO: 37)
GGAGTGAGGGAAACGGCCCCGTTTTAGAGCTAGAAATAGCAAGTTAAAA
TAAGGCT*GTCCGTTATCAACTTG*AAAAGTGGCACCGAGTCGGTGCTT
TT Off-Target 1:
                                      (SEQ ID NO: 38)
GGAGGGAGGGAAACAGCCCC FANCF
On-target sgRNA:
                                      (SEQ ID NO: 39)
GCTGCAGAAGGGATTCCATGGTTTTAGAGCTAGAAATAGCAAGTTAAAA
TAAGGCTAGTCCGTTATCAACTTGAAAAAGTGGCACCGAGTCGGTGCTT
TT On-target CRISPR OFF:
                                      (SEQ ID NO: 40)
GCTGCAGAAGGGATTCCATGGTTTTAGAGCTAGAAATAGCAAGTTAAAA
TAAGGCT*GTCCGTTATCAACTTG*AAAAGTGGCACCGAGTCGGTGCTT
TT Off-Target 2:
                                      (SEQ ID NO: 41)
GCTGCAGAAGGGATTCCAAG VEGFA
On-target sgRNA:
                                      (SEQ ID NO: 42)
GGTGAGTGAGTGTGTGCGTGGTTTTAGAGCTAGAAATAGCAAGTTAAAA
TAAGGCTAGTCCGTTATCAACTTGAAAAAGTGGCACCGAGTCGGTGCTT
TT
```

-continued

Figure 29:
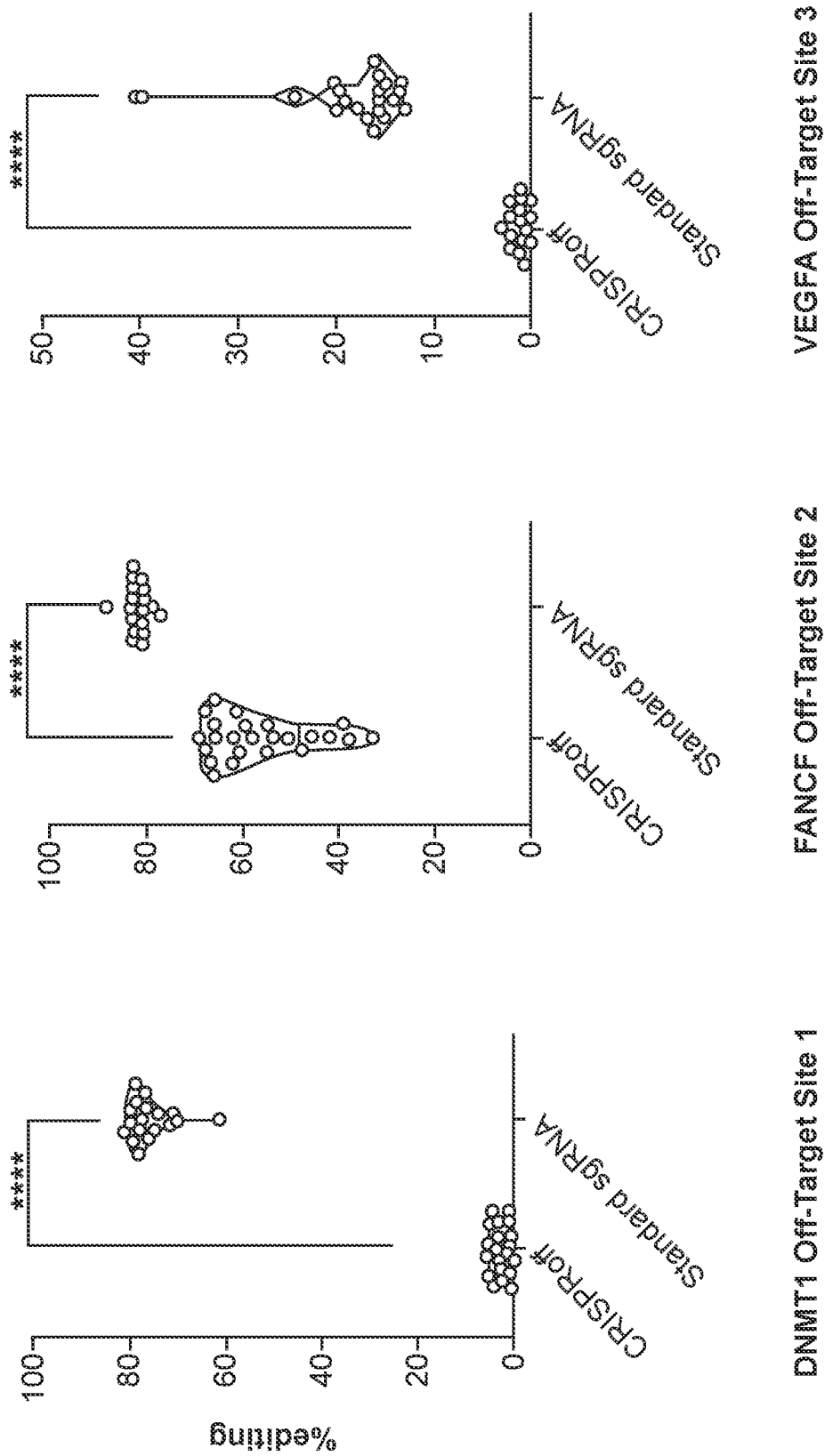
FIG. 29 shows a series of scatterplots comparing off-target editing activity using either CRISPR OFF sgRNAs or modified sgRNAs at top predicted off-target sites across three gene targets. CRISPR OFF sgRNAs caused significantly fewer off-target indels than sgRNAs modified only to include 2'-O-methyl analogs and 3' phosphorothioate internucleotide linkages at the first three 5' and 3' terminal RNA nucleotides. (****$p<0.0001$, Student's unpaired t-test, n=24 technical replicates)

On-target CRISPR OFF:
(SEQ ID NO: 43)
GGTGAGTGAGTGTGTGCGTGGTTTTAGAGCTAGAAATAGCAAGTTAAAA
TAAGGCT*GTCCGTTATCAACTTG*AAAAGTGGCACCGAGTCGGTGCTT
TT Off-Target 3:
(SEQ ID NO: 44)
GCTGAGTGAGTGTATGCGTG ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv. CRISPR ribonucleoproteins (RNPs) were formed using a 30 pmol:10 pmol ratio between sgRNA: Cas9. RNPs were then transfected into HEK293T cells. 48 hours post-transfection, cells were harvested and genomic DNA was harvested from the cell in n=24 biological replicates. The cells were not exposed to UV light. Editing is expressed by percentage of sequences that are not wildtype. The X axis indicates whether the off-target editing was produced by a Cas9 in complex with a sgRNA comprising 3-(4,4'-Dimethoxytrityl)-1-(2-nitrophenyl)-propan-1-yl-[(2-cyanoethyl)-(N,N-diisopropyl)]-phosphoramidite ("CRISPRoff"), or by a Cas9 in complex with a sgRNA without a 3-(4,4'-Dimethoxytrityl)-1-(2-nitrophenyl)-propan-1-yl-[(2-cyanoethyl)-(N,N-diisopropyl)]-phosphoramidite ("standard sgRNA"). The Y axis indicates the percent of the off-target site that was edited. As can be seen in FIG. 29, the off-target editing observed for a CRISPR enzyme complexed with a sgRNA targeting DNMT1 without a 3-(4,4'-Dimethoxytrityl)-1-(2-nitrophenyl)-propan-1-yl-[(2-cyanoethyl)-(N,N-diisopropyl)]-phosphoramidite is greater than a CRISPR enzyme complexed with a CRISPR-OFF sgRNA with a p-value≤0.0001; the off-target editing observed for a CRISPR enzyme complexed with a sgRNA targeting FANCF without a 3-(4,4'-Dimethoxytrityl)-1-(2-nitrophenyl)-propan-1-yl-[(2-cyanoethyl)-(N,N-diisopropyl)]-phosphoramidite is greater than a CRISPR enzyme complexed with a CRISPR-OFF sgRNA with a p-value≤0.0001; the off-target editing observed for of a CRISPR enzyme complexed with a sgRNA targeting VEGFA without a 3-(4,4'-Dimethoxytrityl)-1-(2-nitrophenyl)-propan-1-yl-[(2-cyanoethyl)-(N,N-diisopropyl)]-phosphoramidite is greater than a CRISPR enzyme complexed with a CRISPR-OFF sgRNA with a p-value≤0.0001. The editing efficiency at the target site of each of the aforementioned CRISPR-OFF sgRNAs was the same or 1-3% lower than of the editing efficiency at the target site of each of the aforementioned standard sgRNAs as measured by ICE as described above. The results illustrate that use of the sgRNAs with the 3-(4,4'-Dimethoxytrityl)-1-(2-nitrophenyl)-propan-1-yl-[(2-cyanoethyl)-(N,N-diisopropyl)]-phosphoramidite in the nexus and stem loop 1 in editing assay results in lower off-target editing activity relative to use of the sgRNAs lacking the 3-(4,4'-Dimethoxytrityl)-1-(2-nitrophenyl)-propan-1-yl-[(2-cyanoethyl)-(N,N-diisopropyl)]-phosphoramidite in the nexus and stem loop 1.

Example 10: Analysis of Time-Dependent Activity of Cas9 in Complex with CRISPR OFF in U2OS Cells FIGS. 29-32 are graphs depicting a time-dependent activity of Cas 9 in complex with "CRISPRoff" targeting DNMT1, GRK1, and VEGFA contrasted against the lack of time-dependent activity of Cas9 in complex with "standard sgRNA." Cells were exposed to UV light every two hours for 48 hours. ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv.

Example 11: Generation of Edited K562 Cell Lines

K562 cells were transfected with Cas9 and sgRNAs comprising photocleavable linkers and were subjected to UV light to cleave the linkers. Cas9 was complexed with two different sgRNAs comprising phosphoramidite (3-(4,4'-Dimethoxytrityl)-1-(2-nitrophenyl)-propan-1-yl-[(2-cyanoethyl)-(N,N-diisopropyl)]-phosphoramidite) incorporated at positions 57 and 74 (CRISPR OFF) with target binding regions targeting EMX1 (GAGTCCGAGCAGAAGAAGAA) (SEQ ID NO: 4) and GRK1 (GCCGTCAAAGCTGCCTCGGG) (SEQ ID NO: 33) to produce two experimental populations. Cas9 was also complexed with 2 different sgRNAs without photocleavable linkers (standard) with the target binding regions described above. To form each of the 4 complex solutions, 10 pmol of Cas9 protein was mixed with 30 pmol of sgRNA. Each solution was diluted to 20 µL using transfection buffer and allowed to mix for 15 minutes at room temperature. K562 cells were harvested using TrypLE for 5 minutes at room temperature to singularize the cells. The populations were counted to determine the appropriate number of cells followed by centrifugation at 100×g for 3 minutes. The resulting pellets were then resuspended in nucleofection buffer at a concentration of 200,000 cells per 5 µL. The cell suspension as then added to the precomplexed Cas9 sgRNA solution and transfected. Each experimental population was split into two wells to form paired replicates of control and treatment cells. Four hours after transfection, treatment cells were exposed to UV light for ~one minute and 15 seconds (with a bandpass filter to limit wavelengths to those greater than 345 nm). The cells were subsequently returned to the incubator. 48 hours post transfection, control and treatment samples were harvested and genomic DNA was extracted. Genomic DNA was subjected to PCR using Amplitaq and primers specific to on-target and off-target loci. Sequencing data was analyzed using ICE for the presence of edits. ICE (Inference of CRISPR Editing) measured the amount of gene editing by analyzing Sanger sequencing traces and mapping level of sequence breakdown to determine indel formation frequencies, as described in Hsiau et al. "Inference of CRISPR Edits from Sanger Trace Data", Jan. 14, 2019 bioRxiv. Editing is expressed by the percentage of sequences that are not wildtype.

Figure 27:
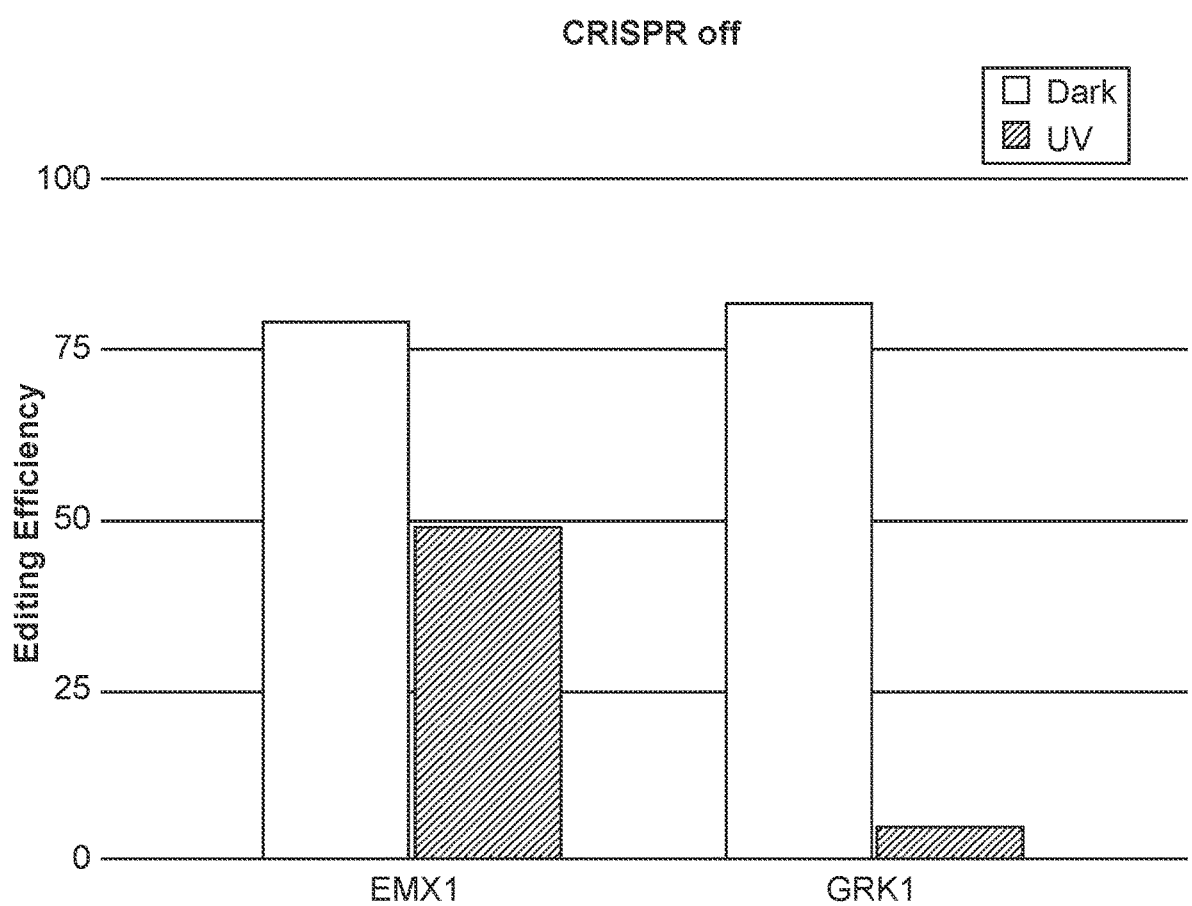
FIG. 27 shows results of an experiment wherein CRISPR OFF complexes are used to cleave a gene sequence. The X axis indicates the gene targeted by the guide sequence as well as the version of the guide sequence, and the Y axis indicates the percent of DNA sequences containing the targeted genes that were edited.

FIG. 27 shows a graph of the editing efficiency of Cas9 with two different CRISPR OFF sgRNAs. The grey bars indicate the editing efficiency of the Cas9 in complex with the CRISPR OFF sgRNA without UV light exposure. The black bars indicate the editing efficiency of the Cas9 in complex with CRISPR OFF sgRNA after UV light exposure.

Figure 28:
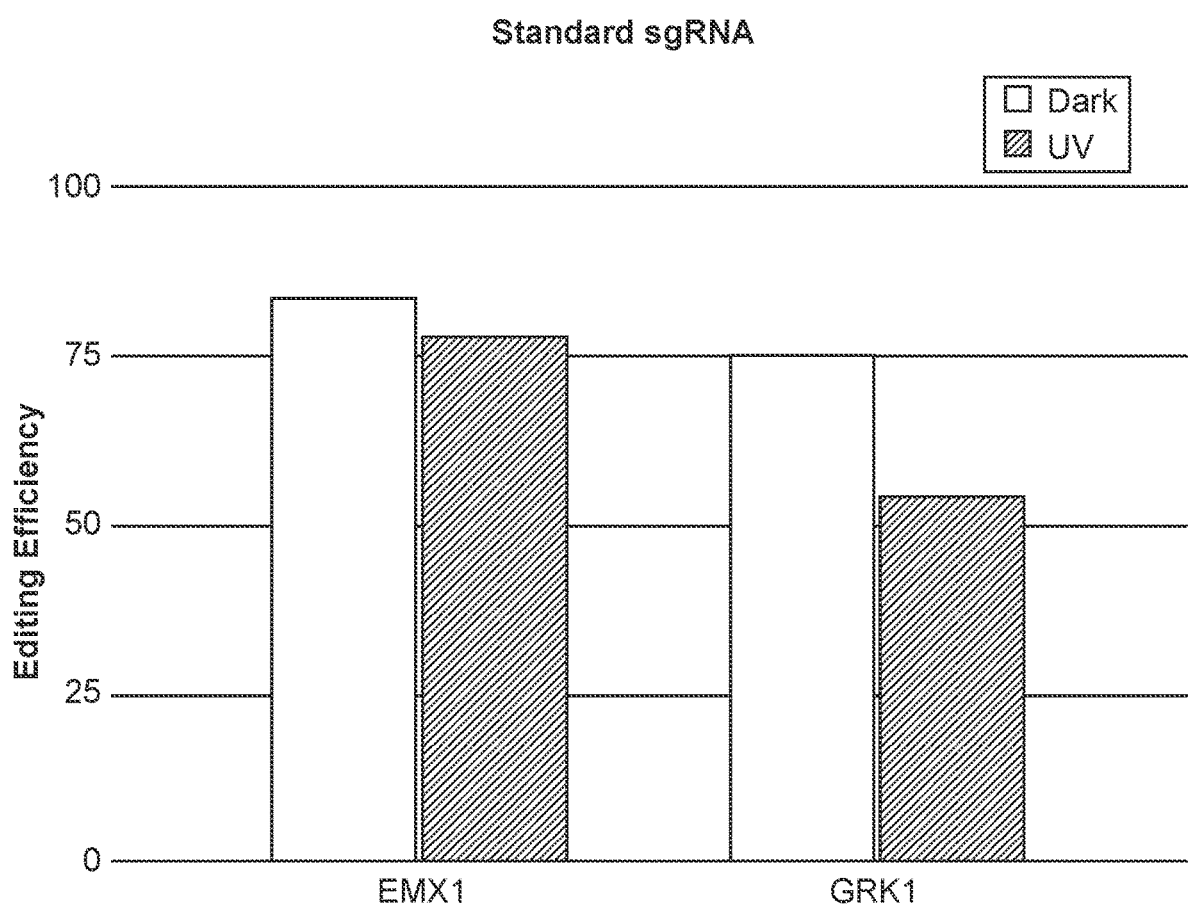
FIG. 28 shows results of an experiment ran as a control for the experiment corresponding to FIG. 27, wherein CRISPR complexes comprising a standard sgRNA are used to cleave a gene sequence. The X axis indicates the gene targeted by the guide sequence as well as the version of the guide sequence, and the Y axis indicates the percent of DNA sequences containing the targeted genes that were edited.

FIG. 28 shows the editing efficiency of Cas9 with 2 different standard sgRNAs without a photocleavable linker, with the same target binding region as the sgRNAs in FIG. 27. The grey bars indicate the editing efficiency of the Cas9 in complex with the standard sgRNA without UV light exposure. The black bars indicate the editing efficiency of the Cas9 in complex with standard sgRNA after UV light exposure.

Example 12: Transcriptional Regulation

A modified activatable (CRISPR ON) sgRNA polynucleotide comprising a 5' polynucleotide leader sequence that forms a 10 bp stem loop and an unnatural nucleotide to crosslink the polynucleotide to a CRISPR effector protein is crosslinked to an inactive Cas9 nuclease (dCas9) fused with a transcription activator domain of VP64. A photocleavable element is inserted 3' of the polynucleotide leader sequence and immediately 5' of the guide sequence. The CRISPR complex comprising the sgRNA crosslinked with dCas9 fusion enzyme is transfected into HEK 293T cells. The 5' polynucleotide leader sequence renders the CRISPR complex unable to efficiently anneal to the promoter of the target sequence complementary to the guide sequence. The target gene has relatively low transcriptional activity. At a desired time, the transfected cell is exposed to UV light, resulting in cleavage of the photocleavable bond and release of the polynucleotide leader sequence. The CRISPR complex now more efficiently binds to the promoter of the target sequence, and more efficient transcription of the target sequence results.

Example 13: Analysis of On-Target Editing by CRISPR-OFF Cas9 Complexes in HEK293 Cells with and without Exposure to UV Light Human embryonic kidney cells (HEK293) were maintained between passage 5-20 in Advanced Modified Eagles Medium (Life Technologies) and 10% v/v FBS. Cells were passaged biweekly at a 1:8 ratio with TrypLE (Life Technologies).

HEK 293 cells were transfected with Cas9 and sgRNAs comprising photocleavable (PC) linkers and were subjected to light filtered with a 345 nm bandpass filter to cleave the linker. Cas9 was complexed with 23 different sgRNAs comprising a photocleavable linker (1-(7-(diethylamino)-2-oxo-2H-chromen-4-yl)propyl), incorporated at positions 57 and 74 (CRISPR OFF) with target binding regions targeting

```
AAVS1
                                   (SEQ ID NO: 45)
(GGGGCCACUAGGGACAGGAU),

BUB1B
                                   (SEQ ID NO: 46)
(AGUGAAGCCAUGUCCCUGGA),

CAMK1_sg1
                                   (SEQ ID NO: 47)
(UGCCAGGAUCACCUCCGAGA),

CAMKI_sg2
                                   (SEQ ID NO: 48)
(GCGUCCUCUUAUCUUCUGCC),

CEL
                                   (SEQ ID NO: 49)
(AACCAGUUGCAGGCGCCCCA),

Chr8q23_sg1
                                   (SEQ ID NO: 50)
(UUAUAGUUACGAUGUUUGAU),
```

```
-continued
CXCR4
                                   (SEQ ID NO: 51)
(GAUAACUACACCGAGGAAAU),

DNMT1
                                   (SEQ ID NO: 52)
(GGAGUGAGGGAAACGGCCCC),

EMX1
                                   (SEQ ID NO: 53)
(GAGUCCGAGCAGAAGAAGAA),

FAM163A
                                   (SEQ ID NO: 54)
(CUGCAGGGCUCGCUGGUGAG),

FANCF
                                   (SEQ ID NO: 55)
(GCUGCAGAAGGGAUUCCAUG),

GAA
                                   (SEQ ID NO: 56)
(AGGAGCCGGUGGGAGCAGGG),

GRK1
                                   (SEQ ID NO: 57)
(GCCGUCAAAGCUGCCUCGGG),

ITGA7
                                   (SEQ ID NO: 58)
(GGUGCUGGAGGGCGAGGCUG),

IRAK4
                                   (SEQ ID NO: 59)
(GUCCUGUCUUUGUCACAGAA),

MAPRE1
                                   (SEQ ID NO: 60)
(UUCUCUGCAGAUAAUUCCUG),

MIP
                                   (SEQ ID NO: 61)
(GCUGGGGUCCUCACUGCGCU),

OMP
                                   (SEQ ID NO: 62)
(GAACUGUAGCCGCUGCUGCU),

OPN1SW
                                   (SEQ ID NO: 63)
(ACAGGGGCAAUGUGGUACUG),

PRGN
                                   (SEQ ID NO: 64)
(CAGAUGCCUGCUCAGUGUUG),

PRKAG3
                                   (SEQ ID NO: 21)
(AGCAAGAAAACAGCAGCUCA),

STK3_sg1
                                   (SEQ ID NO: 66)
(AAAGCAAUACACAAGGAAUC),

STK3_sg2
                                   (SEQ ID NO: 67)
(CCAUAAUGCAGCAAUGUGAC), and VEGFA
                                   (SEQ ID NO: 68)
(GGUGAGUGAGUGUGUGCGUG)
to produce 23 experimental
``` populations. Each experimental population was then split into three groups, one to be kept in the dark, one to be exposed to ambient light, and one to be exposed to light filtered with a 345 nm bandpass filter to limit wavelengths to those greater than 345 nm. To form each of the 4 complex solutions, 10 pmol of Cas9 protein was mixed with 30 pmol of sgRNA. Each solution was diluted to 20 μL using transfection buffer and allowed to mix for 10 minutes prior to transfection. Four hours after transfection, treatment cells were exposed to either ambient light for 20 minutes or to light filtered with a 345 nm bandpass filter to limit wavelengths to those greater than 345 nm, for 60 seconds. 48 hours post transfection, samples were harvested and genomic DNA was extracted.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Figure 38:
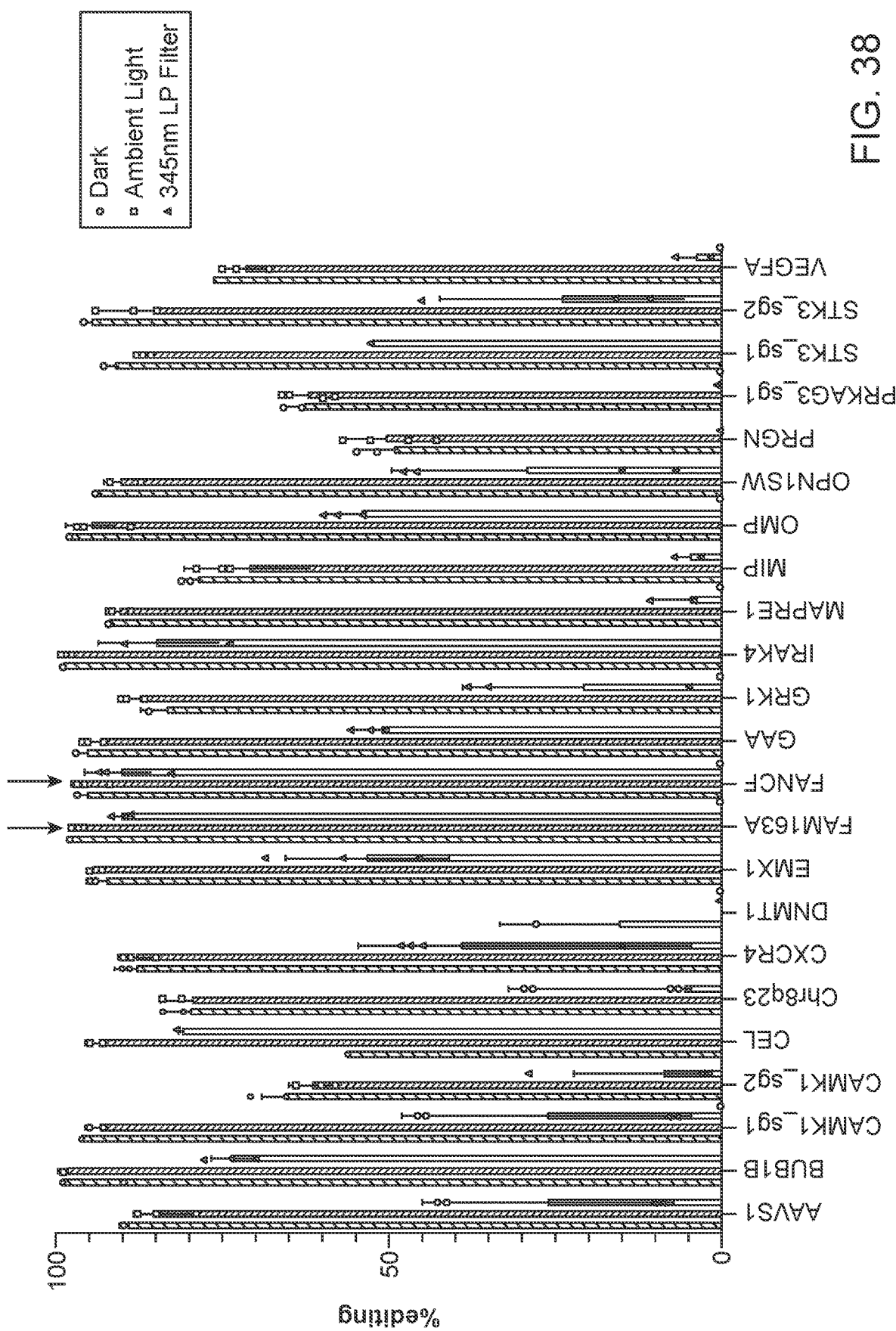
FIG. 38 is a graph comparing the performance, quantified as percent editing, of 23 guide RNAs in HEK293 cells, targeting 23 different target sites, comprising the photocleavable sites of FIG. 34, comparing three conditions: without light, with ambient light, or with light at a wavelength greater than 345 nm.

FIG. 38 shows a graph of the editing efficiency of Cas9 with the 23 different CRISPR OFF sgRNAs. From left to right, for each sgRNA: the black bars (circles), indicate the editing efficiency of the Cas9 in complex with the CRISPR OFF sgRNA without light exposure; the grey bars (squares), indicate the editing efficiency of the Cas9 in complex with CRISPR OFF sgRNA after ambient light exposure; the light grey bars (triangles), indicate the editing efficiency of the Cas9 in complex with CRISPR OFF sgRNA after exposure to light with wavelengths greater than 345 nm. As is pointed out with arrows, FANCF and FAM163 sites show no decrease in editing following exposure. The lamp used was 600 W, intensity was 90-120 mW/cm². Cas9 from Aldevron, with a nuclear localization signal (NLS-Sp.Cas9-NLS), was used in all experiments.

Figure 39:
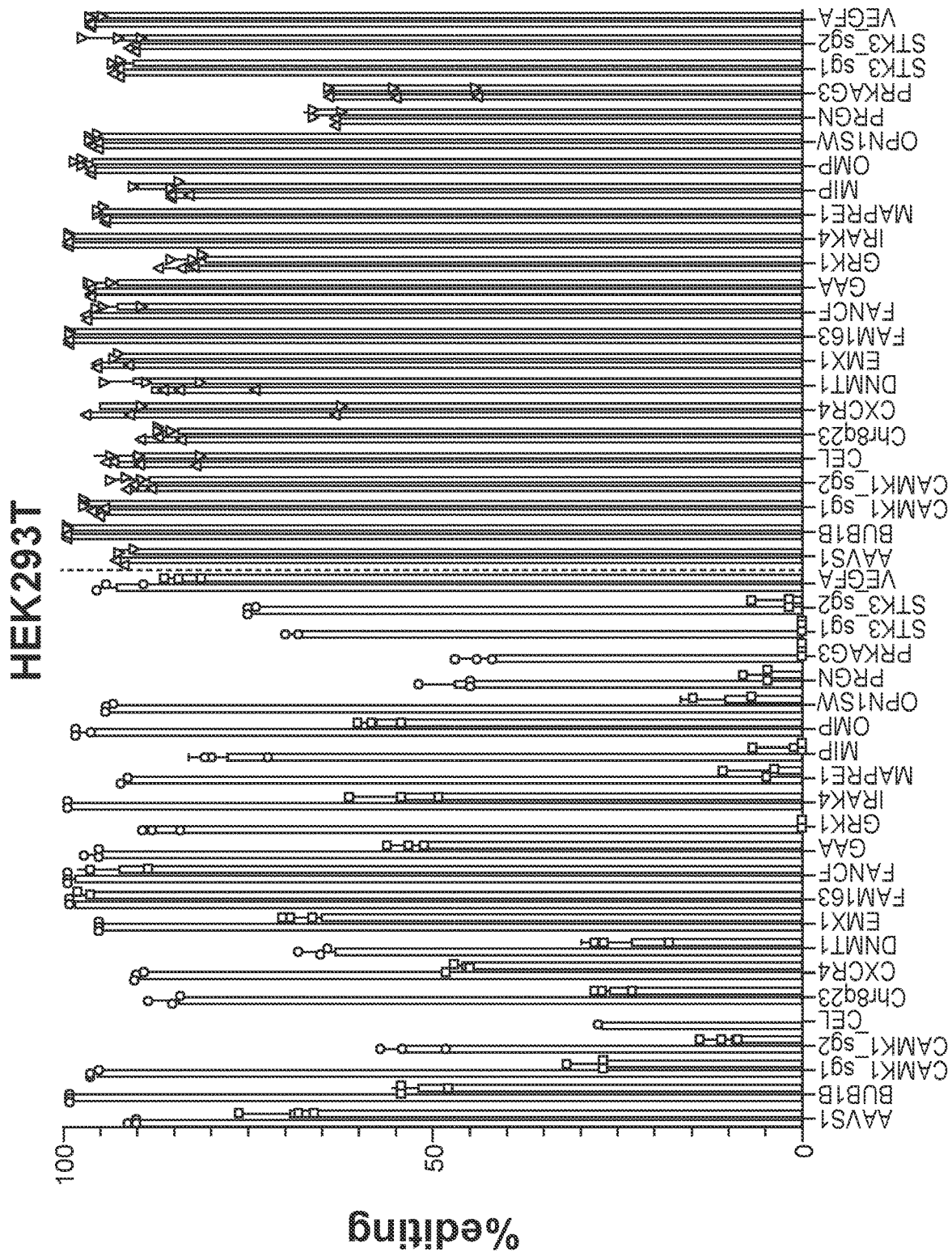
FIG. 39 is a graph comparing the performance, quantified as percent editing, of 23 guide RNAs in HEK293 cells, targeting 23 different target sites, comprising photocleavable linkers at positions 57 and 74, comparing three conditions: without light, with ambient light, or with light at a wavelength greater than 345 nm as compared to sgRNA without photocleavable sites.

FIG. 39 shows a graph of the editing efficiency of Cas9 with the 26 different CRISPR OFF sgRNAs as compared to unmodified sgRNAs with the same target binding sequence.

Figure 46:
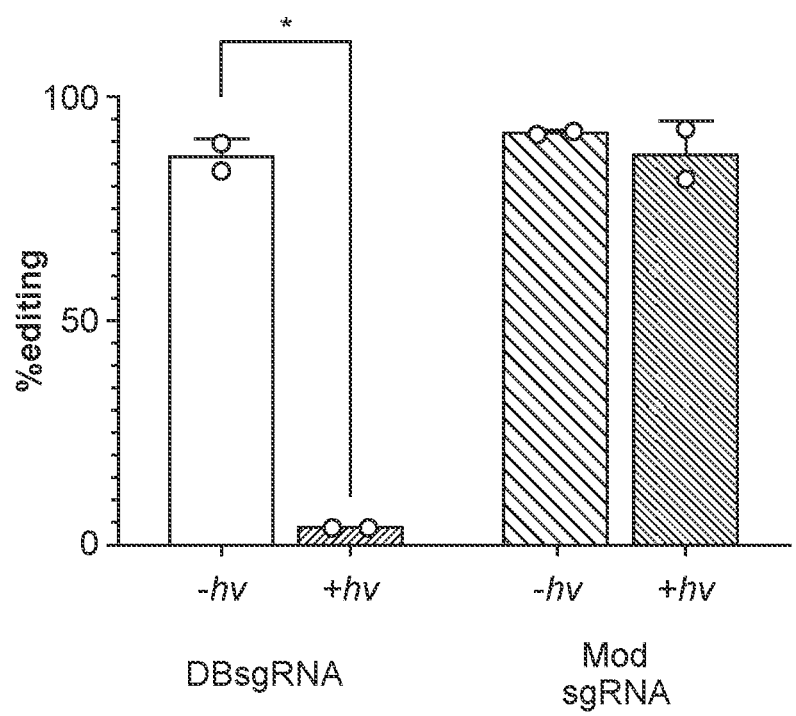
FIG. 46 is a graph showing that the percent editing by the polynucleotide of FIG. 34 significantly decreases upon exposure to light as compared to an sgRNA without photocleavable linkers.

FIG. 46 shows a graph demonstrating the decrease in percent editing observed in cells expressing CRISPR OFF in complex with a Cas9 after exposure to light as compared to cells expressing CRISPR OFF in complex with Cas9 without exposure to light and cells expressing Cas9 in complex with standard sgRNA with and without exposure to light.

Figure 47:
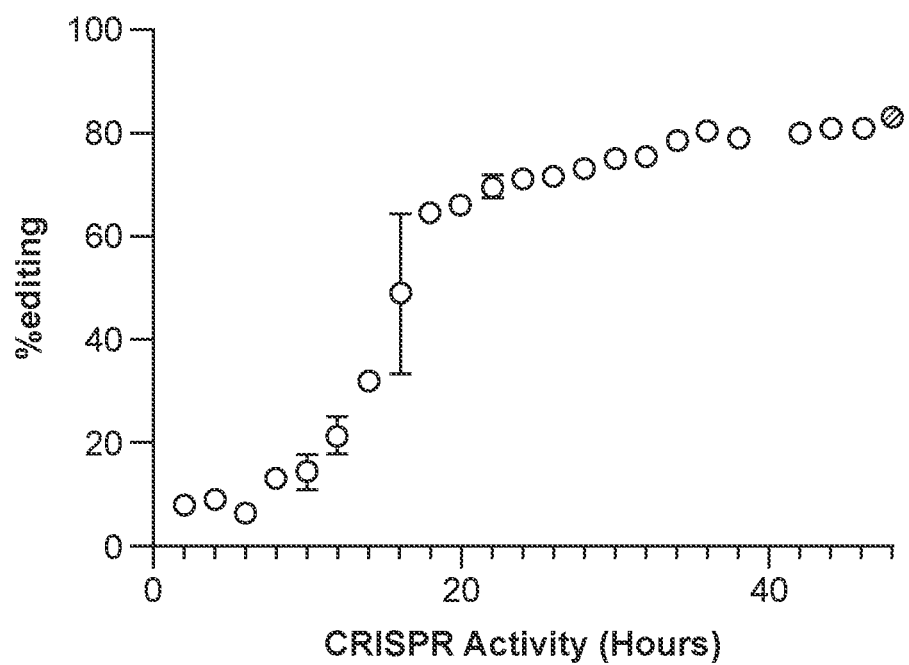
FIG. 47 is a graph showing the change in percent editing activity observed in HEK293 cells by the polynucleotide of FIG. 34 in complex with a Cas9 nuclease over time, with each time point representing the time at which a population of HEK293 cells tested were exposed to light.

FIG. 47 shows a graph demonstrating the increase in percent editing observed over increasing periods of time before the Cas9-CRISPR OFF complex expressed by the cell tested is inactivated with light.

Figure 53:
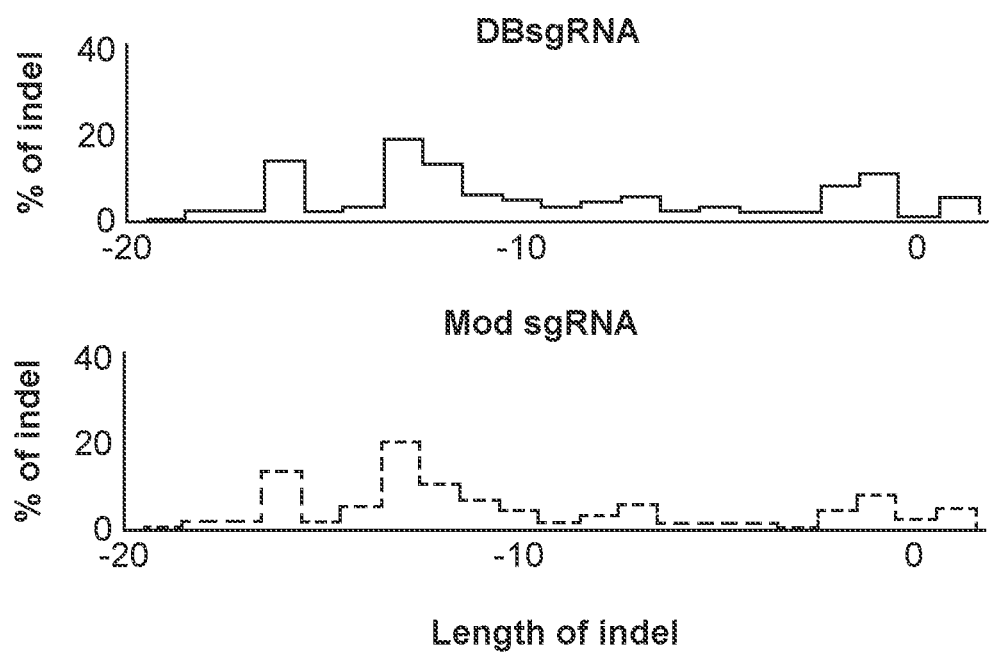
FIG. 53 is an indel profile of the CRISPR OFF polynucleotide in complex with a Cas9 nuclease targeting CAMK1 as compared to a standard sgRNA in complex with a Cas9 nuclease.

FIG. 53 is an indel profile of the aforementioned polynucleotide in complex with a Cas9 nuclease targeting CAMK1 as compared to a standard sgRNA in complex with a Cas9 nuclease.

Figure 51:
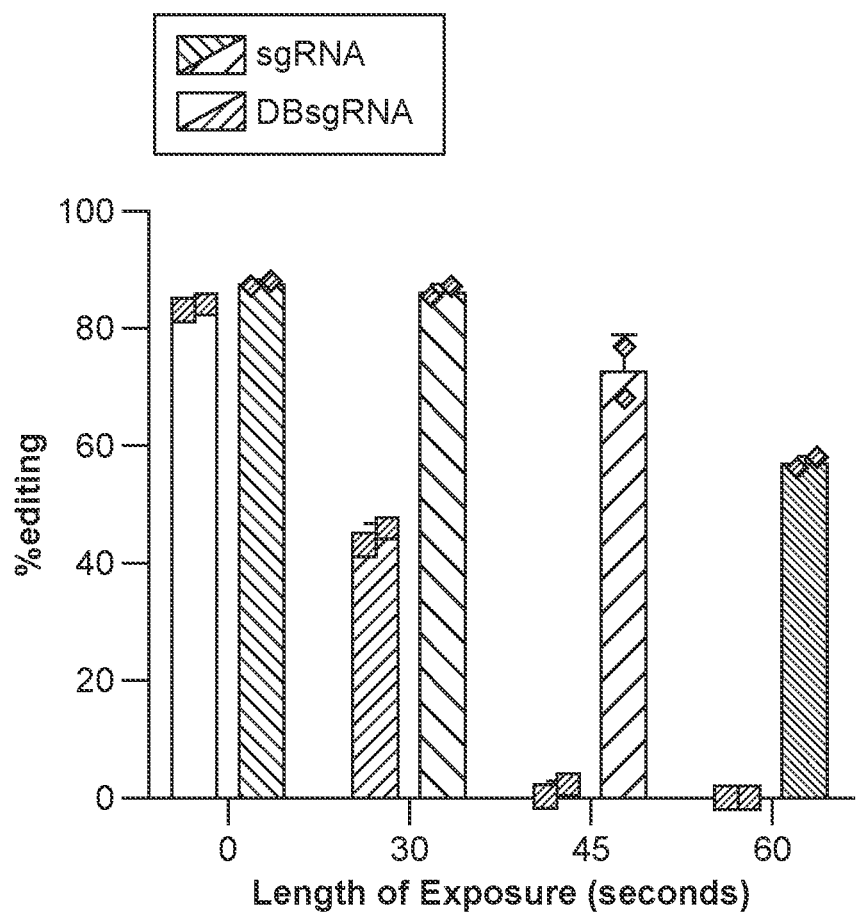
FIG. 51 shows a graph of the effect of light exposure duration on the ablation of editing, wherein complete ablation is achieved between 45-60 seconds.

FIG. 51 shows a graph of the effect of light exposure duration on the ablation of editing, wherein complete ablation is achieved between 45-60 seconds.

Figure 52:
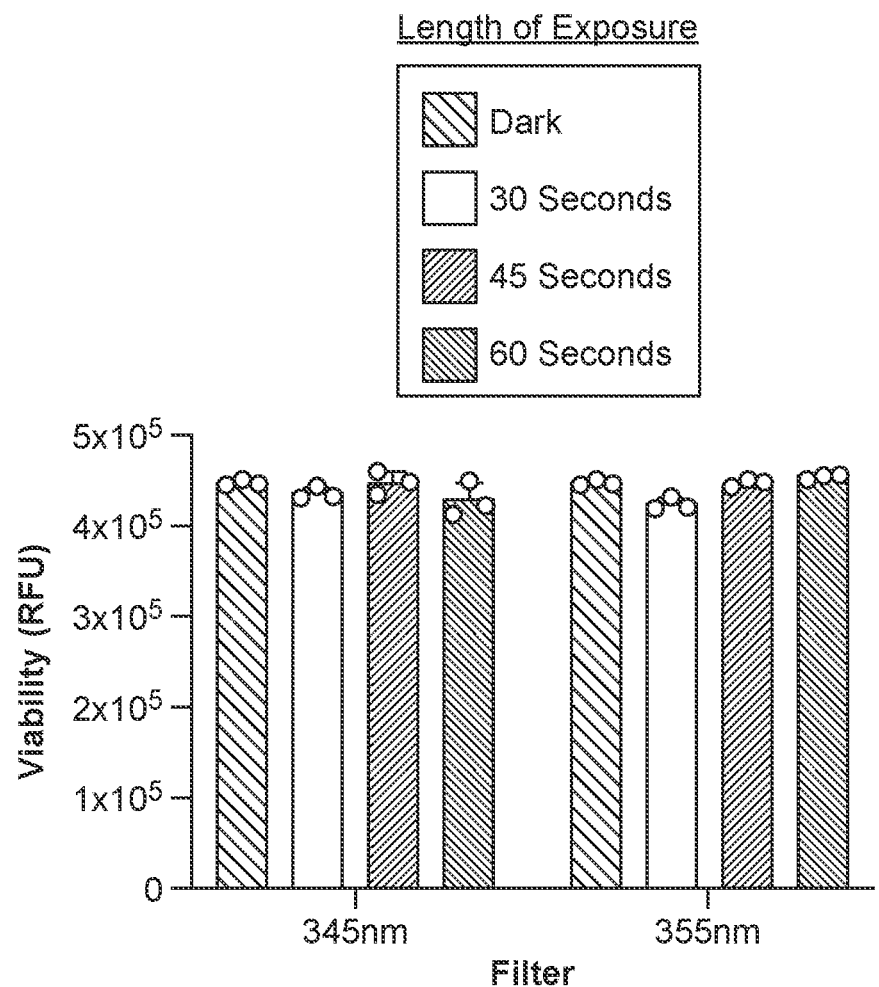
FIG. 52 is a graph showing the effect of increasing exposure time of cells to wide spectrum light on cell viability.

FIG. 52 is a graph showing the effect of increasing exposure time of cells to wide spectrum light on cell viability.

TABLE 1

Target Sequence Primers

| Target | Primer F | Primer R | Primer Seq |
| --- | --- | --- | --- |
| AAVS1 | GCCCCTATGTCCACTTC AGG (SEQ ID NO: 69) | CTCAGGTTCTGGGAGAGG GT (SEQ ID NO: 70) | CTCCATCGTAAGCAAACCTTA GAGG (SEQ ID NO: 71) |
| BUB1B | AGAAATCCTCCCACTTC GGC (SEQ ID NO: 72) | GCAGATTCTTGTGCCAGT GC (SEQ ID NO: 73) | CAGCTAACAAAGAAGCTTAGG CATATAATA (SEQ ID NO: 74) |
| CAMK1_sg1 | ACAACCCTGCCAAGTGG AAA (SEQ ID NO: 75) | ACTAGGGGAGGGTCATCC AC (SEQ ID NO: 76) | CATTTTATAAAGGGGCAATTTA AGGCTTAG (SEQ ID NO: 77) |
| CAMK1_sg2 | ACAACCCTGCCAAGTGG AAA (SEQ ID NO: 75) | ACTAGGGGAGGGTCATCC AC (SEQ ID NO: 76) | CATTTTATAAAGGGGCAATTTA AGGCTTAG (SEQ ID NO: 77) |
| CEL | CTGAGGGTGTAGAGGGG AGG (SEQ ID NO: 81) | GTTCTACCTGGCACCTGT CC (SEQ ID NO: 82) | CCTGAGAGCTCATGAACAAGC AT (SEQ ID NO: 83) |
| Chr8q23_sg1 | CTCGTCAAAACAAGGGT AAGCA (SEQ ID NO: 84) | GTTTGAGTTGACCAAACG CA (SEQ ID NO: 85) | CAAGGGTAAGCAAAGAAATAA AATCTCTTC (SEQ ID NO: 86) |
| Chr8q23_sg2 | ACCTGTCACATTGCTGC ATT (SEQ ID NO: 87) | GTTTGAGTTGACCAAACG CA (SEQ ID NO: 85) | TTGATTATTTCCTGAAGATCTG ATTCAACA (SEQ ID NO: 89) |
| CXCR4 | TTGTGCCCTTAGCCCAC TAC (SEQ ID NO: 90) | CCAGAAGGGAAGCGTGA TGA (SEQ ID NO: 91) | GTACTTGTCCGTCATGCTTCTC AGTTT (SEQ ID NO: 92) |
| DNMT1 | GATCAAGCTTTGTATGT TGGCCAA (SEQ ID NO: 93) | AATCCAGAATGCACAAAG TACTGC (SEQ ID NO: 94) | GATCAAGCTTTGTATGTTGGCC AA (SEQ ID NO: 93) |
| EMX1 | CAGCTCTGTGACCCTTT GTTTG (SEQ ID NO: 96) | ACTAAACTACAGTGGTGC CTGG (SEQ ID NO: 97) | CAGCTCTGTGACCCTTTGTTTG (SEQ ID NO: 96) |
| FAM163A | GAGTGGTGGGAGGGGA AAAG (SEQ ID NO: 99) | CATGTCAGCCGTCCGTAT GT (SEQ ID NO: 100) | CTTGCAAAGCTGGGATTAGAA ACTT (SEQ ID NO: 101) |
| FANCF | GATATTTCCAAAGCGAA AGGAAGC (SEQ ID NO: 102) | ATCAGAGAGTCCTCCTGG AGATTT (SEQ ID NO: 103) | GATATTTCCAAAGCGAAAGGA AGC (SEQ ID NO: 102) |
| GAA | GGTGAGTCTCCTCCAGG ACT (SEQ ID NO: 105) | CAGACTGTGCAAGTGCTC TG (SEQ ID NO: 106) | CTTTTCTCGCCCTTCCTTCTGG (SEQ ID NO: 107) |

TABLE 1-continued

Target Sequence Primers

| Target | Primer F | Primer R | Primer Seq |
|---|---|---|---|
| GRK1 | GTCTCTCTCGTCCAGCAAGGG (SEQ ID NO: 108) | ATGTCTTTCCAGAGCTCCAGGG (SEQ ID NO: 109) | GTCTCTCTCGTCCAGCAAGGG (SEQ ID NO: 108) |
| ITGA7 | GGTTGTCGCCAAACCTTCAC (SEQ ID NO: 111) | GGGATTGGGGAGTCAAGAGC (SEQ ID NO: 112) | GAGTCAAGAGCACAAGAAACATGAGAACAT (SEQ ID NO: 113) |
| IRAK4 | GCTTCTTGTGTGTGCTGTGAG (SEQ ID NO: 114) | GCCTGTGATTGCTGCACAAA (SEQ ID NO: 115) | CAAGTTTCTAGTTTAACTTTTTCACAACCA (SEQ ID NO: 116) |
| MAPRE1 | GGTACTCTTGAAGGCAAACTGC (SEQ ID NO: 117) | CGCTGAATGAATATCTGGAACGC (SEQ ID NO: 118) | ACTGCATGAAACTTGCTTTATAAATTTAGG (SEQ ID NO: 119) |
| MIP | TCAGCCAACCATTACCGTGT (SEQ ID NO: 120) | TAAAGGGGACTGTCCACCCA (SEQ ID NO: 121) | CATTACCGTGTTGAGTGCTAGGTTTC (SEQ ID NO: 122) |
| OMP | TTGAGAACTGAGTGGGGCTG (SEQ ID NO: 123) | GCGTGTCATGAGGTTGGTGA (SEQ ID NO: 124) | TTGAGAACTGAGTGGGGCTG (SEQ ID NO: 123) |
| OPN1SW | CCCCTAACCCCTTTTTCCCC (SEQ ID NO: 126) | GTTTTGTGGGGTGGGAGGAT (SEQ ID NO: 127) | CTAACCCCTTTTTCCCCTGCAGTAC (SEQ ID NO: 128) |
| PRGN | TGAGCTGGGTGGCCTTAACA (SEQ ID NO: 129) | CATTGGCAGGGCCCTTTTATC (SEQ ID NO: 130) | CCAGATGGTCAGTTCTGCCC (SEQ ID NO: 131) |
| PRKAG3_sg1 | ATGTAGGGAGACTGAGGCCA (SEQ ID NO: 132) | GCCCATTGGAAGCTTGCAAA (SEQ ID NO: 133) | TTGGGTCCAACTCTGTGTTATGGAG (SEQ ID NO: 134) |
| STK3_sg1 | ACGGCAAAACCCTGTCTCAA (SEQ ID NO: 135) | TCCACAGAAAACTCATAGTAGACTT (SEQ ID NO: 136) | AAACAAGGGTAAGCAAAGAAATAAAATCTC (SEQ ID NO: 137) |
| STK3_sg2 | AAGCCATCCTCATCTGCCTT (SEQ ID NO: 138) | ACACAAGGAATCCGGTCAAGT (SEQ ID NO: 139) | GGAGAAACCCATCTCTACTAAAAATACAAA (SEQ ID NO: 140) |
| VEGFA | GAAGCAACTCCAGTCCCAAATATG (SEQ ID NO: 141) | GTTCACAGCCTGAAAATTACCCAT (SEQ ID NO: 142) | GAAGCAACTCCAGTCCCAAATATG (SEQ ID NO: 141) |

Example 14: Analysis of On-Target Editing by CRISPR-OFF Cas9 Complexes in U2OS Cells with and without Exposure to UV Light U2OS cells were maintained between passage 5-15 in RPMI 1640 supplemented with 10% v/v FBS. Cells were passaged weekly at a 1:4 ratio with TrypLE. All cells were maintained at 37° C. and 5% CO2.

U2OS cells were transfected with Cas9 and sgRNAs comprising photocleavable (PC) linkers and were subjected to light filtered with a 345 nm bandpass filter to cleave the linker. Cas9 was complexed with 18 different sgRNAs comprising a photocleavable linker (1-(7-(diethylamino)-2-oxo-2H-chromen-4-yl)propyl), incorporated at positions 57 and 74 (CRISPR OFF) with target binding regions targeting

```
AAVS1
                                         (SEQ ID NO: 45)
(GGGGCCACUAGGGACAGGAU),

BUB1B
                                         (SEQ ID NO: 46)
(AGUGAAGCCAUGUCCCUGGA),

CAMK1_sg1
                                         (SEQ ID NO: 47)
(UGCCAGGAUCACCUCCGAGA),

CAMK1_sg2
                                         (SEQ ID NO: 48)
(GCGUCCUCUUAUCUUCUGCC),

Chr8q23_sg1
                                         (SEQ ID NO: 50)
(UUAUAGUUACGAUGUUUGAU),

Chr8q23_sg2
                                         (SEQ ID NO: 144)
(AGUCUACUAUGAGUUUUCUG),

DNMT1
                                         (SEQ ID NO: 52)
(GGAGUGAGGGAAACGGCCCC),

EMX1
                                         (SEQ ID NO: 53)
(GAGUCCGAGCAGAAGAAGAA),

FAM163A
                                         (SEQ ID NO: 54)
(CUGCAGGGCUCGCUGGUGAG),

FANCF
                                         (SEQ ID NO: 55)
(GCUGCAGAAGGGAUUCCAUG),
```

GRK1
(GCCGUCAAAGCUGCCUCGGG), (SEQ ID NO: 57)

ITGA7
(GGUGCUGGAGGGCGAGGCUG), (SEQ ID NO: 58)

IRAK4
(GUCCUGUCUUUGUCACAGAA), (SEQ ID NO: 59)

PRGN
(CAGAUGCCUGCUCAGUGUUG), (SEQ ID NO: 64)

PRKAG3
(AGCAAGAAAACAGCAGCUCA), (SEQ ID NO: 21)

STK3_sg1
(AAAGCAAUACACAAGGAAUC), (SEQ ID NO: 66)

STK3_sg2
(CCAUAAUGCAGCAAUGUGAC), and (SEQ ID NO: 67)

VEGFA
(GGUGAGUGAGUGUGUGCGUG) (SEQ ID NO: 68)

to produce 18 experimental populations. Each experimental population was then split into three groups, one to be kept in the dark, one to be exposed to ambient light, and one to be exposed to light filtered with a 345 nm bandpass filter to limit wavelengths to those greater than 345 nm. To form each of the 4 complex solutions, 10 pmol of Cas9 protein was mixed with 30 pmol of sgRNA. Each solution was diluted to 20 μL using transfection buffer and allowed to mix for 10 minutes prior to transfection. Four hours after transfection, treatment cells were exposed to either ambient light for 20 minutes or to light filtered with a 345 nm bandpass filter to limit wavelengths to those greater than 345 nm, for 60 seconds. 48 hours post transfection, samples were harvested and genomic DNA was extracted.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Figure 40:
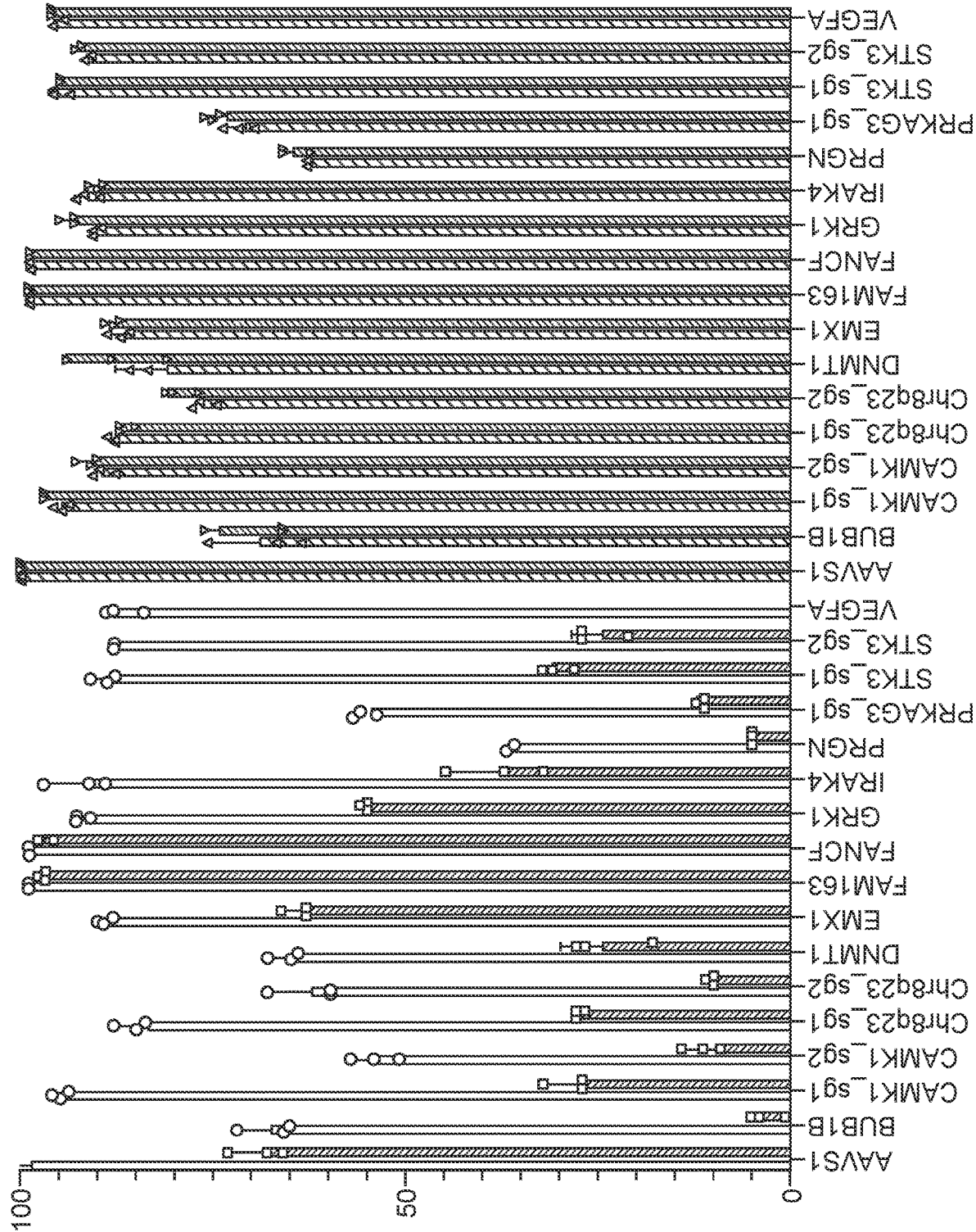
FIG. 40 is a graph comparing the performance, quantified as percent editing, of 18 guide RNAs in Hep3B cells, targeting 18 different target sites, comprising photocleavable linkers at positions 57 and 74, comparing three conditions: without light, with ambient light, or with light at a wavelength greater than 345 nm as compared to sgRNA without photocleavable sites.

FIG. 40 shows a graph of the editing efficiency of Cas9 with the 18 different CRISPR OFF sgRNAs as compared to unmodified sgRNAs with the same target binding sequence.

Example 15: Analysis of On-Target Editing by CRISPR-OFF Cas9 Complexes in Hep3b Cells with and without Exposure to UV Light Hep3B cells were maintained between passage 5-20 in Advanced Modified Eagles Medium (Life Technologies) and 10% v/v FBS. Cells were passaged biweekly at a 1:8 ratio with TrypLE (Life Technologies).

Hep3b cells were transfected with Cas9 and sgRNAs comprising photocleavable (PC) linkers and were subjected to light filtered with a 345 nm bandpass filter to cleave the linker. Cas9 was complexed with 23 different sgRNAs comprising a photocleavable linker (1-(7-(diethylamino)-2-oxo-2H-chromen-4-yl)propyl) incorporated at positions 57 and 74 (CRISPR OFF) with target binding regions targeting

AAVS1
(GGGGCCACUAGGGACAGGAU), (SEQ ID NO: 45)

BUB1B
(AGUGAAGCCAUGUCCCUGGA), (SEQ ID NO: 46)

CAMK1_sg1
(UGCCAGGAUCACCUCCGAGA), (SEQ ID NO: 47)

CAMKI_sg2
(GCGUCCUCUUAUCUUCUGCC), (SEQ ID NO: 48)

CEL
(AACCAGUUGCAGGCGCCCCA), (SEQ ID NO: 49)

Chr8q23_sg1
(UUAUAGUUACGAUGUUUGAU), (SEQ ID NO: 50)

CXCR4
(GAUAACUACACCGAGGAAAU), (SEQ ID NO: 51)

EMX1
(GAGUCCGAGCAGAAGAAGAA), (SEQ ID NO: 53)

FAM163A
(CUGCAGGGCUCGCUGGUGAG), (SEQ ID NO: 54)

FANCF
(GCUGCAGAAGGGAUUCCAUG), (SEQ ID NO: 55)

GAA
(AGGAGCCGGUGGGAGCAGGG), (SEQ ID NO: 56)

GRK1
(GCCGUCAAAGCUGCCUCGGG), (SEQ ID NO: 57)

ITGA7
(GGUGCUGGAGGGCGAGGCUG), (SEQ ID NO: 58)

IRAK4
(GUCCUGUCUUUGUCACAGAA), (SEQ ID NO: 59)

MAPRE1
(UUCUCUGCAGAUAAUUCCUG), (SEQ ID NO: 60)

MIP
(GCUGGGGUCCUCACUGCGCU), (SEQ ID NO: 61)

OMP
(GAACUGUAGCCGCUGCUGCU), (SEQ ID NO: 62)

OPN1SW
(ACAGGGGCAAUGUGGUACUG), (SEQ ID NO: 63)

PRGN
(CAGAUGCCUGCUCAGUGUUG), (SEQ ID NO: 64)

```
                -continued
PRKAG3
                              (SEQ ID NO: 21)
(AGCAAGAAAACAGCAGCUCA), STK3_sg1
                              (SEQ ID NO: 66)
(AAAGCAAUACACAAGGAAUC), STK3_sg2
                              (SEQ ID NO: 67)
(CCAUAAUGCAGCAAUGUGAC), and VEGFA
                              (SEQ ID NO: 68)
(GGUGAGUGAGUGUGUGCGUG)
to produce 23 experimental
``` populations. Each experimental population was then split into three groups, one to be kept in the dark, one to be exposed to ambient light, and one to be exposed to light filtered with a 345 nm bandpass filter to limit wavelengths to those greater than 345 nm. To form each of the 4 complex solutions, 10 pmol of Cas9 protein was mixed with 30 pmol of sgRNA. Each solution was diluted to 20 μL using transfection buffer and allowed to mix for 10 minutes prior to transfection. Four hours after transfection, treatment cells were exposed to either ambient light for 20 minutes or to light filtered with a 345 nm bandpass filter to limit wavelengths to those greater than 420 nm, for 60 seconds. 48 hours post transfection, samples were harvested and genomic DNA was extracted.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Figure 41:
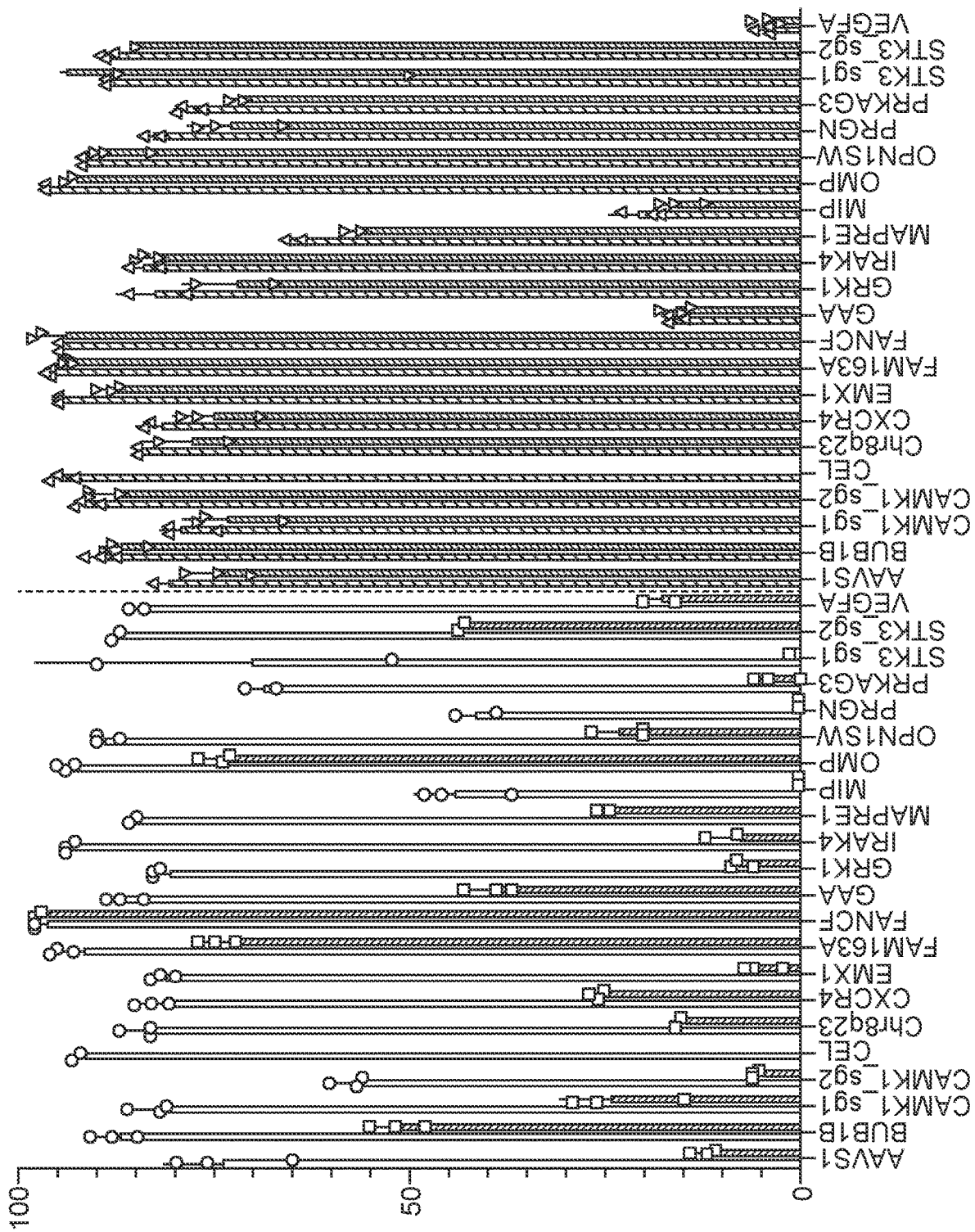
FIG. 41 is a graph comparing the performance, quantified as percent editing, of 13 guide RNAs in U2OS cells, targeting 13 different target sites, comprising photocleavable linkers at positions 57 and 74, comparing three conditions: without light, with ambient light, or with light at a wavelength greater than 345 nm as compared to sgRNA without photocleavable sites.

FIG. 41 shows a graph of the editing efficiency of Cas9 with the 23 different CRISPR OFF sgRNAs as compared to unmodified sgRNAs with the same target binding sequence.

Figure 34:
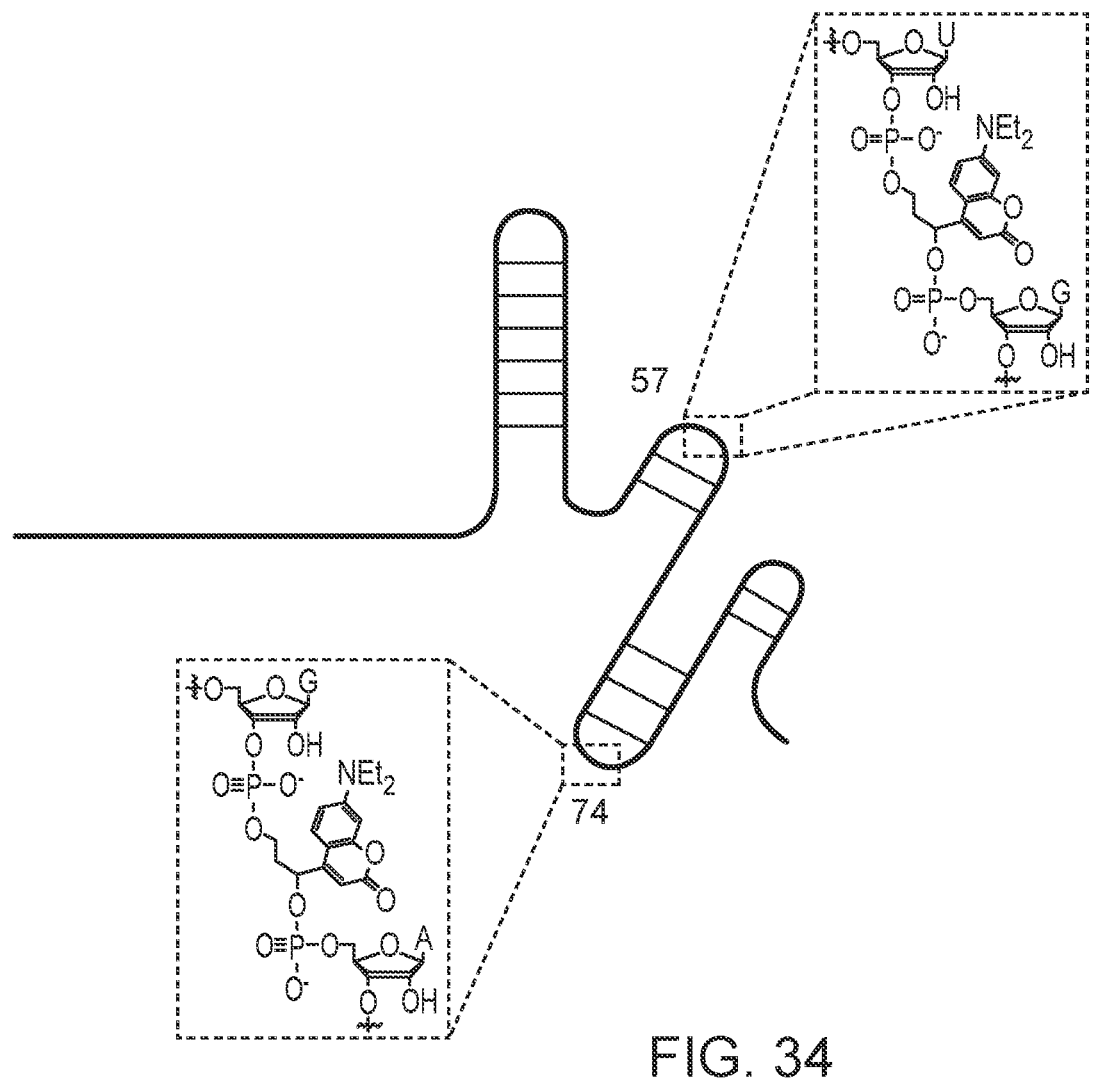
FIG. 34 illustrates exemplary positions at which a modification comprising a coumarin linker can be made to a CRISPR polynucleotide.
Figure 35:
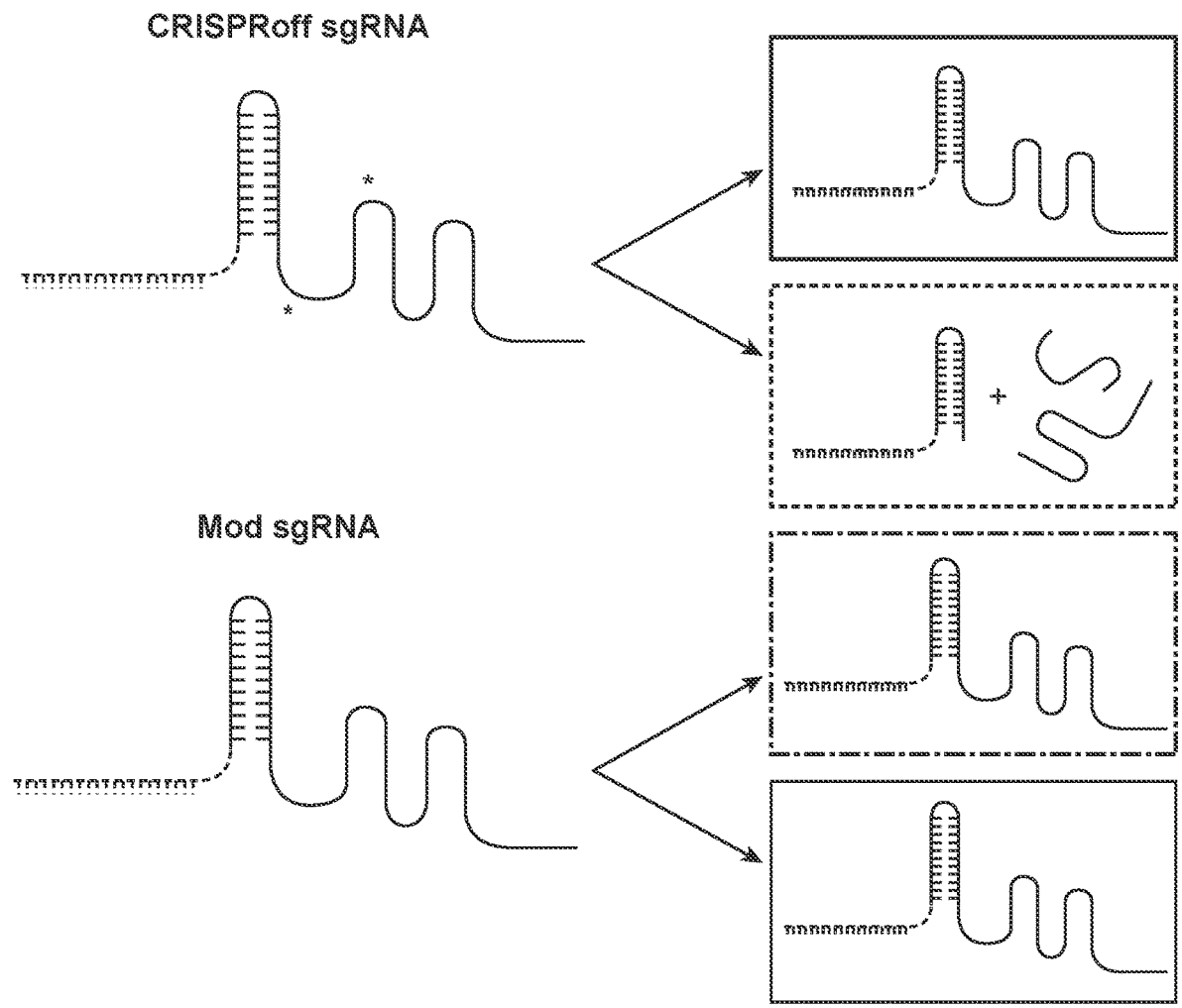
FIG. 35 illustrates exemplary positions at which a modification comprising a cleavable linker can be made to CRISPR polynucleotide as compared to a modified sgRNA without cleavable linkers.

Example 16: Exposure of CRISPR OFF sgRNA with a Coumarin Linker to Visible Light FIG. 34 is a diagram of a CRISPR polynucleotide comprising a coumarin linker, diethylaminocoumarin (1-(7-(diethylamino)-2-oxo-2H-chromen-4-yl)propyl) at positions 57 and 74 of an sgRNA. The coumarin linker is significantly red-shifted and can be used to cleave oligonucleotides using visible light. Coumarin linker release occurs through the formation of a tight ion pair, followed by a reaction of coumarinylmethyl cation with water and other available nucleophiles.

Electrospray Ionization

RNA samples in TE buffer (3 uM) were analyzed by mass spectrometry (Agilent 1290 Infinity II liquid chromatography system (LC) coupled with Agilent 6530B Q-TOF mass spectrometer (MS)) in a negative ion polarity mode. LC is performed with gradient elution (buffer A: 50 mM HFIP; 15 mM Hexylamine 2% MeOH; buffer B: MeOH, 0.75 mL/min, 2-95% B in 1.05 min) on a Acquity UPLC BEH C18 VanGuard Pre-column (1.7 um, 2.1×5 mm). Electrospray ionization performed with a dual ESI source (gas temp 325° C., drying gas 12 L/min, nebulizer 40 psi, Vcap 4 kV, fragmentor 250, skimmer 65). Data acquired in 100-3200 m/z range and deconvoluted in 4000-35000 m/z range.

Figure 36A:
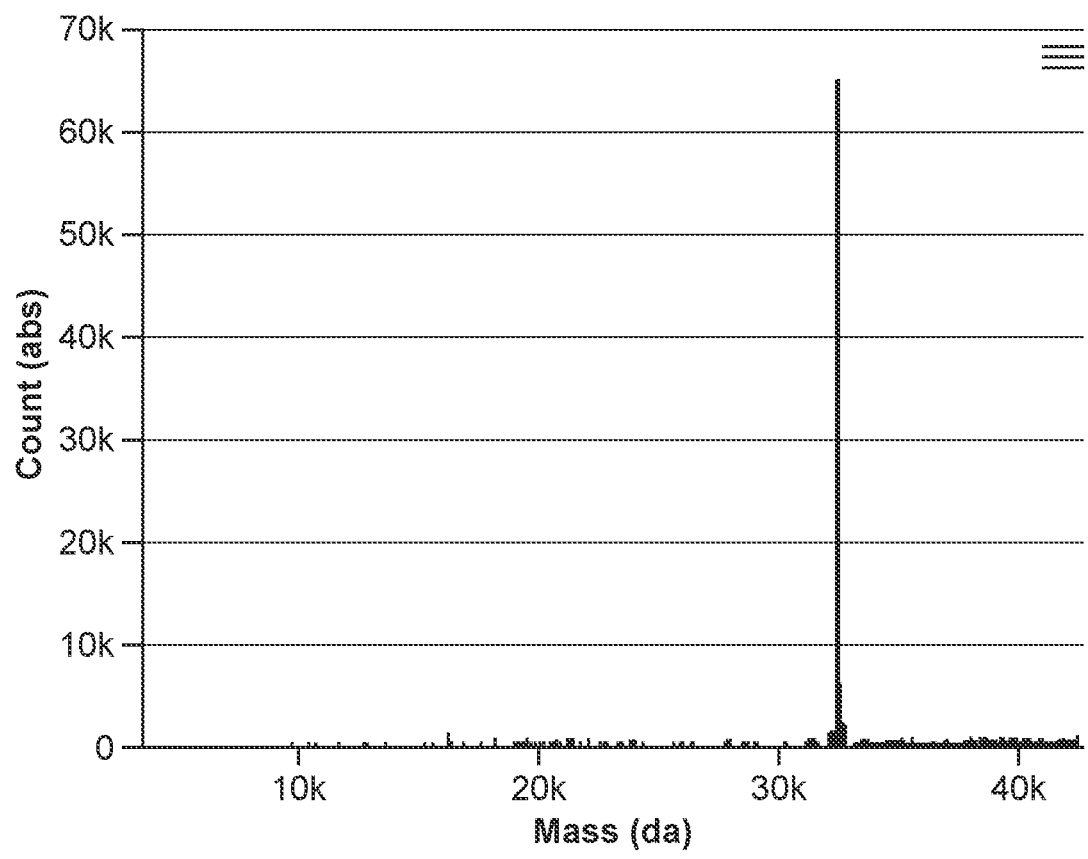
FIG. 36A is an Electrospray Ionization (ESI) Mass Spectrometry trace of an intact CRISPR polynucleotide of FIG. 34 demonstrating that fragmentation is not observed in the absence of light.

FIG. 36A is an ESI trace of the CRISPR OFF sgRNA described above, targeting VEGFA (GGUGAGUGAGUGU-GUGCGUG) (SEQ ID NO: 68) before exposure to light.

Figure 36B:
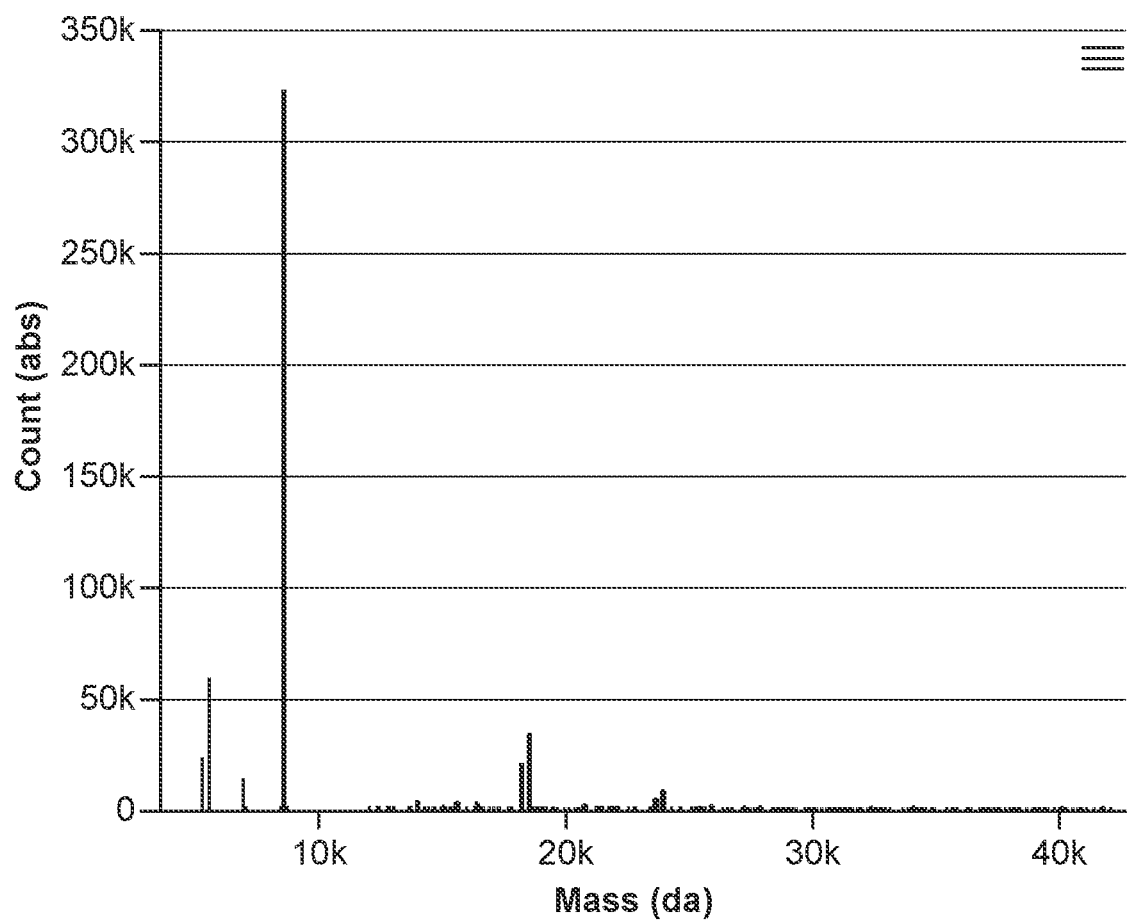
FIG. 36B is an Electrospray Ionization (ESI) Mass Spectrometry trace of a CRISPR polynucleotide of FIG. 34 following photocleavage, demonstrating that the polynucleotide is cleaved at both photocleavable sites upon exposure to light at a wavelength greater than 420 nm.
Figure 37:
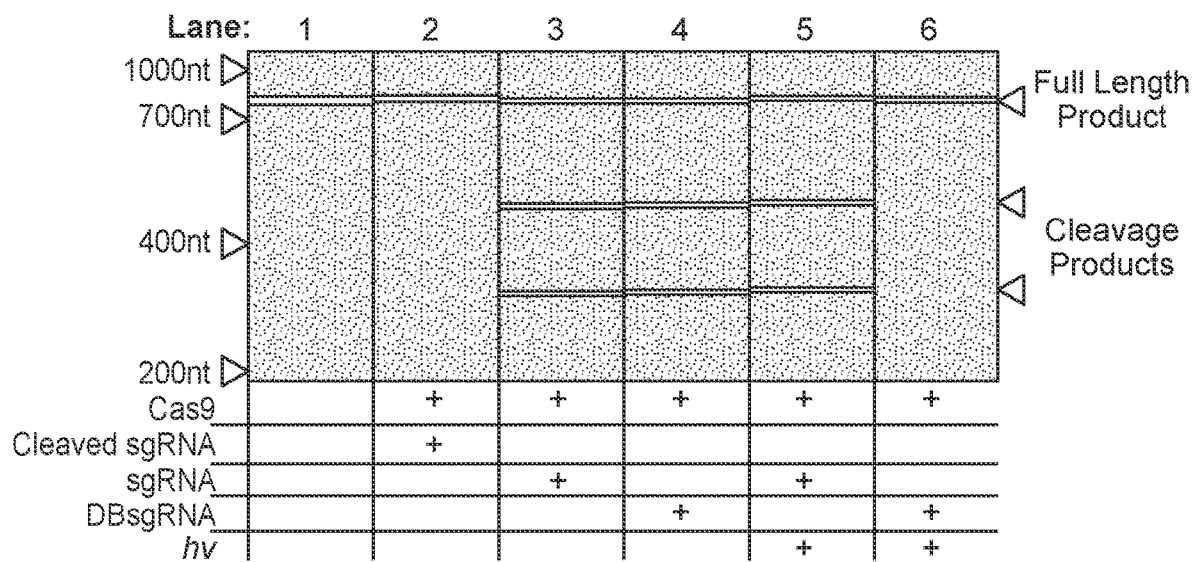
FIG. 37 is picture of a gel showing the comparison of polynucleotide fragments corresponding to the fragments created after the cleavage of photocleavable linkers at positions 57 and 74 after exposure to UV light, fragments created after exposure to UV light, and intact sgRNA.

FIG. 36B is an ESI trace of the CRISPR OFF sgRNA described above after exposure to light filtered through a 420 nm longpass filter. CRISPR OFF sgRNA not subjected to the light retained the same molecular weight as unmodified sgRNA. Fragmentation was not observed for CRISPR OFF sgRNA not subjected to light. FIG. 20B demonstrates that the CRISPR off sgRNA was cleaved at both photocleavable sites upon exposure to 420 nm light.

Example 17: Exposure of CRISPR OFF sgRNA with a UV Cleavable Linker to UV Light

Electrospray Ionization

RNA samples in TE buffer (3 uM) were analyzed by mass spectrometry (Agilent 1290 Infinity II liquid chromatography system (LC) coupled with Agilent 6530B Q-TOF mass spectrometer (MS)) in a negative ion polarity mode. LC is performed with gradient elution (buffer A: 50 mM HFIP; 15 mM Hexylamine 2% MeOH; buffer B: MeOH, 0.75 mL/min, 2-95% B in 1.05 min) on an Acquity UPLC BEH C18 VanGuard Pre-column (1.7 um, 2.1×5 mm). Electrospray ionization performed with a dual ESI source (gas temp 325° C., drying gas 12 L/min, nebulizer 40 psi, Vcap 4 kV, fragmentor 250, skimmer 65). Data acquired in 100-3200 m/z range and deconvoluted in 4000-35000 m/z range.

Figure 57A:
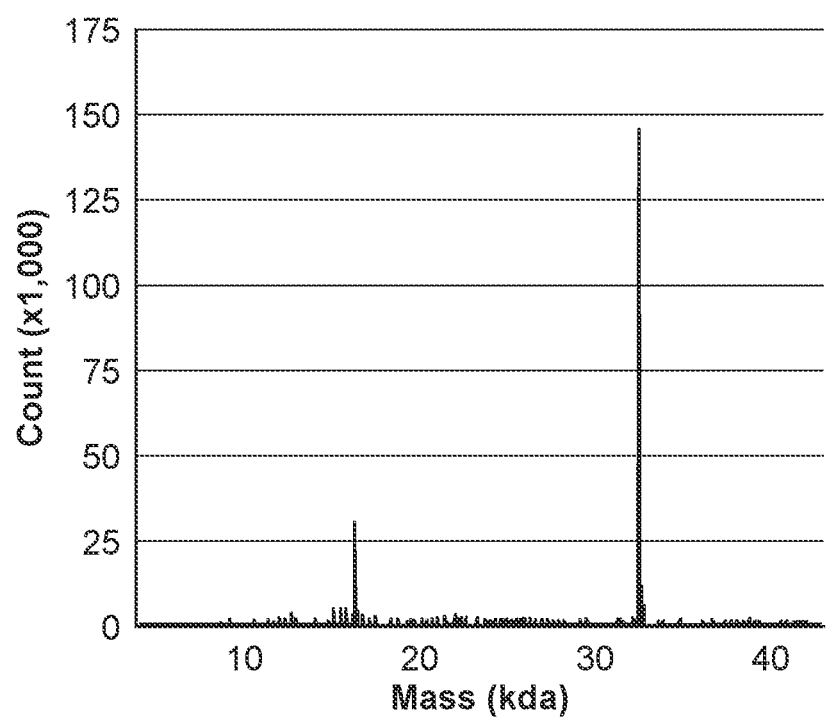
FIG. 57A is an Electrospray Ionization (ESI) Mass Spectrometry trace of an intact CRISPR OFF polynucleotide with photocleavable linkers at positions 57 and 74, demonstrating that fragmentation is not observed in the absence of light.

FIG. 57A is an ESI trace of the CRISPR OFF sgRNA targeting VEGFA (GGUGAGUGAGUGUGUGCGUG) (SEQ ID NO: 68) with photocleavable linkers at positions 57 and 74 before exposure to UV light.

Figure 57B:
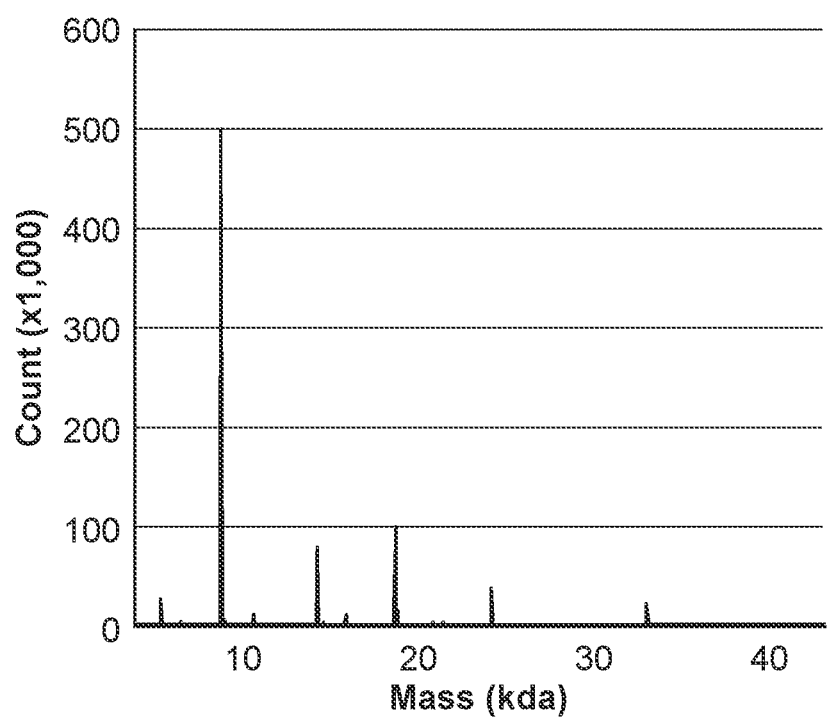
FIG. 57B is an Electrospray Ionization (ESI) Mass Spectrometry trace of a CRISPR OFF polynucleotide with photocleavable linkers at positions 57 and 74, following photocleavage, demonstrating that the polynucleotide is cleaved at both photocleavable sites upon exposure to light at a wavelength greater than 345 nm.

FIG. 57B is an ESI trace of the CRISPR OFF sgRNA of FIG. 41A after exposure to light filtered through a 345 nm bandpass filter. CRISPR OFF sgRNA not subjected to the light retained the same molecular weight as unmodified sgRNA. FIG. 57B demonstrates that the CRISPR off sgRNA was cleaved at both photocleavable sites upon exposure to 345 nm light.

Example 18: Inactivation of Cas9 in Complex with CRISPR OFF sgRNA with UV Light 10 pmol NLS-Cas9-NLS protein (Aldevron) was combined with 30 pmol synthetic sgRNAs in 20 uL total volume and allowed to complex for 10 minutes. During this incubation, cells were harvested and counted. To the RNP solution 5 μL of cell solution at a concentration of 4*10⁴ cells/μL was added and gently mixed.

Cell+RNP solution was transfected using the 4D-Nucleofector system (Lonza) in the 20 μL format. Transfections were done according to manufacturer protocol. Following transfection, cells were recovered in culture media and plated into 96-well plates.

CRISPR OFF inactivation was performed using a Sunray 600 UV Flood Lamp (Uvitron International). 345 nm and 355 nm 6.5"×6.5" colored glass alternative longpass filters were obtained from Newport.com and mounted using custom 3D-printed containers.

Inactivation using an upright microscope was performed using a Zeiss Axios Observer with a Colibri 7 Flexible Light Source and 385 nm LED.

Figure 54:
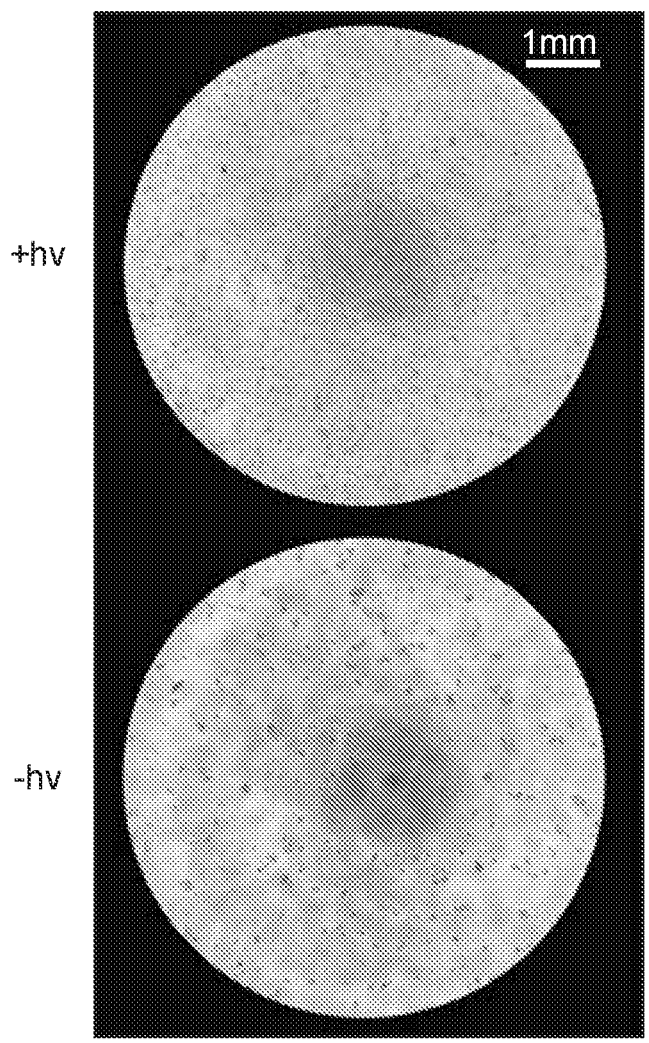
FIG. 54 is a picture of a cell culture wherein the polynucleotide of FIG. 34 in complex with a Cas9 nuclease is used to target an essential gene. The cell culture exposed to light (+hv) demonstrates a higher confluency than the cell culture not exposed to light indicating that the lack of inactivation caused a high degree of cell death.

FIG. 54 is a picture of a cell culture wherein CRISPR OFF in complex with a Cas9 nuclease is used to target an essential gene. The cell culture exposed to light (+hv) demonstrates a higher confluency than the cell culture not exposed to light indicating that the lack of inactivation caused a high degree of cell death.

Figure 42:
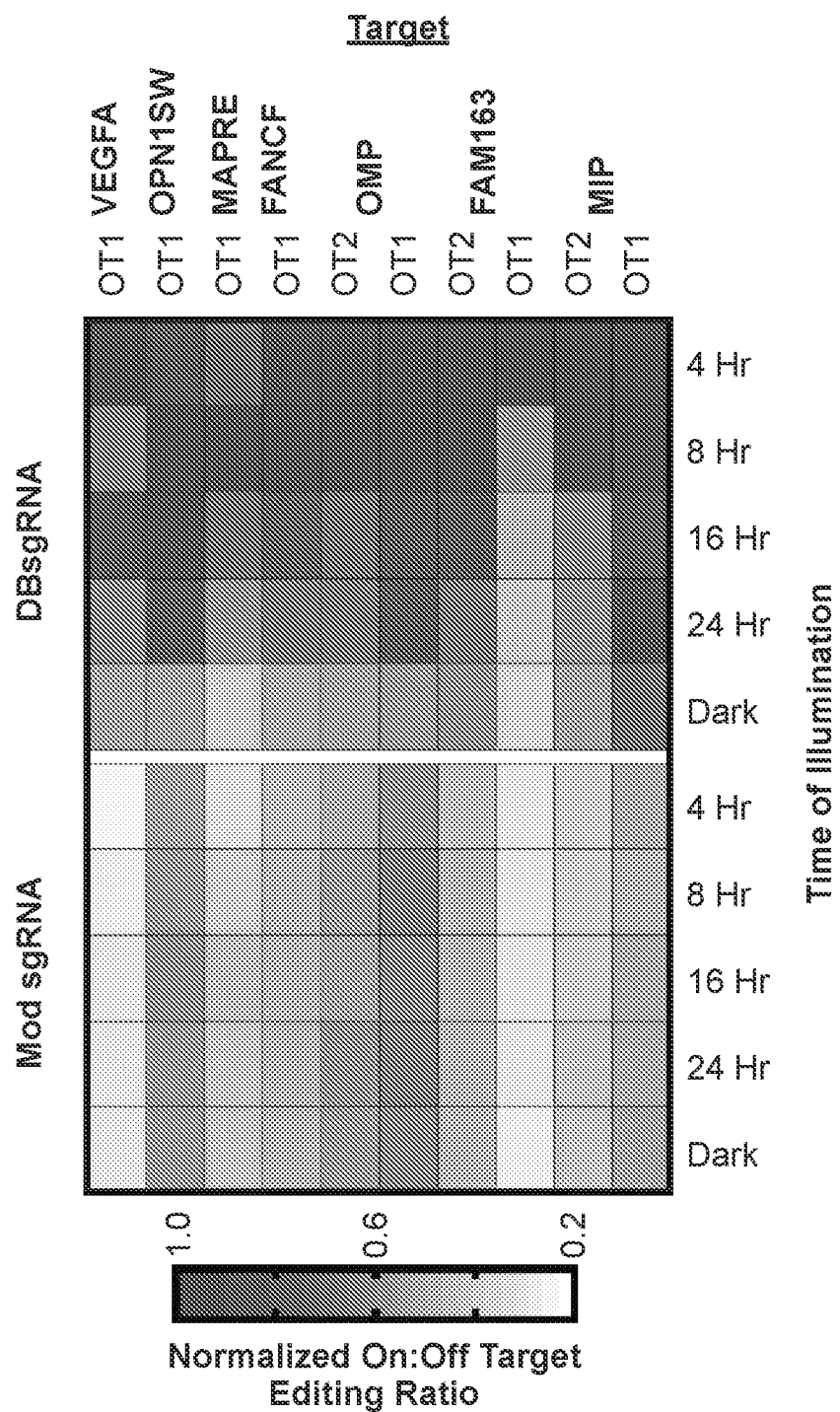
FIG. 42 illustrates relationship between the amount of time that a sgRNA is active and the ratio of on-target editing to off-target editing, demonstrated by an increase in off-target editing the longer sgRNA is allowed to be active, with unmodified sgRNA as the control.

FIG. 42 shows the modulation of the ratio of on-target editing to off-target editing by inactivation of the CRISPR OFF sgRNA before off-target editing occurs, compared to the ratio seen with standard sgRNA. Inactivation of the CRISPR OFF sgRNA was achieved by illuminating cells at discrete times post transfection. Target sites were chosen that had significant levels of off-target editing at one or two sites within the genome as can be seen in Table 2.

Figure 55:
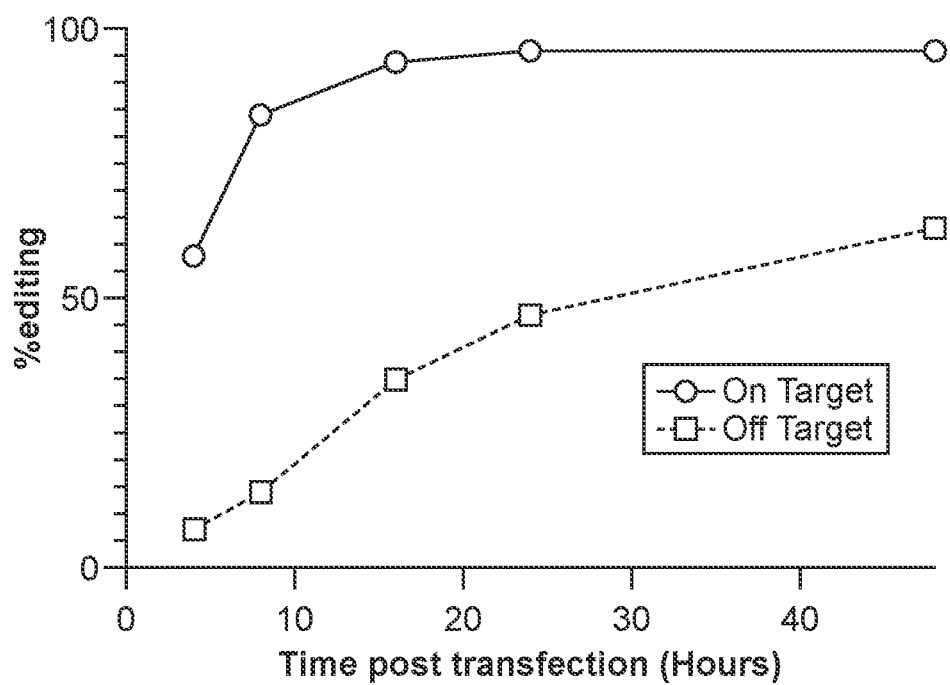
FIG. 55 is a graph showing the ratio of on-target:off-target editing at various time points post transfection.
Figure 56:
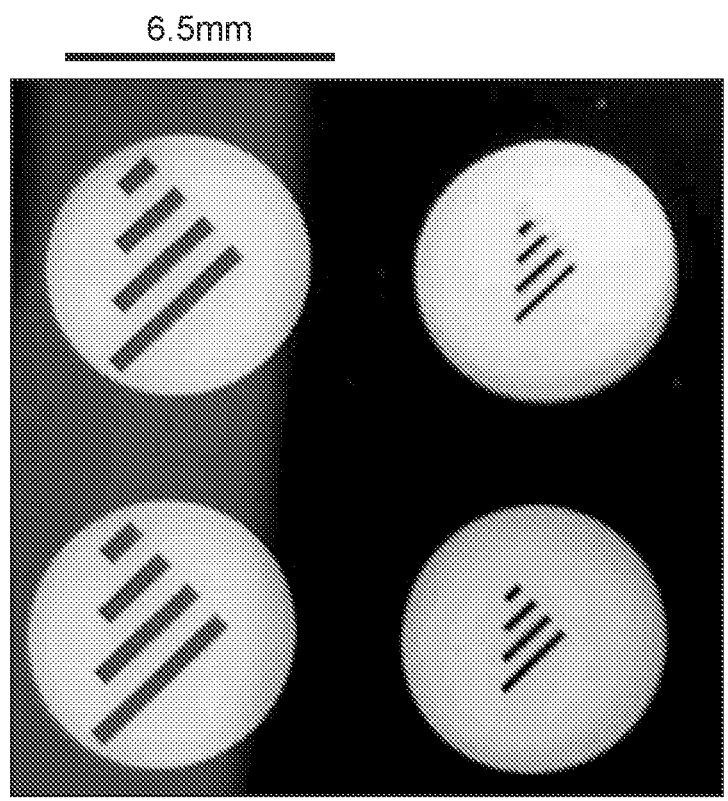
FIG. 56 is a picture of the thin film mask applied to the cell culture of FIG. 44 such that clear areas allowed light to pass through, inactivating the editing activity of the Cas9 nuclease in complex with CRISPR OFF, and dark areas are opaque to allow editing to proceed unimpeded.

FIG. 55 is a graph showing the ratio of on-target:off-target editing at the various time points in HEK293 cells post transfection.

TABLE 2

Off-target sites

| Target | Target Sequence |
| --- | --- |
| MIP_OT1 | AGTGGGGTCCTCACTGCACT (SEQ ID NO: 145) |
| MIP_OT2 | TGTGGGGCACTCACTGCGCT (SEQ ID NO: 146) |
| FAM163_OT1 | CTGCAGGGCCCGCTGGAGAG (SEQ ID NO: 147) |
| FAM163_OT2 | CTGCAGGGGACACTGGTGAG (SEQ ID NO: 148) |
| OMP_OT1 | AGGCTGTAGCCCCTGCTGCT (SEQ ID NO: 149) |
| OMP_OT2 | GAACTACAGCCACTGCTGCT (SEQ ID NO: 150) |
| FANCF_OT1 | GCTGCAGAAGGGATTCCAAG (SEQ ID NO: 41) |
| MAPRE_OT1 | ATCTCTGCAGATAATCCCTG (SEQ ID NO: 152) |
| OPN1SW_OT1 | TTAGAGGCAATGTGGTACTG (SEQ ID NO: 153) |
| VEGFA_OT1 | TGTGGGTGAGTGTGTGCGTG (SEQ ID NO: 154) |

TABLE 3

Off-target sequencing primers

| Target | Primer F | Primer R | Primer Seq |
| --- | --- | --- | --- |
| MIP_OT1 | CTCACAGCAAGGTCGACCAC (SEQ ID NO: 155) | CACCCCTACACACTGCCTTT (SEQ ID NO: 156) | CATTCGAAATCCTATGCTGAGCTTTCATAG (SEQ ID NO: 157) |
| MIP_OT2 | CGGCTCCAGTGCTCTTTCTT (SEQ ID NO: 158) | GGAGGGTACGCAAGGTTTGG (SEQ ID NO: 159) | GCCTTTCTGACTCCCATCCTTC (SEQ ID NO: 160) |
| FAM163_OT1 | GTGGATAGGAGCATCTGCCC (SEQ ID NO: 161) | GTGGGAGAAGGAGGTCATGC (SEQ ID NO: 162) | CCTCCCCATATGCTTGGAGTAAG (SEQ ID NO: 163) |
| FAM163_OT2 | GCCCACATTTGCACTGACTC (SEQ ID NO: 164) | GATCATGGTGATGTGCGCAC (SEQ ID NO: 165) | AGACAAGACACCACAGCAATTCCAATTTTG (SEQ ID NO: 166) |
| OMP_OT1 | AGATCCTGGGGGTCTCTGTG (SEQ ID NO: 167) | CGCCTGCTTATCATTTGGC (SEQ ID NO: 168) | GAACTAGAGACTTATGAGTGGTTCTAAGAT (SEQ ID NO: 169) |
| OMP_OT2 | TTGCAACACCAGGGCTTTCT (SEQ ID NO: 170) | CTTCACAGGCTTCAGGGAGG (SEQ ID NO: 171) | TAGCATTTCCTTCTTTAGAGGTTGATTATG (SEQ ID NO: 172) |
| FANCF_OT1 | AGTTTCACATCCCTGTCTTACCTC (SEQ ID NO: 173) | AGACTCACAACATCCATCAGAACA (SEQ ID NO: 174) | AGTTTCACATCCCTGTCTTACCTC (SEQ ID NO: 173) |
| MAPRE_OT1 | ACAGTTTGTGGGCTTTTTGGT (SEQ ID NO: 176) | GCATTCTGCCCTGTTTGTGG (SEQ ID NO: 177) | CATTTTGAGCAAGGTCAGAAGGAC (SEQ ID NO: 178) |
| OPN1SW_OT1 | TGGCCATAGGAAGCACAGTC (SEQ ID NO: 179) | ATGATCCCCTGTCTCTGCT (SEQ ID NO: 180) | CTACCTCCCTCTCCTTAGCTTCTC (SEQ ID NO: 181) |
| VEGFA_OT1 | AGGGACTTGAGTATCTGCAGTTTT (SEQ ID NO: 182) | TGAAGAGATATCTGCACCCTCATG (SEQ ID NO: 183) | AGGGACTTGAGTATCTGCAGTTTT (SEQ ID NO: 182) |

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Example 19: GFP Knockout Using Cas9-CRISPR OFF 10 pmol NLS-Cas9-NLS protein (Aldevron) was combined with 30 pmol synthetic sgRNAs in 20 uL total volume and allowed to complex for 10 minutes. During this incubation, cells were harvested and counted. To the RNP solution 5 μL of cell solution at a concentration of 4*10$^4$ cells/μL was added and gently mixed.

Cell+RNP solution was transfected using the 4D-Nucleofector system (Lonza) in the 20 μL format. Transfections were done according to manufacturer protocol. Following transfection, cells were recovered in culture media and plated into 96-well plates.

CRISPR OFF inactivation was performed using a Sunray 600 UV Flood Lamp (Uvitron International). 345 nm and 355 nm 6.5"×6.5" colored glass alternative longpass filters were obtained from Newport.com and mounted using custom 3D-printed containers.

Inactivation using an upright microscope was performed using a Zeiss Axios Observer with a Colibri 7 Flexible Light Source and 385 nm LED.

Figure 43:
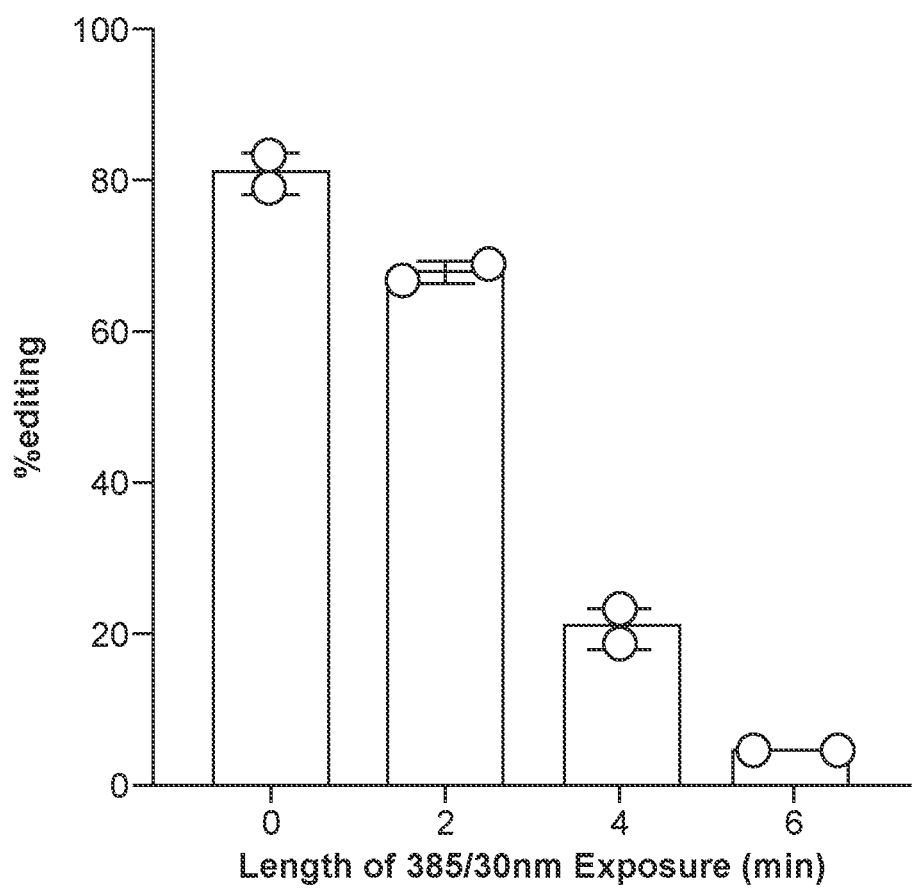
FIG. 43 is a graph showing that the percent editing observed in cells decreases with increased exposure to light at 385 nm.

FIG. 43 is a graph showing that the percent editing observed in cells decreases with increased exposure to light at 385 nm.

Figure 44:
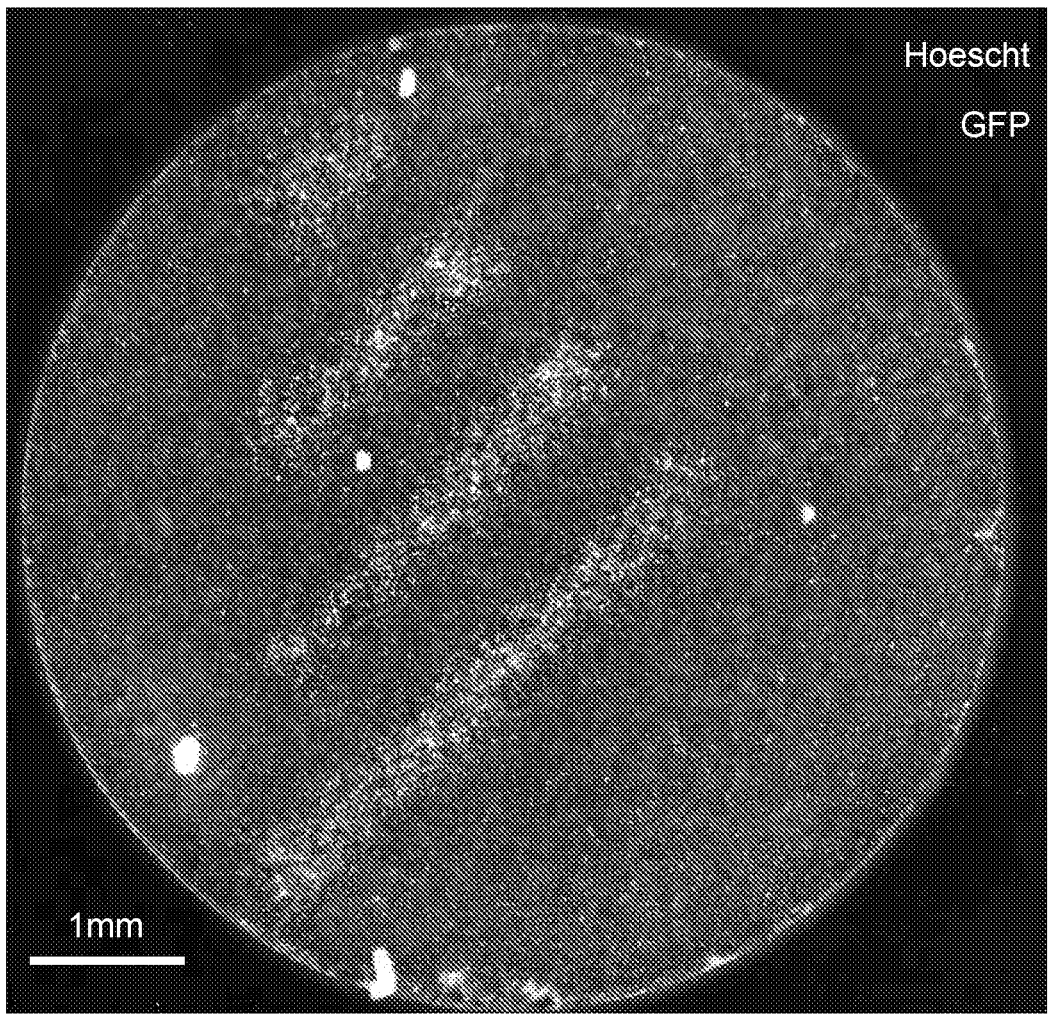
FIG. 44 is an image of a plate of cells selectively masked to prevent some cells from being exposed to light such that the GFP gene is knocked out in those cells kept in the dark, whereas those cells exposed to light express GFP.

FIG. 44 shows a cell culture wherein a mask was used to selectively expose cells expressing CRISPR OFF sgRNA to light to inactivate the gene encoding GFP in cells exposed to light, meanwhile allowing cells unexposed to light to continue to express GFP.

FIG. 24 is a picture of the thin film mask applied to the cell culture of FIG. 44 such that clear areas allowed light to pass through, inactivating the editing activity of the Cas9 nuclease in complex with CRISPR OFF, and dark areas are opaque to allow editing to proceed unimpeded.

Figure 48:
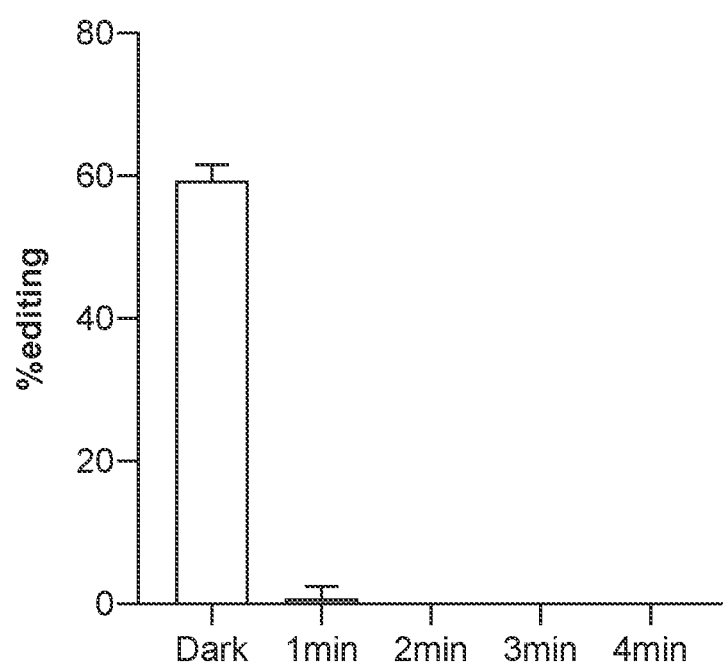
FIG. 48 is a graph showing the time frame in which the CRISPR polynucleotide of FIG. 34 is inactivated by exposure to light with a wavelength of 430±23 nm using the same protocol as FIG. 27.
Figure 49:
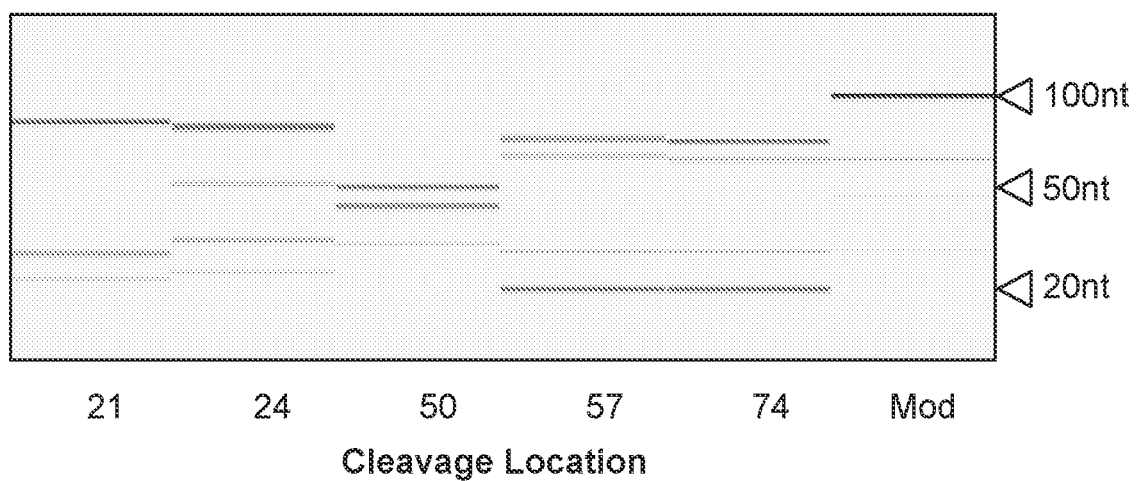
FIG. 49 is a gel showing the cleavage products obtained when a cleavable linker is activated at different locations along the sgRNA.

Example 20: Inactivation of Cas9 in Complex with CRISPR OFF sgRNA with Visible Light FIG. 48 shows how quickly the CRISPR OFF sgRNA targeting MIP, with a coumarin linker at positions 57 and 74, is inactivated by an LED light source. The HEK293 cells transfected with a CRISPR OFF sgRNA with a coumarin linker were split into five independent wells. After four hours, paired replicates were covered to remove ambient light, or exposed to a 430±23 nm LED for 1 min, 2 min, 3 min, or 4 min. One minute was sufficient to inactivate gene-editing. A Colibri 7 light source with 100% intensity of a 430±23 nm LED was used with a standard inverted fluorescent microscope which could illuminate a single well at a time.

Example 21: Testing of Multiple Linker Locations on a sgRNA

RNP Formation and Delivery 10 pmol NLS-Cas9-NLS protein (Aldevron) was combined with 30 pmol synthetic sgRNAs in 20 uL total volume and allowed to complex for 10 minutes. During this incubation, cells were harvested and counted. To the RNP solution 5 μL of cell solution at a concentration of 4*10$^4$ cells/μL was added and gently mixed.

Cell+RNP solution was transfected using the 4D-Nucleofector system (Lonza) in the 20 μL format. Transfections were done according to manufacturer protocol. Following transfection, cells were recovered in culture media and plated into 96-well plates.

CRISPR OFF Inactivation

CRISPR OFF inactivation was performed using a Sunray 600 UV Flood Lamp (Uvitron International). 345 nm and 355 nm 6.5"×6.5" colored glass alternative longpass filters were obtained from Newport.com and mounted using custom 3D-printed containers.

Inactivation using an upright microscope was performed using a Zeiss Axios Observer with a Colibri 7 Flexible Light Source and 385 nm LED.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Table 1. Following Sanger sequencing, presence of indels was analyzed via ICE (Synthego).

Figure 50A:
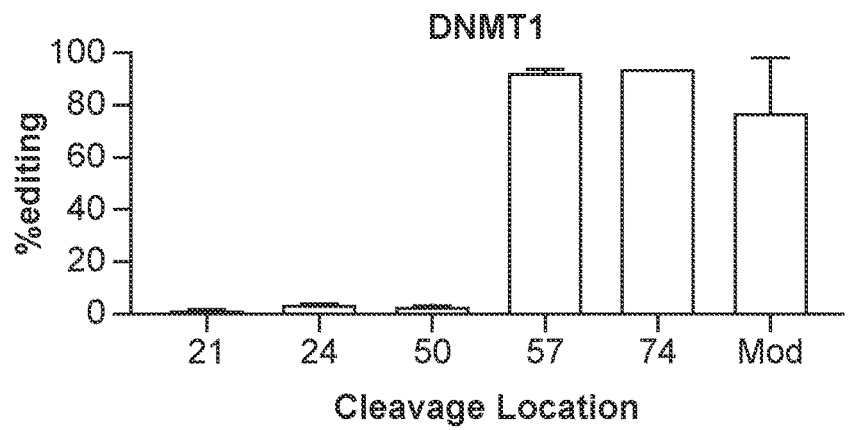
FIG. 50A-C show graphs of the editing activity of various CRISPR OFF cleavable linker locations when targeting different genes.
Figure 50B:
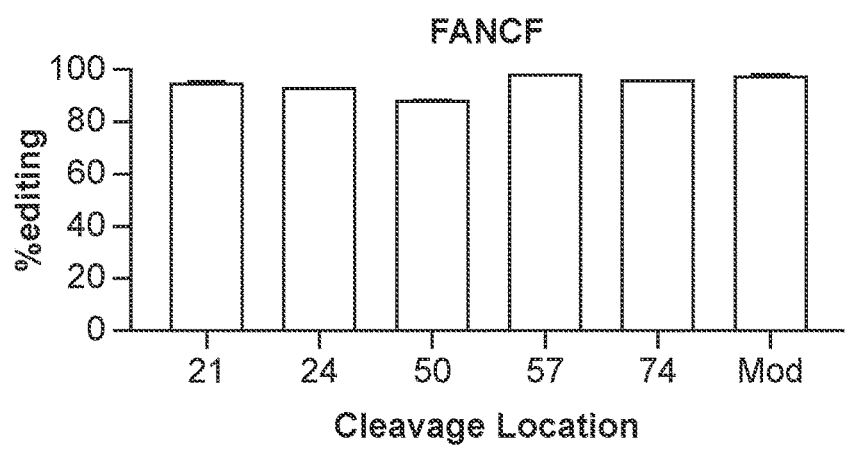
Figure 50C:
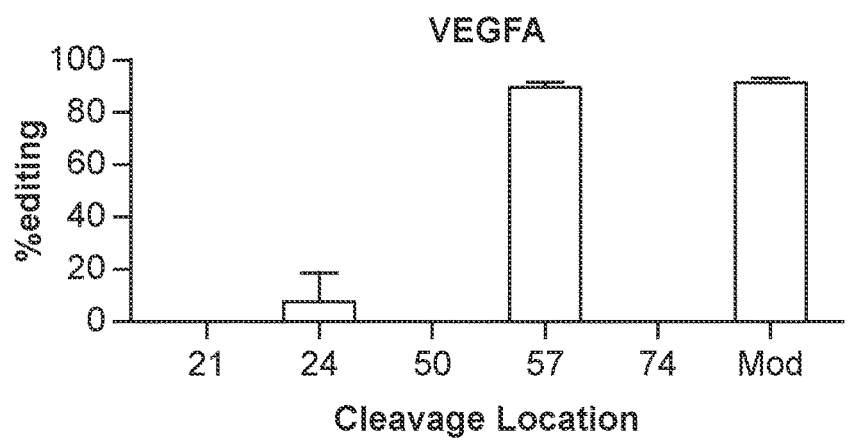

FIGS. 50A-50C show the percent editing observed by eighteen different sgRNAs, in complex with a Cas9 nuclease as described above. FIG. 50A shows the percent editing observed in six different sgRNAs in complex with a Cas9 nuclease, each targeting DNMT1. The sgRNAs are standard (Mod) or have a single cleavable linker at position 21, 24, 50, 57, or 74. FIG. 50B shows the percent editing observed in six different sgRNAs in complex with a Cas9 nuclease, each targeting FANCF. The sgRNAs are standard (Mod) or have a single cleavable linker at position 21, 24, 50, 57, or 74. FIG. 50C shows the percent editing observed in six different sgRNAs in complex with a Cas9 nuclease, each targeting VEGFA. The sgRNAs are standard (Mod) or have a single cleavable linker at position 21, 24, 50, 57, or 74.

Example 22: Droplet PCR to Detect the Fragmentation of CRISPR OFF after Exposure to Light Digital Droplet PCR Cellular RNA was extracted using RNA QuickExtract (Lucigen) without DNase. RNA was quantified using RiboGreen (Thermo Fisher) and normalized.

CRISPR OFF inactivation was performed using a Sunray 600 UV Flood Lamp (Uvitron International). 345 nm and 355 nm 6.5"×6.5" colored glass alternative longpass filters were obtained from Newport.com and mounted using custom 3D-printed containers.

Inactivation using an upright microscope was performed using a Zeiss Axios Observer with a Colibri 7 Flexible Light Source and 385 nm LED.

Total RNA was reverse transcribed using iScript Advanced cDNA Synthesis Kit (BioRad) with 0.4 uM reverse primer for transcription. Reverse transcription product was amplified using 2× EvaGreen ddPCR Mastermix and thermal cycled at 95° C. for 3 minutes followed by 40 cycles of 95° C. for 30 seconds and 52.4° C. for 1 minutes. Signal was then stabilized at 4° C. for 5 minutes followed by inactivation at 90° C. for 5 minutes. Droplets were then read by a QX200 Droplet Digital PCR System (BioRad).

TABLE 4 ddPCR reagents:

| Primer Name | Sequence |
|---|---|
| sgRNA_F | AGAGCTAGAAATAGCAAGTTAAA (SEQ ID NO: 185) |
| sgRNA_R | GACTCGGTGCCACTTT (SEQ ID NO: 186) |

Figure 45:
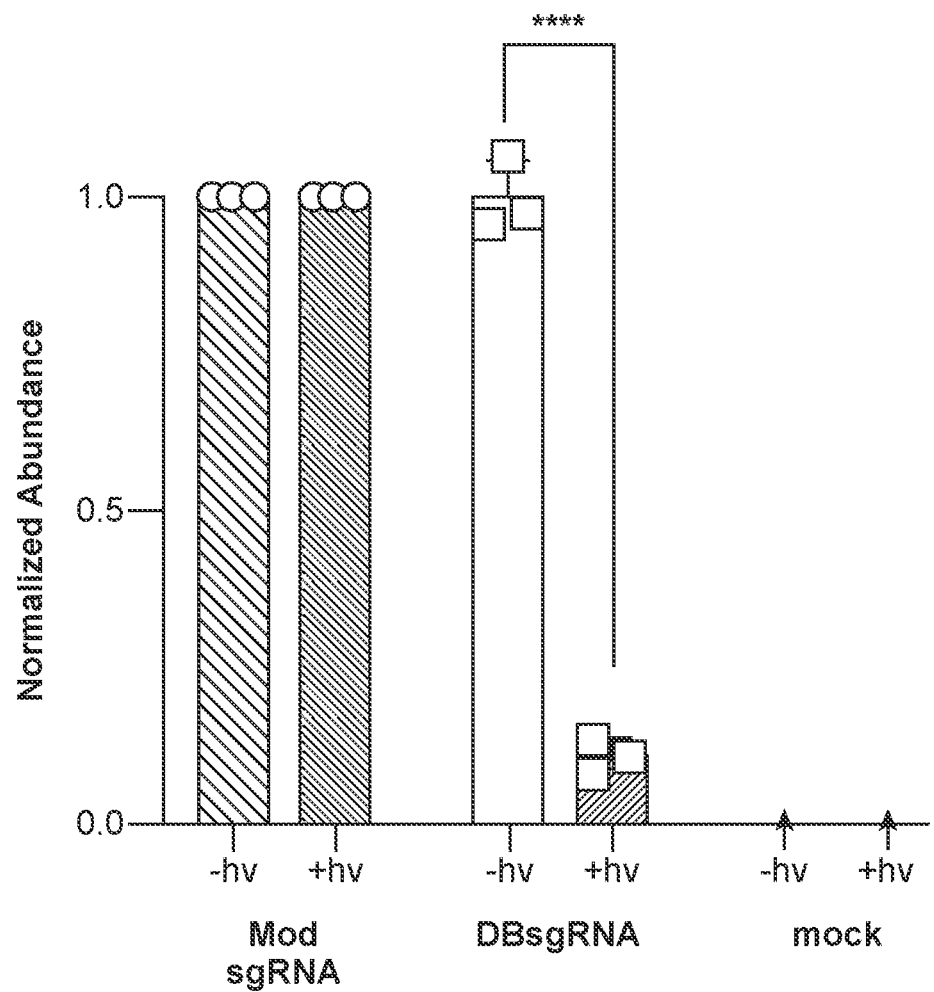
FIG. 45 is a graph showing that the polynucleotide of FIG. 34 decreases in abundance significantly when exposed to light, as compared to sgRNA without photocleavable linkers.

FIG. 45 shows a graph demonstrating the decrease in abundance of CRISPR OFF after exposure to light as compared to standard sgRNA.

Example 23: Preparation of 1-(7-(diethylamino)-2-oxo-2H-chromen-4-yl)propyl

The phosphoramidite compound 3 (3-(bis(4-methoxyphenyl)(phenyl)methoxy)-1-(7-(diethylamino)-2-oxo-2H-chromen-4-yl)propyl (2-cyanoethyl) diisopropylphosphoramidite) is synthesized, following a method disclosed in Wenzel et al. (2003) (NUCLEOSIDES, NUCLEOTIDES & NUCLEIC ACIDS, Vol. 22, Nos. 5-8, pp. 1579-1581), by reacting aldehyde compound 1 (7-(diethylamino)-2-oxo-2H-chromene-4-carbaldehyde) with allyltrimethylsilane in the presence of TiCl$_4$. Next, the diol compound 2 (7-(diethylamino)-4-(1,3-dihydroxypropyl)-2H-chromen-2-one) is generated by ozonolysis of the previous compound and reductive workup with NaBH$_4$. Dimethoxytritylation of 2 followed by phosphitylation yields the phosphoramidite compound 3 in excellent yields.

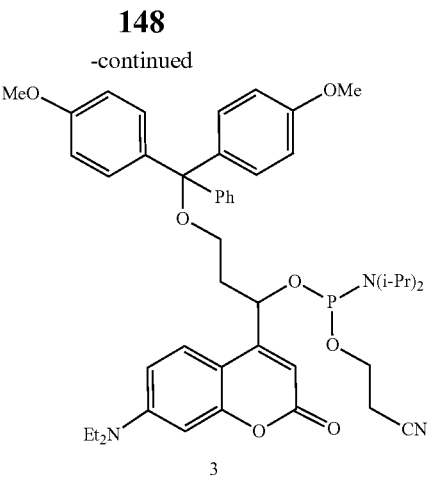

Example 24: Linking 1-(7-(diethylamino)-2-oxo-2H-chromen-4-yl)propyl to a Nucleotide The DMT (DMT=4,4'-dimethoxytrityl) protecting group of the RNA bearing linker formed after addition of compound 3 is removed in an acid-catalyzed detritylation reaction. The detritylated RNA is ready to react with a nucleotide, which is added in the form of a nucleoside phosphoramidite monomer. An appropriate nucleoside phosphoramidite is mixed with an activator (tetrazole or a derivative), both of which are dissolved in acetonitrile. The diisopropylamino group of the nucleoside phosphoramidite is protonated by the activator and is thereby converted to a good leaving group. It is rapidly displaced by attack of the deprotected hydroxyl group of the detritylated RNA on its neighboring phosphorus atom, and a new phosphorus-oxygen bond is formed, creating a phosphite triester bond (as shown in the figure immediately below). Nucleoside phosphoramidites are reasonably stable in an inert atmosphere and can be prepared in large quantities.

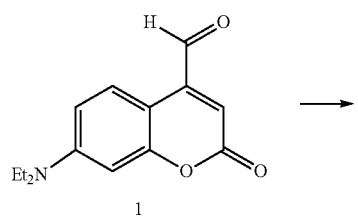

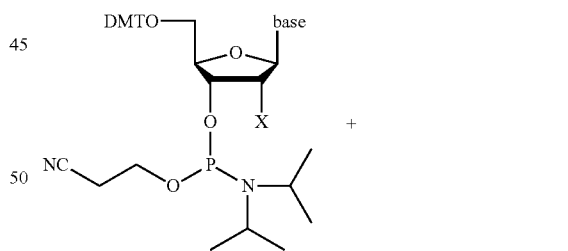

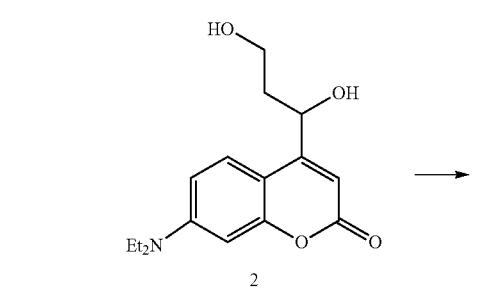

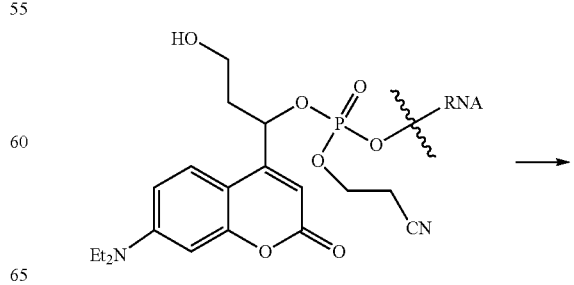

149

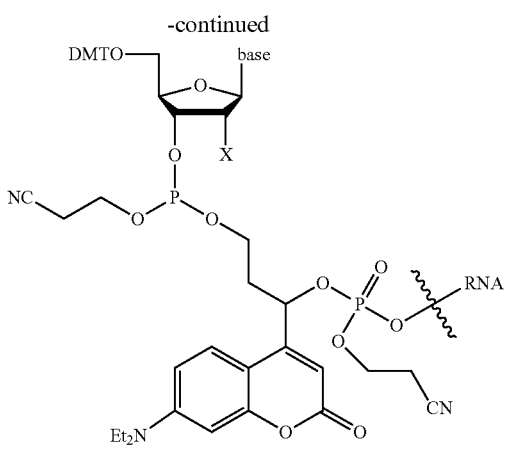

X can be H, OTBDMS (O-tert-butyldimethylsilyl ether), or OMe.

In some embodiments, the diisopropylamino group of the phosphoramidite linker compound 3 is protonated by the activator, and is thereby converted to a good leaving group. It is rapidly displaced by attack of the 3' or 5' hydroxyl group of the nucleoside base, and a new phosphorus-oxygen bond is formed (as shown in the figure immediately below)

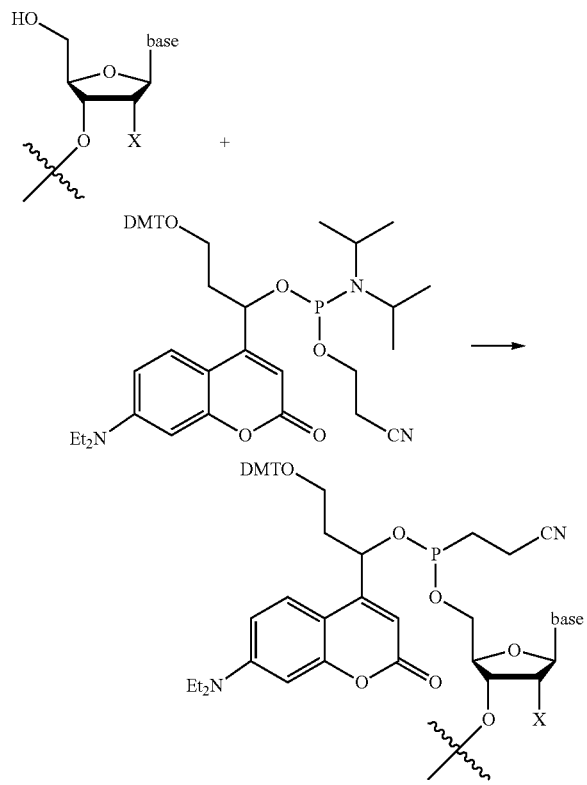

X can be H, OTBDMS (O-tert-butyldimethylsilyl ether) or OMe.

One of skill in the art will understand the phosphoramidite method described in the preceding example generally includes four steps: step 1 (detritylation), step 2 (coupling), step 3 (capping), and step 4 (oxidation).

150

Example 25: Inactivation of Cas9 Linked with CRISPR OFF sgRNA with UV Light

NLS-Cas9-NLS protein (Aldevron) is combined with synthetic CRISPR OFF sgRNA comprising a linker configured to form a covalent bond with the Cas9 and a photocleavable linker at position 54 and 74. The sgRNA is covalently linked to the Cas9 nuclease through the linker to from a linked RNP complex.

Cells are transfected with the linked RNP complex. Following transfection, cells are recovered in culture media and plated into 96-well plates. The cells are incubated for 48 hours to permit the RNP complex to edit the target sequence.

The CRISPR complex is inactivated using a Sunray 600 UV Flood Lamp (Uvitron International) with 345 nm and 355 nm 6.5"×6.5" colored glass alternative longpass filters. Cells are harvested at time intervals before use of the flood lamp and after.

Alternatively, inactivation using an upright microscope is performed using a Zeiss Axios Observer with a Colibri 7 Flexible Light Source and 385 nm LED. Nucleic acid is extracted from the harvested cells and is used to measure editing efficiency at the time intervals.

Example 26: Target Editing Using CRISPR ON V1 sgRNA Variants

Figure 58:
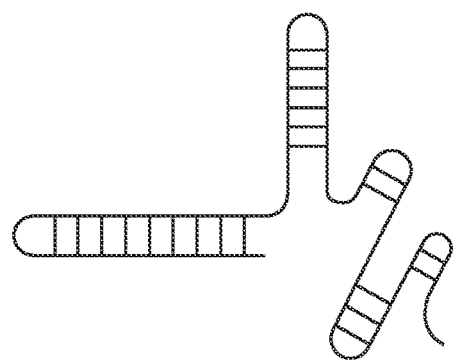
FIG. 58 shows the structure of CRISPR ON V1 sgRNA. The sgRNA structure is identical to *Streptococcus pyogenes* Cas9 (SpCas9) sgRNA but contains a 20 nucleotide (nt) sequence complementary to protospacer (backtrack) sequence followed by a 4 nt loop structure immediately 5' of protospacer.
Figure 59:
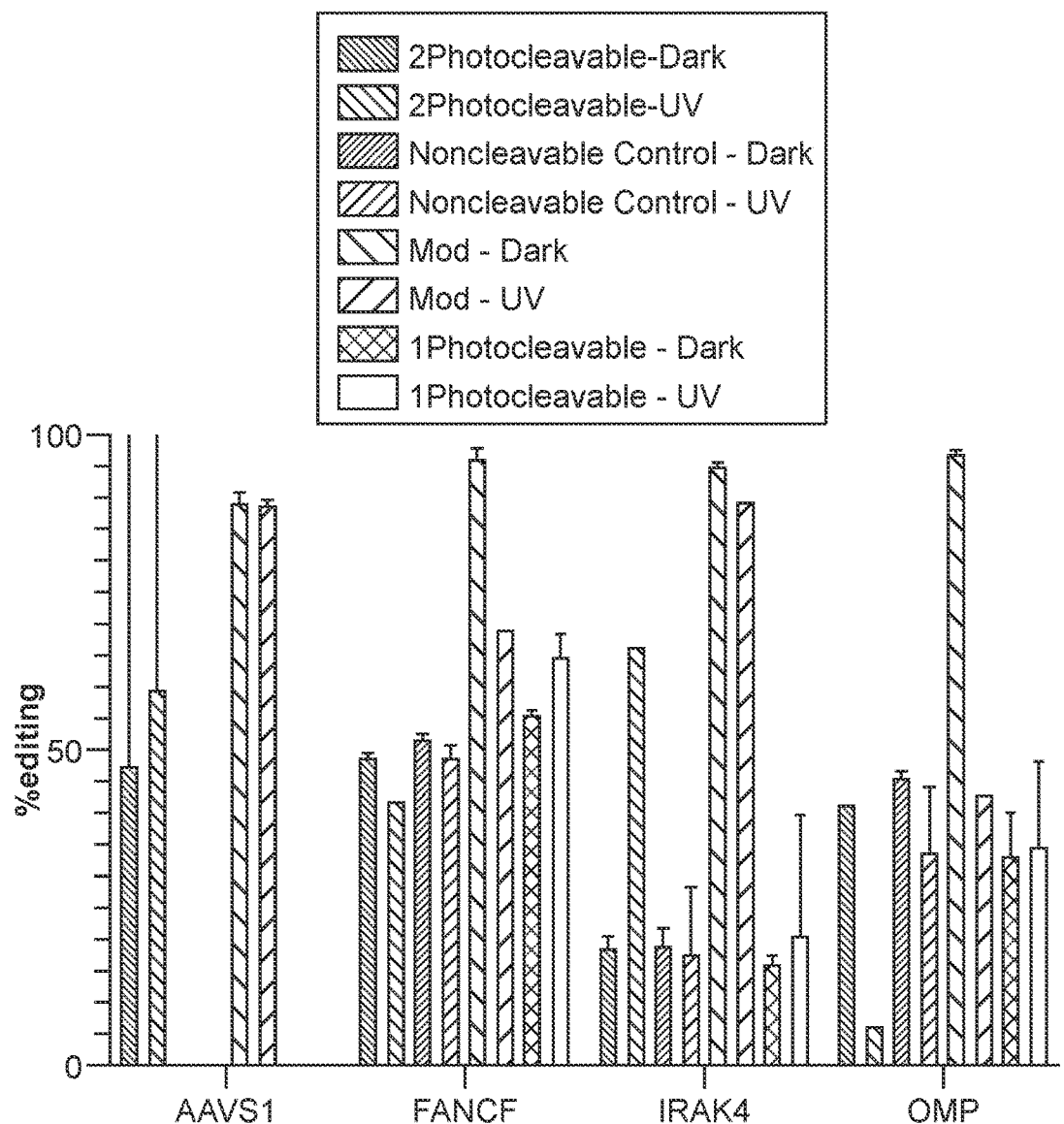
FIG. 59 shows editing using three variants of CRISPR ON V1 sgRNAs targeting four unique loci. The three variants included: one that was not expected to respond to light stimulus (Noncleavable Control), one containing a single photocleavable linker in at position 24 from the 5' end of the sgRNA (1Photocleavable), and one containing 2 photocleavable linkers at positions 11 and 24 (2Photocleavable).

FIG. 58 shows the structure of CRISPR ON V1 sgRNA, which is identical to Streptococcus pyogenes Cas9 (SpCas9) sgRNA but it contains a 20 nucleotide (nt) sequence complementary to protospacer (backtrack) sequence followed by a 4 nt loop structure immediately 5' of protospacer. FIG. 59 shows target editing using three variants of CRISPR ON V1 sgRNAs targeting four unique loci. The three variants included: one that was not expected to respond to light stimulus (Noncleavable Control), one containing a single photocleavable linker in at position 24 from the 5' end of the sgRNA (1Photocleavable), and one containing 2 photocleavable linkers at positions 11 and 24 (2Photocleavable). CRISPR ON sgRNAs were mixed with SpCas9 to form RNPs and transfected into HEK293. After 4 hours, cells were split into two experimental groups, one subjected to photoirradiation, and one group left in the dark. 48 hours post-transfection, genomic DNA was isolated from both groups and analyzed for the presence of indels. Incorporation of a complement to protospacer sequence decreased editing efficiency at all targets analyzed. Incorporation of photocleavable linkers into the hairpin and, optionally, into a complement to protospacer did not result in a full disruption of editing but also did not allow for the full recovery of editing after exposure to light.

Example 27: Target Editing Using CRISPR ON V2 sgRNA

Figure 60:
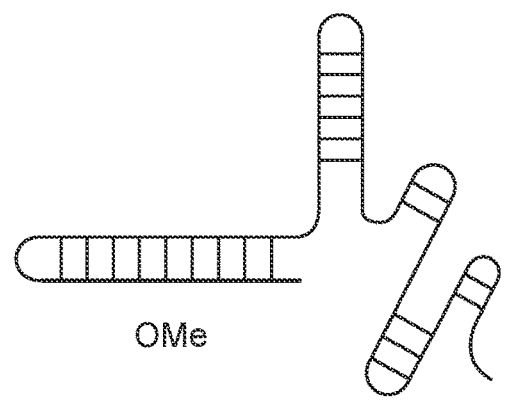
FIG. 60 shows the structure of CRISPR ON V2 sgRNA. CRISPR ON V2 uses the same structure as CRISPR ON V1 but it replaces the backtrack sequence (first 20 nt of RNA, complementary to protospacer) with 2'-O-Methyl (2' O-Me) RNA. 2' O-Me RNA binds more tightly to RNA and is less likely to be displaced during R-Loop formation.

FIG. 60 shows the structure of CRISPR ON V2 sgRNA, which uses the same structure as CRISPR ON V1 but it replaces the backtrack sequence (first 20 nt of RNA, complementary to protospacer) with 2'-O-Methyl (2' O-Me) RNA. 2' O-Me RNA binds more tightly to RNA and is less likely to be displaced during R-Loop formation. FIG. 61 shows a comparison of editing activity between standard sgRNA (Mod), CRISPR ON V1 (RNA) and CRISPR ON V2 (O-Me). CRISPR ON RNPs were transfected in to HEK293s and allowed to recover. 48 hours post transfection, genomic DNA was harvested and analyzed for the presence of indels. CRISPR ON V2 significantly reduced the induction of indels at all 5 loci tested. CRISPR ON RNPs were transfected in to HEK293s and allowed to recover. 48 hours post transfection, genomic DNA was harvested and analyzed for the presence of indels. CRISPR ON V2 significantly reduced the induction of indels at all 5 loci tested.

Example 28: Target Editing Using CRISPR ON V3 sgRNA

FIG. 62 shows the structure of CRISPR ON V3 sgRNA, which is built upon CRISPR ON V2 but it incorporates photocleavable linkers in the middle of the protospacer backtrack (position 11) and immediately 5' of protospacer sequence (position 24). FIG. 63 shows editing using CRISPR ON V3 sgRNA (K11,24) targeting five unique loci in comparison to CRISPR ON V2 variant containing a single photocleavable linker at position 24 (K24), CRISPR ON V2 (O-Me) and standard sgRNA (Mod). Incorporation of photocleavable linkers into CRISPR ON V3 allowed for partial recovery of editing activity. RNPs containing CRISPR ON V3 sgRNAs were transfected into HEK293 cells. 4 hours post transfection, pools were split into two groups, of which one was exposed to light while the other remained in the dark. 48 hours post transfection, DNA was extracted from all groups and analyzed for the presence of indels. CRISPR ON V3 sgRNAs left in the dark displayed consistently low to non-detectable levels of editing. The same samples when exposed to light had increased levels of indels detected in the genomic DNA. This increase in indel presence was not seen in the guides lacking the photocleavable linkers.

Example 29: Target Editing Using CRISPR ON V4 sgRNA Variants

FIG. 64 shows the structure of CRISPR ON V4 sgRNA, which builds on CRISPR ON V3 but introduces additional photocleavable linkers to ensure efficient displacement of the backtrack region by the DNA target. Photocleavable residues are placed at positions 23 and 24 to increase the probability of backtrack release from the sgRNA. Additional photocleavable residues are placed at position 6 and 14 to aid in dissociation. FIG. 65 shows editing using CRISPR ON V4 sgRNA variants in comparison to 5RP (comprising the additional sequence 5'-UCUCCCUGAGCUUCAGG-GAG-3' (SEQ ID NO: 187) at the 5' of the sgRNA), CRISPR ON V2 (Me) and standard sgRNA (Mod) at two loci. The CRISPR ON V4 sgRNAs variants included photocleavable linkers at nucleotides: 3, 23 and 24 (K3, 23, 24); 6, 11, 16, 23 and 24 (K6, 11, 16, 23, 24); 6, 14, 23 and 24 (K6, 14, 23, 24). RNPs formed with CRISPR ON V4 sgRNAs were transfected in HEK293 cells. 1-hour post transfection, cells were split in two groups. One group was exposed to targeted light while the other remained in the dark. 48-hours post transfection DNA was isolated from both groups and analyzed for the presence of indels. Addition of photocleavable linkers at position 23 and 24 appeared to increase the recovery of the editing efficiency at all targets. Further optimization by inclusion of photocleavable linkers at positions 6 and 14 allowed for efficient recovery of editing activity similar to that of the standard (Mod) sgRNAs.

Materials and Methods

CRISPR ON sgRNA Synthesis

All RNAs were synthesized using Synthego's CRISP-Revolution platform via solid phase phosphoramidite chemistry, and their identities were confirmed via electrospray ionization mass spectrometry (ESI-MS).

Cell Culture

Human embryonic kidney cells (HEK293) were maintained between passage 5-20 in Advanced Modified Eagles Medium (Life Technologies) and 10% v/v FBS. Cells were passaged biweekly at a 1:8 ratio with TrypLE (Life Technologies). All cells were maintained at 37° C. and 5% $CO_2$.

RNP Formation and Delivery 10 pmol *Streptococcus Pyogenes* NLS-SpCas9-NLS protein (Aldevron Cat #9212) was combined with 30 pmol synthetic sgRNAs (Synthego) in 20 uL total volume and allowed to complex for 10 minutes. During this incubation, cells were harvested and counted. To the RNP solution 5 μL of cell solution at a concentration of $4*10^4$ cells/μL was added and gently mixed.

Cell+RNP solution was transfected using the 4D-Nucleofector system (Lonza) in the 20 μL format. HEK293 transfections were conducted in SF buffer using protocol CM-130. Following transfection, cells were recovered in culture media and plated into 96-well plates. To create paired replicates, transfections were stamped into a second 96-well plate and allowed to recover independently.

sgRNA Activation

CRISPR ON activation was performed a custom Arduino controlled lightboard. Light board contained 24 unique individually controlled LEDs with 420-430 nm. 96-well plates were irradiated for 4-7 minutes to activate sgRNAs.

Genomic Analysis

Genomic DNA was isolated using DNA QuickExtract (Lucigen) following manufacturer protocol. After harvesting, extract solution was incubated at 65° C. for 15 minutes, 68° C. for 15 minutes followed by 98° C. for 10 minutes. Genomic PCR was performed using AmpliTaq Gold 360 Master Mix (Thermo Fischer) using primer sequences found in Supplementary Table 2. Following Sanger sequencing, presence of indels was analyzed via ICE (Synthego).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in any combination in practicing the invention. It is intended that the following claims define the scope of the invention and that methods and structures within the scope of these claims and their equivalents be covered thereby.

What is claimed is:

1. A CRISPR complex comprising a single guide RNA (sgRNA) covalently bound to a CRISPR effector protein via an adenosine nucleotide or a deoxyadenosine nucleotide at position 22 and a modified uridine nucleotide or a modified deoxyuridine nucleotide at position 49 (the nucleotide positions being numbered consecutively from 5' to 3' from nucleotide position 1 at the 5' end of the target binding region of the sgRNA, wherein the target binding region consists of 20 nucleotides).

2. The CRISPR complex of claim 1, wherein the CRISPR effector protein is Cas9.

3. The CRISPR complex of claim 1, wherein the CRISPR complex comprises nuclease activity.

4. A method of editing a target gene in one or more cells comprising administering the CRISPR complex of claim 1 to the one or more cells comprising the target gene, thereby editing the target gene in the one or more cells.

5. A method of preparing the CRISPR complex of claim 1, the method comprising reacting the sgRNA and the CRISPR effector protein under conditions whereby the unnatural nucleotide of the sgRNA covalently binds to the CRISPR effector protein.

6. A single guide (sgRNA) comprising a crispr RNA (crRNA) region comprising a target binding region and a tracrRNA region that comprises a CRISPR effector protein binding region, wherein the tracrRNA region comprises an unnatural nucleotide that covalently binds to the CRISPR effector protein when the sgRNA binds to the CRISPR effector protein, wherein the sgRNA comprises an adenosine nucleotide or a deoxyadenosine nucleotide at position 22 and a modified uridine nucleotide or a modified deoxyuridine nucleotide at position 49 (the nucleotide positions being numbered consecutively from 5' to 3' from nucleotide position 1 at the 5' end of the target binding region of the sgRNA, wherein the target binding region consists of 20 nucleotides).

7. The sgRNA of claim 6, wherein the tracrRNA region comprises a CRISPR effector protein binding region for Cas9.

8. A system for preparing a CRISPR complex, the system comprising as components: (i) the sgRNA of claim 6 and (ii) a CRISPR effector protein to which the sgRNA covalently binds.

* * * * *